(12) United States Patent
Glenn et al.

US007052896B2

(10) Patent No.: US 7,052,896 B2
(45) Date of Patent: May 30, 2006

(54) LACTOBACILLUS RHAMNOSUS POLYNUCLEOTIDES, POLYPEPTIDES AND METHODS FOR USING TH

(76) Inventors: Matthew Glenn, Genesis Research & Development Corporation Limited, 1 Fox Street, Parnell (NZ); Ilkka J. Havukkala, Genesis Research & Development Corporation Limited, 1 Fox Street, Parnell (NZ); Leonard N. Bloksberg, Genesis Research & Development Corporation Limited, 1 Fox Street, Parnell (NZ); Mark W. Lubbers, New Zealand Dairy Research Institute, Private Bag 11029, Palmerston North (NZ); James Dekker, New Zealand Dairy Research Institute, Private Bag 11029, Palmerston North (NZ); Anna C. Christensson, Department of Applied Microbiology, Lund University, P.O. Box 124, SE-22100 Lund (SE); Ross Holland, New Zealand Dairy Research Institute, Private Bag 11029, Palmerston North (NZ); Paul W. O'Toole, Institute of Molecular Biosciences, Massy University, Palmerston North (NZ); Julian R. Reid, New Zealand Dairy Research Institute, Private Bag 11029, Palmerston North (NZ); Timothy Coolbear, New Zealand Dairy Research Institute, Private Bag 11029, Palmerston North (NZ)

( * ) Notice: Subject to any disclaimer, the term of this patent is extended or adjusted under 35 U.S.C. 154(b) by 967 days.

(21) Appl. No.: 09/971,536

(22) Filed: Oct. 2, 2001

(65) Prior Publication Data
US 2002/0159976 A1 Oct. 31, 2002

Related U.S. Application Data

(63) Continuation-in-part of application No. 09/634,238, filed on Aug. 8, 2000, now Pat. No. 6,544,772, and a continuation-in-part of application No. 09/724,623, filed on Nov. 28, 2000, now Pat. No. 6,476,209.

(30) Foreign Application Priority Data
Aug. 8, 2001 (NZ) .................. PCT/NZ01/00160

(51) Int. Cl.
C12N 9/18 (2006.01)
A23L 2/66 (2006.01)
A23C 19/093 (2006.01)
(52) U.S. Cl. .................. 435/197; 435/183; 435/195; 435/198; 426/534
(58) Field of Classification Search ............. 435/197, 435/198, 195, 183; 426/534
See application file for complete search history.

(56) References Cited

U.S. PATENT DOCUMENTS

| 6,379,663 B1 | 4/2002 | Gill et al. |
| 6,476,209 B1 | 11/2002 | Glenn et al. |
| 6,544,772 B1 | 4/2003 | Glenn et al. |

FOREIGN PATENT DOCUMENTS

| WO | WO 01/77335 A2 | 10/2001 |
| WO | WO 02/44383 A1 | 6/2002 |

OTHER PUBLICATIONS

Choo et al. A cold-adapted lipase of an Alaskan psychrotroph, Pseudomonas sp. strain B11-1: gene cloning and enzyme purification and characterization. Appl Environ Microbiol. vol. 64, No. 2, pp. 486-491, Feb. 1998.*
Uniprot Entry for O52270, printed on Jun. 13, 2005.*
Stentz, Régis, et al., "Molecular Cloning and Analysis of the *ptsHI* Operon in *Lactobacillus sake*", *Applied and Environmental Microbiology*, vol. 63, No. 6, pp. 2111-2116 (1997).
Luesink, Evert J., et al., "Molecular Characterization of the *Lactococcus lactis ptsHI* Operon and Analysis of the Regulatory Role of HPr", *Journal of Bacteriology*, vol. 181, No. 3, pp. 764-771 (1999).
Groisillier, Agnés, et al., "Comparison of partial malolactic enzyme gene sequences for phylogenetic analysis of some lactic acid bacteria species and relationships with the malic enzyme", *International Journal of Systematic Bacteriology*, vol. 49, pp. 1417-1428 (1999).
GenBank Accession No. AF098777, submitted Jun. 2, 1999.
Kunji, Edmund R.S., et al., "The proteolytic systems of lactic acid bacteria", *Antonie van Leeuwenhoek*, vol. 70, pp. 187-221 (1996).
Branny, Pavel, et al., "An operon encoding three glycolytic enzymes in *Lactobacillus delbrueckii* subsp. *bulgaricus*: glyceraldehyde-3-phosphate dehydrogenase, phoshoglycerate kinase and triosephosphate isomerase", *Microbiology*, vol. 144, pp. 905-914 (1998).
GenBank Accession No. AJ000339, submitted May 8, 1998.
Hidalgo, Elena, et al., "Molecular Cloning and DNA Sequencing of the *Escherichia coli* K-12*ald* Gene Encoding Aldehyde Dehydrogenase", *Journal of Bacteriology*, vol. 173, No. 19, pp. 6118-6123 (1991).

(Continued)

*Primary Examiner*—Terry McKelvey
*Assistant Examiner*—Jennifer Dunston
(74) *Attorney, Agent, or Firm*—Speckman Law Group PLLC; Ann W. Speckman; Janet Sleath

(57) ABSTRACT

Novel polynucleotides isolated from *Lactobacillus rhamnosus*, as well as probes and primers, genetic constructs comprising the polynucleotides, biological materials, including plants, microorganisms and multicellular organisms incorporating the polynucleotides, polypeptides expressed by the polynucleotides, and methods for using the polynucleotides and polypeptides are disclosed.

22 Claims, 65 Drawing Sheets

OTHER PUBLICATIONS

GenBank Accession No. P33898, submitted Jul. 15, 1999.

Schmidt, G., et al., "Molecular characterisation of the dnaK operon of *Lactobacillus sakei* LTH681", *Systematic and Applied Microbiology*, vol. 22, No. 3, pp. 321-328 (1999).

Massa, R.B., EBI Dbfetch, Accession No. AJ617682, submitted Dec. 15, 2003.

Pastar, I., EBI Dbfetch, Accession No. AJ496666, submitted Oct. 5, 2003.

NCBI Database, Accession No. ZP_00046718, submitted Sep. 30, 2004.

* cited by examiner

Fig. 1. Nucleotide sequence containing L. rhamnosus strain HN001 esterase gene AA7 showing ATG initiation and translation stop codons (boxed)

```
GTGTTAAATC CAAGGATCGT TAAAAAACGG GCTTAAAATC AAACGATTAG ACTGTCGGGT  60
GACGCACCGG CAGTCTTTTT GCGTTAATAT AGGAATAACC TTTTAACACG ATTCGTTAAC 120
ACGAGGAAAT GGAGGCATTC GTTA ATG GCA GATGAAGAGG CAATGTTGGC AAAGGTTCAA 180
GCGAGCTGGG CGCAAACGGC TGCTCGGGAT AAGGCACGGT ACGCGGATGA ACGGGTACCG 240
GAAGATGTTC ATTGGGAGAC GGAATATCGG TACGAACAGT CGGCTGATCC GCAGCAAACC 300
CTGAACCTGT ACTATCCGGC CAAAAGACGC AACGCAACCA TGCCGACCGT CATCGATATT 360
CATGGTGGCG GTGGTTTTA TGGTGATCGT AATTTGAATC GTAATTATTG CCGCTATTTG 420
GCTAGTCAAG GATACGCAGT GATGGGTATG GGCTATCGGT TGTTACCGGA TGTTGATTTA 480
CGCGGCCAGA TTCAAGACAT CTTTGCTAGT CTGCGCTGGT TATCGCATTT TGGCCCTCAA 540
CGCGGATTTG ACCTTGACCA TGTGCTTTTG ACCGGGGATT CAGCTGGCGG CCACCTGGCG 600
TCCTTGGTTG CCTGCATCCA GCAGAGTGCG GAGTTACAGG AACTCTTTGG CGTGAGTCGG 660
GTTAATTTCA ACTTCACCCT GGTGGCGCTG GTTTGTCCAG TCGCAGAACC AAGTAAGCTT 720
CCCGAAGCAG CCGGTGACAT GAGCGATATG GCCGCGTTTT ATCTGGACAA GTTAAGCGGC 780
GGCGATCAGG CACTGGCCGA TCACCTGAAT TTCTCGCAGG TTGTCAAGGG TTTGGACCTG 840
CCGCCGTTTA TGCTGATTGG CGGGCAAAAT GACAGCTTTT ACTTGCAAAG CCAAGCCTTG 900
TTGAAGGTGT TCGATGCTAA TCACGTCACC TATACAACGA AGCTATGGCC GGCAAGTGCG 960
GGGCCACACC TCAAGCATGT GTTTAATGTT CAACATTGGG AATGGCCGGA AAGTATTGAG 1020
ACGAACTTGG AGATGCTGCG GACGTTTGAT GCGTTAAGCA AGCAGCAAGA TCAAGCTGAA 1080
GAAAACGAAT TTGAA TAG TC TGCGGAAGTG GCAGTCATAG CAGCCGCTCA TCCGGCGATA 1140
GAAAAGACT CAGAGGCGAT CTGAGTCTTT TTAGATTAAA AAAACCGCGC AGTTTGAAGG 1200
CTACGCGGAG GAAATGGC                                             1218
```

Fig. 2. The amino acid sequence of HN001 esterase AA7

```
MADEEAMLAK VQASWAQTAA RDKARYADER VPEDVHWETE YRYEQSADPQ QTLNLYYPAK  60
RRNATMPTVI DIHGGGWFYG DRNLNRNYCR YLASQGYAVM GMGYRLLPDV DLRGQIQDIF 120
ASLRWLSHFG PQRGFDLDHV LLTGDSAGGH LASLVACIQQ SAELQELFGV SRVNFNFTLV 180
ALVCPVAEPS KLPEAAGDMS DMAAFYLDKL SGDQALADH LNFSQVVKGL DLPPFMLIGG 240
QNDSFYLQSQ ALLKVFDANH VTYTTKLWPA SAGPHLKHVF NVQHWEWPES IETNLEMLRT 300
FDALSKQQDQ AEENEFE                                                317
```

Fig. 6. Nucleotide sequence containing L. rhamnosus strain HN001 autoaggregation gene AG5 showing ATG initiation and translation stop codons (boxed).

```
TTCGAAGTTT AAAGAACTAG GTT|TGG|ATCA TGATCTCTTA AAGGCAATCG CCCAGTCAGG    60
TTTTGAGGAA GCGACGCCGA TTCAAGCGGA GACGATCCCA CTGGTTCTGG AAGGCAAAGA   120
TGTCATCGGT CAAGCCCAGA CCGGTACCGG GAAAACGGCA GCATTTGGCT TGCCAATTCT   180
GCAACACATC GATAAAGCCG ACCGGAGTAT CCAAGCATTG GTCATTTCCC CAACTCGGGA   240
ATTGGCGATT CAGACCCAAG AAGAGCTTTA CCGTTTAGGC CGCGACAAGA AGATCAAGGT   300
TCAGGCTGTC TATGGCGGCG CTGATATTCG CCGCCAGATT CGTCAGCTTG CTGACCATCC   360
GCAAATTGTG GTTGGACAC CTGGTCGGAT TCTTGATCAT ATTGGTCGTC ATACCTTAAA   420
GTTGGAACAC CTTGATACCT TGGTGTTAGA TGAAGCCGAT GAAATGCTCG ATATGGGCTT   480
CATTGACGAT ATTGAAAAGA TTGTTGAACA AATGCCGACC GAGCGTCAAA CATTACTGTT   540
CTCCGCGACG ATGCCGGCAG CGATCATGCG CTTAACCAAC AAGTTCATGA AGAACCTGT   600
GATTGTCAAG ATTAAGGCTA AGGAACTGAC AGCAGATACC GTTGAGCAAT ATTATGTTCG   660
GGCCAAGGAC TATGAAAAGT TCGATGTCAT GACACGACTG TTTGACGTTC AGGATCCGGA   720
CTTGGCACTG ATTTTTGGAC GGACCAAGCG TCGTGTTGAC GAACTGACAC GGGGATTAAA   780
GGCACGCGGC TATCGGGCTG AAGGTATTCA CGGCGATTTA ACCCAGCAAA AGCGAATGAG   840
CGTTTTGCGG CAGTTCAAGA GCGGCCAATT GGATTTTCTG GTTGCAACCG ATGTCGCTGC   900
TCGTGGGTTG GACATTTCTG GTGTCACCCA TGTTTACAAC TATGATATCC CGCAAGATCC   960
GGATTCCTAT GTTCACCGTA TCGGTCGGAC GGGACGCGCC GGACATAAAG GGGTATCCGT  1020
AACCTTTGTC ACGCCAAATG AAATTGAATA TCTGCACACC ATTGAAGATC TCACCAAGAA  1080
GCGGATGTTA CCCATGAAGC CGCCGACAGC TGAAGAAGCA TTAATGGGCC AGATCTCCAG  1140
CGGCTTAGCA ACCATCAAGG AACAAGTTGA AGCTAACGAT ACCGAAAAGT ATGAAGCAAT  1200
GGCTGAAACC TTGTTGGAAA ACTACACCCC GTTGCAGCTG GTTTCGGCGT ATCTCAAGGC  1260
AGTCAGCCCT GACGATGCGA GTGCCGTTCC GGTTAAAATT ACACCAGAAC GTCCATTACC  1320
ACGCCGCGGC CGCAACAATC ACGGCCATGG CAACAATCGT GGCGGTTATA AAGGCGGCTA  1380
CAAAGGCAAG CGACGCGATG GCGGCTATCA AGGTAATCGC GATGGCAAGC GCAGTTACGA  1440
CAAGAAGCGC AACTTTGGCG ACAAACGTAA AAACGTTAAG CGTAATTTCA AAATCCGTAC  1500
GGGTGAA|TAA| TCACCAGTAC GTTAATAGAC CGGTCA                           1536
```

Fig. 7. The amino acid sequence of HN001 autoaggregation protein AG5

```
LDHDLLKAIA  QSGFEEATPI  QAETIPLVLE  GKDVIGQAQT  GTGKTAAFGL   50
PILQHIDKAD  RSIQALVISP  TRELAIQTQE  ELYRLGRDKK  IKVQAVYGGA  100
DIRRQIRQLA  DHPQIVVGTP  GRILDHIGRH  TLKLEHLDTL  VLDEADEMLD  150
MGFIDDIEKI  VEQMPTERQT  LLFSATMPAA  IMRLTNKFMK  EPVIVKIKAK  200
ELTADTVEQY  YVRAKDYEKF  DVMTRLFDVQ  DPDLALIFGR  TKRRVDELTR  250
GLKARGYRAE  GIHGDLTQQK  RMSVLRQFKS  GQLDFLVATD  VAARGLDISG  300
VTHVYNYDIP  QDPDSYVHRI  GRTGRAGHKG  VSVTFVTPNE  IEYLHTIEDL  350
TKKRMLPMKP  PTAEEALMGQ  ISSGLATIKE  QVEANDTEKY  EAMAETLLEN  400
YTPLQLVSAY  LKAVSPDDAS  AVPVKITPER  PLPRRGRNNH  GHGNNRGGYK  450
GGYKGKRRDG  GYQGNRDGKR  SYDKKRNFGD  KRKNVKRNFK  IRTGE       495
```

Fig. 8. Phase contrast photomicrographs showing obvious clumping of washed L. rhamnosus strain HN001 cells in the presence of AG5 autoaggregation protein tagged with GST (Fig. 8A) and no clumping of washed L. rhamnosus strain HN001 cells in the presence of an irrelevant (non-adhesion) HN001 protein tagged with GST (Fig. 8B)

A

B

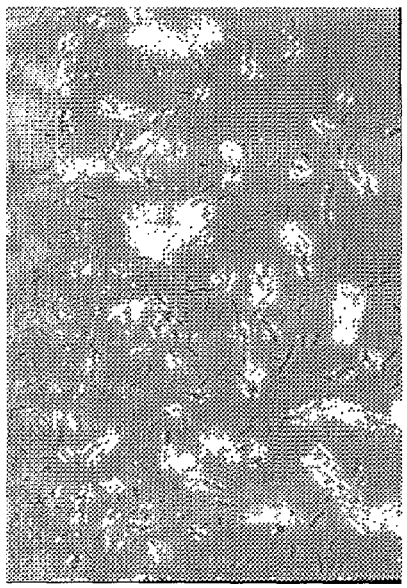

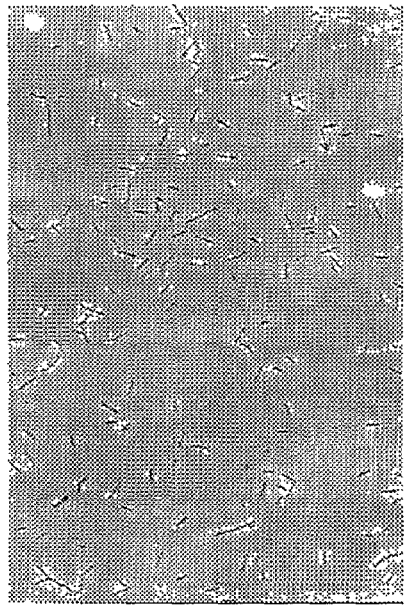

Fig. 9. Nucleotide sequence containing L. rhamnosus strain HN001 malic enzyme gene AA5 showing ATG initiation and translation stop codons (boxed)

```
ACGGCTATTG TGACGGCTTG TCAGAGTGGG ATGGGCGGTA CTGGCGACGT GGCTATTCTC   60
AGTACGGCGA ATCGGATGAA TCTGATGCCA TTTGCTCAGG TGGCAACACG CTTGGGTGGC  120
GCGATTACCG TTATTACCAT GACGGCGATT CTGCGGATGA TCTTTTAAAT CGACTAGTTT  180
CGAAACTTAA GGAGG ATG AT TCACATGGCA AAGAAGGATT TTAATCAACT AGCGCTAGAT  240
CAAGCAAAAG TAAATGGCGG AAAATTGAGT GTGGAACCGA AAGTACCAAT TGAGACGCGC  300
GATGATTTGA GTATTGCGTA TACTCCAGGC GTCGGGGCAG TTTCTTCTGC TATTGCCAAG  360
GATCAGTCGC TCGTTTATGA CTTAACCACT AAGAAAAATA CGGTTGCAGT TGTCAGTGAC  420
GGTTCGGCGG TTTTAGGGTT AGGCAATATC GGTGCCGAGG CTGCGATGCC GGTGATGGAA  480
GGAAAAGCCG CTTTGTTCAA ACGGTTTGCT AAGGTTGATG CCGTGCCGAT TGTGTTGGAT  540
ACGCAAGACA CTGAAGCAAT CATTGCGGCG GTAAAGCCA TTGCACCAAC ATTTGGCGGG  600
ATCAATCTTG AGGATATCAG TGCGCCACGA TGTTTTGAAA TCGAAGCACG ACTCATTGAT  660
GAGCTCAACA TCCCGGTGTT CCACGATGAT CAACATGGCA CTGCGATTGT GGTGCTCGCC  720
GCTTTGTACA ATGCCTTGAA AGTAGCGGAT AAAAAGATTG AAGACATTCG CGTGGTGGTT  780
AATGGCGGCG GCTCAGCGGG GCTATCCGTT GCCCGGCGAT TCTTGGCAGC CGGAGTCAAA  840
CACGTCATGG TGGTGGATAA GGTGGGCATT TTAGCTAAAA AGAACGCTGA TCAACTGCCA  900
CCACATCAAG CGGGATTGCC T TAA                                         924
```

Fig. 10. The amino acid sequence of HN001 malic enzyme AA5

```
MIHMAKKDFN QLALDQAKVN GGKLSVEPKV PIETRDDLSI AYTPGVGAVS  50
SAIAKDQSLV YDLTTKKNTV AVVSDGSAVL GLGNIGAEAA MPVMEGKAAL 100
FKRFAKVDAV PIVLDTQDTE AIIAAVKAIA PTFGGINLED ISAPRCFEIE 150
ARLIDELNIP VFHDDQHGTA IVVLAALYNA LKVADKKIED IRVVVNGGGS 200
AGLSVARRFL AAGVKHVMVV DKVGILAKKN ADQLPPHQAG LP         242
```

Fig. 13. Nucleotide sequence containing L. rhamnosus strain HN001 malate dehydrogenase gene AG3 showing TTG initiation and translation stop codons (boxed)

```
AAAGCAATCG GTTCGATCAT CATCGCATTT GTTGCCATGA TTTTGGCTTT GCTTTGGCCA  60
CCGTTAACGA TCATACTGGA CTTGGTAATG TTACTCTTGT GGGCCATCCC GGATCAGCGG  120
GTTGAACGGC ATTTGCTACA TGGCCCGAAA AACTAAACTT TGTGAAAAGG GGTTTTTATC  180
TTGGCAAGAA CCATTGGTAT TATCGGTATT GGACATGTTG GGGTGACAAC AGCATTTAAT  240
CTCGTTAGCA AGGGGATTGC GGATCGTCTG GTGCTAATTG ACCAAAAGGC TGATTAGCT  300
GAAGGCGAAA GTTATGATTT GAAGGATGCA CTTGGTGGAT TGCCGACTTA TACCGAGATT  360
ATCGTCAATG ATTACGATGC TTTGAAAGAT GCAGATGTTG TCATTTCCGC GGTTGGCAAT  420
ATCGCTGCGA TTTCAAACGG CGATCGAATT GGTGAAACCC AAACGTCAAA ACAAGCATTA  480
GACGATGTGG CACCAAAGTT GAAAGCGTCC GGATTCCATG GCGTTTTGCT GGATATCACC  540
AATCCTTGTG ATGCTGTCAC CAGCTATTGG CAATATTTAC TTGACCTACC AAAGTCCCAG  600
ATTATTGGCA CCGGCACCTC GCTGGATACT TATCGGATGC GGCGCGCGGT TGCTGAATCG  660
CTAAATGTGA ATGTCGCCGA TGTTCGCGGT TATAACATGG GTGAGCATGG TGAGTCACAA  720
TTTACGGCGT GGTCAACGGT GCGGGTTAAC AACGAGCCAA TCACGGATTA TGCGCAAGTA  780
GATTATGATC AATTAGCTGA TGCGGCGCGG GCTGGCGGCT GGAAGATTTA TCAGGCCAAA  840
CATTATACCA GCTACGGTAT TGCCACCATT GCTACTGAAA TGACACAGGC GATTATCAGT  900
GATGCCAAGC GGATTTTTCC GTGCGCTAAC TATGATCCTG AATTCGGTAT CGCCATCGGT  960
CATCCGGCGA CGATTGGCAA GCTCGGTGTT GTTAACACGC CTAAGTTGAA GCTTACCGAT  1020
GAAGAGCGTG CTAAGTATGT TCATTCCGCG GGCATCATTA AAGCTACAGT GGAAAAGATG  1080
AAGTAAGATT AATCCAGTAG CATTGATGTC ATGCATAAAA AGACGCCAAA TTGTGACCGG  1140
TATTCTCTAA CGTTTTACTC CAACGTTGAG GGTGCTGATC AAATCGGCGC CTTTTTACTA  1200
GAGTTAATTT DAATGTTACG CCTTAATAAG GAGTTTTTCG GGTATGGTTA AAAAATATAC  1260
GTTGGTGACT GTTGA  1275
```

Fig. 14. The amino acid sequence of HN001 malate dehydrogenase AG3

```
LARTIGIIGI GHVGVTTAFN LVSKGIADRL VLIDQKADLA EGESYDLKDA  50
LGGLPTYTEI IVNDYDALKD ADVVISAVGN IGAISNGDRI GETQTSKQAL  100
DDVAPKLKAS GFHGVLLDIT NPCDAVTSYW QYLLDLPKSQ IIGTGTSLDT  150
YRMRRAVAES LNVNVADVRG YNMGEHGESQ FTAWSTVRVN NEPITDYAQV  200
DYDQLADAAR AGGWKIYQAK HYTSYGIATI ATEMTQAIIS DAKRIFPCAN  250
YDPEFGIAIG HPATIGKLGV VNTPKLKLTD EERAKYVHSA GIIKATVEKM  300
K  301
```

Fig. 15. Nucleotide sequence containing L. rhamnosus strain HN001 dihydrodipicolinate synthase gene AI2 showing ATG initiation and translation stop codons (boxed)

```
ATG CAAAGAG CAGAATTAAT CACCGCGATT GTGACACCGT TAACGACCG CGATGAAATT    60
GACTATGATA GTATGCAACG GTTAGTCGAT CATCTCATTG ATCAAGGCAC TGACGGGTTT   120
GTGGTTGGAG CTACGACGGG TGAAGGGCCT ACGTTGAGTC ATGATGAAAA GATCACCCTT   180
TACACCCGTT TTGTGGCCAT GGTTCACGGG CGCGCACTCG TCATTGCCAA TTCAGGGTCT   240
AACAACACCC GCGAAACCAC TGATTTTACG CATGAAGTCG GTGGAATTGC CGGAATTGAT   300
GCTACTTTGG TTGTGGTTCC GTATTACAAC AAGCCGGATC AAGATGGCAT GATCGCGCAC   360
TATACCACGG TTGCGGCAAG TGCGCAAAAA CCGATCATTA TTTACAACAT TCCAGGGCGA   420
ACCGGCGTAA ACATGTTACC GGAAACCGTG GCAACGCTGG CACAAAACCC CATGATTCAA   480
GGGATCAAGC AGTGCGGCAG TCTGGCAGCA CTCAGCGATA TCATCGACCG AACCAAACAC   540
GATGCCTTCA ATGTCTGGAC CGGCGAAGAT GCTCAAGCGC TGACGATCAA AACACTGGGC   600
GGGATGGGCG TTATTTCAGT TGCCTCCCAC CTATATGCCC ATAGCATCCG GGAAATGTAT   660
CGTGCGCTCG ATCGCGGTGA CATCACCACT GTAGCTGCAT ACAACGGCA ACTGTTACCG   720
AAAATGGCCG CGTTATTCCA TTTTCCATCC CCAGCGCCTA CCAAAGCCGC ACTTAATGCT   780
TTGGGATTCA AAGTCGGCAG CCCGCGTTTA CCGCTACTGC CATTAACAGC GGCACAACAA   840
CAAGAATTAG CCCATCTGTT AGGGGTTTCG GAACTATCAG CAATTGAAGC GGAGGTGCTT   900
GCA TGA    906
```

Fig. 16. The amino acid sequence of HN001 dihydrodipicolinate synthase AI2.

```
MQRAELITAI VTPFNDRDEI DYDSMQRLVD HLIDQGTDGF VVGATTGEGP    50
TLSHDEKITL YTRFVAMVHG RALVIANSGS NNTRETTDFT HEVGGIAGID   100
ATLVVVPYYN KPDQDGMIAH YTTVAASAQK PIIIYNIPGR TGVNMLPETV   150
ATLAQNPMIQ GIKQCGSLAA LSDIIDRTKH DAFNVWTGED AQALTIKTLG   200
GMGVISVASH LYAHSIREMY RALDRGDITT VAALQRQLLP KMAALFHFPS   250
PAPTKAALNA LGFKVGSPRL PLLPLTAAQQ QELAHLLGVS ELSAIEAEVL   300
A    301
```

Fig. 17. Nucleotide sequence containing L. rhamnosus strain aspartate aminotransferase gene AH9 showing GTG initiation and translation stop codons (boxed)

```
GTG CATTTAG CAAAAAGAAT CCTCAACGTC GCACCGTCAG CGACATTGGC CTTAAGTAAT    60
CAGACGAAAG ACTTAAAGGC AAAAGGTGCC GACGTCATTG ATTTGTCTAT TGGCCAACCA   120
GATTTTTCAA CCCCTAAGGC GATTGATGAC GCAGCTATTG CGGCGATTCA GGCTGGTAAT   180
GCCAGTTTCT ATACGGCAGC AACCGGTATT CCGGAATTAA AGCAGGCGAT TAGTGACCGG   240
ATATTTGCCC AAGACGGTAT TCGTTATGAT CATCGTCAAA TCGTTGCAAC CACCGGCGCT   300
AAGTTTGCTT TGTATGCCTT ATTTCAGGTT TTCTTAAACC CAGGCGATGA GGTGCTGATT   360
CCTGTTCCAT ACTGGGTTTC CTACGAGGAA CAGATTAAAT TGGCGAGCGG CGTGCCACAT   420
CTGGTCATGC CGGCAGTCGG ACATAAAGTC AGTGTCGATG ATCTTGAGGC GGCTCGGACC   480
GATAAAACCC GGGCATTGAT TATCAATTCG CCACAAAACC CAAGTGGCGT TGTCTATGAT   540
CGCACGGAAC TGACCTTAAT TGGCAATTGG GCGCTGAAGC ATCATATTTT GGTAGTGACT   600
GACGATATTT ACCGAGATCT GATTTATAAC GGTACGACTT ACACCTCAAT GATTAGTATC   660
GATCCCGATA TCGCAGCGAA TACTGTTTTA ATTTCCGGCG TCTCCAAGTC ATATGCGATG   720
ACGGGTTGGC GGATTGGTTA TGCCGCCGGT CCGGAAAAGC TGATTCAGGC CATGGCGACC   780
TTTATTAGCC ACACGACCTC TAATCCGGCA GCAGTTTCCG AATACGCCGC GGTGGCAGCT   840
TTAACTGGCG ATCAGCAGGT TGTTGAAAAG ATGCGCCGTG CTTTTGAAGA ACGGCTGAAT   900
CTTTTCTATG ATCTTCTGGC AGATATTCCC GGTTTCGATA TGGGAGATAA ACCGCAAGGC   960
GCCTTCTATC TTTTCCCGAA TATTAAGCGT GCCGCTCAAT TGAGTCATTA TGGTACGGTT  1020
GATGATTTTA TCAGTGCACT GTTGACCGAA ACCGGGGTTG CCATTGTTCG TGCTGGACGG  1080
GCGTTTGGCA TGCCGGATCA TGCGCGGATT AGTTATTGTA AAGATTTGGC CAGTCTGAAA  1140
GAGGCCGCCC GGCGTATCCG GGAGTTTGTT GGTAAA TAA T TATTGAAGTG GGGAGTTAAC  1200
GCATGACGGA AAAGATTCGC ATTATTGATG CAAAAGAACA TGTGAAC   1247
```

Fig. 18. The amino acid sequence of HN001 aspartate aminotransferase AH9

```
VHLAKRILNV APSATLALSN QTKDLKAKGA DVIDLSIGQP DFSTPKAIDD    50
AAIAAIQAGN ASFYTAATGI PELKQAISDR IFAQDGIRYD HRQIVATTGA   100
KFALYALFQV FLNPGDEVLI PVPYWVSYEE QIKLASGVPH LVMPAVGHKV   150
SVDDLEAART DKTRALIINS PQNPSGVVYD RTELTLIGNW ALKHHILVVT   200
DDIYRDLIYN GTTYTSMISI DPDIAANTVL ISGVSKSYAM TGWRIGYAAG   250
PEKLIQAMAT FISHTTSNPA AVSEYAAVAA LTGDQQVVEK MRRAFEERLN   300
LFYDLLADIP GFDMGDKPQG AFYLFPNIKR AAQLSHYGTV DDFISALLTE   350
TGVAIVPGRA FGMPDHARIS YCKDLASLKE AARRIREFVG K   391
```

Fig. 19. Nucleotide sequence containing L. rhamnosus strain HN001 serine dehydratase subunits α (AF8) and β (AF7). ATG translation initiation codons and termination codons are shown, boxed for AF8, shaded for AF7.

```
AACATCAGGG TGGTAAAATC ACACTGATTA AGGAACGGGT TGTCGGCTTG AACGACTGAA   60
AACTTCGACT TCGGTCATCT AAAGGAGAAA ACTATGCCAG ATGTACGTTT TCACAGCGTC  120
TTTGATATTA TTGGACCGGT TATGGTGGGG CCAAGTAGCT CACATACAGC CGGGGCAGCG  180
CGGATTGGTA AAGTCGTGCG CGACATTTTT GGCGAACCCC CGGAGACGAT TACGATTTAC  240
CTTTACGAAT CATTTGCCAA AACCTATCGC GGTCATGGTA CCGATGTGGC GCTAGTAGCA  300
GGGCTGTTGG GGATGGCACC CGATGATCCG CGGTTGCCGG AATCGCTGAA GTTGGCCTAT  360
GACCAAGGCA TTAAAGTGAG TTTTGTGCCG AAAAGCGATA AGGTTGATCA TCCTAACACG  420
GCACATATTG TCTTGCAAGC CGGTGATCAC CGGTTAGCGG TCACTGGGGT TTCCATTGGT  480
GGCGGGAATA TTCAGATCAC GGAAATCAAT GGGTTTAAGA TATCGTTGAG CATGGGTCAG  540
CCGACTTATA TCACCATTCA TGACGATGTG CCGGGGATGA TTGCACAGGT CACCAAGATT  600
TTCTCCGATG CCGGCATTAA TATCGGGACA ATGACGGTGA CCCGCACTGC TAAAGGGGAA  660
CAGGCAATTA TGATCATTGA AACGGATGAT TATCATGATG ATATTTTGGC CAAATTGAAA  720
TTATTACCGC ATATGCGCAA TGTCACTTAC TTTGAGTGAT GACGCGCTAA CAACTGGTTA  780
CGAACTGGCT AATAAAGGAG CTTATCATGT TTATACCGT TAAAGAACTT GTAGAACAAA  840
GTCATGCCTT CTCCTCGGTT GCCGAACTCA TGGTGCATAC GGAAGTCGAA AACTCAACGC  900
GGACTGAAGC ACAGATCCGT CATTTAATGA GCCGTAATCT GGAAGTGATG GAACGCTCGG  960
TTAAGGAAGG CATTGCCGGG GTCAAAAGTG TCACCGGGTT AACCGGCGGC GAGGCCAAAA 1020
AGCTGAACCA TTATATTGCT GATGACCGGT TCATGAGCGG TAAACCGATC ATGGAGGCTG 1080
TTCGCAATGC AGTGGCAGTT AATGAAGTGA ACGCTAAAAT GGGGCTGATT TGTGCGACGC 1140
CGACTGCGGG ATCGGCAGGA GTTCTGGCCG GTGTTTTGTT GGCGATGCGT GATCGCCTGC 1200
ACCTGACGCA TGATCAGCAG CTTGATTTTC TTTTTACCGC TGGTGCATTT GGCTTGGTCA 1260
TTGCAAATAA TGCCGGGATT GCCGGAGCAG AAGGCGGGTG CCAGGAAGAA GTTGGCTCGG 1320
CCAGTGCGAT GGCTGCGGCG GCGTTGGTTT GTGCTAATGG CGGCAGTGCC GAACAGGCAC 1380
CCACCGCCGT TGCGATTACG TTGCAAAACA TGCTGGGGTT GGTTTGTGAC CCAGTTGCCG 1440
GCTTGGTGGA GGTTCCGTGT GTGAAGCGAA ATGCATTGGG AGCAAGTCAA GCCATGATTT 1500
CCGCTGATAT GGCATTGGCC GGTTGCATCA GTGTGATTCC GGCCGATGAG GTGATTGAAG 1560
CGGTTAACCG CGTCGGCATG CAGTTGCCAG CAACATTGCG GGAAACCGGC GAGGGCGGCC 1620
TAGCAACGAC ACCAACTGGC TTACGGCTGA AAGAACAAAT CTTCGGCAAA AAGAATTGT 1680
GATTCAATGA CGGCACGACA AATTTTTGCC CGGCATGAGT TTTATTAAA CGGCGTTACT 1740
GGCAACAAGG TATTTGGAAA GGGTCAATCG TGATTAATTT ATATATTATT CGACATGGTG 1800
AAACAGCAGG CAATGTGCGC CGCTTAATTC AAGGCGTGAC GAATTCACAC TTGAATGCGC 1860
GCGGACGTAA ACAGGCGTAT GCTTTG 1286
```

Fig. 22. Amino acid sequence of L. rhamnosus strain HN001 serine dehydratase subunit α AF8 (A) and subunit β AF7 (B).

(A)
```
MFYTVKELVE QSHAFSSVAE LMVHTEVENS TRTEAQIRHL MSRNLEVMER  50
SVKEGIAGVK SVIGLTGGEA KKLNHYIADD RFMSGKPIME AVRNAVAVNE 100
VNAKMGLICA TPTAGSAGVL AGVLLAMRDR LHLTHDQQLD FLFTAGAFGL 150
VIANNAGIAG AEGGCQEEVG SASAMAAAAL VCANGGSAEQ AATAVAITLQ 200
NMLGLVCDPV AGLVEVPCVK RNALGASQAM ISADMALAGC ISVIPADEVI 250
EAVNRVGMQL PATLRETGEG GLATTPTGLR LKEQIFGKK  289
```

(B)
```
MPDVRFHSVF DIIGPVMVGP SSSHTAGAAR IGKVVRDIFG EPPETITIYL  50
YESFAKTYRG HGTDVALVAG LLGMAPDDPR LPESLKLAYD QGIKVSFVPK 100
SDKVDHPNTA HIVLQAGDHR LAVTGVSIGG GNIQITEING FKISLSMGQP 150
TYITIHDDVP GMIAQVTKIF SDAGINIGTM TVTRTAKGEQ AIMIIETDDY 200
HDDILAKLKL LPHMRNVTYF E  221
```

Fig. 23. Nucleotide sequence containing L. rhamnosus strain HN001 histidinol-phosphate aminotransferase gene AG2 showing ATG initiation and translation stop codons (boxed)

```
GTGAAGGAAA AATGAGTCGC TTAAAAGAGC GCGATAAAAT CAACAAATAT TGACAACCGA    60
TTGCCAGCCA GCGCTCACGT TTGAAGCTCG GCCAAACCAA ACAAGATCAC AAGGAGGCGT   120
TGTTT[ATG]TT TAAACCCACC ATTCATCAAC TTCATCCCTA TACGCCAGAA AAGCCTCTTG   180
CCGTATTAAA AGAAGAACTT GGCTTGCCAC AGCTGGTGCG GATGTCAGCA AACGAAAACC   240
CATTCGGTAC CAGCGTCAAA GTTCAGCAGG CCGTGACCAA CTGGAATTTT ACGCAAAGTC   300
GTGATTACCC CGATGGCTAT GCCAGTCAAC TACGCACCGC GGTGGCAAAA CATTTAGACG   360
TTGCCGCAGA GCAGTTGGTT TTTGGCAATG GTCTGGATGA AGTCATTGCC TTAATTGCCC   420
GCACTTTTTT GAGCCCGGGG GATGAAGTCA TTGAACCATG GCCAACATTT TCCGAGTACC   480
GCTTGCATGC CCAAATTGAA GGGGCCACCG TGATTGATGT GCCCGTCACT GAAACTGGCA   540
ATTTTGATTT ATCTGCAATG GCGCAGGCGC TAACCGCGAA AACGAAACTG ATTTGCGTGT   600
GCAACCCAAA TAACCCCACG GGCACGCTGC TGTCAATTGC GACACTGACC GAATGGCTGC   660
GACAGATACC AAAAGACGTG CTGGTTTTAA TGGATGAGGC TTATATTGAG TTCACTGATG   720
ACTATCCAGC CACGAGCGCT ATCAGCTTAT TATCAAAGTT CCAAACCTC GTCGTGCTGC   780
GAACATTTTC AAAAATCTAT GGACTGGCGA ATTTCCGGGT CGGCTTCGGT GTTTTTCCTA   840
AACAACTTGT TAACTACTTG CAAACCGTTC GGCTGCCTTA CAATTTAAGC AGCATTGCCC   900
AAGTTAGCGC ACAGGCGGCC TTGGCTGATC AAGATTTTGT CGCGATGACA CGCAAGCGAG   960
TGCAGCAAGC GCGCGATAGT TGGGAACGCT TTTTAACCCA AACTGGACTG CCACACACCC  1020
GGAGCCAAAC CAACTTTCAA TTCTTTCAGG CCCCAAAAAT GCAGGCATCG GCTTTAAAAA  1080
AGCGCCTGCT ACAACAAGGT TTTCTTGTCC GTGATGGCTT AAAACCCGGC TGGCTGCGCG  1140
TCACGTTTGG CACTGAGGTA CAAAACACGG CGGTACAGCG CATCATTGAA ACTTTTCAGG  1200
CAGAACTCAC TGGGCCAAAT GCGCTGAAG[T GA]TTGGAACC GCCACCATGC AGGCGTAAAC  1260
TAAAGGTGTG GTTAATGGCT CATCTGAAAG GAAGCATTTA TTTTGAAAAT TGCCAAATTA  1320
AACAACCATC CCTATCTGAT AACGTCTGCA                                  1350
```

Fig. 24. The amino acid sequence of HN001 histidinol-phosphate aminotransferase AG2

```
MFKPTIHQLH PYTPEKPLAV LKEELGLPQL VRMSANENPF GTSVKVQQAV    50
TNWNFTQSRD YPDGYASQLR TAVAKHLDVA AEQLVFGNGL DEVIALIART   100
FLSPGDEVIE PWPTFSEYRL HAQIEGATVI DVPVTETGNF DLSAMAQALT   150
AKTKLIWVCN PNNPTGTLLS IATLTEWLRQ IPKDVLVLMD EAYIEFTDDY   200
PATSAISLLS KFPNLVVLRT FSKIYGLANF RVGFGVPPKQ LVNYLQTVRL   250
PYNLSSIAQV SAQAALADQD FVAMTRKRVQ QARDSWERFL TQTGLPHTRS   300
QTNFQFFQAP KMQASALKKR LLQQGFLVRD GLKPGWLRVT FGTEVQNTAV   360
QRIIETFQAE LTGPNALK                                      378
```

Fig. 25. Nucleotide sequence containing L. rhamnosus strain HN001 malY-aminotransferase gene AJ6 showing ATG initiation and translation stop codons (boxed)

```
GGATGGTGCA GGGGCTTAGG CTTCTGTGCC TTTTTAGAAA GAAGCG ATG A AATTGACAAT    60
TTATGACTTT GATCATGTTA TCGATCGCCG GGTACGTTT AGCACTCAAT GGGATTATAT   120
TGCTGATAGG TTTGGCCGTA ACGATATCCT GCCCTTTTCG ATCTCCGATA CAGATTTTCC   180
AGTACCAGTT GAAGTGCAAG ATGCGCTAAA AGAACGGTTA ACACATCCAA TTTATGGCTA   240
TACACGATGG AATCATGCTA CTTACAAAGA CAGTATTGTT CACTGGTTCG AGCGTGATGG   300
TCATACAAAG ATAAACCCGG ATTGGATTGT TTATAGCCCT AGCGTTGTTT TTACGATTGC   360
TACACTCATT CGAATGAAGA GCGATCCCGG GGACGGAGTG GCTGTGTTTA CGCCTATGTA   420
TGATGCCTTC TATGGTACGA TTAAACAGAA CGATCGAGTG TTGATCCCGA TTCGATTAGC   480
AGCTGCAGAT GAAGGCTATG TGATTGATTG GGATAGTTTG GCAACGGTAC TTGCTGAAAA   540
GCAGACAAAA ATATTCTTAC TAACAAATCC GCATAACCCG ACAGGACATG TTTTTACAAA   600
ATCGGAATTA GCACGCCTTT ATGACTTGTG TCAGGCAGCC CATGTTTTCT TGATCTCTGA   660
TGATATTCAC CGCGATATTG TTTATCCGGG TCATTCGTAC GAACCAATGA CAAATGTCGG   720
CACAAGTGAT GTTGCACTCT GCTGCTCAGG GTCAAAGACA TTTAACACAC CAGGCCTGAT   780
TGGCTCATAT GCCTTCTTAC CAGATCATGA TGTAAGGGCA CAATTTTTGA CGGAATTAAA   840
GCAGAAAAAT GCTCTGTCTT CTGTAAGCAT CTTTGGCATG CTGGCGCAAA TTGCGGCTTA   900
TAACGGTTCA GAGGATTACG TGGAACAACT GACTGCCTAT ACAAAAAATA ATATGGAGTT   960
GGTTGCTAGT TATTTAGAGG AAAATTTGCC GGAATTGCAG TTTTCGTTAC CGGATGCCAC  1020
GTACTTAGCC TGGATAAATG TGTCTAAACT GAGATTAACG TCAGAGGAAC TTCAACATCG  1080
GTTAGTAAAC GGCGGCCATG TTGGCATTAT GGCGGGCAAA ACTTATGGTG ATACCAGATA  1140
TCTAAGGATG AATATTGCCT GTCCAAAGAA GAAGTTAGTG ATGGGGCTAG AACGTTTAAA  1200
GAAGGGAATT AGGGGA TAA T ATGCTCTTAC TCAGAGAAAT CAAAATCTTA CGCCGCCTGT  1260
CCC  1263
```

Fig. 26. The amino acid sequence of HN001 malY-aminotransferase AJ6

```
MKLTIYDFDH VIDRRGTFST QWDYIADRFG RNDILPFSIS DTDFPVPVEV    50
QDALKERLTH PIYGYTRWNH ATYKDSIVHW FERDGHTKIN PDWIVYSPSV   100
VFTIATLIRM KSDPGDGVAV FTPMYDAFYG TIKQNDRVLI PIRLAAADEG   150
YVIDWDSLAT VLAEKQTKIF LLTNPHNPTG HVFTKSELAR LYDLCQAAHV   200
FLISDDIHRD IVYPGHSYEP MTNVGTSDVA LCCSGSKTFN TPGLIGSYAF   250
LPDHDVRAQF LTELKQKNAL SSVSIFGMLA QIAAYNGSED YVEQLTAYTK   300
NNMELVASYL EENLPELQFS LPDATYLAWI NVSKLRLTSE ELQHRLVNGG   360
HVGIMAGKTY GDTRYLRMNI ACPKKKLVMG LERLKKGIRG    410
```

Fig. 27. Nucleotide sequence containing L. rhamnosus strain HN001 malY-aminotransferase gene AJ7 showing ATG initiation and translation stop codons (boxed)

```
ATGACTGATT GGGTACTTGA TGACGGTGGA CATGGTTCTA CTGG[ATG]CGT ACAATGACAA   60
CAAAAGCAAG AAAGCAGGGA TCATTGATGG AAGATTTGCC AACTGATATT GCAACGTTTG  120
TGGACACGCA CTTAGTTGAT CGCCATAATA GCAATGCTGT GAAGTGGGAC GGTCTGAAAG  180
AAGAATTTGG CCGGGCTGAC TTGTTGCCTA TGTGGATTGC CGACACTGAG TTTAAGGCGC  240
CTCAAGCAGT TTTGGATGCA TTGACAGTTC GCGTCAAGGA AGGGACGTTT GGCTATTCCA  300
TTCGCCCGCA GTCTTATTAC GAAGCCTTCA TTAACTGGCA AAAGGAACGA CATGGCATTA  360
CGGTTGAACC TGAGTGGATG CGTTTTGGCG TTGGCGTTGT CAAATCACTG TATGCGATGG  420
TGAACTGGCT GACAGAACCT GGTGATCCGG TCCTCATCAT GCAGCCGGTT TATTATCCCT  480
TTATGAATGC CATTAATGAT CTTGGACGTA AAGTCGTATC AGTTGACTTG CAATTAACCG  540
CTGATGGTTG GCGCATGGAT TTTGACCAAT TAGAAAAGAC CTTGGCGGCG AATGAAATTA  600
AAGCGATGAT TCTGTGTTCA CCGCACAATC CGGTTGGTCG GATCTGGACC CGAGATGAGT  660
TAGAACAACT TTTTGCCATC ACAAGTCGGT ATGATGTGAC AGTGGTTTCT GATGAAATTC  720
ACGGTGATCT TGAAGTGAGT GGGCCGAAGT TTACATCCGC TTTACAGGTC GCTGAAGGTA  780
AAGCTCGAAA AAAGCTTGTT GTGCTCAATG CGCCGTCAAA AACATTTAAT TTAGCCGCCT  840
TGCTGAATTC ACACATTATT ATTCCCGATC AAGCGTTGCG TACGAGTTAT GATGCCTTCA  900
TTAAGCAGCT GCATCCGGTT GATACGAGCT TGATGGGGCA AGTGGCCGGT GAAGCTGCTT  960
ATCGGCATGG CGCTGCTTGG TTAGATCAGG TCTTACAAGT GGTTCGCTAC AATTATCGGC 1020
AACTGCAAGC TGGTTTAGCC GCGGCGGCCC CACAAGCGAC CCTGGCCGAC TTACAAGGGA 1080
CTTATTTGGC TTATGTTGAT ATCGGTGCTT ATGTTGCGCC AAGTCAGATC AAAGACTTTG 1140
TTGAAGGTGT GTGCGGATTG GCTGTTGATT ATGGTGCATG GTTTTCACCG CAAACGGCAA 1200
CTTATATTCG TTTAAATTTA GCTACTGATC CTAAGCTTGT TGCCGAGGCG ATTAACCGAC 1260
TAACCACTCA TTTGGCACAG CAGCCGCAGC GG[TGA]TCGGG ACAAGAATTA AATTGCCTTT 1320
TTCAAGATAA AACTCGAATT CAAAGAGACG GAATGG  1356
```

Fig. 28. The amino acid sequence of HN001 malY-aminotransferase AJ7

```
MRTMTTKARK QGSLMEDLPT DIATFVDTHL VDRHNSAVK  WDGLKEEFGR   50
ADLLPMWIAD TEFKAPQAVL DALTVRVKEG TFGYSIRPQS YYEAFINWQK  100
ERHGITVEPE WMRFGVGVVK SLYAMVNWLT EPGDPVLIMQ PVYYPFMNAI  150
NDLGRKVVSV DLQLTADGWR MDFDQLEKTL AANEIKAMIL CSPHNPVGRI  200
WTRDELEQLF AITSRYDVTV VSDEIHGDLE VSGPKFTSAL QVAEGKARKK  250
LVVLNAPSKT FNLAALLNSH IIIPDQALRT SYDAFIKQLH PVDTSLMGQV  300
AGEAAYRHGA AWLDQVLQVV RYNYRQLQAG LAAAAPQATL ADLQGTYLAY  360
VDIGAYVAPS QIKDFVEGVC GLAVDYGAWF SPQTATYIRL NLATDPKLVA  420
EAINRLTTHL AQQPQR  436
```

Fig. 29. Nucleotide sequence containing L. rhamnosus strain HN001 cystathione β-lyase gene AC8 showing ATG initiation and translation stop codons (boxed)

```
CCAAGTAATC ATGCCATTCA GCTAGCAAAC ATTGCCCGTC AACCTGCTTC ATTGACGGGC    60
ATACATAAAA GAACACTATT CATTAAAGGA GGTCGGGTTT CAATGACCCA ATTCAATACC   120
AAACTCGTTC ATGGACCACA ACTAAATGTC GACCAAGCCG GTGCCATCGT GCCACCAGTA   180
TACCAAAGTG CCATGTTCCG CTTTGCTCCT GATGGTCAGG AAACCCACTG GGACTATGCG   240
CGCAGTGGTA ACCCGACCCG TGAATACCTG GAACGTCAGA TTGCTACGCT AGAAAATGGC   300
GATGCTGGCT TTGCGTTTTC CAGCGGTGTT GCAGCGATTG CAACGGTGCT CGCGATTTTC   360
CCCGACCACA GTCACTTCAT TATTGGTGAT TCGCTCTACA GTGGCACCGA TCGCCTCATC   420
AACCAGTATT TTTCTCAACA CGGCCTGACC TTTACACCGG TGGATACGCG TGATCTGGCA   480
GCGGTGGAAG CCGCCATCCG CCCCGAAACT AAAGCAATTT TCTTTGAGAC TTTTTCCAAT   540
CCGCTCCTCA AGTCAGCAG CGTCAAGGCC ATCAGTGCCC TCGCCAAAAC CCATGATCTG   600
TTAACGATTG TCGACAACAC GTTCTTAACC CCTTATTACC AGCGGCCACT TGACCTCGGT   660
GCCGACATCG TTCTACACAG CGCCACCAAA TACCTCGGTG GCCACGGTGA CCTCATCGCC   720
GGCCTCGTTG TCTCCGCTCA CCCCGACCTC AGCGAGAAGC TCGCTTTCCT GCAAAACACG   780
ATCGGTGCCA TTTTAAGCCC GCTTGACTGT AGCCTCGTCA CCCGCGGCAT TGCCACCCTC   840
TCCGTTCGCC TTGATCGTGA AACTGCAAAC GCCCAAGCCG TCGCCGAATT TCTAGCGCAG   900
CACCCAGACG TCGCCCACGT TTACTACCCC GGACTTAAAA ACGATCCCGG TTACGCATTA   960
GCCCAAAAAG AAACCACGGG TGCCAGCGGA CTCCTGACGA TCAAACTAGC CGACAACATT  1020
GATCCCTTAA AGTTCGTTAA CAGCACCAAA ATTTTCGACT TTGCCGACTC ACTTGGCACC  1080
GTCTCCAGTC TAGTCAAACT ACCTTGGTTT AAGCTCCCGG AAGACAAACG CGCCGATTTT  1140
GGTTTGACAC CGCAACATGT CCGGATTGCA ATTGGCTTGG AGGATCAGCA GGACTTGATT  1200
GACGATCTGC AGCAGGCACT GGTTGCAGCG GAAAAATAGT ATCCAAAATA ATATCTATTA  1260
CTTTTGCTAA ATAGGC  1276
```

Fig. 30. The amino acid sequence of HN001 cystathione β-lyase AC8

```
MTQFNTKLVH GPQLNVDQAG AIVPPVYQSA MFRFAPDGQE THWDYARSGN    50
PTREYLERQI ATLENGDAGF AFSSGVAAIA TVLAIFPDHS HFIIGDSLYS   100
GTDRLINQYF SQHGLTFTPV DTRDLAAVEA AIRPETKAIF FETFSNPLLK   150
VSSVKAISAL AKTHDLLTIV DNTFLTPYYQ RPLDLGADIV LHSATKYLGG   200
HGDLIAGLVV SAHPDLSEKL AFLQNTIGAI LSPLDCSLVT RGIATLSVRL   250
DRETANAQAV AEFLAQHPDV AHVYYPGLKN DPGYALAQKE TTGASGLLTI   300
KLADNIDPLK FVNSTKIFDF ADSLGTVSSL VKLPWFKLPE DKRADFGLTP   350
QHVRIAIGLE DQQDLIDDLQ QALVAAEK 378
```

Fig. 33. Nucleotide sequence containing L. rhamnosus strain HN001 phosphoenolpyruvate hydratase AK4 showing ATG initiation and translation stop codons (boxed)

```
TCTGGTTTCA ATATTAAACA GCCTTCTGGC AAAAAGGAGA AGAATAT ATG  TCTATCATTA     60
CTGATGTATT GGCACGCGAA GTTTTAGACT CACGTGGCAA CCCTACTGTT GAAGTTGAAT   120
TGTATACCGA AGATGGCGGT TTCGGCCGCG CATTAGTTCC ATCAGGTGCT TCAACCGGTG   180
AACATGAAGC CGTTGAATTG CGTGATGGCG ATAAGGATCG TTTTGGCGGC AAGGGTGTTT   240
TGAAGGCCGT TGACCACGTA AACAATGAAA TTGCTAAGGC TGTGATTGGC CTTGACGTCA   300
CCGAACAACG CTTGATTGAC CAAACCATGA TCGATCTTGA TGGCACGCCT AATAAAGGCA   360
AGCTCGGTGC CAATGCGATT TTGGGTGTTT CCTTGGCTGC TGCCCGTGCT GCGGCTGATG   420
AAGTTGGTCT GCCATTGTAT CAATATCTTG GCGGCCCGAA TGCTCATGTT TTGCCAACGC   480
CAATGATGAA CGTTCTTAAT GGTGGTGCAC ATTCAACTAA CACCGTTGAC TTCCAGGAAT   540
TCATGATCAT GCCTGTTGGT GCCAAGAGTG TTCGTGAAGC CGTTCGGATG GGTTCAGAAA   600
CCTTCCACGC ATTGCAGGCA CTGCTCAAGA GCAAGGGTGA CATCACTGCT GTTGGTGATG   660
AAGGCGGCTT TGCACCTAAC TTGAAGGATA ACGAAGAAGC TTTCGAATTG CTTGTTGAAG   720
CGATCAAGAA GGCTGGCTAC AAGCCGGGTG ATGACATTGC TTTGGCCTTC GACGTTGCTG   780
CTTCAGAAAT GTACGATGCT GATACCAAGA CGTACACAAC CAAGTGGTCC AACCCTGACA   840
AGAAGTACAC AACCGAAGAA TGGACCAACA TGATTGACGG CTACATTAAC AAGTATCCGA   900
TCGTTTCTGT TGAAGATCCA ATCGATGAAA ACGACTGGGA AGGCTGGCAG ACATTCACCG   960
AGAAGATGGG CGACAAAGTC CAAATCGTTG GTGATGACCT GTTTGTTACC AACACCGATT  1020
ACCTGAAGAA GGGTATTGAC ATGGGTGTTG CTAACTCCAT CCTGATCAAG TTGAACCAAA  1080
TCGGTACATT GACAGAAACC TTCGAAGCAA TCGAAATGGC CAAAGAAGCT GGTTACACGG  1140
CTGTTGTTTC ACATCGTTCA GGTGAAACCG AAGATACCAC GATTGCTGAC TTGGTTGTTG  1200
CAACCAACGC CGGTGAAATC AAGACTGGTT CAATGAGCCG GACTGACCGG ATTGCCAAGT  1260
ACAATCAGTT GATGCGCATC GAAGATCAAT TAGGTGCTCA ATCACAATAC AAGGGTCGCA  1320
AGTCCTTCTA CAACGTTAAA GCAATTGAC T AA TTAACGCT TGACGTTAAC ATGAAAAGCA  1380
CGTCACTTCA AATGGTGGCG TGTTTTTTCT ATTCTTAGCT TAAGCAAAAG ATGAACTTGC  1460
TCACGCTTTG TGACTGAGGG CTGTCTGGTG CCGGTGCAAG CA             1502
```

Fig. 34. Amino acid sequence of *L. rhamnosus* strain HN001 phosphoenolpyruvate hydratase AK4

```
MSIITDVLAR EVLDSRGNPT VEVELYTEDG GFGRALVPSG ASTGEHEAVE   50
LRDGDKDRFG GKGVLKAVDH VNNEIAKAVI GLDVTEQRLI DQTMIDLDGT  100
PNKGKLGANA ILGVSLAAAR AAADEVGLPL YQYLGGPNAH VLPTPMMNVL  150
NGGAHSTNTV DFQEPMIMPV GAKSVREAVR MGSETFHALQ ALLKSKGDIT  200
AVGDEGGFAP NLKDNEEAFE LLVEAIKKAG YKPGDDIALA FDVAASEMYD  250
ADTKTYTTKW SNPDKKYTTE EWTNMIDGYI NKYPIVSVED PIDENDWEGW  300
QTFTEKMGDK VQIVGDDLFV TNTDYLKKGI DMGVANSILI KLNQIGTLTE  350
TFEAIEMAKE AGYTAVVSHR SGETEDTTIA DLVVATNAGE IKTGSMSRTD  400
RIAKYNQLMR IEDQLGAQSQ YKGRKSFYNV KAID                   434
```

Fig. 35. Nucleotide sequence containing *L. rhamnosus* strain HN001 tagatose bisphosphate aldolase AK1 showing ATG initiation and translation stop codons (boxed)

```
TATAGCACGC CAAGCCAAGC AGCTCGCAGG TGGTTTTTGG GTTAAAGCTT CTATTATTGA   60
CTGACTTTCT TTGAGTTTCA TGAAAATGAT CGGCGAAAAA TGTCTATTAT TGTCATTTTG  120
TTCTATACTA ATCGTGTACT GAACATTTAA GGATTACCTA GGAGGTATTT TTAC ATG TCT  180
GTTAAACTTA CTGCTGGTCA GTTAGAGCAT TTGAAGCAAT TGTCCAATGA CAACAACGTC  240
ATCTCGGCTT TAGCCATTGA CCAACGCGGT TCCCTGAAGA AGATGCTTGC AGCTGCAGCG  300
AACAAGCCAG CTGACGAAAC CACGATTGTT GATTTCAAGA AAGCTGTTTC TGAAGAATTA  360
ACCAAATACG CCAGCGCGAT TCTGCTTGAT CCAGAATACG GCCTGCCAGC TGCCAAGGTT  420
CGCGATCCTA AGTCCGGCCT CTTGCTTTCC TATGAAAAGA CCGGCTACGA TGCGACTGAA  480
CCTGGCCGTT TCCAGATTT GATTGATAAC CAAAGTGCTT TGCGCATCAA GAACGAAGGC  540
GGCGATGCAG TCAAGTTCTT ACTGTACATT GACCCTGACG AACCTGATAG TATCAACGAT  600
CGTAAATATG CGTTTGTTGA ACGGGTTGGT GCTGAAGCTA AGCTAATGA TCTGCCACTG  660
TTCTTGGAAT TAGTTTCCTA CGATGGCAAG ACCAACGAAA CCGGCACCGC TGCATGGGCA  720
AAAGCAAAGC CTGAAAAAGT TATCAAGATC ACTAAGGAAT TCAGCAAGGC GCAATACAAC  780
GTTTCTGTTT TGAAGCTTGA AGTTCCGGTT GATCAAAAGT TTGTTGAAGG TTACACCGAT  840
GAAGGCGTAA CGCCGGTTTA CAGCAAGGAA GAAGCTGCTA AGTACTACAA GGCTCAATCC  900
GATGCAACCG ATTTGCCATT CATCTTCCTG TCCGCTGGTG TTTCCAACGA ATTGTTCCTT  960
GAAGAACTCA AATTTGCTAA GGAAGCCGGT TCAACCTTTA ACGGTGTGCT TTGCGGCCGG 1020
GCAACCTGGA AGCCAGGCGT TAAGCCATTT GCTGCTGAAG GCGAAGCTGC CGGCAAGAAG 1080
TGGCTGCAAA CGGAAGGTAA AGCTAACATC GATCGTTTGA CAAGGTTTT GGCTGACACT 1140
GCTACTCCTT GGACAGACAA GGTTGAAGGC TAA TTCTTTT TAACTAATTA ATCGTTCAAA 1200
AACCAGCCAC AGATGCGGCT GGTTTTTTAT ATGGTGAGCG TGAGCCAGCC CGCT         1254
```

Fig. 36. Amino acid sequence of *L. rhamnosus* strain HN001 tagatose bisphosphate aldolase AK1

```
MSVKLTAGQL EHLKQLSNDN NVISALAIDQ RGSLKKMLAA AANKPADETT  50
IVDFKKAVSE ELTKYASAIL LDPEYGLPAA KVRDPKSGLL LSYEKTGYDA 100
TEPGRFPDLI DNQSALRIKN EGGDAVKFLL YIDPDEPDSI NDRKYAFVER 150
VGAEAKANDL PLFLELVSYD GKTNETGTAA WAKAKPEKVI KITKEFSKAQ 200
YNVSVLKLEV PVDQKFVEGY TDEGVTPVYS KEEAAKYYKA QSDATDLPFI 250
FLSAGVSNEL FLEELKFAKE AGSTFNGVLC GRATWKPGVK PFAAEGEAAG 300
KKWLQTEGKA NIDRLNKVLA DTATPWTDKV EG                   332
```

Fig. 37. Nucleotide sequence containing L. rhamnosus strain HN001 phosphoglycerate kinase AK6 showing TTG initiation and translation stop codons (boxed)

```
TGTTGATGGT AAGCTTAATT GAAACATCAT CTTTAGGAAA ATGAAGGAGG TCATATCTTT    60
TGGCTAAATT AATCGTTTCA GATTTAGACG TTAAAGACAA AAAAGTCTTG ATTCGCGTTG   120
ACTTCAACGT GCCGATCAAA GACGGCGTTA TCGGTGATGA CAATCGGATC GTGGCAGCAT   180
TGCCAACCAT CCAATATGTC ATTGATCACG GCGGCAAGGC AATTCTGCTG TCTCACCTTG   240
GCCGGGTTAA GACCGAAGAA GATAAGGCAA AGCTGACCTT GAAGCCTGTT GCAGAACGCC   300
TTAGTGAATT GCTGAAGAAG CCAGTTACAT TTGTACCAGC TACCCGTGGT AAAGAATTGG   360
AAGACGCGAT CGCAAAGTTA AATGACGGCG ACGTACTTTT GATGGAAAAT ACGCGGTTTG   420
AAGATCTTGA CGGTAAAAAA GAATCCGGCA ACGATCCTGA ACTCGGCAAG TACTGGGCAA   480
GCTTAGGCGA CTTGTTTGTC AATGATGCCT TTGGTACCGC TCACCGTAAG CATGCTTCAA   540
ACGTTGGTAT TGCCTCCAAC ATGAAACAAA CTGCTGCCGG CTTCTTGATG GAAAAAGAAA   600
TCAAGTTCTT GGGTGACGCT GTGGACAATC AAAGCATCC ATTCATCGCA ATTTGGGTG    660
GTGCTAAGGT TTCCGATAAG ATCGGTGTGA TTGAAAACCT GGTTCCTAAA GCTGACAAGA   720
TTCTCATCGG CGGCGGCATG ACTTATACCT TCTATGCTGC CAAGGGTATG AGCATCGGTA   780
ATTCACTGGT TGAAAAGGAC AAGATCGACT TAGCTAAGAA GATCATGGAC CAAGCCGGTG   840
ACAAGCTGCT TTTGCCTGTT GATTCTGTGG TTGCCCCAGA ATTTTCTAAC GATGCACCGC   900
ATAAGGTTGT TGAAGGCGAC ATTCCGGATG GCTACATGGC GTTGGATATC GGCCCTAAGA   960
CGATTCAGGA ATTCAAGGAT GCACTTAAGG GTGCCAAGAC AGTTGTCTGG AACGGCCCAA  1020
TGGGTGTCTT TGAAATGAGT AACTATGCTG AAGGCACACT TGAAGTTGGT CGTGCTCTTG  1080
GTGATTTGAA GGATGCAACT ACGATCATCG GTGGCGGCGA CTCAACAGCT GCAGCTAAGC  1140
AACTTGGCAT TGCACCTAAG ATTACCCACA TCTCCACTGG TGGCGGTGCT AGCCTTGAAT  1200
ACCTTGAAGG CAAGACCTTA CCAGGTATTG CAGCCATTTC TGACAAGTAA TTGTTAGTGA  1260
TGCTGATCTA ACAGTCATTA TCGACATGCA TGATGCATGT CGGTACATAA TGAAAGGAAG  1320
GTATGTCATG CGGACACCAT TCATTGCTGG TAACTGGAAA ATGAATAAGA ATCCTAAGGA  1380
GACGCAAGCC TTCTTAGATG CTGTTAA                                     1407
```

Fig. 38. Amino acid sequence of *L. rhamnosus* strain HN001 phosphoglycerate kinase AK6

```
LAKLIVSDLD VKDKKVLIRV DFNVPIKDGV IGDDNRIVAA LPTIQYVIDH   50
GGKAILLSHL GRVKTEEDKA KLTLKPVAER LSELLKKPVT FVPATRGKEL  100
EDAIAKLNDG DVLLMENTRF EDLDGKKESG NDPELGKYWA SLGDLFVNDA  150
FGTAHRKHAS NVGIASNMKQ TAAGFLMEKE IKFLGDAVDN PKHPFIAILG  200
GAKVSDKIGV IENLVPKADK ILIGGGMTYT FYAAKGMSIG NSLVEKDKID  250
LAKKIMDQAG DKLLLPVDSV VAPEFSNDAP HKVVEGDIPD GYMALDIGPK  300
TIQEFKDALK GAKTVVWNGP MGVFEMSNYA EGTLEVGRAL GDLKDATTII  350
GGGDSTAAAK QLGIAPKITH ISTGGGASLE YLEGKTLPGI AAISDK      396
```

Fig. 39. Nucleotide sequence containing *L. rhamnosus* strain HN001 triosephosphate isomerase AK5 showing ATG initiation and translation stop codons (boxed)

```
AGATTACCCA CATCTCCACT GGTGGCGGTG CTAGCCTTGA ATACCTTGAA GGCAAGACCT   60
TACCAGGTAT TGCAGCCATT TCTGACAAGT AATTGTTAGT GATGCTGATC TAACAGTCAT  120
TATCGACATG CATGATGCAT GTCGGTACAT AATGAAAGGA AGGTATGTCA TGCGGACACC  180
ATTCATTGCT GGTAACTGGA AAATGAATAA GAATCCTAAG GAGACGCAAG CCTTCTTAGA  240
TGCTGTTAAG GGTAAGTTAC CTGATGCAAG CAAAGTTGAA ACAGTCATTG GCGCACCTGC  300
CATTGATCTA ACGACACTGG TTGCCGGTGC AGAAGGTACT CCTTTGAAGA CAGCGGCGGA  360
AAACTGCTAC TTTGAAGACG AAGGTGCTTT TACCGGCGAA ACCAGCCCGA AGCCTTAAA   420
AGAAATGGGC GTTGATTACG TCATTATCGG TCACAGTGAA CGTCGCGGTT ATTTCCACGA  480
AACCGACGAA GATATCAACA GAAGGCTAA  GGCCATCTTT AAGAACAATC TTTTGCCGAT  540
TATCTGCTGT GGTGAAAGTT TGGCTCAGCG TGAAGCCGGT CAAACCGAAG ACTGGGTTGC  600
TTCTCAAATC GAAGCAGCTT TGGCAGGCTT AAGTGCCGAC CAAGTTAAGG TTTCGGTTTT  660
GGCTTATGAA CCAATCTGGG CTATCGGCAC TGGTAAAACA GCAACTGCAG ATCAAGCACA  720
AGAAGTTGTT GCTCACATCC GTGCAACCGT TGAGAAGTTG TATAATAAAG ATACGGCAGA  780
TGCTGTTCGG ATTCTTTACG GCGGCTCTGT TAAACCAGCG AACGTCAAGG AATTAATGGC  840
TAAGCCTGAT ATTGATGGTG GTTTAGTTGG TGGCGCTTCG ATGGATCCTG ACAGTTTCAT  900
CGCCTTGGCT AACTACCAAG ATTAATCTGG TTTCAATATT AAACAGCCTT CTGGCAAAAA  960
GGAGAAGAAT AT                                                      972
```

Fig. 40. Amino acid sequence of L. rhamnosus strain HN001 triosephosphate isomerase AK5

```
MRTPFIAGNW KMNKNPKETQ AFLDAVKGKL PDASKVETVI GAPAIDLTTL  50
VAGAEGTPLK TAAENCYFED EGAFTGETSP KALKEMGVDY VIIGHSERRG  100
YFHETDEDIN KKAKAIFKNN LLPIICCGES LAQREAGQTE DWVASQIEAA  150
LAGLSADQVK VSVLAYEPIW AIGTGKTATA DQAQEVVAHI RATVEKLYKK  200
DTADAVRILY GGSVKPANVK ELMAKPDIDG GLVGGASMDP DSFIALANYQ  250
D  251
```

Fig. 41. Nucleotide sequence containing L. rhamnosus strain HN001 phosphoryl carrier protein HPR AA9 showing ATG initiation and translation stop codons (boxed)

```
TTGTTTTGGG TACGAGTACG CACACAAACT ATTCGGAAAA ACACTAGAAA AATCTAGTTA  60
ATACGAAGGA GCAGATCAGT CATGGAAAAA CGCGAATTTA ACATTATTGC AGAAACCGGG  120
ATTCACGCAC GTCCGGCAAC CTTGTTGGTA CAAGCAGCTA GCAAGTTCAA CTCAGATATC  180
AACTTGGAAT ATAAAGGTAA GAGCGTTAAC TTGAAGTCCA TCATGGGTGT TATGAGTTTG  240
GGCGTTGGTC AAGGTGCCGA TGTTACAATC TCTGCTGAAG GCGCTGACGA AGCCGATGCA  300
ATCGCTGCAA TTACGGACAC AATGAAAAAG GAAGGCTTGG CTGAATAATG GCTGAACATT  360
TGAAGGGAAT CGCTGCTAGT GATGGGATCG CCACAGCGAA GGCCTATTTA CTGGTTCAAC  420
CTGATTTATC ATTTGACAAA AAGACCGGTTG ATGATCCTTC AAGGAGATC GACCGGCTAA  480
AGCAGGCACT T                                                       491
```

Fig. 42. Amino acid sequence of L. rhamnosus strain HN001 phosphoryl carrier protein HPR AA9

```
MEKREFNIIA ETGIHARPAT LLVQAASKFN SDINLEYKGK SVNLKSIMGV  50
MSLGVGQGAD VTISAEGADE ADAIAAIIDT MKKEGLAE  88
```

Fig. 43. Nucleotide sequence containing L. rhamnosus strain HN001 glyceraldehyde-3-phosphate dehydrogenase AK7 showing ATG initiation and translation stop codons (boxed)

```
CCACAAACTC GATTTTAACT GGGGCAACCC GTAGAATAA  ACCTTATTTC CTAAAGGAGG    60
AAATTTTAGC [ATG]ACTGTTA AGATTGGTAT TAATGGTTTT GGCCGTATCG GTCGTTTGGC  120
ATTCCGTCGT ATTTACGAAT TGGGTGCAAA GAGCAATGAC ATTCAGGTTG TTGCGATCAA  180
CGATTTGACC AGCCCAACCA TGCTGGCTCA CTTGCTGAAG TATGATTCAA CCCACGGTAC  240
TTTCCCTGGT GAAGTTAGTG CAACCGATAA CGGTATTGTC GTTGACGGTA AGAATACCG   300
TGTCTACGCA GAACCGCAAG CCCAGAACAT TCCTTGGGTT AAGAACGACG GCGTTGACTA  360
CGTTCTTGAA TGCACAGGCT TCTATACTTC TGCTGAAAAG TCACAAGCTC ACTTGGATGC  420
AGGCGCAAAG CGTGTTCTGA TTTCTGCCCC AGCTGGCAAG ATTAAGACTA TCGTTTATAA  480
CGTTAATGAT GACACCTTGA ATGCAGACGA CAAGATCGTT TCTGCAGGTT CTTGCACGAC  540
CAACTGCTTG GCACCAATGG CTTACTTCCT GAACCAGGAA TTCGGCATTG AAGTTGGTAC  600
CATGACCACC GTTCATGCCT ACACCTCAAC TCAGATGTTG CTTGACGGCC CAGTTCGTGG  660
CGGCAACCTG CGTGCTGCAC GTTCAGCTGC TGCTAACACG ATTCCTCACA GCACTGGTGC  720
TGCTAAGGCT ATCGGTTTGG TTATCCCAGA ATTGAACGGC AAGTTACAGG GTCATGCACA  780
GCGTGTTTCT GTTGTTGACG GTTCCTTGAC TGAATTGGTT TCCATCTTGA AGACCAAGAA  840
CGTTACGGCT GACCAAGTCA ACGAAGCTAT CAAGAAGCAC ACCGAAAACA ACCCTAGCTT  900
TGGCTGGAAC GAAGACGAAA TCGTATCTTC CGATGTTATC GGTACGACAT ACGGTTCAAT  960
CTTCGATCCT ACTCAGACCG AAGTTACAAC TGCCGGTGAC TATCAATTAG TTAAGACGGT 1020
TGCTTGGTAC GATAACGAAT ATGGCTTTAC TTGCCAGATG ATCCGTACCT TGCTGAAATT 1080
TGCTACTCTC [TAA]TCCGGAG TAACGCTTTT CTAACCGCAA CATCCGAAGC GGAGGGAGCT 1140
TTACTCCCTC CGCTTTTTTT GGAAAGACCA TTAAAAGG                         1178
```

Fig. 44. Amino acid sequence of L. rhamnosus strain HN001 glyceraldehyde-3-phosphate dehydrogenase AK7

```
MTVKIGINGF GRIGRLAFRR IYELGAKSND IQVVAINDLT SPTMLAHLLK  50
YDSTHGTFPG EVSATDNGIV VDGKEYRVYA EPQAQNIPWV KNDGVDYVLE 100
CTGFYTSAEK SQAHLDAGAK RVLISAPAGK IKTIVYNVND DTLNADDKIV 150
SAGSCTTNCL APMAYFLNQE FGIEVGTMTT VHAYTSTQML LDGPVRGGNL 200
RAARSAAANT IPHSTGAAKA IGLVIPELNG KLQGHAQRVS VVDGSLTELV 250
SILKTKNVTA DQVNEAIKKH TENNPSFGWN EDEIVSSDVI GTTYGSIFDP 300
TQTEVTTAGD YQLVKTVAWY DNEYGFTCQM IRTLLKFAIL 340
```

Fig. 45. Nucleotide sequence containing L. rhamnosus strain HN001 sorR transcription regulator AL3 showing ATG initiation and translation stop codons (boxed), and repeated sorR-response elements recognized by the sorR protein (underlined).

```
TCATTCACAA ATGTTAAACT TAAGTTGTTA CTAATTTCAC TTTTGATTAT AATTGGAATG  60
TAATCGGTTA CAACGTGACT GTTGATAAT TTCACATTTG TGATTCGAG GTGACATCAA 120
TGTCAAATTT GCCTAAACGG TATGATCGTG CAACTTTAGT CAAGATATCC GATCTTTACT 180
ACATGCACGG TCTAACTCAA CAAGAAATAT CTAACATTGC CCATATTCAC AGAACCGAAA 240
TAAGTCGAAT TCTGAAGGCG GCTAGGGATG AAGGCGTGGT ATCTATCGCA ATCAATCCCG 300
AAACCACCGC CGTCAGCCAA CTTATTGATT TTTTAAACA AAAATACAAT TTGCGAGAGG 360
CCGTTATAGT CCCGGCTTCT GAAAATGGAG GCAATGAGTT AAACGCTTTG AGTGTTTACG 420
CATCAATGTT TTTATCAAGA ATCATTAAAA GTGGTGACGT AATTGGGTTA AGTTGGGGTT 480
CAACGCTTTC AAGTGTTATC AGTCAATTTC CAACAGATAA AGGCCTTCGT GATATTAAAG 540
TTGTTCCGCT GGTGGGTGGC CCAATGGGAA GAATACCTTC GACTATCAT GTGAGCTATC 600
TGACACACCG GCTCGCCAAT CGGCTAAACG GAACAGCGTT TGTCTTGGAT TCCCCTGCCT 660
TTGTCAGATC AAAAGCGCTT CGTAAAGAGC TTCTCGCCAA CCCCAACACG CAAGAAATCT 720
TAGGATTGTG GAATCGTGTC AATATCGCGA TCTTTGGCAT CGGAAGTTCA CTAATTACAG 780
ATTCTCCTGA TTGGCAAGCG TTCTATGAGA ACACAAACTT CAAGTCTTAT TTCAGTGCCG 840
ATATGGTCGG AGATATTCTT TCACACCCTT TCGACAAGGA TGGAAAATTA GCTCGCGATA 900
TCGACTCCAT TCTTGTTGCC TTTCCTTTTT CGGCATTGCG AAAAGTACCA CACTCCGTTG 960
GAATTGCTTT TGGGGAAGAA AAGGTAAATG CTATCCTTGC CGCTCTTCGA GGTGGTCTCT 1020
TAAACACTTT AATTACTACC GAAGCAACAG CAAAGGCAAT CAAAGAGTTG TCCTAA      1076
```

Fig. 46. Amino acid sequence of L. rhamnosus strain HN001 sorR transcription regulator AL3

```
MSNLPKRYDR ATLVKISDLY YMHGLTQQEI SNIAHIHRTE ISRILKAARD  50
EGVVSIAINP ETTAVSQLID FFKQKYNLRE AVIVPASENG GNELNALSVY 100
ASMFLSRIIK SGDVIGLSWG STLSSVISQF PTDKGLRDIK VVPLVGGPMG 150
RIPSNYHVSY LTHRLANRLN GTAFVLDSPA FVRSKALRKE LLANPNTQEI 200
LGLWNRVNIA IFGIGSSLIT DSPDWQAFYE NTNFKSYFSA DMVGDILSHP 250
FDKDGKLARD IDSILVAFPF SALRKVPHSV GIAFGEEKVN AILAALRGGL 300
LNTLITTEAT AKAIKELS 318
```

Fig. 47. Nucleotide sequence containing L. rhamnosus strain fpg gene AL4 showing ATG initiation and translation stop codons (boxed).

```
GACTCGGCTT GTTTCACTTG TGGTACCTTT GAAAGTCGAA AGTCATTATG GACCGACCTG   60
GTTTGATGCG AAATAAGGAG AACTC[ATG]CC TGAATTACCT GAAGTTGAAA CGGTTCGCCG  120
TTCCTTGTTA CCGTTAGTCA AAAATAAAAA AATCACCGCG ATTAGCACAA ACTGGGAGAA  180
AATCCTAATT AATGGTCTGG CAACCTTTCA AAACAGGTT GTGGGCGCTG CTGTCAACAC   240
GATTGATCGC CGCGGTAAGT ATTTACTGAT TCGGCTTAAC AACGGCATGA CGATTGTCAG  300
TCATTTGCGC ATGGAAGGCC GCTATTACGT TGTTTCGGAT GCCAAAACGC CGCTGGATAA  360
GCATGATCAT GTGACGTTTA CCTTTCAGGA TGGCAGCCAG TTGCGTTACC GCGATCTGCG  420
CAAGTTTGGC CGGATGCGGC TGATTCACAC GGGTCAGGAG CAATTGGTGC CAGCGCTGGC  480
CAAGCTAGGA CCGGAGCCGA CTGCTGCTAC TTTTAGCGAA AGTGACTTTG CCCAGAAACT  540
AAAACGGCAT CATAAAGCCA TTAAATCGGT TTTGCTGGAT CAAACTGTTG TGGCCGGAAT  600
TGGTAATATT TACGCGGATG AGGTCTTATG GCTCAGCAAG CTCAATCCGC TGCAGCCAGC  660
TAATACCTTA ACCAAGGCGG AGGTTCACAC GTTACATGAT GCGATTATCA AGGAATTGGA  720
CGACGCCATT GCCGCTGGCG GTACCAGTGC CCATACTTAC GTTGATGCAA AAGGCAACCG  780
CGGTTCGTTT CAGGACGCTT TGCATGTCTA TGATCGTGAA GGGACGCCTT GTGATCGTTG  840
CGGCACCACG ATTGTCAAAA TTAAAGTCGG TCAACGCGGC ACGCATTATT GCCCGCATTG  900
CCAGCCGTTA CGTCGAAGGG GGCAACTGGC A[TGA]CCTTTT TGTTAGGGCT GACGGGCGGC  960
ATTGCGTCAG GCAAGTCAAC GGTAAGCCGG ACATTTAAAG CAGCTGGGTT TCCAGTGGTG 1020
GATGC                                                               1025
```

Fig. 48. The amino acid sequence of HN001 fpg AL4.

```
MPELPEVETV RRSLLPLVKN KKITAISTNW EKILINGLAT FQKQVVGAAV   50
NTIDRRGKYL LIRLNNGMTI VSHLRMEGRY YVVSDAKTPL DKHDHVTFTF  100
QDGSQLRYRD LRKFGRMRLI HTGQEQLVPA LAKLGPEPTA ATFSESDFAQ  150
KLKRHHKAIK SVLLDQTVVA GIGNIYADEV LWLSKLNPLQ PANTLTKAEV  200
HTLHDAIIKE LDDAIAAGGT SAHTYVDAKG NRGSFQDALH VYDREGTPCD  250
RCGTTIVKIK VGQRGTHYCP HCQPLRRRGQ LA                     282
```

Fig. 49. Nucleotide sequence containing the *L. rhamnosus* strain HN001 acetoin dehydrogenase gene *AP1* showing ATG initiation and translation stop codons (boxed)

```
GCGTGGTGTA AGATTCGGTA AGGCTAGAGC AAAGCGGTTG TGTGAAGTGT GAATCCAGCA   60
AGCTGAATTC CTGAATTGAT GAAAGGAAGA CGGATATGTA TCGAGATCTG AATGGTAAGG  120
TTGCAGTCGT GACTGGTGGC TCCAAAGGCA TTGGCGCGGG CATTGCAGAA CGGTTTGGCC  180
AAGAGCATAT GGCCGTTGTG ATTAATTATT TAGGTGATCA CGAAGGCGCG CGAAAAACAG  240
CCGATACAGT GATCAAAAAT GGCGGTCAGG CAGTCAGTAT TCATGCAGAT GTTTCGACAG  300
AAGCGGGCAT AGCGAGTTTG GTTAAAACTG CCGAGTCCGA ATTTGGCCGC CTTGATGTCT  360
GGGTCAATAA TGCAGGCATG GAAATTAAAG CACCGACGCA TGAAGTGTCT CTGGATGACT  420
GGAATAAAGT CATTGCGATT AATCAAACCG GGGTCTTTTT AGGCGCCCGG GCTGCTTTGA  480
ATTATTTTCT CGACCATCAC CAGCCAGGCA ATATTATTAA CATCTCATCG GTCCATGAAC  540
AGATTCCCTG GCCAACGTTT GCCAGTTATG CTGCAGCTAA AGGGTCGGTT AAGCTTTTCA  600
CGGAGACGAT TGCGATGGAA TACGCTAACC GCGGAATTCG GGTCAACGCT ATCGGCCCCG  660
GTGCCATTGA GACGCCGATT AATGCGGAAA AGTTTGCTGA TAAGGCGCAG TATGACCAAA  720
CAGTCGCCAT GATTCCCCAA GGACGGCTAG GCAAACCGGA AGATGTTGCC GCCGGAGCAG  780
CCTGGCTGGC ATCGACAGAG TCAAGTTACG TCACTGGCAC GACCCTATTT ATTGACGGCG  840
GGATGACATT ATATCCTGCG TTTAAGACG GACAGGGCTG ATCAATGTTG CGAAGATGCA  900
AAAAGTCGCC ATCTCGATTA TGAAATGGCG ACTTTTTGTG TACGGGTTAG AATTCGCGTT  960
TTTTATACAG CACGGTGCTT AACCACCAAG AGAAGATGAA                       1000
```

Fig. 50. The amino acid sequence of HN001 acetoin dehydrogenase AP1.

```
MYRDLNGKVA VVTGGSKGIG AGIAERFGQE HMAVVINYLG DHEGARKTAD   50
TVIKNGGQAV SIHADVSTEA GIASLVKTAE SEFGRLDVWV NNAGMEIKAP  100
THEVSLDDWN KVIAINQTGV FLGARAALNY FLDHHQPGNI INISSVHEQI  150
PWPTFASYAA AKGSVKLFTE TIAMEYANRG IRVNAIGPGA IETPINAEKF  200
ADKAQYDQTV AMIPQGRLGK PEDVAAGAAW LASTESSYVT GTTLFIDGGM  250
TLYPAFKDGQ G   261
```

Fig. 52. Nucleotide sequence containing the *L. rhamnosus* strain HN001 aflatoxin $B_1$ aldehyde reductase gene *AI7* showing ATG initiation and translation stop codons (boxed).

```
ACTAATGTGG ATGACGGCGT GGCGAACTTT TTAACGGATT TTTTTGAGAA GTGAGCTTTT   60
TCCGTAAAAA GTGGGGTTTC TGGTTGATTG TTAGCGAAAC GTTTGCCACC ATAGAGATGG  120
TAAACGTTTT TATTTTGCGG TCGTTTGAGG AGGGCTTTAA TCATGTATCA TGCAGCAGCT  180
GATCGTTATG AGAAAATGCC GGTTCGCCAT GCTGGTAAGA CAGGGTTGAT GTTGCCGGTT  240
ATTTCGTTGG GATTGTGGCA GCATTATGGC AACTTGGATC CATTTGGCCC GCGACGCTCG  300
GTGATTTTGG ATGCGTTTGA TCGTGGCGTT TTTCATTTTG ATGTCGCTAA TCATTATGGT  360
AATGGTGATC GTGAACCGGG ATTTGGCTCT AGTGAAAGGT TACTCGGGCA GATTCTGGCC  420
ACGGATTTAA AACCGTATCG AGACGAATTG GTGATTAGTA CCAAGGTGGG TTATGAGATT  480
CACCCTGGTC CATACGGTGT CGGGACGTCG CGTAAAGCAG TTATTCAAGG CTTGAATGAT  540
TCACTCAAGC GCTTGCAGTT GGATTATGTC GATATTTACT ATGCCCACCG ATTTGACGAT  600
ACCGTGGCCT TGGAAGAGAC GGTTAATGCG CTGGATCAAA CGGTGCGTGA CGGTAAGGCG  660
TTGTATATTG GTATTTCCAA CTATGATACG AAGCAGACCA AAGAAGCAAT TGCGATGTTT  720
AAAGATCTGC ACACGCCTTT TGTACTGAAT CAATACAGTT ACAACATGTT TAATCGCACC  780
GCTGAAACGT CCGGCTTGAT CGATGCATTA AAAGCTGATG GTGCCGGGTT GATTGCATAC  840
GGACCGTTAT CAGAAGGCTT GTTATCAGAT CGCTACCTAA AGGGAATTCC GGATACTTTC  900
AAAATCCATC CAACCAACAA GGCCACTTTT GCTAAGGGCA AAGAGGCTGT GGTTAAGCAA  960
CTAAATGCGC TTAATGAAAT TGCGCATGAT CGTGACCAAA CCCTGAGTCA AATGGCCTTG 1020
GCGTGGTTGT TACGGGATCC GGTTGTCACA AGTGTGATCA TTGGGACGAC CTCAGTTGAA 1080
CACCTTCAGG ATAACCTTAA AGCAACGGAA CATCTGACCT TTACTGCTGA AGAGATTCAA 1140
CAAATTGATG ATATTTTAAA TGCTTAGTTG ACGTTTGGCT GTAAAAGGCT AAGCGTAAGT 1200
ATAAAAAAAC GGCTTCGGAG TGTTTTTTGA CTCCGGAGCC GTTTTATTTT TGAGGAACAA 1260
TGCTTGACAG GTGCTCT                                                1277
```

Fig. 53. The amino acid sequence of HN001 aflatoxin $B_1$ aldehyde reductase AI7.

```
MKLTIYDFDH VIDRRGTFST QWDYIADRFG RNDILPFSIS DTDFPVPVEV   50
QDALKERLTH PIYGYTRWNH ATYKDSIVHW FERDGHTKIN PDWIVYSPSV  100
VFTIATLIRM KSDPGDGVAV FTPMYDAFYG TIKQNDRVLI PIRLAAADEG  150
YVIDWDSLAT VLAEKQTKIF LLTNPHNPTG HVFTKSELAR LYDLCQAAHV  200
FLISDDIHRD IVYPGHSYEP MTNVGTSDVA LCCSGSKTFN TPGLIGSYAF  250
LPDHDVRAQF LTELKQKNAL SSVSIFGMLA QIAAYNGSED YVEQLTAYTK  300
NNMELVASYL EENLPELQFS LPDATYLAWI NVSKLRLTSE ELQHRLVNGG  350
HVGIMAGKTY GDTRYLRMNI ACPKKKLVMG LERLKKGIRG   380
```

Fig. 57. Nucleotide sequence containing the L. rhamnosus strain HN001 aromatic aminotransferase gene AH7 showing ATG initiation and translation stop codons (boxed).

```
TATGACGTTG CGTGTCGATA GGCAAATGGA CTATGCTATT GCATGCTAT  TATAACGCGT    60
TTGCCAGCGT AAAAGTCAGT TAGGCAATCT TTTAGTTGTA GCCGTCTAAC TCCGACTTCT   120
AACTGCATCG GTTCGCGTTT ACATCATAAT GCGCTCTCCT GCCCAGAAAT CGGGTTTGGC   180
TCGCGCTTAC TTTATTAAGG AGATTTGTAT GACATTGCAA CCTTTAAACG AACAACTACC   240
TGCCATCGAG GTTAGTGAGA TTCGACAATT TGACGAAAGT GTCAGTGATA TTCCCGGTAT   300
TTTGAAACTG ACGCTAGGCG AACCTGATTT CAACACCCCG GAACATGTTA AGCAAGCCGG   360
GATCAAAGCC ATTCAGGAAA ATTACTCGCA TTATACCGGG ATGGTTGGTG ATCCGGAGTT   420
ACGCGAAGCC GCACAACATT TTTTTAAAAC GAAATATGCC ACTGACTATC GGGCTACAGA   480
TGAAATTCTG GTGACAGTCG GGGCCACTGA AGCACTGGCA ACCGCCATTA CGACGATCAG   540
TGATCCGGGT GATGCCATGC TGGTTCCGTC ACCAATTTAT CCGGGCTACA TTCCGCTTCT   600
GACGCTGAAT CACGTTACGC CGCTTTATAT GGATACGAGT AAAACCGACT TGTCTTGAC   660
CCCCGAACTC ATTGAGGCCA CCATCACTGC AAATCCTGAC GCTAAAATCA AGGCATTAT   720
CCTTAACTAT CCAAGTAATC CCACCGGTGT CACGTATCGG GCGGCAGAAG TTAAAGCCAT   780
TGCGGACATC GCCGCTAAAC ATAACCTCTA CATTATCTGT GACGAAATTT ATTCTGAACT   840
GACTTATGGT GAGCCGCATG TTTCCATGGG ACAATTGCC TACGATCGTA CATTTATTGT    900
CAACGGTCTG TCTAAATCAC ATGCAATGAC CGGCTGGCGA ATCGGCTTTT TGATGGGTCC   960
CCAGCAGTTA ATCGCGCAAG CCAAAAAGGT GCACCAATAT CTTGTGACTG CCGCAACGAC  1020
CATTGCCCAG CGCGCTGGTA TTGAAGCTCT GACGAACGGT GCAGACGATG CTCAGGTGAT  1080
GAAAGCAGCT TACGTTAAAC GCCGTGATTT TGTTTATGCC GCCCTCATCG ACATGGGCTT  1140
TAGCGTGGCT CGTCCTGATG GTGCCTTTTA TCTTTTTGCA AAAATTCCGA CCCAACTGCA  1200
TCTAAGCTCA CGCGAATTTA CGCACGCCTT GGCACATGAA CAGAAGTTAG CTCTGATTTC  1260
AGGTACCGCT TTTGGCCCCG GCGGCGAAGG TTATATCCGA ATCAGTTACG CGGCATCAAT  1320
GACCGATCTT CAAGAAGCCG TTAAGCGATT GCGCGCGTTC ATGGCCAGCC ACATCGGCTA  1380
ATCAAGCGTA AACGGAAAGA ATCCGCACG                                    1409
```

Fig. 58. The amino acid sequence of HN001 aromatic aminotransferase AH7

```
MTLQPLNEQL PAIEVSEIRQ FDESVSDIPG ILKLTLGEPD FNTPEHVKQA   50
GIKAIQENYS HYTGMVGDPE LREAAQHFFK TKYATDYRAT DEILVTVGAT  100
EALATAITTI SDPGDAMLVP SPIYPGYIPL LTLNHVTPLY MDTSKTDFVL  150
TPELIEATIT ANPDAKIKGI ILNYPSNPTG VTYRAAEVKA IADIAAKHNL  200
YIICDEIYSE LTYGEPHVSM GQFAYDRTFI VNGLSKSHAM TGWRIGFLMG  250
PQQLIAQAKK VHQYLVTAAT TIAQRAGIEA LTNGADDAQV MKAAYVKRRD  300
FVYAALIDMG FSVARPDGAF YLFAKIPTQL HLSSREFTHA LAHEQKLALI  350
SGTAFGPGGE GYIRISYAAS MTDLQEAVKR LRAFMASHIG    390
```

Fig. 59. Nucleotide sequence containing the L. rhamnosus strain HN001 acetate kinase gene AP5 showing ATG initiation and translation stop codons (boxed)

```
ATG GCAAAGA TTCTCGCAGT CAATGCAGGT AGTTCGACCC TGAAGTGGAA GCTTTTTGAT    60
ATGCCGGCTG AAGTGCAGTT GGCTGAGGGG TTGGTCGATC GATTGGGCCA GCCGCAATCG   120
AAGGTTAAAA TTAAATATGG CGACGGTCAG AAGTACGAGA GCGATACCCC AATTGCAAAC   180
TATCAAGAAG CAGTTGCCAG CTTGATGGGT AATATTAAGG CGCTAGGGTT AGTGGAGCAT   240
TTGCACGAGA TTATCGGGGT CGGCCATCGA GTGGTTGCTG GCGGCGAAAT TTTTGCCGAA   300
TCAGTTGTTG TTGATGATGA GACGTTGCTG CAGATTCAGA ATCTGCGCGA CTATGCACCG   360
TTGCATAATC CCGTTGAAGC GGACTATATT TCGGTTTTTC GGAAAATGAT GCCTTGGGCG   420
AATGAAGTGG CAGTTTTTGA CACGGCTTTC CACCAAACAA TGCAACCGGA GAACTTTTTA   480
TATAGCATTC CATACGAATA TTATGAGCAA TATGGTGCGC GGAAGTATGG TGCGCATGGA   540
ACAAGTGTCC GTTATGTGAG CGCTCGTGCT GCTGAAATGT TGGGCAAGCC GCTAGAAGAT   600
CTACGTATGA TTGTCATGCA CTTAGGGTCT GGCTCTAGCA TCACCGCGGT TCAAGGCGGA   660
CAGTCAATTG ATACGTCCAT GGGCTTTACG CCATTAGCAG GTGTCACCAT GGGCACGCGA   720
TCAGGTGATA TTGATCCGTC ATTGGTAGGC TATCTCATGA AGAAGTTGGC GATACCGGAT   780
GTTGGCCAAA TGATTCATAT TCTCAACAAC GATTCCGGTC TGCTAGGTAT CTCCGGACTC   840
AGCAATGATA TGCGTGACTT GGAAGCCGCC GAGGACACCA ATACACGCGC TAAGCTGGCA   900
CTGGATATTT TTGTGAACCG CGTTGTGAAA TACGTTGGCT CTTACGTTGC TTTAATGGAT   960
GGCGTCGACG TGCTGGTCTT CACCGCTGGC ATTGGCGAAA ACGGTGACGA GATCCGTGAT  1020
AAGATTATGC GGTCGCTTGA TTACCTCGGC GCCAAAATCG ACAATGATCT GAATTACAAG  1080
TCACATGGCG TTGAAGCAGA TCTAAGCACG GCAGATTCAA CCGTGAAAAC GCTGCTGGTA  1140
CCGACAAATG AAGAACTTAT GATTGTACGC GATGTGATGG CACTGAGCTA A           1191
```

Fig. 60. The amino acid sequence of HN001 acetate kinase AP5

```
MAKILAVNAG SSTLKWKLFD MPAEVQLAEG LVDRLGQPQS KVKIKYGDGQ    50
KYESDTPIAN YQEAVASLMG NIKALGLVEH LHEIIGVGHR VVAGGEIFAE   100
SVVVDDETLL QIQNLRDYAP LHNPVEADYI SVFRKMMPWA NEVAVFDTAF   150
HQTMQPENFL YSIPYEYYEQ YGARKYGAHG TSVRYVSARA AEMLGKPLED   200
LRMIVMHLGS GSSITAVQGG QSIDTSMGFT PLAGVTMGTR SGDIDPSLVG   250
YLMKKLAIPD VGQMIHILNN DSGLLGISGL SNDMRDLEAA EDTNTRAKLA   300
LDIFVNRVVK YVGSYVALMD GVDVLVFTAG IGENGDEIRD KIMRSLDYLG   350
AKIDNDLNYK SHGVEADLST ADSTVKTLLV PTNEELMIVR DVMALS       396
```

Fig. 61. Nucleotide sequence containing the *L. rhamnosus* strain HN001 basic surface protein gene *AC9* showing ATG initiation and translation stop codons (boxed)

| | | | | | |
|---|---|---|---|---|---|
| ATGCCATTGT | CTGCACTTTC | TTAGCTTGGG | GTCAGCGGTA | TCTCGAAAAA | TTCACATCAC | 60 |
| GCTACAATGC | CAATGCACAA | ACCACGCAAT | TATAATCCGC | CATTTTGAAA | GGAAGAAAGC | 120 |
| T[ATG]TTAAAG | AAAAAGTTGT | GGTTCCTGTT | GCCGCTTGTG | GCCTTGGTAA | CCTTCACGCT | 180 |
| CACCGCTTGC | ACCAGCGCAT | CATCTGACAC | GTCAAAAAAC | AGCGACGTCA | CCGCCGAACT | 240 |
| CATCAACAAA | AATGAGCTTA | CCATCGGCCT | TGAAGGTACT | TATGCGCCAT | TTTCTTATCG | 300 |
| CAAAGATGGC | AAACTTGAAG | GCTTCGAAGT | GGAACTGGGG | AAAGCCTTAG | CCAAGAAAAT | 360 |
| CGGGGTTAAG | GCAAAATTCG | TGCCCACCCA | ATGGGATTCG | CTGATTGCAG | GATTAGGCAG | 420 |
| CCAGAAATTT | GATCTCGTAC | TGAATGATAT | TAGTGAAACG | CCCGCACGCA | AAAAGGTCTA | 480 |
| CAACTTCACC | ACTCCGTACA | TGTACTCGCG | TTATGCCTTA | ATAACCCGCA | GCGATAACAC | 540 |
| CACCATCAAA | TCGCTTGCCG | ATATTAAAGG | CAAAACATTT | GTCGAAGGCA | CCGGTACACC | 600 |
| CAATGCCGCT | TTAGCCAAAA | AATACGGCGC | TAAGATCACC | CCGTCTGGCG | ACTTTACCGT | 660 |
| ATCGCTTAGC | CTTGTGAAAG | AAAAACGCGC | AGACGGAACC | ATCAACGCCT | CGGCTGCATG | 720 |
| GTATGCCTTT | GCCAAGAATA | ACTCAACCGC | GGGCTTAAAG | AGTCAAACCC | TCAAAGATAG | 780 |
| TGTCGTTAAA | CCCGATGAAG | TAGCTGGCAT | GGTCAGCAAA | AAATCGCCTA | AACTACAAGC | 840 |
| CGCACTTTCA | AAGGGCATTC | AAGAACTACG | CAAAGACGGC | ACGTTGAAAA | AACTGTCGCA | 900 |
| AAAATATTTT | GGCACCGATT | TAACCACCAA | G[TAA]TCATGC | CATTCAGCTA | GCAAACATTG | 960 |
| CCCGTCAACC | TGCTTCATAA | ACGGGCATAC | ATAAAAGAAC | ACTATTCATT | AAAGGAGGTC | 1020 |
| GGGTTTCAAT | GA | | | | | 1032 |

Fig 62. The amino acid sequence of HN001 basic surface protein AC9

| | | | | | |
|---|---|---|---|---|---|
| MLKKKLWFLL | PLVALVTFTL | TACTSASSDT | SKNSDVTAEL | INKNELTIGL | 50 |
| EGTYAPFSYR | KDGKLEGFEV | ELGKALAKKI | GVKAKFVPTQ | WDSLIAGLGS | 100 |
| QKFDLVLNDI | SETPARKKVY | NFTTPYMYSR | YALITRSDNT | TIKSLADIKG | 150 |
| KTFVEGTGTP | NAALAKKYGA | KITPSGDFTV | SLSLVKEKRA | DGTINASAAW | 200 |
| YAFAKNNSTA | GLKSQTLKDS | VVKPDEVAGM | VSKKSPKLQA | ALSKGIQELR | 250 |
| KDGTLKKLSQ | KYFGTDLTTK | 270 | | | |

Fig. 63. Nucleotide sequence containing the *L. rhamnosus* strain HN001 aromatic outer membrane protein A AL8 showing ATG initiation and translation stop codons (boxed)

```
TAGGGGGTCA AAAATGGGAA CCAAAATAGC CGTTAAAATC AACAAGTGGC AAGTGTAGCT   60
CAAGCCAGCA GCAGTGCGAG CG ATG GTCAA GCCAAAGCAA GCAGGGGCTA ATGTGGCAAC  120
GACCACTAAT AGTAAAATTG GCGGCAGTCA AGTAGTGCC AAGGCAGCCA GTGCGTTTAA  180
AGTAGTGCT AGCGTTGAAA GTAGTGGCCA GATCAAAAGC ACTAGTTTAG CCAGTGCTGG  240
CAGTAACGGC GAAAAAGCGA CCAGCGCTCT AAGCAGTAGT GCAGTTGATG CCAGCGATGG  300
TCGTGCGAGT CAGGGTGTTG GCGGCACGTC AAGTGGTAGT TCAGATACTA CGAGTCAGGC  360
AAATGAAGGC AACAGCGCCG CCAGTGTAAC AAGTGCAAGC GCCAATAGTG CCTCTGCAAC  420
AAATACATCT GAAGGTCAAA CTCCAGTTAA TGAAGCGGTA TCAAACGATG CTTCTAGCGC  480
CGATGTCAGC ACCGCGTCAG AGTTTGATGC AGCCATGGCC GATTCAACGG TAAGTGTCAT  540
CAACGTACAG TCCGACTTTG TTATGGATGT TAGTGGTGAT CGCCAATCGT ATGCTTATCG  600
GCCAAACCTA ATCATTAATG GCAATAACCA CACAATTGAT TTCAAAAGA AGTATTTCGA  660
AGCTGATCCT ACAAGTAGTC AGAATGAATC ATTACCATC AACGATTTAA ATATGTACGG  720
TTACAGTTGG TGGGGCCCGG TTACTATCAA GGGCAGTAAG CCGAAAGACG GCATCGATCA  780
TTCGGTAGTG TTCAATAATG TCACATACAC AGGTGCACAA CTGATGTATG GCATTTATAC  840
AAAAGCCTTT ATTAAGGGGA ATACAAAGAT TCAGTCAGTG GGCAGTTATG TTTCCCCGCT  900
GGACGGATCA ACCCAGACAA CCCAAGGCTT AGGCAACCAG CAAAACTTTC AAATTAGTTA  960
TTTAGAGGTT TTGCCTGGCG CTACTTACAC GGGGACAACT ACTGGTGGGA CTAACGTTGA 1020
AGTATATGAT GGCGGTTCAT TTATTGTTGA CAAGGGAGCA ACCGTTAACT TACAACGCAC 1080
GGATGCAAGC AAATCGAATG AACGTGGTAC GAATGCATTG ATTGATACAC AGGGAGGTAA 1140
CGTTGAGTTT AAGGATGGAT CAACCGTTAT CCTTAATAAA AATGCACTTG TGAAAGATGG 1200
CTTTGCACCA ATCTATATTG AAGACGGTGG TAATCTAACC GTTGATAAGA ATGCAACGGT 1260
ATCCATTACC GGTGCAACTG GAAACATCCC GGTAAGAATT GACGGTACCG GAACTGTCAA 1320
CCTCAACGAA GGATCGCACA TGACGATCAC TCAAAATGGT GCGCCTAAAC TTGGCTATGG 1380
CTTTATCAAT ATTAAAGGTA CCGGAGGCTT CTTCGTTGCA AGTGGCAGCA CTTTGGATCT 1440
TAATGTAACG GGTACAGGGA CAAAGAGTGT CAATGCAATT AATGTAGCAA ATGACGGTCA 1500
ACTGAGTTTT GCACAGGATG CTACGGCCAA CTTAACCATT GACGGTGGCA CGGGCGAAGC 1560
GCATTTGTTG AAAGTCGGTG ACGATGCCAA CATTAACATC TATATGCCGA AATCCGTTCT 1620
TTTTAAGATT ACCGATAACG ATGACGCAGA CAGCAGTTTA TTTAAAGTCA GTGGTACCGG 1680
CACGCTAACA GGTCAATATG TGAAAATCAT TCCGGATGAC GGGAATGCCT ATGGGCCATA 1740
TAAGTCCGCT ATCTATACAC TAAAAGGGAA TGGCTCTTCT TCAGATACCG CTACGGTTGA 1800
AGGTGAGACA GCAGAAGATG AACAATCCGG GAAAGCACTT GCCGACACGT TGCGACTGA 1860
CAAAAGCTTG GAGTTCGTCA GTGCCAGTGA TAATTTTATT AAGGTAAATC CAGTTACTGA 1920
TGAAACCACA ACGCTTACAG GTAAAACCAC TGCCGGAGCC TATGTAACGA TTTCAGGTTT 1980
AAAGGGGATT CCAGAAGGCA GCTTAACTGC GAATTCCTAT GATAGTACAA AATATTTGGT 2040
```

```
ACAGGCGGAC AAGGACGGTA ATTGGAGTTA CGAACTGCCG ACTGGGGTTT CGTTACCTGC 2100
CAATGCTTCA TTTGAAGTTA TTTCGAGTGC TGGATTCATT GTGAAAACAG CGACGGTAGT 2160
GATCAACGAT GCCGAAACGC CAAAGCAGGC ATCCAGTGCA GCTGGCAGCT TAATCAACGC 2220
CAATAGTGCT GCTGATGTCA CAGCTTCACA GGCAAAGGCT ACAAGTGCTG CTGCTAGTGA 2280
TGCGGCGAGT TATGCAAGTG AAGCGCAATC GATTGCTGGC AGTCATGCTG ATAATATGGA 2340
AATCAAGTCT CTCGCCAGTG ATGCTGAGAA GCAATCGCAA ATTGCTTTGG CAGCTAGCAA 2400
GTCTGCTGCG GCTAGTTCCA GTGCGGCAGC GTCCGCAGCA ATCGTGGCAA GTAGCGCGGC 2460
TAGTGAAGCG TCATCTGCAG CTGCTGCCGT AAGTAACGCT GATGCATCAG CAAACTCTGC 2520
AGCCGCTGCT TATGATTCCT ACGCTTCTGA GGCCAGTGCC GCTTCTGCTG CTAATGATAG 2580
TTCGGGATAT GCCACTGCAT CATTTGCAGC AAGTTCCGCT GCGGCTGCCA TGAGCGCAGC 2640
GTTATCGACA GCGCAAGTTG CTGCCAAGGT TGCAGTGAGT GATGCAGCAG CAGCGGGTAG 2700
TGCAGCTGCT GTTGCTAGTG CAGCTCAAAG CGACTCCAAG AATAAACAAG CGACTGCAGC 2760
TACAGCAAGA AGTCAAGCAC TTGATGATTT GAATAAGATC AAGTCTCTAA CTGATTACGC 2820
AAGTGGCGCA AGCTCCAGTG CCAGCGAAGC GGGTCAAGCA TCGACTGCAA CATCTGCGTA 2880
TGCTAGTGCT GCAAGTTCGA GTGCCAGTGA AGCCGGTTCA TATGCTCATC AGGCAGGCTC 2940
CAGCGCCAGT GACGCTGTCG GTCAGTCCGG CAGTGCAGCC AACATGCCA GCACCGCTGC 3000
GAGTGCGGCA TCCAGCTATC CGAAGGATAG TGGGATTCAG TCACTAGCCA GTCAGGCTGC 3060
AAGCGAGGCA GCAAAGGCAA GCAGTAACGC GAGTGCCGCA ACCAGCGCCG CGGCCGTTGG 3120
TTTCAGTGCT GCCAGTGATG CAAGTGAACA GGCGAAGACG GCTGCAAGTG CCGATGTGGT 3180
GGCAAGCAGT GCGGCCAGCA CGGCTAACAG TAATGCGAGT GCCGCAGCCA GTGCGACCAA 3240
GGCTGGTGAT AGCAAAGCCG CAGCAGGATT CTCGAGTGCA GCGAGTGCTG CAGCAAGCAG 3300
TGCCAAGGGT GCAGAAGCAG TTGCCAGCGA AGCGGCGAGT GCCGCGGCAT CCGATGACTC 3360
GGTAGCTTCT AGTGCCGCCA GTGCGGCTGC AGGCTTTGAC AAAGCTGCCA GCGCTGCGGA 3420
AGGCGCAGCT TCAAGTGCCG CGAGCGCGGC TGCTAGTTCA GCGGCAGCTC AAGGCACACG 3480
AGGTGGCGCA AGCTCCAGTG CCAGCGAAGC GGGTCAAGCA TCAACCGCAA CATCTGTGTA 3540
TGCTAGTGCT GCAAGTTCGA GTGCCAGTGA AGCCGGTTCA TATGCTCATC AGGCAGGCTC 3600
CAGTGCCAGT GAAGCGACTG CCATGCAAG TAGTGCTACA AGTCAAGCAA GTGCCGCATC 3660
CAGTGCTGCG TCCAGGTACC CAAGTGATAG TGGGATCCAG TCAGATGTAA GTATTGCGTC 3720
CAGTGCAGCA AGTACTGCAT CCAGTGCCGC TAGTGCCGCA CAAAGTGAGG CTTCGACGGC 3780
ATCGTCGGCT GCAAGTCATG CTAGTGAACA AGCAAGTATT GCTTCCAGTG AGGATGTTGT 3840
ATCAAGCAGT GCTGCGAGTG TCGCGTCCAG CGCGGCCAGT GCCGCATCCA GTGCTGCAAA 3900
GGCTGGTAAC AGTAGTGCTG CGGGTATATA CTCTCATGCA GCAAGTGCAG CTGCAAGCAG 3960
TGCTAAGAGC GCTGAAAGTC AAGCAAGCAG TGCCGCCAGT GCTGCTGCTT CTGATGATTC 4020
GGTAGCTTCT AGCGCTGCCA GTGCCGCTTT GTCTGACGAT GCTAAGGCAA GTAGCGCCGC 4080
CGATGTAGCA TCCAGCGCTA CAACTGCTGC CATTAGTTCC GCCACATCCT TGGCTGATCA 4140
CAGTGCCACA GGGTCAACCG CTGGCTCCCA TATTTTGCCA AGTACTGGTG GAGAGACGAC 4200
AGGTAGTATA CCATCGGGTC AGACGCCAAC ACAGACGAAG CCAACACAGA CGAAGCCAAC 4260
ACAAACGAAG CCAACACAAG CCGGTCAAAC AACCCAGACA GGTTCATTAC CGCAAACGGA 4320
```

```
TCATGCAGGG AGGCATATGC TACCGCAGAC CGGTGATGAT GCTGAAAGCG GTACTTCTGT 4380
TTTGGGTTTG CTGATTGTTA GTCTGATGGG ATTGTTTGGT CTTGCGGGAA CCAGACATCA 4440
GAAGGACAAT AAGCCATCAA AG TAA TATTG GATCACTAAT GTCGCCCATA CACTGGTGAT 4500
AAACCAAAAT CTGATGGAAA TAGCTAGTGG TGTAAGAGAT GATTATTCTC TTGCACCACT 4560
TTTTTGTTAA GCACGTTTTT TTATGGATTC TGTGTGCCAA ATGTTTGAAA TTCATGTGGT 4620
TAAATTTGGT TTTGCGGGTA ATCTA                                     4645
```

Fig 64. The amino acid sequence of HN001 outer membrane protein AL8

```
VRAMVKPKQA GANVATTTNS KIGGSQSSAK AASAFKSSAS VESSGQIKST  50
SLASAGSNGE KATSALSSSA VDASDGRASQ GVGGTSSGSS DTTSQANEGN  100
SAASVTSASA NSASATNTSE GQTPVNEAVS NDASSADVST ASEFDAAMAD  150
STVSVINVQS DFVMDVSGDR QSYAYRPNLI INGNNHTIDF QKKYFEADPT  200
SSQNESFTIN DLNMYGYSWW GPVTIKGSKP KDGIDHSVVF NNVTYTGAQL  250
MYGIYTKAFI KGNTKIQSVG SYVSPLDGST QTTQGLGNQQ NFQISYLEVL  300
PGATYTGTTT GGTNVEVYDG GSFIVDKGAT VNLQRTDASK SNERGTNALI  350
DTQGGNVEFK DGSTVILNKN ALVKDGFAPI YIEDGGNLTV DKNATVSITG  400
ATGNIPVRID GTGTVNLNEG SHMTITQNGA PKLGYGFINI KGTGGFFVAS  450
GSTLDLNVTG TGTKSVNAIN VANDGQLSFA QDATANLTID GGTGEAHLLK  500
VGDDANINIY MPKSVLFKIT DNDDADSSLF KVSGTGTLTG QYVKIIPDDG  550
NAYGPYKSAI YTLKGNGSSS DTATVEGETA EDEQSGKALA DTFATDKSLE  600
FVSASDNFIK VNPVTDETTT LTGKTTAGAY VTISGLKGIP EGSLTANSYD  650
STKYLVQADK DGNWSYELPT GVSLPANASF EVISSAGFIV KTATVVINDA  700
ETPKQASSAA GSLINANSAA DVTASQAKAT SAAASDAASY ASEAQSIAGS  750
HADNMEIKSL ASDAEKQSQI ALAASKSAAA SSSAAASAAI VASSAASEAS  800
SAAAAVSNAD ASANSAAAAY DSYASEASAA SAANDSSGYA TASFAASSAA  850
AAMSAALSTA QVAAKVAVSD AAAAGSAAAV ASAAQSDSKN KQATAATARS  900
QALDDLNKIK SLTDYASGAS SSASEAGQAS TATSAYASAA SSSASEAGSY  950
AHQAGSSASD AVGQSGSAAQ HASTAASAAS SYPKDSGIQS LASQAASEAA  1000
KASSNASAAT SAAAVGFSAA SDASEQAKTA ASADVVASSA ASTANSNASA  1050
AASATKAGDS KAAAGFSSAA SAAASSAKGA EAVASEAASA AASDDSVASS  1100
AASAAAGFDK AASAAEGAAS SAASAAASSA AAQGTRGGAS SSASEAGQAS  1150
TATSVYASAA SSSASEAGSY AHQAGSSASE ATGHASSATS QASAASSAAS  1200
RYPSDSGIQS DVSIASSAAS TASSAASAAQ SEASTASSAA SHASEQASIA  1250
SSEDVVSSSA ASVASSAASA ASSAAKAGNS SAAGIYSHAA SAAASSAKSA  1300
ESQASSAASA AASDDSVASS AASAALSDDA KASSAADVAS SATTAAISSA  1350
TSLADQSATG STAGSHILPS TGGETTGSIP SGQTPTQTKP TQTKPTQTKP  1400
TQAGQTTQTG SLPQTDHAGR HMLPQTGDDA ESGTSVLGLL IVSLMGLFGL  1450
AGTRHQKDNK PSK  1463
```

Fig. 65. Nucleotide sequence containing the *L. rhamnosus* strain HN001 aromatic extracellular matrix binding protein AM4 showing ATG initiation and translation stop codons (boxed)

```
CTGCTTAATG GTCACCCATT CCTTGTCAAG CAGAAAACTA ATGATTTCGT AGTGCTTGAG    60
CAGGCTACTT TCCAATAGTT CTTCCATAAA CTTACCTCCC CAAGTAGGTT GTTACTATCA   120
AAACTTGCCT AACGTTAGGC AAGCTTTGAA CTAGAACCAA TCATTGATTT ATTTATACTA   180
ATGACATATT GCATAAGCAT TGCTTGGTTC ACCATAAATT ATAAAGTGAT AATGCTTGTT   240
GTTTCAATTA TTAAGAACTC GCCTTTCAAA ATGTAATAAT TTATATCAAA TATTTTGAGA   300
ATGGGTAGGG TTAACTTAAT TGTTTGCTGT TTTGGGTTCA ATAAAAGGGA GGCATGTTGA   360
AGTGAAAAAG GGGAGACTGA TATTACTATT AGCCACGGGA CTGATTTCAA TTGGTCTTTG   420
GGATTCAAGC GGTGTCGTAT TGGCAGCGAA TAAGCCCCAG GCTGGTGATA TCCATTTGGG   480
TGGTGCCGAT GGTTCGAGCT ATAGGAAGCT TATAAATAGC ATCACATTCC AATATAGCAA   540
CGACGCCGTG GTATATGACG AAGGTACGGA TACCTTCAAA ATTCCAATTC GGTTCGGCTC   600
GCTTGAATCA GATGGCTTGG ATCGGTATTT GGAGTTTGGG TATTCGTTTA ACGATGCCTT   660
ACAAGGAAAA ATCAAGCGGG TTGTGATTTC ACCTGATGGG CTGGTCCCAG CGGTTATTAC   720
AAGTCTTAAC AAGAACAGAG AATTTGCACG GCGCTGGGAT GGTAGTGATG GTAAAAGCGT   780
TAGTCATCAA CTAGGTGGAC GAGCAGATGC CGTCATCTAC ATGCAGGCGC ATAAGATT AT   840
G CCCGAGGAT TGGATTGCTG TTCGGATGGA AACCAATCGG ATTGAAGGGA ACACCCTAT   900
TCATCCAGCA TTTCGATCCA CTCGCATTCT TGAGTACAAC GATTTTGGTC CTGCACTCAA   960
CGCCAAACTT TTAGAAGCCA TGAAGAAAAA GGCGATTGAT GACACGGCCA AGGATCCTAA  1020
ACCGGTTCAA GAAGAAGTTA AGAAAAAGT CGACCCAATC ACGGTTGACG AGGACTTTGA  1080
CAAGCTCATT CAGGAAATCG TTTTAAACGC GCATAAGGAA CAGGCTAAAC GAGATATTGA  1140
TGCCGAAGCC GCCAAAGTCA GCGCTGAAAT TGAGCAGGAT CCGACTTTAA CGGCAACGGA  1200
AAAGGCAAAG CAAAAAGATG GCGTTGCAGC CGAAGCAACC AAGGCCAAGG CGGCAATCGA  1260
CCAAGCGCAA ACCGAAACAG GGGTTCAGCA GGCGCGAGAT GCCGGCATTG CAGCAATCGA  1320
TGCCCAACAT CAGCCTGGAA CCGGACTCAA CGTGCGCCGA GAAGAAGCTA AGCAGGCGAT  1380
TGATGCCGAA GCGGCTAAAG TGACTGCTGA GATTGAGCAG GATTCAACCT TAGCTACTAG  1440
CGAAAAAGCG GCCCAAAAGC AAGGAGTTGC TGATGAAGCC GCGAAAGCCA AGACGGCGAT  1500
TGATCAGGCC CAAACGATTG AAGCCATCGA TAAAGCTAAA GATGATGGGA TTAAAGCAAT  1560
TGATGCCCAA CACAAGCAAG GCGCTGACTT CGATACGCGT AAAGCTCAAG CTAAAGACGC  1620
AATTGATGCC GAAGCGGCCA AGTCAAGGA TGCTATTGAT CAAGACCCGA CTCTGACGGC  1680
CAAAGACAAG ACGGCCCAGA AGCAAGGCGT TGGTGATGAA GCGACCAAAG CTAAGACTGC  1740
CATTGATCAA GCGAAGACCA TTGATGGGGT GATCCAAGCG AAAGATGATG GCATCAAGGC  1800
AATTGATGCC CAACATCAGG CAGGTACCGA TTTGGCGACC CGCAAAGATA GTGCTAAACA  1860
AGCGATCGAT GCCGAAGCGG CCAAAATAAC CGATGCCATC AACCAAGATG ACACGCTAAC  1920
CAGTACCGAA AAGGACGCCC AGAAGCAGGC AGTAGCTGAC GAAGCGGCTA AGCCAAAGC   1980
```

```
AGCGATTGAC CAGGCTCAAA ACGCAGATGC CATTCTTCAG GCCCAAGCTG ATGGGATTAA 2040
AGCCATTGAT GCGAAACATC AAATTGGTGC AGATTTAGAT ACCCAGAAAA CCAAGGCTAA 2100
GCAGGCAATT GACAAGGAAG CCGCCAAAGT TTTAACGGCA ATTGAGCAAG ATCCGACTTT 2160
GACCAGTGCT GAAAAAAAGG CGCAAAAGCA AGGCGTTGCC GATGAAACTG CTAAAGCCAA 2220
GACCGCAATT GATTCGGCGC GGAATGCTGA TGAAATCGCC AAAGCGCAAG CAGATGGGAT 2280
TAAAGCCATC GATGCGCAAC ATCGGCTGGG AATGGATTTA GCTAAGCGTA AAACTGATGC 2340
ACAAGCGGCC ATTGACGCTG AAGCTGCCAA AGTTGGCGAA GCGATTGATC AAGATCCTAC 2400
TTTAACGAGC CAAGAAAAGG CGGCCCAAAA GCAGACCTTT GCTGCTGAAG CAACCAAGGC 2460
TAAAGATACC ATCGCCAAAG CGCAGGATGC CGATGGTGTT ATTCAGGCTG AAAAAGCAGG 2520
CATTCAAGCC ATTGACGATG GCATCAATC AGGTGCACTT TTAGATACGC GCAAAGTTGA 2580
TGCTAAAAAA GCCATTGATG CCGAAGCTGC TAAAATTAAT GACGCCATTG ACCAAGATGT 2640
CACGTTAACC AGCGCTGAGA AAGCCACTCA GAAGCAAAAA GTTACGGATG AAGCAGTCAA 2700
AGCCAAGACA GCGATTGACG CAGCTAAAAA TGCGGACACC GTTGATCAGG CTAAAGCATC 2760
AGGCATCCAA GCCATTGATG CCGTCCATCA AAGCGGCACG CTTTTAGACA CTCGCAAACA 2820
AGATGCCAAA AAGGCGATTG ATGCGGAAGC AGTTAAAGTC ATTGCAGCTA TTGGCCAAGA 2880
TGTGACCTTG ACGCAAGCGG AAAAACTAAC GCAACAGCAA GCAGTCGCTG ATGCAGCAAC 2940
GCAAGCTAAG GCTGCTATTG ATGCTGCCAA GAATGCCGAT GCGGTGGACC AAGCCAAAGC 3000
GGATGGTATC AAGGCGATTG ATGCCCAACA CCAAGCCGGG TTGGCGTTGA ACGAACGCAA 3060
AGAAGCAGCC AAAAAGCTAA TTGCGGAAAC CGCTGATAAG GTGCAGGCTG CGATTGGTCA 3120
GGATGTGACG CTGACTGCGA CCCAGAAAGC AGTGCAAAGA CAGGCGATTA CCGTGGAAGT 3180
CACTAAAGCC AATCAAGCCA TTGATGCGGC TGGCAATGCT GACGCGGTCG ATCAAGCTAA 3240
AAATGCGGGA GTTAAAGCAA TTTATGACCA GCATCAATCC GGTCAGGCAC TCGCAGATCG 3300
GAAGCGTGAT GCCAAACAGG CGATTGATGC CGAGGCGGCA AAAGAAACAG CTGCCATTGA 3360
TCAGGATGCA ACTTTAACCG CGAATGAAAA GGCAAGCCAA AAACAGGCGG TTGCCGATGA 3420
AGCGACTAAA GCCAAAGAAG CGATTGATGC GGCTAAGCAG GCTGATGCAG TCGACCAGGC 3480
CAAGAATGAC GGGATCAGAG CGATTGACGC CAACATCAC GCTGGCCAAG CAGTTGCCGA 3540
TCGTAAAGCC GCTGCTAAGC AAGCCATTGA TGCCGAAGCG GCTAAAGTAA CGGGCAACAT 3600
TGATCAAGAT GAAACCCTCA CAGCGACAGA AAAAGCGGCG CAAAAACAGG CAGTTGCAAC 3660
CGAAGCCGAT AACGCGAAGC AAGCGATCGA CAAAGGGCAA AATGCTGACG CCGTCGACAA 3720
AGCTAAAACA GGCGGCATCA AGCGATTGA CGCTCAGCAC CAGTCTGGGC AGGCAATTAA 3780
AGCGCGCCAA AATGACGCCA AGCAGGCTAT TGATGCTGAA GCCGCAAAAG TAACCAAAGC 3840
GATTGACCAA GATCCAACTT TAACCGCCGC TGAAAAAAAG GCACAGAAGC AAGCAGTCAC 3900
AGATGCGGAA ACTAAAGCTA AGCTGCTAT TGATGCTACG TTAGTGGCCG ATGCGATTGA 3960
CCAAGCTCTG GCTGACGGGA TTAAAACCAT CGATGCCCAA TACCAAACTG GTATAGCATT 4020
GGATAAGCAA AAGGCGGCGG CCAAACAAAC AATTGATGCC GAAGCAGCCA AGGTTAGTGA 4080
AGCAATTGAT CAGGATGTCA CTTTGACAGC CGACCAAAAG GCTACACAAA AGCAGGCAGT 4140
GGCAGATGAA GCAACGAAAG CAAAAGCGGC CATTGACCAA GCCTCTGACG CCGATGCGGT 4200
GATTCAAGCA ACAATTGATG GTATTGAAGC TATTGACGCG CAACACCAGT CCGCAACGGC 4260
```

```
ACTTGACAAG CAAAAGCAGC AAGCAAAACA GGCCATTGAT GCTGAAGCGG CCAAAGTAAG 4320
TAAGGCGATC GATCAAGATG TGACGTTAAC GGCAACGCAA AAAGCTGACC AGAAGCAGGC 4380
TGTGATCGCT GAAGCAGACA AGCCAAAAA GCTTATCGAT GCAGCTGGCA ATGCTGATGG 4440
TATCAAGCAA GCTGAAAGTG ATGGGATCAA AGCAATCGAC GCTCAGCATC AATCCAGTCA 4500
GGCACTCGCA GATCGGAAGC GTGATGCTAA AACTGCCATT GATGCCGAAG CGGCAAAAGA 4560
AACAGCTGCT ATTGATCACG ATGCCACCTT AACCGCGAAT GAAAAGGCAA GCCAGAAACA 4620
GGCGGTTACG GATGAAGCAA CTAAAGCCAA AAAGCGATT GATGCGGCTA AGCAGGCTGA 4680
TGCAGTCGAC CAGGCCAAGA CTGACGGGAT CAAAGCGATT GACGCCCAAC ATCACTCCGG 4740
GCAAGCTCTT GACGATCGTA AGCCGATGC CAAGCAGGTC ATTGATGCTG AAGCAGCCAA 4800
GGTGACGGCA GCGATTGATC AGGATAACAC GTTGACCAAA GCCCAAAAAG CTGCCCAGAA 4860
ACAAGGGGTT GCGACAGAAG CCGACAAAGC TAAGCAAGCC ATTGATGCTG CCGGGGATGC 4920
CGATGCTGTA GATCAAGCAA AGACAGCCGG GATTCAAGCC ATCGATGCTC AGCACAAAGC 4980
CGGTAAAACC ATTGATAGCC GTCATGATGA CGCTAAGCAA GCGATTGATG AAGAAGCGGC 5040
TAAGGTGATT AAAGCGATTG ACCAGGATCC AACTCTGACC GCTGCCCAAA AAGAAGCACA 5100
AAAGCAAGCG GTAGCAACTG AAGCCGATAA AGCTAAAAAA GCAATTGACG CTGCAGGCGA 5160
TGCGGATGCT GTAGATCAGG CAAAACAGC CGGCATCAAG GCTATCGATG AGCAACACAA 5220
GTCAGGACAA ACAGTTGATG CACGAAAAGA AGATGCCAAA AAGGCCATTG ATGCTGAAGC 5280
CGGTAAAGTT ACTGATGCAA TTGATCACGA CGCCACTTTG ACGGCTGCTC AAAAAGAAGC 5340
GCAGAAGCAG GCAGTTGCTG ATGAGGCTGA TAAAGCTAAA AAAGCGATTG ATGCAGCTGG 5400
AAATGCGGAT GCTATTGATC AGGCAAAATC TGCTGGTATC AAGGCAATTG ACGAACAACA 5460
CAAGTCAGGA CAAAGCATCG ATACTCGTAA AGATGACGCT AAGAAAGCTA TTGATGGAGA 5520
AGTTGCTAAG ATAACTGATG CGATCGATCA TGACCCAACA CTGACCGATG CTGAAAAGGC 5580
AACACAAAAG CAGGCCGTCA TCGCTGAAGC TGACAAGGCC AAGAAGGCAA TTGATGCAGC 5640
CGGTGATGCT GATGCCGTTG ACCAGGCACA AAAGGCTGGC ATCAAGGCGA TCGACCAGCA 5700
ACACAAATCC GGGCAAGCAC TAGCAATCCG GAAAGATGCT GCTAAGAAAG CCATTGATGA 5760
AGAAGCTGCT AAAGTAAGCG AAGCCATTGA TCATGATGTA ACGTTGACGG ACAGCGAAAA 5820
GGGCACTCAG AAGCAAGCTG TTGCTGACGA GGCCAAGAAA GCTAAGCAGG CGATTGATAC 5880
TGCCGACAAT GCTGATGGCG TTGATCAAGC AGTGACCAAA GGCATTCAGA TCATTGACGC 5940
GCAGCACCAG TCCGGCCAAG CGCTCACCGA TCGTAAGGCT GCTGCGAAAA AAGCCATTGA 6000
TGCCGAAGCT GCAAAGGTAG CCAAGCTAT TGAGCAGGAT CCAACACTGA CGGCAACAGA 6060
AAAGAAGCGT CAAAAACAAG CCGTTGCAGA CGAAGCAACA AAGGCCAAAG CGGCGATTGA 6120
TACTGCTGCT AATGCTTCAG CGGTTGACCA AGCAAAAAAT GCCGGTATTA AGGCCATTGA 6180
TGCTCAACAC GTCTCTGGTA AAGCTTTTGA CTTAAGCAAG GACGAAGCCA AGAAAGCGAT 6240
TGATGCTGAA GCTACCAAAG TTCAAGGTGA AATTGATCAG GACCCGACTC TGACCGCTAC 6300
TGCCAAGAAA CAGCAAAAAG AAGCAGTGCC GACAGAAGCC GGTAAAGCAA AACAGGCATT 6360
TGATCAGGCT AAAAATATCG AGGAGGTACG ACCGCCAAAG ACGAAGGCAT CAAAGCGATT 6420
GATGCGCAAC ATCAGTCAGG ACAAGCAGTT GCACACG[TAA] AGACGATGCA AAGAAAGCAA 6480
TCGACGACGA AGCTGCTAAA GTGACCGAAG CAATTGATCA TGATTCGTCA TTGACTGATG 6540
```

```
CTGAAAAGAA GGCTCAGAAA CAAGGCGTTG TAACAGAAGC TGACAAAGCG AAGAAAGCGA 6600
TTGATGCAGC TGGCAGTGCC GATGCAGTCG ATCAGGCCAA AGATGCAGGC ATCAAGGCCA 6660
TCGACGCGCA ACATCAGTCA GGACAAGCAG TTGCAACACG TAAAGACGAT GCAAAGAAAG 6720
CGATTGACGA CGAAGCTGCT AAAGTCATCA AGGCAATTGA TCAAGATCCC AACATTGACT 6780
GACGCAGAAA AAACGGCGCA AAAGCAAGCA GTTGCAACAG AAGCTGACAA AGCGAAAAAA 6840
GCCATTGATG CGGCAAAAGG TGCCGATGCA GTAGACAAAG CCAAAGCAGC TGGTATCAAG 6900
GCAATTGATG CCCAGCACCG CTCCGGTCAA ACCATCGCGG CGCAAAAAGA TGCGGCCAAA 6960
AAGGCAATTG ACGACGAAGC TGCTAAAGTC ATCAAGGCAA TTGATCAAGA TCCAACATTG 7020
ACTGATGCAG AAAAGGCAGC GCAAAAGCAA GCAGTTGCCG CAGAAGCTGA TAAAGCAAAG 7080
AAAGCGATTG ACGCAGCTGG TAACGCTGAT GCGGTGAACC AAGCCAAAGT AGCTGGCATT 7140
AAGGCAATTA ACGACCAACA TCGTGCCGGC AAGGGACAAA AGGTCACCAA AGCAACACCT 7200
CTGCCAACGA CTAAGGCACC TGAGACGCCT GCAGCACCTA AAACAAAAGT TATCACCTCA 7260
TCAGAAGGCA ACCTTCCGAA AACAGGGGAG CAACAATCTC TGTGGATGGT GGTCCTAGGC 7320
GCTTTGTTGA GTCTGTTCTC AGGATTGTGG TTCGCCAAAA AGAAAGCGTC ACATTAGGCG 7380
TTGAGATCAA GATTCTTAAG CTCAAAAAGT TGCAGTTATG AATGGTAGGG AAACCTCATC 7440
ATAGAAAGCT GATTTTCGG AAACTGACAG CCGGCAAGTG AGACGTTTTA TCTCATTTGT 7500
CGGCTGTTTT TCTGGCTATA CCTGTTGATG ATTTTTAAAT ATTGATTCA TTTTTAAATT 7560
CAGCGGTCCA GTTGATTGAC ATGGTATAGC CCAACCGCTA CGCTTAAAGC ATGACAAAGA 7620
AGGGTGTGAG CTTATGGCA                                                7639
```

Fig. 66. The amino acid sequence of HN001 extracellular matrix binding protein AM4

```
MQAHKIMPED WIAVRMETNR IEGKHPIHPA FRSTRILEYN DFGPALNAKL   50
LEAMKKKAID DTAKDPKPVQ EEVKEKVDPI TVDEDFDKLI QEIVLNAHKE  100
QAKRDIDAEA AKVSAEIEQD PTLTATEKAK QKDGVAAEAT KAKAAIDQAQ  150
TETGVQQARD AGIAAIDAQH QPGTGLNVRR EEAKQAIDAE AAKVTAEIEQ  200
DSTLATSEKA AQKQGVADEA AKAKTAIDQA QTIEAIDKAK DDGIKAIDAQ  250
HKQGADFDTR KAQAKDAIDA EAAKVKDAID QDPTLTAKDK TAQKQGVGDE  300
ATKAKTAIDQ AKTIDGVIQA KDDGIKAIDA QHQAGTDLAT RKDSAKQAID  350
AEAAKITDAI NQDDTLTSTE KDAQKQAVAD EAAKAKAAID QAQNADAILQ  400
AQADGIKAID AKHQIGADLD TQKTKAKQAI DKEAAKVLTA IEQDPTLTSA  450
EKKAQKQGVA DETAKAKTAI DSARNADEIA KAQADGIKAI DAQHRLGMDL  500
AKRKTDAQAA IDAEAAKVGE AIDQDPTLTS QEKAAQKQTF AAEATKAKDT  550
IAKAQDADGV IQAEKAGIQA IDDGHQSGAL LDTRKVDAKK AIDAEAAKIN  600
DAIDQDVTLT SAEKATQKQK VTDEAVKAKT AIDAAKNADT VDQAKASGIQ  650
AIDAVHQSGT LLDTRKQDAK KAIDAEAVKV IAAIGQDVTL TQAEKLTQQQ  700
AVADAATQAK AAIDAAKNAD AVDQAKADGI KAIDAQHQAG LALNERKEAA  750
KKLIAETADK VQAAIGQDVT LTATQKAVQR QAITVEVTKA NQAIDAAGNA  800
DAVDQAKNAG VKAIYDQHQS GQALADRKRD AKQAIDAEAA KETAAIDQDA  850
TLTANEKASQ KQAVADEATK AKEAIDAAKQ ADAVDQAKND GIRAIDAQHH  900
AGQAVADRKA AAKQAIDAEA AKVTGNIDQD ETLTATEKAA QKQAVATEAD  950
NAKQAIDKGQ NADAVDKAKT GGIKAIDAQH QSGQAIKARQ NDAKQAIDAE 1000
AAKVTKAIDQ DPTLTAAEKK AQKQAVTDAE TKAKAAIDAT LVADAIDQAL 1050
ADGIKTIDAQ YQTGIALDKQ KAAAKQTIDA EAAKVSEAID QDVTLTADQK 1100
ATQKQAVADE ATKAKAAIDQ ASDADAVIQA TIDGIEAIDA QHQSATALDK 1150
QKQQAKQAID AEAAKVSKAI DQDVTLTATQ KADQKQAVIA EADKAKKLID 1200
AAGNADGIKQ AESDGIKAID AQHQSSQALA DRKRDAKTAI DAEAAKETAA 1250
IDHDATLTAN EKASQKQAVT DEATKAKKAI DAAKQADAVD QAKTDGIKAI 1300
DAQHHSGQAL DDRKADAKQV IDAEAAKVTA AIDQDNTLTK AQKAAQKQGV 1350
ATEADKAKQA IDAAGDADAV DQAKTAGIQA IDAQHKAGKT IDSRHDDAKQ 1400
AIDEEAAKVI KAIDQDPTLT AAQKEAQKQA VATEADKAKK AIDAAGDADA 1450
VDQAKTAGIK AIDEQHKSGQ TVDARKEDAK KAIDAEAGKV TDAIDHDATL 1500
TAAQKEAQKQ AVADEADKAK KAIDAAGNAD AIDQAKSAGI KAIDEQHKSG 1550
QSIDTRKDDA KKAIDGEVAK ITDAIDHDPT LTDAEKATQK QAVIAEADKA 1600
KKAIDAAGDA DAVDQAQKAG IKAIDQQHKS GQALAIRKDA AKKAIDEEAA 1650
KVSEAIDHDV TLTDSEKGTQ KQAVADEAKK AKQAIDTADN ADGVDQAVTK 1700
GIQIIDAQHQ SGQALTDRKA AAKKAIDAEA AKVGQAIEQD PTLTATEKKR 1750
QKQAVADEAT KAKAAIDTAA NASAVDQAKN AGIKAIDAQH VSGKAFDLSK 1800
```

```
DEAKKAIDAE ATKVQGEIDQ DPTLTATAKK QQKEAVPTEA GKAKQAFDQA    1850
KNIEEVRPPK TKASKRLMRN ISQDKQLHT    1879
```

Fig. 67. Nucleotide sequence containing the L. rhamnosus strain HN001 aromatic high-molecular-weight adhesion protein AL7 showing ATG initiation and translation stop codons (boxed)

```
GATTCAGCAG CAAGCACGAG TGATGCAACC GATTCGAAAT CGCTAGCGAC AGATTCAGCA    60
GCAGTCAAAC CGCAAACGGT GACCCAAGAA GACCGCTCAC TTGCATCCGC AGCTGTTCAG   120
ACAACTTCGG CCGCAGCATC ATCGGCGGCT TCATCTGCAT CGTCACAAGC ATCCTTAGCA   180
GCACAATCGG CAACAACAAC TCAGGTCAAC ACGCAAGCTC CGGCCAATGC AACAGCTGCT   240
GAAAATACGC AGACCATTGG CGACTATACC TACAGTCTTG ATACGGCAAA CGGTACAGCA   300
ACGGTTACCG GCCGCGCCAA CGCCAATGTC ACCGATATTA ACATTGGCGC GTCTGTTACC   360
TATAATGGCC AAACTTTTAA AGTGACGGCG ATTAACAATG GCGCTTTTGC AACGCTTAAT   420
AATTTGGGTA ATGTTAACGT GGCTGATACT GTCACGTCCA TTGGCGAAAA TGCTTTTGCA   480
TACAGTCAGT TTACGGGCAA CATTACAATT GAAATGCAG AAAGTCTCGG CAAAGCCGCA    540
TTTGCCGGAA TTAAGGCAGG GTCAGTCACG CTGAAGAAGA CGGCTAACAT TTCAGAGCGC   600
GCCTTTTATT TTGCTAACGT GAAAGATATA ACGATTGCAG ACGCTCAGAC TATAGAGGCA   660
CAGGCATTCT TTAGTCTTAC AGCTTCATCT TTAAAAATTG ATGGTCAAGC CGATATTGGC   720
GAGTCTGCTT TTGAATCTGC CAATATTGCT GGGGATGTCA CCGTTAATCG TGCAAAGACG   780
ATCGGAAAAA ATGCATTCGC CACTTTAAAG GCGCATTCGT TGACGTTGGA CAATCTAACG   840
ACGCTTGATG AAGGTGCCTT TGGTGGTGCT GTATTCACTG GTAATCTTAC AATTAATGGC   900
GCAAAAACTA TTGGCAAGTC CGCATTCGCT TATGACAAAG TAACCGGAGA TGTCACGGTG   960
AGCGGCTCAC CTGCCATTGG TGAAATTGCC TTTTATGGGA TTCAGGCGGC GACAATCACG  1020
ATTGATGGCG CCCAAACCAC TTTCGATAAG ACCGCGTTTG GATTTGCCAC GGCGGATCAC  1080
GTAACAGTCA ATGTAGCCAC CCTTGATCAT GAGGCATTTT ATCATCTTTA TACTGACCAA  1140
CTAACCCTTG GTCCTGATGT TCGAGATATT ACAGATGGCG CTTTTCAGTT TATTCAAAAT  1200
ACCAAAAAAA CAGAGAGTAA CGCTGAAAAT GATACTACGG ACGTTCAAAT AGCAGTGTTG  1260
AACCTGCCAG CTAATGTCAA AACAATCAGC GGCTCGGCTT TTTATGGTTC GAAAGTTAAA  1320
ACGATCGCAG TTGCAGAAAA CAGTCAATTG ACAACTCTCG GATTTCAGGC GTTTGCATTT  1380
TCCACTGCTA CGGCGATTAA CTTACCCGAT TCGCTGGAGC AGATTGGTGA TCAGGCGTTT  1440
TATGGCGGGA AGCTTGTGAA AGTAGCGTTT GGACCCAAAT TGCAATCAAT TGGTAATCTG  1500
GCCTTTACTG AATTTGGCCC GTTGGAAAAT GTTGACTTTA CTCGGGCCAC GGCGCTCGAA  1560
ACAATTGGTG ATAGTGCGTT TGCCTACAAT ACGATTAACA ATGCGATCAC GTTACCACCT  1620
AAGCTATTAA CGATCGGAAA TGCGGCCTTT GTCGGGAATA AAATTCCAAA ACTGGTTCTG  1680
GATGATCGGT TAAAGACAAT CGGTGACACT GCTTTTGGCT ATAACCAGAT CCAGGACGCA  1740
CTCGATGTTC CTGACAGCGT GACCGACATC GGTAAGTATG CATTTGTTTA CAACTCTATC  1800
AGTAATTTAA CGTTAGGAAA TGGACTGAAA ACGATTGGCC AGGAAGCATT TGAAGCCAAT  1860
GTTATTTTAA ATGCGCAAAC GATACCAAGC AGTGTTACGA GTATTGGCGC CAAGGCATTT  1920
AAGGCTAATT TGATTCCTAA AGTTGTTGTT GAGGGCACGC CAACCATTGG CAATGATGCT  1980
```

```
TTTTCGAATA ACCGGATCAC TGTGCTGAAA GCAGCGACAG CCAAGCCGAC AACCCCGGAT 2040
GCTTTGGAGC AGAATGCCGA TGCCTATACA GACTCGGCGC ACGTAAGTCT AAGTGATTTC 2100
TTTGATGTGG CCATTTCCGG AGTGACCCAC CAAAACATCG TTGTTTCAAA CATCAAAGGA 2160
GTTAATGGCG CTACGGTAAC TTTTGATACG GCAAGTAAGT CGTTTAAA AT G CCAGCTAAG 2220
ACGCAGGGAT TTAATTTCGA TTGGTCTTTG AAAGGGCAAG ACGGTGTTAC CTACACAGGC 2280
CACTACATTG TTCATCTCGA TGATCCAGTG ATTCGTGCCC ATGACATCAG CCTATTTACT 2340
GGCCAGGTAT GGAAGCCGGA ACTGAATTTT GAAAACGCGA TTAAAAGCGA CGGTACTGAG 2400
GTTCCATTGA GTGAGTTGAC TTGGTCAGTG ACGGATGAAA AAGGCAATGT GGTAGCATCT 2460
AAGGATAAAA ATGGGGTTGT CACCGGTCAT GTGGATAATA GCCAGCCAAC GACTTATGTG 2520
GTCACCTATA CCTATGGTGC AGAAAGCGGT TCTGCTAAAA TCAATTACAA GCAACGGTTA 2580
GCGGCTTCAT ATGCTTGAC TGGTACTCAG ACCGTCACCG CAACAGGAAG TCCGATTACC 2640
GTCGATGTCT CCCAATTTGC ACTGAGTTTG GGTGACGGTT TTGATGCGGG GAAATTAGAA 2700
TTAAGTGATC TTAATTTCTT TGATGCCGAT GGTAAGCCGG TAGCCGCAGA TGCTCTGATT 2760
AAAACTGGCG TCTACAGTGT GGAATTATCA GAAGCTGCGT GGGCACGGAT CGCCAAATTA 2820
ACAAATGATG AAGGCCAGTC TGCTGCGGGT TATGATTTTA CCGGAACAAG TACGGCACAA 2880
TTAATCATCG GTCTAACGGC TACAGGTCAT TTGAGCGATA GCGGTTTTGT TTATGACGGC 2940
AAAACAACAG CCAGTCAGTC TAAAGATTTG GCGGTCACGG TGACATTGAG TGATGGCACT 3000
CAGAAAGAAA TGAACCTGAC CTCAGAAGAC TTCTCATTAG TTGAAAAAGA TTCAGCTAAC 3060
GTTGGCACGT ACCATTATTT GTTAAACAGC GTTGGTTTCG CTCGTTTACA AGCGTTACTA 3120
GGTGATACCG TGACGATTGA TCAAACTGCC ATCAATCAAA ATTCCGGAAA AATCACCATT 3180
ACGCCAGCAC CGGCTACAGT TAATAGTAAT AGTACGGATT TTGAATATGA TGGCAAAACC 3240
AAGGCCAGTG AGGCTAAAGG TATTCAAGCT ACAGTCAAAC TAGGCGAAAC TGGAAAAACG 3300
ATTGACCTGA CGTCAGCTGA CATTGTTGTT GAGAATGATG GTGTAGATGC AGGCAAGTAC 3360
AGCTATGAGC TGAGTGACGC TGGTAAAGCT AAATTGCAAG CCGCAACTGG AAATAACTAT 3420
CAGTTGACTG CAGACGATCT GGCTAAAGTC ACGGGAGCTA TCACGATTAC GCCAGCTACC 3480
ACCTCAGTTG ATAGCAATGA CGTTTCATTT GAATACGATG GTAAGACCAA GGCCAGTGAA 3540
GCTGCAGGTA TTCAAGCCAC AATCAAGCTC GACACTGGTA AAGTTGTAGA CTTGACCGCG 3600
GCCGATATTA TCGTTACCAA TGATGACGTA AACGCTGGTC AGTACAGCTA TCAACTAAGT 3660
GATGCTGGTA AGGCTAAGTT ACAAGCCGCA ACTGGAAATA ACTATCAGTT GACTGCAGAC 3720
GATTTGGCCA AGGTTGCTGG AACTATCACG ATCACGCCAG CCGTTACCAC AGTTGATAGT 3780
AGTGACGTAT CATTCGAATA TGACGGCAAG ACCAAGGCCA GTGAAGCCAA GGGTATTCAA 3840
GCTACAATCA AGCTGGACAC TGGTAAAGTT GTAGACTTGA CCGCGGCCGA TATTATCGTT 3900
ACCAACGATG ACGTAAACGC TGGTCAGTAC AGCTATCAAC TAAGTGATGC TGGTAAGGCT 3960
AAGTTACAAG CCGCAACCGG AAATAACTAC CAACTCACGG CAGACGATTT AGCTAAAGTC 4020
ATGGGAACCA TCACGATCAC GCCAGCCGCT GTCACAGCAG ACAGCAATGA CCTTTCGTTC 4080
GAATATGATG GTAAAACGAA AGCCAGTGAA GCCAAAGGTA TTCAAGCCAT GGTAAAACTA 4140
GGCGAGACTG AAAAAACGGT TGACCTGACG TCAGCTGACA TTGTTGTTGC CAACGATGAC 4200
GTAAACGCCG GTCAGTACAG CTATCAGCTA AGTGATGCTG GTAAGGCTAA GCTGCAAGCT 4260
```

```
GCAACTGGAA ATAACTATCA GTTGACTGCA GACGGTTTGG CTAAGGTTGC TGGAACAATC 4320
ACAATCACGC CAGCTACCAC TACAGCGGAT AGCAATGACG TTTCATTTGA ATACGATGGT 4380
AAGACCAAGG CCAGTGAAGC CAAGGGTATT CAAGCCACAA TCAAATTAGG CGAAATTGAA 4440
AAAACGGTTG ACCTATCGTC AGCTGACATT ATCGTTGCCA ATGACGGAGT AATCGTTGGC 4500
AAATACACTT ACAGTCTGAG CGACAGCGGC AAATCTAAAT TACAGGCGGC AACAGGAAGT 4560
AATTATCAGT TAACGACAGA AGTTTTGGAT AAGGTTTCAG GAAGCATTAC AATCACCCCT 4620
GCTGGAGCAA TCGCAACAGG CAAGGATGCT CACTTTGAGT ACGATGGAAA AACGAAAGCC 4680
AGTGAAGCTA AAGGCATTCA AGCGATTTTG ACCATTGACG GGACTGAAAA GACTGTTGAC 4740
CTGACCGCGG CTGACATTGT TGTTGCGGAG GATGGCGTAG ATGCAGGCAA GTACAGTTAT 4800
CGACTGAGCG ATGCTGGTAA ATCTAAGTTA CAGAGGGAAG CAGGGAGCGA CCATCAGCTA 4860
ACCGCAGACG ACTTGGCTGA AGTCACGGGA ACTATCACGA TCACGCCAGC CATTGCCACA 4920
GCAGATAGTA ATGACGTTTC ATTTGAATAT AATGGCAAGA CCAAGGCCAG TGAAGCTGAA 4980
GGTATTCAAG CCACGGTTAT GCTGGGTGAG TCTGGACAAG TTGTTGCTCT AACATCGGCT 5040
GATGTTGTTG TTGTGAATGA TGGTGTAGAT GCAGGCAAGT ACAGCTATCA GCTGAGTGAT 5100
GCTGGTAAAG CTAAGCTACA AGCCGCAACC GGAAATAACT ACCAGCTCAC GGCAGACGAT 5160
TTAGATAAAG TCACGGGAAC CATCACGATC ACGCCAGCTA CCACCACAGT TGATAGCAAT 5220
GACGTTTCAT TCGAATATGA CGGCAAGACC AAGGCCGGTG AAGCTAAGGG TATTCAAGTT 5280
ACAGTCAAAC TAGGCGAAAC TGAAAAAACG GTTGACCTGA CGTCAGCTGA CATTGTTGTT 5340
GCCAACGATG ACGTAAACGC TGGTCAGTAC AGCTATCAGC TAAGTGATGC TGGTAAGGCT 5400
AAGTTACAAG CCGCAACTGG AAATAACTAC CAGCTAACTG CAGACGATCT GGCTAAAGTC 5460
ACGGGAACCA TCACGATCAC GCCAGCCGTT ACCACAGCAG ATAGCAATGA CGTTTCATTC 5520
GAATATGACG GCAAGACCAA GGCCAGTGAA GCTAAGGGTA TTCAAGTTAT AGTCAAACTA 5580
GGCGAAACTG AAAAAACGGT TGACCTGACG TCAGCTGACA TTGTTGTAGC CAACGATGAT 5640
GTAAACGCTG GTCATTACAG CTATCAGCTA AGTGATGCTG GTAAGGCTAA GTTGCAAGCC 5700
GCAACCGGAA ATAACTATCA ACTAACTGCA GACGATTTGG CCAAGATCAC TGGAACCATC 5760
ACGATTACCC CAGCCGTTGC CACAGCAGAT AGCAATAACG TTTCATTTGA ATATAACGGC 5820
AAGACCAAGG CCAGTGAAGC TCGGGGCATT CAAGCCACAG TCAAACTAGG CGAAAATGGA 5880
AAAACGGTTG CGCTAACCGC GGCTGACATT GTTGTCGTCA ATGACGGGGT CAATGCTGGC 5940
CAGTACGACT ATAAGTTAAG TGCTGCTGGT ATGACAAAGC TACGCCAGGC AACAGGAACT 6000
AATTATCAAT TCAAAAAGGA GGACTTAACC AAACTTGGCG GCACGGTCAC GATCACGCCA 6060
GCTACGGCAT TAGCTGATCT GAATGATGTT TCATTTAGTT ATGATGGACA AACTAAGGCG 6120
AGTCAGGCAC ACGACTTAAC TGCCAACATC AAACTTGGTA CTAAGGTTGT TTCGGTACAT 6180
CTGAACGCCA CAGACATTCT TGTAACCGAT GATGGTGTGG GCGTAGGTCA GTACCAATAC 6240
AAATTGGATG CTAACGGGAT CGCTAAATTA CGTCAGGCAT CAGGTGATAA TTACCAATTT 6300
GATGCCAAAG TCTTGGCGGG ATTGACTGGT ACGATTACAA TCAAACCGGT TACCGGTGCG 6360
GTGACAGTTA ATGACACATC TTTTGTTTAT GATGGTCATA CTAAAGCAAG TGCTGCCGCG 6420
GGATTACAGG CAAGTCTTTA CCTGCCGCAA GCCGAGGCCA AGCAACGAT ACAACTGACA 6480
CGGGAAGATA TCCTTGTGAC AAATGACGGC ACAGCAGCAG GTACGTATCG TTATCGGTTG 6540
```

```
AGCCAAACCG GTATCGCCAA GTTACAGAAG GCTGTTGGCA AGAACTACGA GTTAGATCAA 6600
GATGAATTGG CGGGATTGAC CGGCACCATT ACGATTACGC CGCTGACGGT GAATGCCACA 6660
GTTAATCATG GTCAGTTCCA ATACAACGGT GTCACTCGTG CAAGTCAAGC AGGCGGATTA 6720
GCGATAACTG TCCAACTGCC AGAAAAGTCT CAAAAGATCG CCTTGACGAA CACAGATATT 6780
GCAGTTGAAA ACGACAGCGT CAATGTCGGG ACGTACACGT ATCATTTGAC AGCAAGCGGG 6840
CTGGCTAAAT TGGCCGTAGC GATTGGTCCT AATTATCAGG TTACTGATCA AACGTTCAGC 6900
GGCACCATCA CCATTACACC AGCGCCTATA TCTGCAACGC TCAGTGGTCT TCAAAAGAAA 6960
ACTTACGATG CCAGCCAGG CGCTTTGAAT GACGACTATT ATCGGTTAGT TTTGGGTGAC 7020
GGAACTGAAA TTCAGCTTCA AGCCGGCGAT CTGATCTTTG TAGACGGTCA AGCTCCTGTT 7080
AATCCGGGAA GCTATGCGGT AGCTCTCAGC ACATCTGGCC TGCAACGAAT CAAGGCGTCG 7140
TTGCCAAATA ATCTGTTGAA AAATGTTAAC ACGCAGCAGG CTATTTTTGA GATTGTTGCC 7200
TTGCCAAGTC CTGATCCCGG GACCGGAACA ACGCCGGATA CGCCGGATCA TCACTTGCCG 7260
AATACAGGTA CTGGCACCCA ACAGTCCGAG ATTTCACGC ATAATGGAAC GAAACATCGA 7320
CTTCCACAAA CAGGCGATAC CCAGTCACAA ACACTAAGCC TCATGGATT GTTGCTGGCA 7380
ACGATGAGCG GCTTATTCGG ATTAGCTGGC CGGAAACGGA AGCGCACCG TTAAACGTTT 7440
TGTTAGAAAT GTAGTGATTA AAAAGATCCT ATCACGATGA GTTCTGCTCA TGTGGTGGGA 7500
TCTTTTGTTA TGGCAAAAAC TAGGCGCAAA AGCTTACAGT GGTACCGCTG CGCCTTGGGT 7560
TAACCCTGAT TTGATTTTGG CAAAAGCCGG GTCTGTTAGG AAAGCACTGA TGAGTTGCCG 7620
CATATTGATG TTACTATCCT GAATCTCCGG CATGTTTGGC GTAATGCTTG TGCCTGTCAC 7680
AGTAAGATTG TACTGGCTGG CGAGACTGGT GATAGCTTGC TTGGACTGAT ACATGTTGTA 7740
GAGTTTAACG GTTTC                                                 7755
```

Fig. 68. The amino acid sequence of HN001 high-molecular-weight adhesion protein AL7

```
MPAKTQGFNF DWSLKGQDGV TYTGHYIVHL DDPVIRAHDI SLFTGQVWKP    50
ELNFENAIKS DGTEVPLSEL TWSVTDEKGN VVASKDKNGV VTGHVDNSQP   100
TTYVVTYTYG AESGSAKINY KQRLAASYAL TGTQTVTATG SPITVDVSQF   150
ALSLGDGFDA GKLELSDLNF FDADGKPVAA DALIKTGVYS VELSEAAWAR   200
IAKLTNDEGQ SAAGYDFTGT STAQLIIGLT ATGHLSDSGF VYDGKTTASQ   250
SKDLAVTVTL SDGTQKEMNL TSEDFSLVEK DSANVGTYHY LLNSVGFARL   300
QALLGDTVTI DQTAINQNSG KITITPAPAT VNSNSTDFEY DGKTKASEAK   350
GIQATVKLGE TGKTIDLTSA DIVVENDGVD AGKYSYELSD AGKAKLQAAT   400
GNNYQLTADD LAKVTGAITI TPATTSVDSN DVSFEYDGKT KASEAAGIQA   450
TIKLDTGKVV DLTAADIIVT NDDVNAGQYS YQLSDAGKAK LQAATGNNYQ   500
LTADDLAKVA GTITITPAVT TVDSSDVSFE YDGKTKASEA KGIQATIKLD   550
TGKVVDLTAA DIIVTNDDVN AGQYSYQLSD AGKAKLQAAT GNNYQLTADD   600
LAKVMGTITI TPAAVTADSN DLSFEYDGKT KASEAKGIQA MVKLGETEKT   650
VDLTSADIVV ANDDVNAGQY SYQLSDAGKA KLQAATGNNY QLTADGLAKV   700
AGTITITPAT TTADSNDVSF EYDGKTKASE AKGIQATIKL GEIEKTVDLS   750
SADIIVANDG VIVGKYTYSL SDSGKSKLQA ATGSNYQLTT EVLDKVSGSI   800
TITPAGAIAT GKDAHFEYDG KTKASEAKGI QAILTIDGTE KTVDLTAADI   850
VVAEDGVDAG KYSYRLSDAG KSKLQREAGS DHQLTADDLA EVTGTITITP   900
AIATATADSNDV SFEYNGKTKA SEAEGIQATV MLGESGQVVA LTSADVVVVN   950
DGVDAGKYSY QLSDAGKAKL QAATGNNYQL TADDLDKVTG TITITPATTT  1000
VDSNDVSFEY DGKTKAGEAK GIQVTVKLGE TEKTVDLTSA DIVVANDDVN  1050
AGQYSYQLSD AGKAKLQAAT GNNYQLTADD LAKVTGTITI TPAVTTADSN  1100
DVSFEYDGKT KASEAKGIQV IVKLGETEKT VDLTSADIVV ANDDVNAGHY  1150
SYQLSDAGKA KLQAATGNNY QLTADDLAKI TGTITITPAV ATADSNNVSF  1200
EYNGKTKASE ARGIQATVKL GENGKTVALT AADIVVVNDG VNAGQYDYKL  1250
SAAGMTKLRQ ATGTNYQFKK EDLTKLGGTV TITPATALAD LNDVSFSYDG  1300
QTKASQAHDL TANIKLGTKV VSVHLNATDI LVTDDGVGVG QYQYKLDANG  1350
IAKLRQASGD NYQFDAKVLA GLTGTITIKP VTGAVTVNDT SFVYDGHTKA  1400
SAAAGLQASL YLPQAEAKAT IQLTREDILV TNDGTAAGTY RYRLSQTGIA  1450
KLQKAVGKNY ELDQDELAGL TGTITITPLT VNATVNHGQF QYNGVTRASQ  1500
AGGLAITVQL PEKSQKIALT NTDIAVENDS VNVGTYTYHL TASGLAKLAV  1550
AIGPNYQVTD QTFSGTITIT PAPISATLSG LQKKTYDGQP GALNDDYYRL  1600
VLGDGTEIQL QAGDLIFVDG QAPVNPGSYA VALSTSGLQR IKASLPNNLL  1650
KNVNTQQAIF EIVALPSPDP GTGTTPDTPD HHLPNTGTGT QQSEISTHNG  1700
TKHRLPQTGD TQSQTLSLMG LLLATMSGLF GLAGRKRKAH R           1741
```

Fig. 69. Nucleotide sequence containing the L. rhamnosus strain HN001 aromatic PEB1 AJ4 showing ATG initiation and translation stop codons (boxed)

```
GCA ATG ACCA CACAATCCGG CTTCTACCCA CGCTGGCTGG CGCTCACGAG GAGGGACATT  60
AAAATGGCAA AAATGTGGAA ACGCATGCTC CTGCCACTGG TGTTGTTACT ATTGATGATA  120
CCGTTAAGCA GCTGTGGCAA AAGTGTGGCG GATCGTGATA TTTTAGCGAA CGCCAAGGCA  180
ACCAATACGA TTATTTGGGG CGTCAAGGCC GATACCCGTC TGTTTGGCTT GATGAACATT  240
AAAACCGGTA AAATTGAAGG CTTTGATGTT GATATGGCCA AGGCGATTAC CAAGCAGATT  300
TTAGGCAAAA AAGGGAACGC CCAGCTGGTT CAGGTGACCA GTGATACCCG CGTGCCGATG  360
ATTAAAGGTG GGAACCTGGA CGCGGTGATC GCTACCATGA CGATTACCCC GGAGCGCCAA  420
AAGATTCTGG ACTTTTCCGA TGTTTACTTT AATGCCGGGC AAAGTCTTTT AGTTAAAAAA  480
GGCAGTCCGA TTAAGTCAGT GAAGGATTTG AAGAAAGGCA CCAAAGTTAT CGGCGTGCAA  540
GGGTCCAATT CAGTTGATAA TGTTAAAAAA GCTGCTCCCG ACACCACTGT TCTGCAGTTA  600
GCCGATTATG CGCAGGCGTT TACCGCTTTG AAATCAGGCC AAGGTGATGC CTTGACCACT  660
GACAATGGGA TTTTATACGG GATGTCAGAA CAGGATAAGA ACTATATTGT CACCGGGGGC  720
ACCTTCACTA AAGAGCCATA CGGGATTGCG ATTAACAAAG GCCAGAAGCC GTTTGTCAAC  780
GCGGTTAATA AGGCGATCAA ACAACTCAAA CAAAACGGGA CTTATGCAAA GCTAATCAAG  840
AAGTGGTTCG GCGATGTGCC AGGATTCAGT CTTAAGGAGG TGGAA TAA CA TGTGGTCAAT  900
TCTTACCAAT AATTGGAACA CCTTTCTTTC CGGACTTGGT TTCACGTTAG CAGCGAGCAT  960
TTAG                                                                964
```

Fig. 70. The amino acid sequence of HN001 PEB1 AJ4

```
MAKMWKRMLL PLVLLLLMIP LSSCGKSVAD RDILANAKAT NTIIWGVKAD   50
TRLFGLMNIK TGKIEGFDVD MAKAITKQIL GKKGNAQLVQ VTSDTRVPMI  100
KGGNLDAVIA TMTITPERQK ILDFSDVYFN AGQSLLVKKG SPIKSVKDLK  150
KGTKVIGVQG SNSVDNVKKA APDTTVLQLA DYAQAFTALK SGQGDALTTD  200
NGILYGMSEQ DKNYIVTGGT FTKEPYGIAI NKGQKPFVNA VNKAIKQLKQ  250
NGTYAKLIKK WFGDVPGFSL KEVE 274
```

Fig. 72. Nucleotide sequence containing L. rhamnosus strain HN001 Dihydrodipicolinate reductase gene AI3 showing ATG initiation and translation stop codons (boxed)

```
ATGATTCACG TTCTTGTCGC CGGTTTTCGC GGTGCCATGG GTCAAAAAACA GTCAAAATG     60
GTTCAGTCAC AAAAAGATTT CGCATTAAGT GCCGTTTTTG ATCCCAAAGCA ACTGCCGCT   120
GATGCCCAAA AATATGGACT ACCAGCTGAT ACAAAAGTGC TCACGAGCTAT GATCAGCTC   180
AATCCCGACA TTGCCGATGT GTGGGTTGAT TTTACCAATC CCACTGCCGTC GCTGCCAAC   240
ATTGAAGCCG CGATCAAAGC AGGCATTCAC CCAGTCGTTG GCACAAGCGGC ATGACGCAA   300
GCCGATCAAA ACCGCTTAAT CGAACTCGCC CAAGCCCGTC ATATCGGCGGT CTAATCGCC   360
CCAAACTTCG GCCTTTCCGC GGTTCTCTTA ATGAAGTTCG CGCAGGAAGCC GCCGCCTAC   420
TTCCCTGACG CCGAAATTAT CGAGATGCAT CATCAGGACA AGCCGATGCG CCATCAGGT   480
ACCGCCATCG CCACTGCGCA CAAAATCGCC GCCGGACGCA CCCAAAAGCCA TTGTCCACC   540
ATCGACAACG ACGCCCGCGG CCAACGCATT GATGACGTCC CGGTCCACGCC GTCCGCTTA   600
CCAGGTTACA TCGCCCACGA ACAAGTCCTC TTCGGCGGTC CCGGTGAAGCC CTCACCATC   660
CGCCAAGACT CCTTCGATCG CCAAAGCTTC ATGCAAGGGG TCGCCGTTGCC ATTCGCAAG   720
GTTCAGGCAG CGGATCATTT GGTTGTGGGG TTGGAAAATT TCTTGTAG              768
```

Fig. 73. The amino acid sequence of HN001 Dihydrodipicolinate reductase AI3

```
MIHVLVAGFR GAMGQKTVKM VQSQKDFALS AVFDPKATAA DAQKYGLPAD    50
TKVLTSYDQL NPDIADVWVD FTNPTAVAAN IEAAIKAGIH PVVGTSGMTQ   100
ADQNRLIELA QARHIGGLIA PNFGLSAVLL MKFAQEAAAY FPDAEIIEMH   150
HQDKADAPSG TAIATAHKIA AGRTQKPLST IDNDARGQRI DDVPVHAVRL   200
PGYIAHEQVL FGGPGEALTI RQDSFDRQSF MQGVAVAIRK VQAADHLVVG   250
LENFL                                                    255
```

Fig. 74. Nucleotide sequence containing L. rhamnosus strain HN001
Fructose-bisphosphate aldolase gene AM8 showing ATG initiation and
translation stop codons (boxed)

```
ATGTGTTATC AGCGTGACCG TTTCCTTTCA AACCGGTCAG CAAAACCGTC ACGTTCTCAT    60
CATTTTCTCG CCCTTTTCTT TTGTCATTTA TGGTAGAATA CAACAGTTGT GAATTGTATA   120
TTTCGTAGGA GGATATCTAC ATGCCATTAG TTAACGCTGC AGAGCTTGTA AAAGCTGCAC   180
ATAAAGGTCA CTACTGTATC GGTGCCTTCA ACACCAACAA CTTGGAATGG ACTCGTGCCA   240
TTCTCGCCGG CGCTCAAGAA TTGAACGTTC CGGTTATCAT CCAGACTTCC ATGGGTGCTG   300
CTAAGTACAT GGGTGGCTAT GAATTCTGCC AAACCATGAT CGAAGCTGCC GTTAAAGCCA   360
TGGACATCAC CGTTCCTGTT GTGATTCACT TGGACCACGG TAACTATGAA GCAGCCAAGG   420
AAGCTATTGC TGCTGGCTAC AACTCAGTTA TGTTTGACGG CCACGACCTC GACTTTGAAG   480
ATAACTTGGA AAAGACCAAG GAAATCGTTA AGCTGGCCCA CGCCAAGGGC ATTTCCGTTG   540
AAGCTGAAGT TGGTTCCATC GGCGGTGAAG AAGACGGTGT TGTCGGCGAA GGTGAATTAG   600
CTGACGTTGA AGAAGCCAAG ACTTTGGCAG CTACCGGGAT CGACTTCCTG GCAGCCGGCA   660
TTGGTAACAT CCACGGCCAA TATCCAGACA ACTGGAAAGG CCTGCACTTC GACCGCTTAC   720
AAGAATTGAA CGACGCTGTT AAGATGCCGC TCGTTCTCCA CGGTGGTTCC GGTATCCCTC   780
AAGAACAAGT TCAAAAGGCG ATCACCATGG GCATTTCCAA GTTGAACATC AACACCGAAT   840
GCCAACTTGC CTTTGCTAAG GCAACACGTG AATACATCGA AGCTGGTAAG GATCAACAAG   900
GCAAGGGCTT TGACCCTCGT AAGATGCTCA AGCCAGGCAC CGATGCGATC ACCGATACCT   960
TCAAGGAAAT CACCGGCTGG ATTGGCAACA AGCCAGTTAA GATGGTTCCT GAAGCACTTT  1020
AATTTTTTAA TCAAAGACCA TTTAAAGAAC CCACTCGCTG AAATTGCGAG TGGGTTCTTT  1080
TCGTCTCTCG TACTTAAGCT GTTAAGGATA AGCGCTGCCG CTGTGACTGA ATTTAGGATG  1140
ACGTACGCTT AGTCCTCTAC CTCATCCCAT GCTCGGTCTT CATCAGTCAC AGCATCTCTG  1200
AATCCTTGCC AATCAGCGGC AGTGGCAAAT AAATCAGATC GCAGCGGTGT CAGCACA     1257
```

Fig. 75. The amino acid sequence of HN001 Fructose-bisphosphate aldolase
AM8

```
MPLVNAAELV KAAHKGHYCI GAFNTNNLEW TRAILAGAQE LNVPVIIQTS    50
MGAAKYMGGY EFCQTMIEAA VKAMDITVPV VIHLDHGNYE AAKEAIAAGY   100
NSVMFDGHDL DFEDNLEKTK EIVKLAHAKG ISVEAEVGSI GGEEDGVVGE   150
GELADVEEAK TLAATGIDFL AAGIGNIHGQ YPDNWKGLHF DRLQELNDAV   200
KMPLVLHGGS GIPQEQVQKA ITMGISKLNI NTECQLAFAK ATREYIEAGK   250
DQQGKGFDPR KMLKPGTDAI TDTFKEITGW IGNKPVKMVP EAL;         293
```

Fig. 76. Nucleotide sequence containing L. *rhamnosus* strain HN001 dnaK chaperone gene AM9 showing initiation and translation stop codons (boxed)

```
AACTAGTGGA TCCCCCGGGC TGCAGGAAAG CATTGCTGAT CTTAATGAGC AATTGAAAAC      60
CAGCAAGCAT GATGGTGAAC AACTGAAGCA AGAGCGTGAT GCATTCGAAG ACAAGTATTT     120
GCGCGCAGCT GCAGAGATTC AAAACATGAA TGCGCGGTTC GAAAAGAGC  AGCAAAAAAT     180
GTTGAAATAT GACGGCCAGA AGTTAGCCAA GGCGATTTTG CCGGTAGTTG ACAATCTAGA     240
GCGTGCGCTT GCAACCGAAG CCAAAGATGA CAGTGCGGCC TCACTCAAAA AAGGTGTGCA     300
GATGGTTTAC GATCATCTGG AACGCGCCTT GAAGGAAAAT GGCATCACTG CGATTGATGG     360
TGCTGGCGAC AAGTTTGATC CGAATACCCA ACAGGCAGTA CAAACCGTGG CGGCGGACGA     420
CAAACATCCC GCTGACACGG TCGCGCAGGT GTTACAAAAA GGGTATTATC TCAAGGATCG     480
GGTTCTGCGC CCTGCTATGG TCGTTGTCGC TAAATAATTA ATCTGAAATA AAGAAGGTAT     540
AAAAAT ATG A GTAAAGTTAT TGGTATTGAC TTAGGAACCA CCAACTCTGC AGTTGCGGTT     600
TTGGAAGGCA ATCAGCCAAA AATCATCACC AACCCGGAAG GCAATCGCAC CACGCCATCT     660
GTTGTCGCAT TTAAAGATGG TGAAATCCAA GTTGGTGAAG TGGCAAAACG CCAGGCGATC     720
ACTAATCCGG ATACCATCGT GTCAATTAAG CGTCACATGG GCGAAGCTAA CTATAAAGTT     780
AAGGTTGGCG ATAAGAATA  CACCCCGCAA GAAATTTCAG CGATGATTTT ACAGTACATC     840
AAAAAATTTT CTGAAGACTA TCTGGGCGAA CCGGTTAAAG ATGCGGTTAT CACAGTTCCG     900
GTTTACTTTA ATGACAGTGA GCGTCAGGCA ACAAGGATG  CCGGTAAGAT CGCTGGTTTG     960
AATGTTCAAC GGATTATCAA CGAACCAACC GCGTCAGCCT TGGCATATGG TTTGGATAAA    1020
GGCGACAAAG AGAAAAGATT TGGTTTACGA CTTTGTCGAC GGCACATT TG A TGTTTCCAT   1080
CGTGCAGTTA GGTGATGGTG TTTTGACAGT GCTGTCAACC TTTGGCGAAT ATCCATTACT    1140
TTGTGTACGA AGG                                                      1153
```

Fig. 77. The amino acid sequence of HN001 dnaK chaperone AM9

```
MSKVIGIDLG TTNSAVAVLE GNQPKIITNP EGNRTTPSVV AFKDGEIQVG      50
EVAKRQAITN PDTIVSIKRH MGEANYKVKV GDKEYTPQEI SAMILQYIKK     100
FSEDYLGEPV KDAVITVPVY FNDSERQANK DAGKIAGLNV QRIINEPTAS     150
ALAYGLDKGD KEKRFGLRLC RRHI                                 174
```

Fig. 78. Nucleotide sequence containing L. rhamnosus strain HN001 6-phospho-β-galactosidase gene A05 showing translation stop codon (boxed)

```
TGCAAATTGC CACGGATACC CAGACACAAG TCATTGCAGA CGGCGTTGTT ACCAAGTATA    60
CGCCAGCCAA TGCCATGATC GTTGCCACTC ATCGGCACAC AGCCAAACAG TTGCTGGCCG   120
CAGCAGGAAT ACCAGTTGCA CGTGGGGCTA AGTTTACTAA ATGGCCGGAT GCCAAAGCAG   180
CTTTTGAGCA CAGCTTTGCG CATAAAAGTA TTGTGGTGAA ACCCGAGGCA CGCAGCCAAG   240
GCAAAGCGGT TGAGCAGTTT TCGATACCAC CGACTGAAAA GCAGTTTGAC CGAGCCTTTC   300
ATGAAGCCAA TCGCCATCAT GGGGTGCTCA TTGAAATGAT GGCACGCGGC ACGACCTACC   360
ATTTTACCAT CATCGGGCAA CAAGTGCTCA GCGTCTTGGA AACAGCAGCA GCTAATGTTG   420
TAGGCGATGG GCGCAAAGCC ATTAAGGAAT TGATCGCCTT GAAAAATGGT CACCGCGCGA   480
CTTCCCGGCA ATTGCAGCTT GACGCCAGTG CACGGCGTCA GTTAAAGGCT CAAGCGTTAA   540
CACCCGAGAC TGTGCTTCAA CGCGGGCAGC AGGTTTTCTT AACCACTGCC GCGCATCCGC   600
AAACCGGTGG CGATTTGTAT GACGTGACGG ACGAGATTGA TGACAGTTAC AAGCAACTGG   660
CGCTAAAAGC TGCTGCCACG CTTGATTTGC CGGTAGCAGC TGTCGACATT GTGATTGATA   720
ATCTGTATGC ACCGTATGAT CCGGAGGCAG ATGGGCAGGC AATCGTGATT AGCCTCAATC   780
CGGTACCGGA TCTCGCTGTG CCGTTGCATC CGGACATGGG CGAATCACGC GCACTTGCCC   840
CGGCATTGCT AAACTGGCTG TTTGCTGTGA GA TAA GTAAA CGAGGTCATA TTAAAACCGA   900
CCTCAGCATG GTAAATTTGC TCTAAGGTCG GTTGGTTACA CCGTTCATGA TCATGCTTCT   960
GCGCGTTACG GTCACGATGC TGACATTTAG GTGCGGCCAC ACTCCATTAT ATTGGTTAAG  1020
TTGCGCCAAA CGTCTTTAGC GGTTGCTTAG ATAGGTTAAA ACCACTTTTT CTTAGGCTTT  1080
TCTTGCGTGT CATCAAGTGG CGGTAAGGTG ATGTTAGCCT GATTGATGGC AGTGGCTGCC  1140
ACAATAAGTA GCCCTGGCGC GGTATCGGCA GTTTGCGCCG TTTCGTTAGC AACCAATGTA  1200
AATGGCACAT TGGCATCGGT GAGGAGCTTC ATGTAAGGAC CGGTAATGGC ATTATCAAGT  1260
TTGCCGTTGA GTAGGGCTTT ATAGTTGCGG TCATGGAAAT CTTTTAATAA TGGGGCAACC  1320
TGATGCTGTC GTTTGGGATC AGCCAGTTCC TGATTGCTGA TACATAAAGC GACCCGTTCA  1380
CGTAACGAGC CCATGTACTT GCGGCGTTCG TCGGGTTTGG TTTGCGGTGG GCCGTATAGT  1440
GCACTGTTGA GATGTTCCTG CATATTGTCT TCTGCCATGA TGAAAAGCCT CCTTATGATG  1500
GGTTTGATCA AATAACGATT TAACGATCCT TGGTGAACCG TCTTGTTGTG TGAACGCGAG  1560
TCGTAATGTT GAAACCTGAC AACGCGTTGC AATATGACCT CATTGTAACA TGTTCTAGCG  1620
TAAAGAAAGG AATGACGAAA GGGTGTTTAC CAGTAACGAC TTTGCGGTTT TTGCTGCGCC  1680
AACGCTAAGT GCGCGGATGG CCTTGATCCG GCAACAGTTG GATC                   1724
```

Fig. 79. The amino acid sequence of HN001 6-phospho-β-galactosidase A05

| | | | | | |
|---|---|---|---|---|---|
| QVIADGVVTK | YTPANAMIVA | THRHTAKQLL | AAAGIPVARG | AKFTKWPDAK | 50 |
| AAFEHSFAHK | SIVVKPEARS | QGKAVEQFSI | PPTEKQFDRA | FHEANRHHGV | 100 |
| LIEMMARGTT | YHFTIIGQQV | LSVLETAAAN | VVGDGRKAIK | ELIALKNGHR | 150 |
| ATSRQLQLDA | SARRQLKAQA | LTPETVLQRG | QQVFLTTAAH | PQTGGDLYDV | 200 |
| TDEIDDSYKQ | LALKAAATLD | LPVAAVDIVI | DNLYAPYDPE | ADGQAIVISL | 250 |
| NPVPDLAVPL | HPDMGESRAL | APALLNWLFA | VR | | 282 |

Fig. 80. Nucleotide sequence containing L. rhamnosus strain HN001
Peptidase gene PepO showing initiation and translation stop codons (boxed)

```
GATCATGATG GGGCAGCAGT CGCCATCAAG CAGTATGCAA TGGGTGAAGG TTAATAAAAA    60
AGCGAGTCGA ATTCCTGATA ATGGAAGTCG ACTCGCTTTT TATTTTAGCC GAAATAGTTT   120
CGTTTAAATC TAATCTTTTA AGTCAATAAT TGCCTGTTCC AACTCCTGTT TCTGAGCTGC   180
AGAGATTTCC GGATATTTTA GCGGCAAAGC GGTGACTTCG CGGTTGATGA TTTGGGACAC   240
AACCAGTCGG GAGTACCACT TATCGTCTGA CGGAATCACG TACCAGGGAT TTGTTTTCGT   300
GGCGGTGTGC TGAATGGCAT CTTGATAAGC TTGCTGGTAA TCATCCCAAA AGCGCCGTTC   360
GTGAATATCC GCCAATGAGA ACTTCCAATT CTTTTCGGGA ATTCGATTC GTTTTAAGAA    420
GCGATTTTTT TGTTCGGCCT TGGAAATGTG TAAGAAGAAC TTGAGCAGCA AGATGCCATT   480
GCGGTGCGCA TAGGTTTCTA GCGCCTTGAT ATCGTTGAAG CGTTTGGCCC ATAAATCGTC   540
ATGGACATCA GCAACGGTGT TGATTCCCGG CAGGTTTTCT TTTAATAGCA ATTCGGGATG   600
AACCCGGTCG ACCAGCACTT CTTCATAATG GGAGCGATTG AACACCGTCA GTTCGCCACC   660
AGCCGGGAAA GCGTTATGGA TGCGCCATAA AAAGTCATGG CCTAGTTCAA GCTCAGTCGG   720
TACTTTAAAC GACACCACTG AGGTTCCCTG CGGATTGACG CCGGACATGA CGTGTTCAAT   780
CATGCTGTCT TTGCCGGCTG CATCCATCCC TTGAAAGATA ATCAAGACGC TGTATTGTTT   840
CTGTGCCGCC AAGTGTTGCT GAACTTTGGA GAGCACCTTG ATGTTATGAT CAATGTCTGC   900
TTTGATCTGC TCTTTTTTAT TTTGAAAATG TTCTGGCGGC GCGGTCGCAA ACGCTTGAAT   960
GTTAAAGGTG CCAGTGCCGT CAAAACGATA TTTTTCCAAT GTCATCTTAT CACCTTCAAT  1020
TTAAGCTTAG TTTCAACATA GTAGTTACGC CAAGGATGTG CAAGCAATTG ACGCCTTGGC  1080
GGATTAAATC TATGCTGAGA TTACGACATG AAAACGGAGG CAATTGCATG ACATTACCAA  1140
GAATTCAAGA TGATTTGTAC CTAGCCGTCA ATGGCGAATG GCAAGCGAAG ACGCCGATTC  1200
CACCTGATAA AAGTGTTGTG AGTGCGGATA GTAATCTGAC CGATGATATT CGCCAAAAAC  1260
TAGTGGCTGA TCTAAGCACG ATGACGAAAA CAGCCAAAAC TTTGCCGCTC CAGTATGCAG  1320
CGCGGTTGTT TGCCAAAGCC AATGACCAAA CCCGCCGTCA GCAGCTAGGC ATTGAGCCAG  1380
TTCGTGATCG GATAAGCTTT TTGATGGCGC TCACGACGCT TGATCAATTT CGCAGCGCTA  1440
TGCCCAAACT GGTTGCTGAT CAATACGTCT TACCGATCAG TCCTTACGTT GATGCTGATA  1500
TGCACGATGC CGAGCATAAT ATTCTGAATC TTGGCGGGCC AGACACAATT TTACCTGATG  1560
CGGCGATGTA CCAACATGAA GATGCCGAAA ATGCGGCGGA TCTGGCAGCG TGGTCGCAGA  1620
TGGCAGCTGC CATGCTGGCT GCGGTAGGAT TCAGTCAGAC TGATCAAACA GCATATGTTG  1680
AAGCGGCTAA ACGATTTGAT CGGCGTTTGG CTGATTATGT GCCAGCAAAT GTTGACTTAG  1740
CGGTAGATAG CACGTATGAC AATCCATTGA GCTGGCAGGC GTTGAAGAT GCGGCCGGTT   1800
ATTTGGGGAT CCCACAAGCC TTTGCAACTT ACATGCCGCA AACACCGGCG AAAGTCAATG  1860
CGGTTGTACC GGCTTATCTT CCGCACTTAA GCAAACTACT GACGCCGGAC AATTATTCAG  1920
AATGGCACGC ATGGATGGTG ATTAACGAAT TGCTAACCTG CGCCACTTAC CTCAGTGATG  1980
ATTTACGTCA ATTGGCCGGA CAGTATGATC GGTTTTTGGC TGGTCAACCT GAGGCGTCAT  2040
CGTGGACGAA ACACGCTTTT GGGATTGCCA ACGAGTATTT TGACGATGTG ATTGGTCAGT  2100
```

```
ATTATGGTCA AACCTACTTT GGTGCCGACG CTAAGGCAGA TGTGACGGCC ATGGTTAAGC  2160
AAATTCTTGC GCAATACCGC GTGCAGCTAG AAAACAACAC TTGGCTGAGT CCGGCTACGA  2220
AGCAAAAGGC GATGCGCAAG TTAGCCACGA TGCAAGTCAA AATGGGGTAT CCGGAGCGAC  2280
TCTTTTCCTT GTATGATCAC TTGAGCGTGG ATGTTGACGA TGATTTGTTG ACGGCAATTC  2340
TGAAACTTAG CGCACAGACG CAGGCCTTTT GGTTTAAACA GTTAGGCCAG ACGGTGGATC  2400
GGAATCAATG GAATATGCCG GGACACTTGG TGAATGCCAG TTATGATCCG CTGAAAAATG  2460
ACATCACTTT TCCCGCTGGT ATCTTGCAGC CGCCGTATTA CTCACTCAAA TGGACCCGGG  2520
CGGAAAACCT CGGAGGGACA GGCGCAACGA TCGGTCATGA AATCTCGCAT TCGTTTGATA  2580
ATAACGGGGC GCTGTATGAT GAATATGGTA ATTTGCATAA CTGGTGGACA CCAGCGGATA  2640
AGCAGGCATT TGATCAGCTG GTAAAAGCGA TGGCGGCACA GTTTGATGGC CGTGACTATG  2700
AAGGAGTCAA GGTCAACGGT ACACTGACCG TTAGTGAAAA CATGGCGGAT AACGCCGGCA  2760
TGGATGTGGC GTTGGCGTTA CTAGGCGATC AGCCGGATGT TAAGGATCTG CAGGCATTCT  2820
TCATCACTTA CGCTCGTTCA TGGGCCACCA AAATGCGACC GGAGCGGGCT AAAACTGTTT  2880
TGCGGCAAGA TGTTCATGCG CCGGCTACCT TACGCGTGAA TGTGCCGGTG CAAAACTTTC  2940
CTGCATGGTA CCAGGCATTT AATGTTCAGC CACAAGATGG TATGTATCGG CAACCACAGA  3000
AGCGGCTGAC GATTTGGCAT CAG TAA TATT TAAATAAAAG AGTTTTATGT GAACCTTTTT  3060
CGAGAACCGC GAGATCAACT GTGTGTCACA CTGTTCATGG GGAAGCGTAA ACAAAAAGGC  3120
AACGATTGCC GTGAGACAAT CGTTGCCTTT TTTCAATCTT GGGACAGGTC GTGGTAATAA  3180
TGTAGCCAGC CGGTTTCGCG TTCGCCGATT TGATC                              3215
```

Fig 81. The amino acid sequence of HN001 Peptidase PepO

```
MTLPRIQDDL YLAVNGEWQA KTPIPPDKSV VSADSNLTDD IRQKLVADLS      50
TMTKTAKTLP LQYAARLFAK ANDQTRRQQL GIEPVRDRIS FLMALTTLDQ     100
FRSAMPKLVA DQYVLPISPY VDADMHDAEH NILNLGGPDT ILPDAAMYQH     150
EDAENAADLA AWSQMAAAML AAVGFSQTDQ TAYVEAAKRF DRRLADYVPA     200
NVDLAVDSTY DNPLSWQAFE DAAGYLGIPQ AFATYMPQTP AKVNAVVPAY     250
LPHLSKLLTP DNYSEWHAWM VINELLTCAT YLSDDLRQLA GQYDRFLAGQ     300
PEASSWTKHA FGIANEYFDD VIGQYYGQTY FGADAKADVT AMVKQILAQY     350
RVQLENNTWL SPATKQKAMR KLATMQVKMG YPERLFSLYD HLSVDVDDDL     400
LTAILKLSAQ TQAFWFKQLG QTVDRNQWNM PGHLVNASYD PLKNDITFPA     450
GILQPPYYSL KWTRAENLGG TGATIGHEIS HSFDNNGALY DEYGNLHNWW     500
TPADKQAFDQ LVKAMAAQFD GRDYEGVKVN GTLTVSENMA DNAGMDVALA     550
LLGDQPDVKD LQAFFITYAR SWATKMRPER AKTVLRQDVH APATLRVNVP     600
VQNFPAWYQA FNVQPQDGMY RQPQKRLTIW HQ                        632
```

LACTOBACILLUS RHAMNOSUS POLYNUCLEOTIDES, POLYPEPTIDES AND METHODS FOR USING THEM

CROSS-REFERENCE TO RELATED APPLICATIONS

This application is a continuation-in-part of U.S. patent application Ser. No.: 09/634,238 filed Aug. 8, 2000, now U.S. Pat. No. 6,544,772, and Ser. No. 09/724,623 filed Nov. 28, 2000, now U.S. Pat. No. 6,476,209. This application claims priority to PCT International Application No. PCT/NZ01/00160 filed Aug. 8, 2001.

TECHNICAL FIELD OF THE INVENTION

This invention relates to polynucleotides isolated from lactic acid bacteria, namely *Lactobacillus rhamnosus*, including full-length sequences encoding polypeptides, as well as probes and primers specific to the polynucleotides; genetic constructs comprising the polynucleotides; biological, materials, including microorganisms and multicellular organisms, incorporating the polynucleotides; polypeptides encoded by the polynucleotides; and methods for using the polynucleotides and polypeptides.

BACKGROUND OF THE INVENTION

The present invention relates to polynucleotides isolated from a specific strain of lactic acid bacteria, namely *Lactobacillus rhamnosus* HN001 (*L. rhamnosus* HN001). Lactic acid bacteria, and their enzymes, are the major determinants of flavor and fermentation characteristics in fermented dairy products, such as cheese and yogurt. Flavors are produced through the action of bacteria and their enzymes on proteins, carbohydrates and lipids.

*Lactobacillus rhamnosus* strain HN001 are heterofermentative bacteria that are Gram positive, non-motile, non-spore forming, catalase negative, facultative anaerobic rods exhibiting an optimal growth temperature of 37±1° C. and an optimum pH of 6.0–6.5. Experimental studies demonstrated that dietary supplementation with *Lactobacillus rhamnosus* strain HN001 induced a sustained enhancement in several aspects of both natural and acquired immunity (See PCT International Publication No. WO 99/10476).

In addition, *L. rhamnosus* HN001, and certain other Gram-positive bacteria can specifically and directly modulate human and animal health (See, for example, Tannock et al., *Applied Environ. Microbiol.* 66:2578–2588, 2000; Gill et al., *Brit. J. Nutrition* 83:167–176; Quan Shu et al., *Food and Chem. Toxicol.* 38:153–161, 2000; Quan Shu et al., *Intl. J. Food Microbiol.* 56:87–96, 2000; Quan Shu et al., *Intl. Dairy J.* 9:831–836, 1999; Prasad et al., *Intl. Dairy J.* 8:993–1002, 1998; Sanders and Huis in't Veld, *Antonie van Leeuwenhoek* 76:293–315, 1999; Salminen et al., 1998. In: Lactic Acid Bacteria, Salminen S and von Wright A (eds)., Marcel Dekker Inc, New York, Basel, Hong Kong, pp. 203 –253; Delcour et al., *Antonie van Leeuwenhoek* 76:159–184, 1999; Blum et al., *Antonie van Leeuwenhoek* 76:199–205, 1999; Yasui et al., *Antonie van Leeuwenhoek* 76:383–389, 1999; Hirayama and Rafter, *Antonie van Leeuwenhoek* 76:391–394, 1999; Ouwehand, 1998. In: Lactic Acid Bacteria, Salminen S and von Wright A (eds)., Marcel Dekker Inc, New York, Basel, Hong Kong, pp. 139–159; Isolauri et al., S 1998. In: Lactic Acid Bacteria, Salminen S and von Wright A (eds)., Marcel Dekker Inc, New York, Basel, Hong Kong, pp. 255–268; Lichtenstein and Goldin, 1998. In: Lactic Acid Bacteria, Salminen S and von Wright A (eds)., Marcel Dekker Inc, New York, Basel, Hong Kong, pp. 269–277; El-Nezami and Ahokas, 1998. In: Lactic Acid Bacteria, Salminen S and von Wright A (eds)., Marcel Dekker Inc, New York, Basel, Hong Kong, pp. 359–367; Nousianen et al., 1998. In: Lactic Acid Bacteria, Salminen S and von Wright A (eds)., Marcel Dekker Inc, New York, Basel, Hong Kong, pp. 437–473; Meisel and Bockelmann, *Antonie van Leeuwenhoek* 76:207–215, 1999; Christensen et al., *Antonie van Leeuwenhoek* 76:217–246, 1999; Dunne et al., Antonie van Leeuwenhoek 76:279–292, 1999).

Beneficial health effects attributed to dietary supplementation with these bacteria include the following:

- Increased resistance to enteric pathogens and anti-infection activity, including treatment of rotavirus infection and infantile diarrhea—due to increases in antibody production caused by an adjuvant effect, increased resistance to pathogen colonization; alteration of intestinal conditions, such as pH; and the presence of specific antibacterial substances, such as bacteriocins and organic acids.
- Aid in lactose digestion—due to lactose degradation by bacterial lactase enzymes (such as beta-galactosidase) that act in the small intestine.
- Anti-cancer (in particular anti-colon cancer) and anti-mutagenesis activities—due to anti-mutagenic activity; alteration of procancerous enzymatic activity of colonic microbes; reduction of the carcinogenic enzymes azoreductase, beta-glucuronidase and nitroreductase in the gut and/or faeces; stimulation of immune function; positive influence on bile salt concentration; and antioxidant effects.
- Liver cancer reduction—due to aflatoxin detoxification and inhibition of mould growth.
- Reduction of small bowel bacterial overgrowth—due to antibacterial activity; and decrease in toxic metabolite production from overgrowth flora.
- Immune system modulation and treatment of autoimmune disorders and allergies—due to enhancement of non-specific and antigen-specific defence against infection and tumors; enhanced mucosal immunity; adjuvant effect in antigen-specific immune responses; and regulation of Th1/Th2 cells and production of cytokines.
- Treatment of allergic responses to foods—due to prevention of antigen translocation into bloodstream and modulation of allergenic factors in food.
- Reduction of blood lipids and prevention of heart disease—due to assimilation of cholesterol by bacteria; hydrolysis of bile salts; and antioxidative effects.
- Antihypertensive effect—bacterial protease or peptidase action on milk peptides produces antihypertensive peptides. Cell wall components act as ACE inhibitors
- Prevention and treatment of urogenital infections—due to adhesion to urinary and vaginal tract cells resulting in competitive exclusion; and production of antibacterial substances (acids, hydrogen peroxide and biosurfactants).
- Treatment of inflammatory bowel disorder and irritable bowel syndrome—due to immuno-modulation; increased resistance to pathogen colonization; alteration of intestinal conditions such as pH; production of specific antibacterial substances such as bacteriocins, organic acids and hydrogen peroxide and biosurfactants; and competitive exclusion.
- Modulation of infective endocarditis—due to fibronectin receptor-mediated platelet aggregation associated with *Lactobacillus* sepsis.

Prevention and treatment of *Helicobacter* pylon infection—due to competitive colonization and antibacterial effect.

Prevention and treatment of hepatic encephalopathy—due to inhibition and/or exclusion of urease-producing gut flora.

Improved protein and carbohydrate utilisation and conversion—due to production of beneficial products by bacterial action on proteins and carbohydrates.

Other beneficial health effects associated with dietary supplementation with *L. rhamnosus* include: improved nutrition; regulation of colonocyte proliferation and differentiation; improved lignan and isoflavone metabolism; reduced mucosal permeability; detoxification of carcinogens and other harmful compounds; relief of constipation and diarrhea; and vitamin synthesis, in particular folate.

Peptidases are enzymes that break the peptide bonds linking the amino group of one amino acid with the carboxy group (acid group) of an adjacent amino acid in a peptide chain. The bonds are broken in a hydrolytic reaction. There is a large family of peptidase enzymes that are defined by their specificity for the particular peptides bonds that they cleave (Barrett A J, Rawlings N D and Woessner J F (Eds.) 1998. *Handbook of proteolytic enzymes*, Academic Press, London, UK). The two main families are exopeptidases and endopeptidases.

Exopeptidases cleave amino acids from the N- or C-terminus of a peptide chain, releasing free amino acids or short (di- and tripeptides). Different types of exopeptidases include:

Aminopeptidases—release a free amino acid from the N-terminus of a peptide chain;

dipeptidyl-peptidase (also known as dipeptidyl-aminopeptidases)—release a dipeptide from the N-terminus of a peptide chain;

tripeptidyl-peptidases (also known as tripeptidyl-aminopeptidases)—release a tripeptide from the N-terminus of a peptide chain);

carboxypeptidases—release a free amino acid from the C-terminus of a peptide chain;

peptidyl-dipeptidase—release a dipeptide from the C-terminus of a peptide chain;

dipeptidases—release two free amino acids from a dipeptide; and tripeptidases—release a free amino acid and a dipeptide from a tripeptide.

Endopeptidases hydrolyze peptide bonds internally within a peptide and are classified on the basis of their mode of catalysis:

serine-endopeptidases—depend on serine (or threonine) as the nucleophile in the catalytic reaction;

cysteine-endopeptidases—depend on the sulphydryl group of cysteine as the nucleophile in the catalytic reaction;

aspartic-endopeptidases—contain aspartate residues that act as ligands for an activated water molecule which acts as the nucleophile in the catalytic reaction; and metallo-endopeptidases—contain one or more divalent metal ions that activate the water molecule that acts as the nucleophile in the catalytic reaction.

Peptidases are important enzymes in the process of cheese ripening and the development of cheese flavor. The hydrolysis of milk caseins in cheese results in textural changes and the development of cheese flavors. The raft of proteolytic enzymes that cause this hydrolysis come from the lactic acid bacteria that are bound up in the cheese—either starter cultures that grow up during the manufacture of the cheese, or adventitious and adjunct non-starter lactic acid bacteria that grow in the cheese as it ripens (Law and Haandrikman, *Int. Dairy J.* 7:1–11, 1997).

Many other enzymes can also influence dairy product flavor, and functional and textural characteristics, as well as influencing the fermentation characteristics of the bacteria, such as speed of growth, acid production and survival. (Urbach, *Int. Dairy J.* 5:877–890, 1995; Johnson and Sornuti, *Biotech. Appl. Biochem.* 13:196–204, 1991; E 1 Soda and Pandian, *J. Dairy Sci.* 74:2317–2335, 1991; Fox et al., In Cheese: chemistry, physics and microbiology. Volume 1, General aspects, $2^{nd}$ edition, P Fox (ed) Chapman and Hall, London; Christensen et al., *Antonie van Leeuwenhoek* 76:217–246, 1999; Stingle et al., *J. Bacteriol.* 20:6354–6360, 1999; Stingle et al., *Mol. Microbiol.* 32:1287–1295, 1999; Lemoine et al., *Appl. Environ. Microbiol.* 63:1512–3518, 1997). Enzymes influencing the specific cellular and system characteristics and/or functions are examplified below:

Lysis of cells. These enzymes are mostly cell wall hydrolases, including amidases; muramidases; lysozymes, including N-acetyl muramidase; muramidase; N-acetylglucosaminidase; and N-acetylmuramoyl-L-alanine amidase. DEAD-box helicase proteins also influence autolysis.

Carbohydrate utilization. Lactose, citrate and diacetyl metabolism, and alcohol metabolism are particularly important. The enzymes involved include beta-galactosidase, lactate dehydrogenase, citrate lyase, citrate permease, 2,3 butanediol dehydrogenase (acetoin reductase), acetolactate decaboxylase, acetolactate synthase, pyruvate decarboxylase, pyruvate formate lyase, diacetyl synthase, diacetyl reductase, alcohol decarboxylase, lactate dehydrogenase, pyruvate dehydrogenase, and aldehyde dehydrogenase.

Lipid degradation, modification or synthesis. Enzymes involved include lipases, esterases, phospholipases, serine hydrolases, desaturases, and linoleate isomerase.

Polysaccharide synthesis. Polysaccharides are important not only for potential immune enhancement and adhesion activity but are important for the texture of fermented dairy products. The enzymes involved are a series of glucosyl transferases, including beta-(1-3) glucosyl transferase, alpha-N acetylgalactosaminyl transferase, phosphogalactosyl transferase, alpha-glycosyl transferase, UDP-N-acetylglucosamine C4 epimerase and UDP-N-acetylglucosamine transferase.

Amino acid degradation. Enzymes include glutamate dehydrogenase, aminotransferases, amino acid decarboxylases, and enzymes involved in sulphur amino acid degradation including cystothione beta-lyase.

Sequencing of the genomes, or portions of the genomes, of numerous organisms, including humans, animals, microorganisms and various plant varieties, has been and is being carried out on a large scale. Polynucleotides identified using sequencing techniques may be partial or full-length genes, and may contain open reading frames, or portions of open reading frames, that encode polypeptides. Polypeptides may be identified based on polynucleotide sequences and further characterized. The sequencing data relating to polynucleotides thus represents valuable and useful information.

Polynucleotides and polypeptides may be analyzed for varying degrees of novelty by comparing identified sequences to sequences published in various public domain databases, such as EMBL. Newly identified polynucleotides and corresponding polypeptides may also be compared to polynucleotides and polypeptides contained in public domain information to ascertain homology to known polynucleotides and polypeptides. In this way, the degree of similarity, identity or homology of polynucleotides and polypeptides having an unknown function may be determined relative to polynucleotides and polypeptides having known functions.

Information relating to the sequences of isolated polynucleotides may be used in a variety of ways. Specified polynucleotides having a particular sequence may be isolated, or synthesized, for use in in vivo or in vitro experimentation as probes or primers. Alternatively, collections of sequences of isolated polynucleotides may be stored using magnetic or optical storage medium and analyzed or manipulated using computer hardware and software, as well as other types of tools.

SUMMARY OF THE INVENTION

The present invention provides isolated polynucleotides comprising a sequence selected from the group consisting of: (a) sequences identified in the attached Sequence Listing as SEQ ID NOS: 1–33; (b) complements, reverse sequences and reverse complements of SEQ ID NOS: 1–33 and fragments of SEQ ID NOS: 1–33; (c) open reading frames contained in SEQ ID NOS: 1–33 and their variants; (d) functional domains contained in SEQ ID NOS: 1–33; and (e) sequences comprising at least a specified number of contiguous residues of a sequence of SEQ ID NOS: 1–33 (x-mers). Oligonucleotide probes and primers corresponding to the sequences set out in SEQ ID NOS: 1–33, and their variants are also provided. All of these polynucleotides and oligonucleotide probes and primers are collectively referred to herein, as "polynucleotides of the present invention."

The polynucleotide sequences identified as SEQ ID NOS: 1–33 were derived from a microbial source, namely from fragmented genomic DNA of *Lactobacillus rhamnosus*, strain HN001, described in PCT International Publication No. WO 99/10476. *Lactobacillus rhamnosus* strain HN001 are heterofermentative bacteria that are Gram positive, non-motile, non-spore forming, catalase negative, facultative anaerobic rods exhibiting an optimal growth temperature of 37±1° C. and an optimum pH of 6.0–6.5. A biologically pure culture of *Lactobacillus rhamnosus* strain HN001 was deposited at the Australian Government Analytical Laboratories (AGAL), The New South Wales Regional Laboratory, 1 Suakin Street, Pymble, NSW 2073, Australia, as Deposit No. NM97/09514, dated 18 Aug. 1997.

The polynucleotide sequences disclosed herein are primarily "full-length" sequences, in that they represent a full-length gene encoding a full-length polypeptide and contain an open reading frame. Similarly, RNA sequences, reverse sequences, complementary sequences, antisense sequences and the like, corresponding to the polynucleotides of the present invention, may be routinely ascertained and obtained using the polynucleotides identified as SEQ ID NOS: 1–33 and are included in the terminology "polynucleotide."

The present invention further provides isolated polypeptides, including polypeptides encoded, or partially encoded, by the polynucleotides disclosed herein. In certain specific embodiments, the polypeptides of the present invention comprise a sequence selected from the group consisting of sequences identified as SEQ ID NO: 42–75, and variants thereof. Polypeptides encoded by the polynucleotides of the present invention may be expressed and used in various assays to determine their biological activity. Such polypeptides may be used to raise antibodies, to isolate corresponding interacting proteins or other compounds, and to quantitatively determine levels of interacting proteins or other compounds. The polypeptides of the present invention may also be used as nutritional additives or supplements, and as additives in dairy processing and fermentation processing. Several polypeptides of the present invention also have human and animal health related benefits.

Genetic constructs comprising the inventive polynucleotides are also provided, together with transgenic host cells comprising such constructs and transgenic organisms, such as microbes, comprising such cells.

The present invention also contemplates methods for modulating the polynucleotide and/or polypeptide content and composition of an organism, such methods optionally involving stably incorporating into the genome of the organism a genetic construct comprising a polynucleotide of the present invention. Such modulation may involve up regulating or down regulating expression from one or more polynucleotides of the present invention. Up regulation may be accomplished, for example, by providing multiple gene copies, modulating expression by modifying regulatory elements, promoting transcriptional or translational mechanisms, or the like. Similarly, down regulation may be accomplished using known antisense and gene silencing techniques. In one embodiment, the target organism is a microbe, preferably a microbe used in fermentation, more preferably a microbe of the genus *Lactobacillus*, and most preferably *Lactobacillus rhamnosus*, or another closely related microbial species used in the dairy industry. In a related aspect, methods for producing a microbe having an altered genotype and/or phenotype is provided, such methods comprising transforming a microbial cell with a genetic construct of the present invention to provide a transgenic cell, and cultivating the transgenic cell under conditions conducive to growth and multiplication. Organisms having an altered genotype or phenotype as a result of modulation of the level or content of a polynucleotide or polypeptide of the present invention compared to a wild-type organism, as well as components and progeny of such organisms, are contemplated by and encompassed within the present invention.

The isolated polynucleotides of the present invention may be usefully employed for the detection of lactic acid bacteria, preferably *L. rhamnosus*, in a sample material, using techniques well known in the art, such as polymerase chain reaction (PCR) and DNA hybridization, as detailed below.

The inventive polynucleotides and polypeptides may also be employed in methods for the selection and production of more effective probiotic bacteria; as "bioactive" (health-promoting) ingredients and health supplements, for immune function enhancement; for reduction of blood lipids such as cholesterol; for production of bioactive material from genetically modified bacteria; as adjuvants; for wound healing; in vaccine development, particularly mucosal vaccines; as animal probiotics for improved animal health and productivity; in selection and production of genetically modified rumen microorganisms for improved animal nutrition and productivity, better flavor and improved milk composition; in methods for the selection and production of better natural food bacteria for improved flavor, faster flavor development, better fermentation characteristics, vitamin synthesis and improved textural characteristics; for the production of improved food bacteria through genetic modification; and for the identification of novel enzymes for the production of, for example, flavors or aroma concentrates.

The isolated polynucleotides of the present invention also have utility in genome mapping, in physical mapping, and in positional cloning of genes of more or less related microbes. Additionally, the polynucleotide sequences identified as SEQ ID NOS: 1–33, and their variants, may be used to design oligonucleotide probes and primers. Oligonucleotide probes and primers have sequences that are substantially complementary to the polynucleotide of interest over a certain portion of the polynucleotide. Oligonucleotide probes designed using the polynucleotides of the present invention may be used to detect the presence and examine the expression patterns of genes in any organism having sufficiently similar DNA and RNA sequences in their cells, using techniques that are well known in the art, such as slot blot DNA hybridization techniques. Oligonucleotide primers designed using the polynucleotides of the present invention may be used for PCR amplifications. Oligonucleotide probes and primers designed using the polynucleotides of the present invention may also be used in connection with various microarray technologies, including the microarray technology of Affymetrix (Santa Clara, Calif.).

The polynucleotides of the present invention may also incorporate regulatory elements such as promoters, gene regulators, origins of DNA replication, secretion signals, cell wall or membrane anchors for genetic tools (such as expression or integration vectors).

The polynucleotide sequences, encoded polypeptides and genetic constructs of this invention are useful for improving the properties of microbes that are used in the manufacture of milk-derived products, such as cheeses, yogurt, fermented milk products, sour milks, and buttermilk. Microbial metabolism during fermentation, which results in the breakdown of proteins, lipids and lactose in milk, influences the speed of ripening, the texture and consistency of fermented milk products, and the development of flavors and aromas during ripening. Undesirable flavors in milk products are produced, for example, by the food of milk-producing animals, microbial action, and enzymatic activity during fermentation, and require removal. The present invention provides polynucleotides and polypeptides and methods for their use in modifying the flavor, aroma, texture and health-related benefits of milk-derived products. Methods are described for modulating the polynucleotide content or composition of microbes used in the dairy industry by transforming the microbes with one or more polynucleotides sequences of *Lactobacillus rhamnosus* strain HN001. The inventive polynucleotides also include sequences encoding polypeptides that increase the survivability of microbes during industrial fermentation processes, wherein exposure to osmotic, temperature and other stresses can lead to reduced microbial viability, impaired metabolic activity and suboptimal fermentation conditions. While the present invention is described with particular reference to milk-derived products, it will be recognized that microbes such as *Lactobacillus*, which are used in the dairy industry, are also used in the production of other foods and beverages (e.g., fermented vegetables, beer, wines, juices, sourdough breads). It is expected that the polynucleotides described herein and their methods of use can be used for the processing of these foods and beverages as well.

This invention also provides transgenic microbial populations comprising expressible polynucleotide sequences of *Lactobacillus rhamnosus* strain HN001 which provide health-related benefits. For example, the polypeptides encoded by the inventive sequences include enzymes that detoxify carcinogens, degrade allergenic proteins and lactose, and produce bioactive peptides and biogenic amines. Microbes transformed with these polynucleotide sequences can be taken internally as a probiotic composition or alternatively, the microbes or their encoded polypeptides can be added to products to provide health-related benefits. Non-pathogenic bacteria, preferably lactic-acid producing species of *Bacillus, Lactobacillus, Sporolactobacillus* or *Bifidiobacterium*, that are able to colonize the gastrointestinal tract, preferably the gastrointestinal tract of a mammal, are useful for preventing or reducing pathogen colonization of the gastrointestinal mucosa, and for replacing normal flora that are depleted, for example, by drug therapy. The polynucleotide sequences of this invention can be used to transform microbes for use in a therapeutic composition that is effective for treating or preventing a gastrointestinal condition or disorder caused by the presence of pathogenic microbes in the gastrointestinal tract or by the absence of normal intestinal microbes in the intestinal tract. Such probiotic compositions can be administered alone or in combination with another pharmaceutical agent, depending on the condition that is to be treated.

All references cited herein, including patent references and non-patent publications, are hereby incorporated by reference in their entireties.

BRIEF DESCRIPTION OF THE DRAWINGS

FIG. 1 shows the nucleotide sequence containing *L. rhamnosus* strain HN001 esterase gene AA7 (SEQ ID NO: 3) showing ATG initiation and translation stop codons (boxed).

FIG. 2 shows the amino acid sequence of HN001 esterase AA7 (SEQ ID NO: 44).

FIG. 6 shows the nucleotide sequence containing *L. rhamnosus* strain HN001 autoaggregation gene AG5 (SEQ ID NO: 10) showing ATG initiation and translation stop codons (boxed).

FIG. 7 shows the amino acid sequence of HN001 autoaggregation protein AG5 (SEQ ID NO: 52).

FIGS. 8A and 8B are images of phase contrast photomicrographs. FIG. 8A illustrates an image of a phase-contrast photomicrograph (exposure ⅛ sec, final magnification ×240) showing obvious clumping of washed *L. rhamnosus* strain HN001 cells in the presence of AG5 autoaggregation protein tagged with GST. FIG. 8B illustrates an image of a phase-contrast photomicrograph (exposure ⅛ sec, final magnification ×240) showing no clumping of washed *L.* rhamnosus strain HN001 cells in the presence of an irrelevant (non-adhesion) HN001 protein tagged with GST, as a negative control.

FIG. 9 shows the nucleotide sequence containing *L. rhamnosus* strain HN001 malic enzyme gene AA5 (SEQ ID NO: 2) showing ATG initiation and translation stop codons (boxed).

FIG. 10 shows the amino acid sequence of HN001 malic enzyme AA5 (SEQ ID NO: 43).

Figure 11:
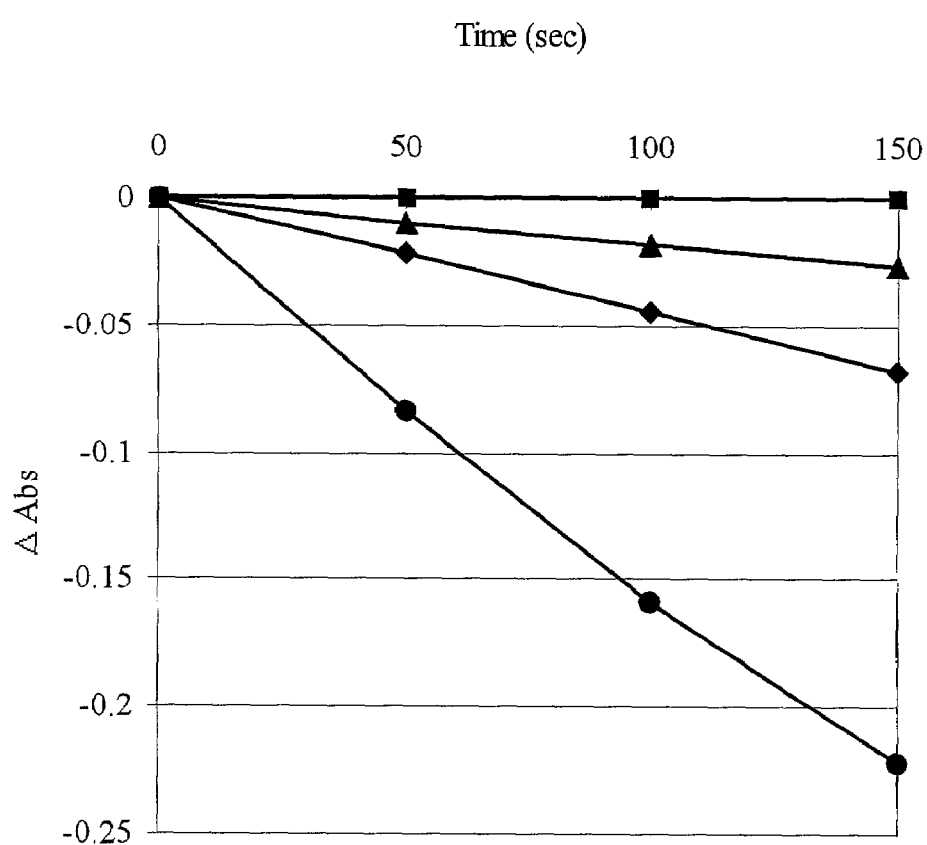

FIG. 11 demonstrates malate enzyme activity measured experimentally as rate of pyruvate reduction by crude lysate preparations of EJ1321 cell transformants. ■ PBS buffer-only; ▲ 3.5 µg wild-type EJ1321 cell lysate; ♦ 3.5 µg cell lysate of EJ1321 transformed with pGEX-6P-3 construct encoding an irrelevant HN001 protein (AD5); ● 3.5 µg cell lysate of EJ1321 transformed with pGEX-6P-3 construct encoding HN001 malic enzyme AA5.

Figure 12:
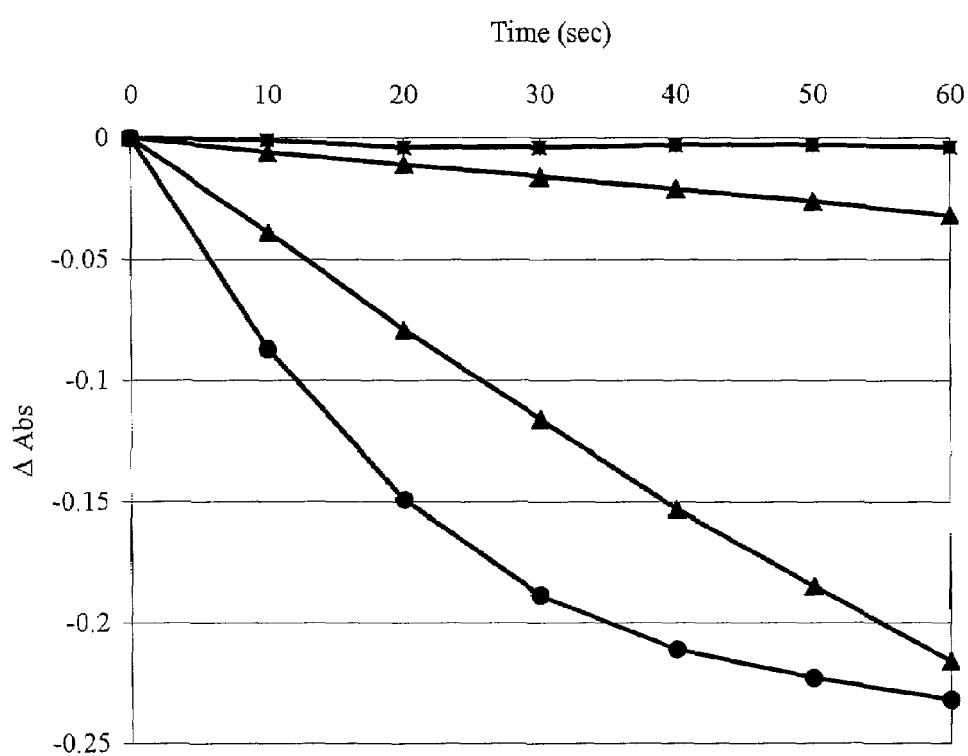

FIG. 12 shows experimental data illustrating the effect of increasing amounts of EJ1321 crude lysate on malic enzyme activity. ■ 5 µl wild-type EJ1321 cell lysate; ▲ 5 µl cell lysate of EJ1321 transformed with pGex-6P-3 encoding AA5; ♦ 50 µl cell lysate of EJ1321 transformed with pGex-6P-3 encoding AA5; ● 200 µl cell lysate of EJ1321 transformed with pGex-6P-3 encoding AA5.

FIG. 13 shows the nucleotide sequence containing *L. rhamnosus* strain HN001 malate dehydrogenase gene AG3 (SEQ ID NO: 9) showing TTG initiation and translation stop codons (boxed).

FIG. 14 shows the amino acid sequence of HN001 malate dehydrogenase AG3 (SEQ ID NO: 51).

FIG. 15 shows the nucleotide sequence containing *L. rhamnosus* strain HN001 dihydrodipicolinate synthase gene AI2 (SEQ ID NO: 13) showing ATG initiation and translation stop codons (boxed).

FIG. 16 shows the amino acid sequence of HN001 dihydrodipicolinate synthase AI2 (SEQ ID NO: 55).

FIG. 17 shows the nucleotide sequence containing *L. rhamnosus* strain aspartate aminotransferase gene AH9 (SEQ ID NO: 12) showing GTG initiation and translation stop codons (boxed).

FIG. 18 shows the amino acid sequence of HN001 aspartate aminotransferase AH9 (SEQ ID NO: 54).

FIG. 19 shows the nucleotide sequence containing *L. rhamnosus* strain HN001 serine dehydratase subunits α (AF8) and β (AF7). ATG translation initiation codons and termination codons are shown, boxed for AF8, and shaded for AF7.

Figure 20:
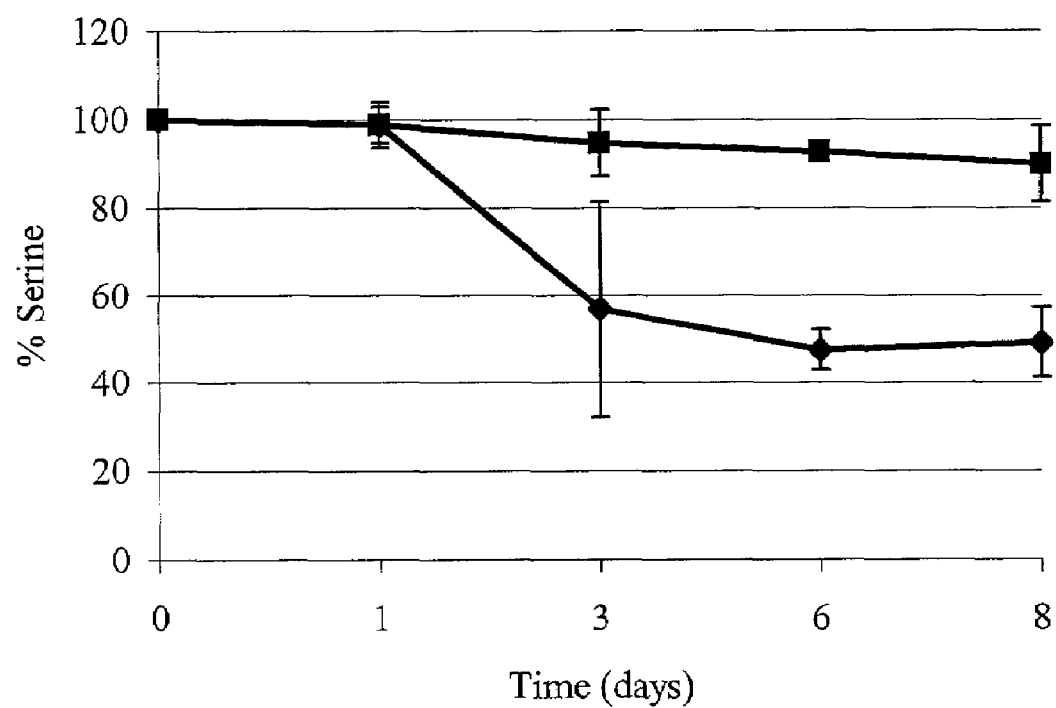

FIG. 20 shows the experimentally measured percentage serine utilisation by HN001 strain in liquid culture with 5 mM initial serine concentration. ■ HN001 transformed with vector only; ♦ pTRKH2 construct containing HN001 serine dehydratase.

Figure 21:
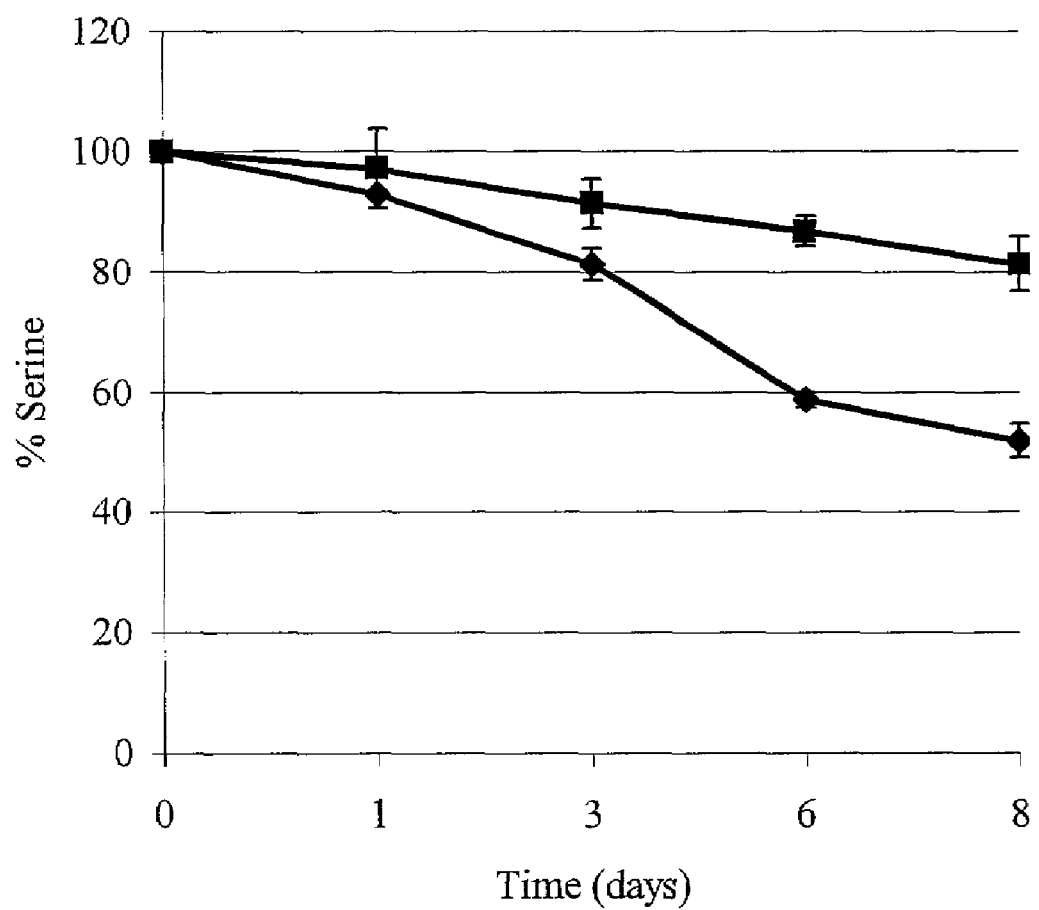

FIG. 21 shows the experimentally determined percentage serine utilisation by HN001 strain in liquid culture with 12 mM initial serine concentration. ■ HN001 transformed with vector only, ♦ pTRKH2 construct containing HN001 serine dehydratase.

FIG. 22A shows the amino acid sequence of *L. rhamnosus* strain HN001 serine dehydratase subunit α (AF8; SEQ ID NO: 49), and FIG. 22B shows the amino acid sequence of *L. rhamnosus* strain HN001 serine dehydratase subunit β (AF7; SEQ ID NO: 48).

FIG. 23 shows the nucleotide sequence containing *L. rhamnosus* strain HN001 histidinol-phosphate aminotransferase gene AG2 (SEQ ID NO: 8) showing ATG initiation and translation stop codons (boxed).

FIG. 24 shows the amino acid sequence of HN001 histidinol-phosphate aminotransferase AG2 (SEQ ID NO: 50).

FIG. 25 shows the nucleotide sequence containing *L. rhamnosus* strain HN001 malY-aminotransferase gene AJ6 (SEQ ID NO: 17) showing ATG initiation and translation stop codons (boxed).

FIG. 26 shows the amino acid sequence of HN001 malY-aminotransferase AJ6 (SEQ ID NO: 59).

FIG. 27 shows the nucleotide sequence containing *L. rhamnosus* strain HN001 malY-aminotransferase gene AJ7 (SEQ ID NO: 18) showing ATG initiation and translation stop codons (boxed).

FIG. 28 shows the amino acid sequence of HN001 malY-aminotransferase AJ7 (SEQ ID NO: 60).

FIG. 29 shows the nucleotide sequence containing *L. rhamnosus* strain HN001 cystathione β-lyase gene AC8 (SEQ ID NO: 5) showing ATG initiation and translation stop codons (boxed).

FIG. 30 shows the amino acid sequence of HN001 cystathione β-lyase AC8 (SEQ ID NO: 46).

Figure 31:
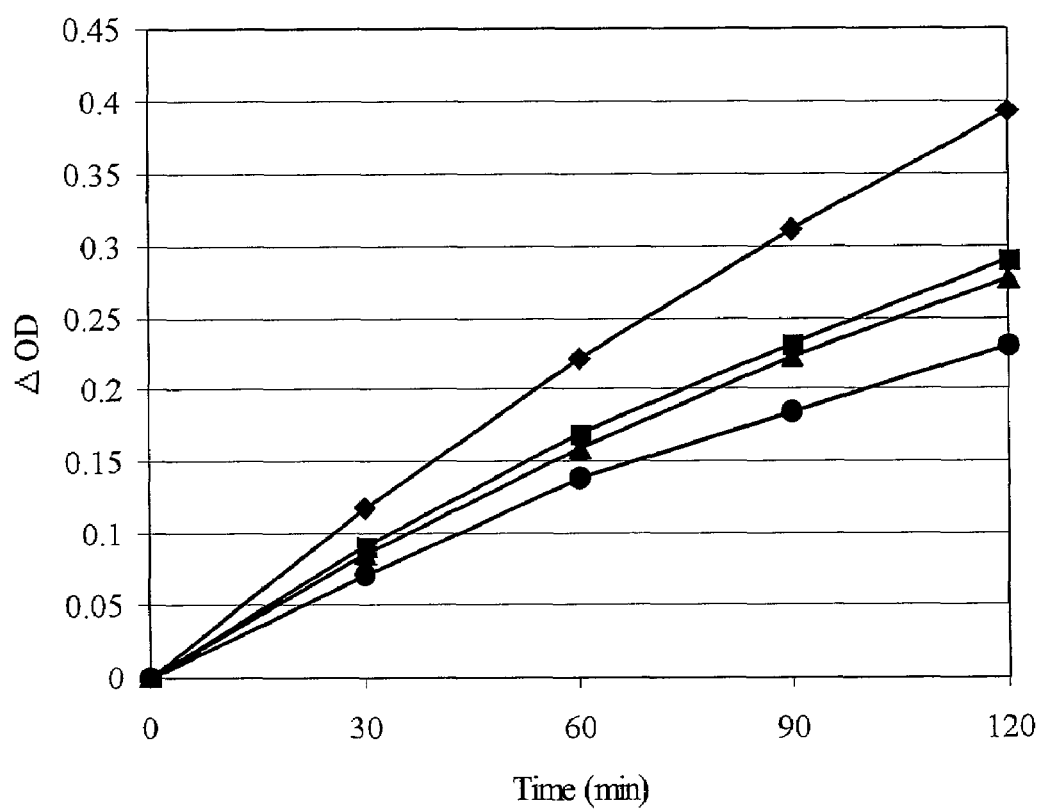

FIG. 31 shows experimental results demonstrating cystathione β-lyase activity measured as rate of mercaptide formation. ♦ 10 µl purified HN001 cystathione β-lyase AC8 fusion protein; ■ 10 µl purified CAT fusion protein; ▲ 10 µl H₂O only; ● 10 µl elution buffer only.

Figure 32:
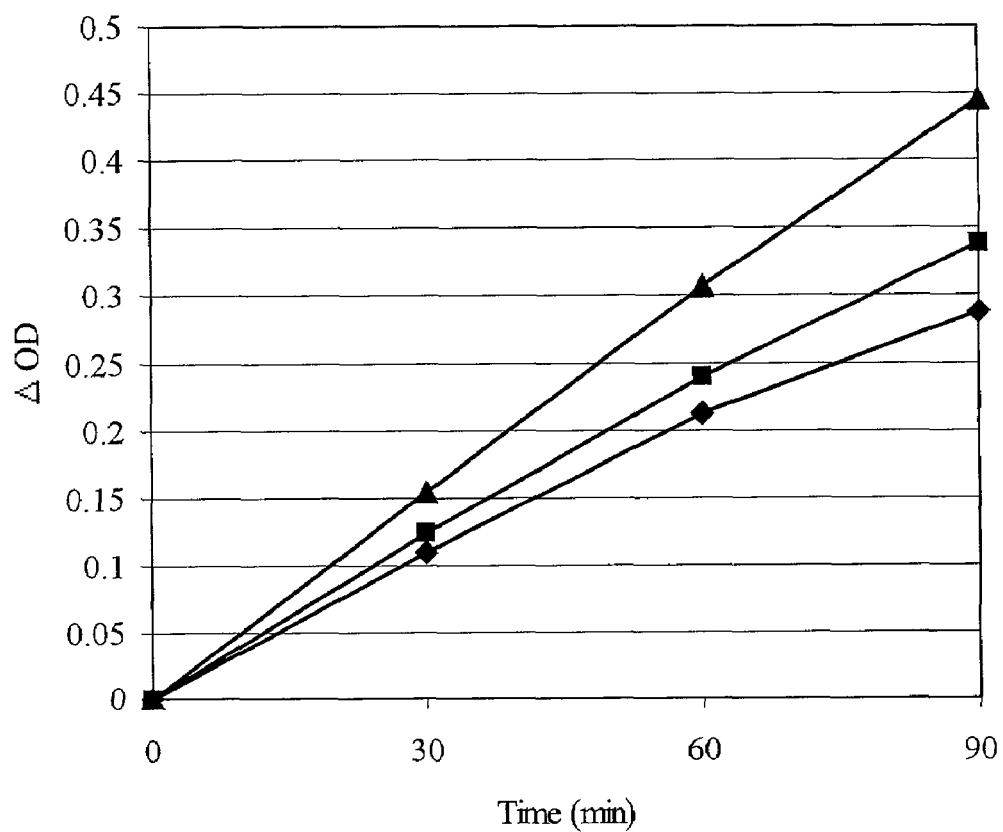

FIG. 32 shows the experimentally determined dose-response of the AC8 fusion protein. Cystathione β-lyase activity of increasing amounts of His-patch/Thio/AC8 fusion protein; 10 µl (♦), 25 µl (■) and 50 µl (▲) purified protein showed increasing rates of mercaptide formation. The increase in mercaptide formation was proportional to amount of AC8 fusion protein added.

FIG. 33 shows the nucleotide sequence containing *L. rhamnosus* strain HN001 phosphoenolpyruvate hydratase AK4 (SEQ ID NO: 20) showing ATG initiation and translation stop codons (boxed).

FIG. 34 shows the amino acid sequence of *L. rhamnosus* strain HN001 phosphoenolpyruvate hydratase AK4 (SEQ ID NO: 62).

FIG. 35 shows the nucleotide sequence containing *L. rhamnosus* strain HN001 tagatose bisphosphate aldolase AK1 (SEQ ID NO: 19) showing ATG initiation and translation stop codons (boxed).

FIG. 36 shows the amino acid sequence of *L. rhamnosus* strain HN001 tagatose bisphosphate aldolase AK1 (SEQ ID NO: 61).

FIG. 37 shows the nucleotide sequence containing *L. rhamnosus* strain HN001 phosphoglycerate kinase AK6 (SEQ ID NO: 22) showing TTG initiation and translation stop codons (boxed).

FIG. 38 shows the amino acid sequence of *L. rhamnosus* strain HN001 phosphoglycerate kinase AK6 (SEQ ID NO: 64).

FIG. 39 shows the nucleotide sequence containing *L. rhamnosus* strain HN001 triosephosphate isomerase AK5 (SEQ ID NO: 21) showing ATG initiation and translation stop codons (boxed).

FIG. 40 shows the amino acid sequence of *L. rhamnosus* strain HN001 triosephosphate isomerase AK5 (SEQ ID NO: 63).

FIG. 41 shows the nucleotide sequence containing *L. rhamnosus* strain HN001 phosphoryl carrier protein HPR AA9 (SEQ ID NO: 4) showing ATG initiation and translation stop codons (boxed).

FIG. 42 shows the amino acid sequence of *L. rhamnosus* strain HN001 phosphoryl carrier protein HPR AA9 (SEQ ID NO: 45).

FIG. 43 shows the nucleotide sequence containing *L. rhamnosus* strain HN001 glyceraldehyde-3-phosphate dehydrogenase AK7 (SEQ ID NO: 23) showing ATG initiation and translation stop codons (boxed).

FIG. 44 shows the amino acid sequence of *L. rhamnosus* strain HN001 glyceraldehyde-3-phosphate dehydrogenase AK7 (SEQ ID NO: 65).

FIG. 45 shows the nucleotide sequence containing *L. rhamnosus* strain HN001 sorR transcription regulator AL3 (SEQ ID NO: 24) showing ATG initiation and translation stop codons (boxed).

FIG. 46 shows the amino acid sequence of *L. rhamnosus* strain HN001 sorR transcription regulator AL3 (SEQ ID NO: 66).

FIG. 47 shows the nucleotide sequence containing *L. rhamnosus* strain fpg gene AL4 (SEQ ID NO: 25) showing ATG initiation and translation stop codons (boxed).

FIG. 48 shows the amino acid sequence of HN001 fpg AL4 (SEQ ID NO: 67).

FIG. 49 shows the nucleotide sequence containing the *L. rhamnosus* strain HN001 acetoin dehydrogenase gene AP1 (SEQ ID NO: 32) showing ATG initiation and translation stop codons (boxed).

FIG. 50 shows the amino acid sequence of HN001 acetoin dehydrogenase AP1 (SEQ ID NO: 74).

Figure 51:
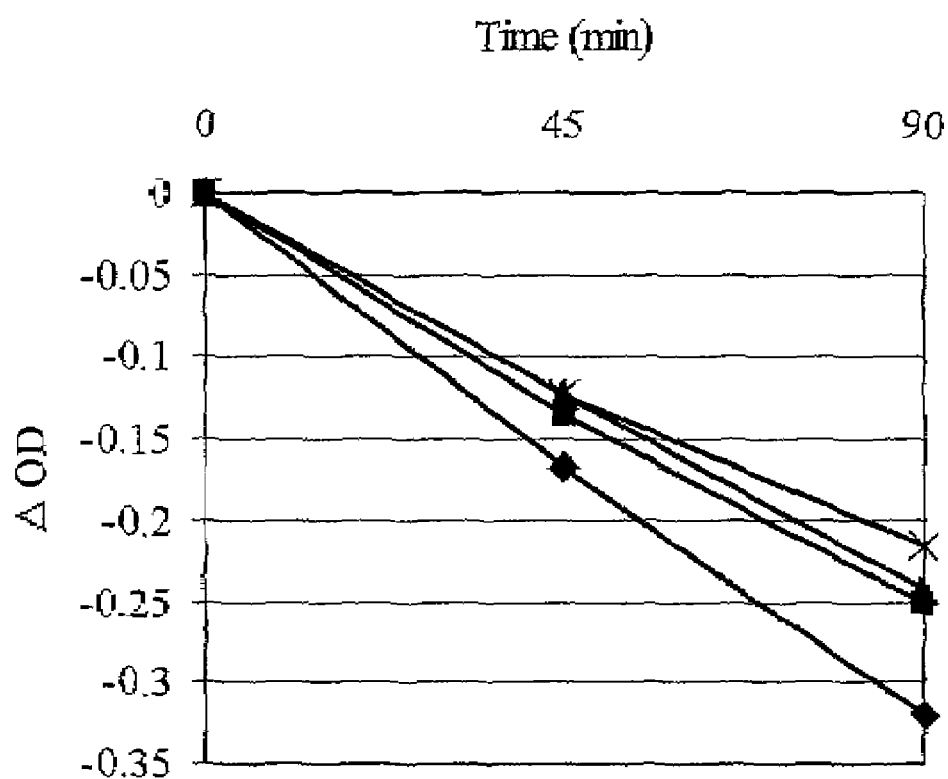

FIG. 51 illustrates the experimental results of an acetoin reductase assay as measured by oxidation of NADH co-factor by OD at 340 nm in the presence of acetoin substrate. ●, elution buffer only; ■, purified irrelevant GST-fusion protein; ▲, purified GST protein; ♦, purified AP1-GST fusion protein.

FIG. 52 shows the nucleotide sequence containing the *L. rhamnosus* strain HN001 aflatoxin $B_1$ aldehyde reductase gene AI7 (SEQ ID NO: 15) showing ATG initiation and translation stop codons (boxed).

FIG. 53 shows the amino acid sequence of HN001 aflatoxin $B_1$ aldehyde reductase AI7 (SEQ ID NO: 57).

Figure 54:
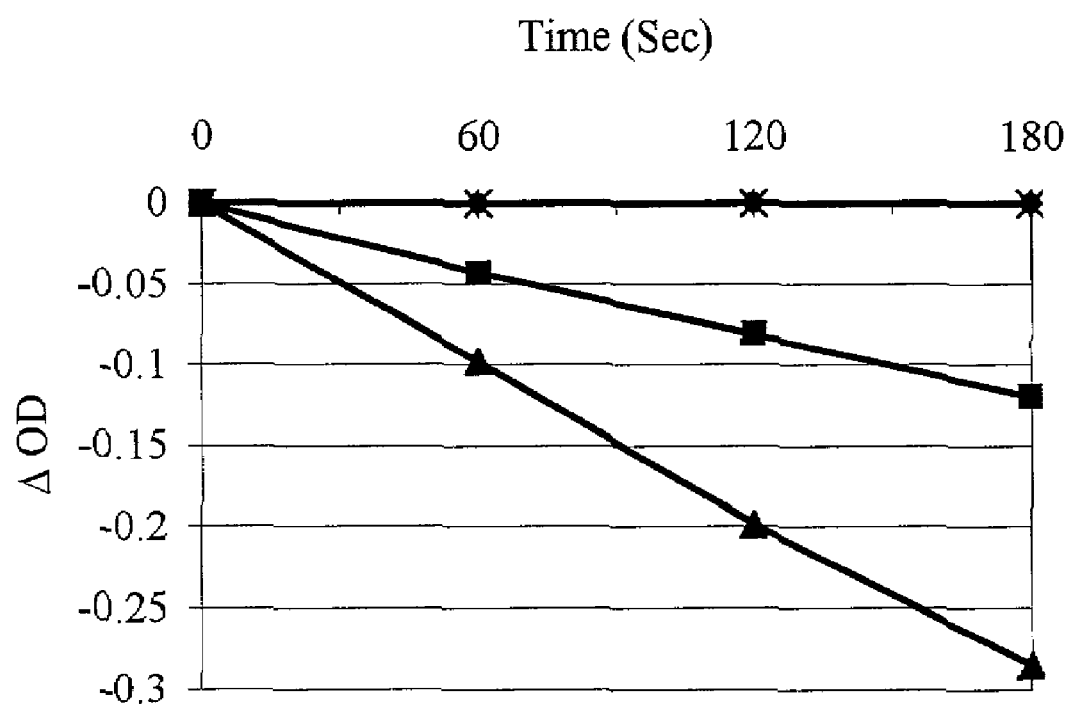

FIG. 54 shows the experimental results of aflatoxin $B_1$ aldehyde reductase assay according to oxidation of the NADPH co-factor in the presence of acetoin substrate. X , water only; +, Sepharose column elution buffer only; ●, irrelevant GST-fusion protein; ■, 10 µl purified AP4-GST fusion protein; ▲ 20 µl purified AP4-GST fusion protein.

Figure 55:
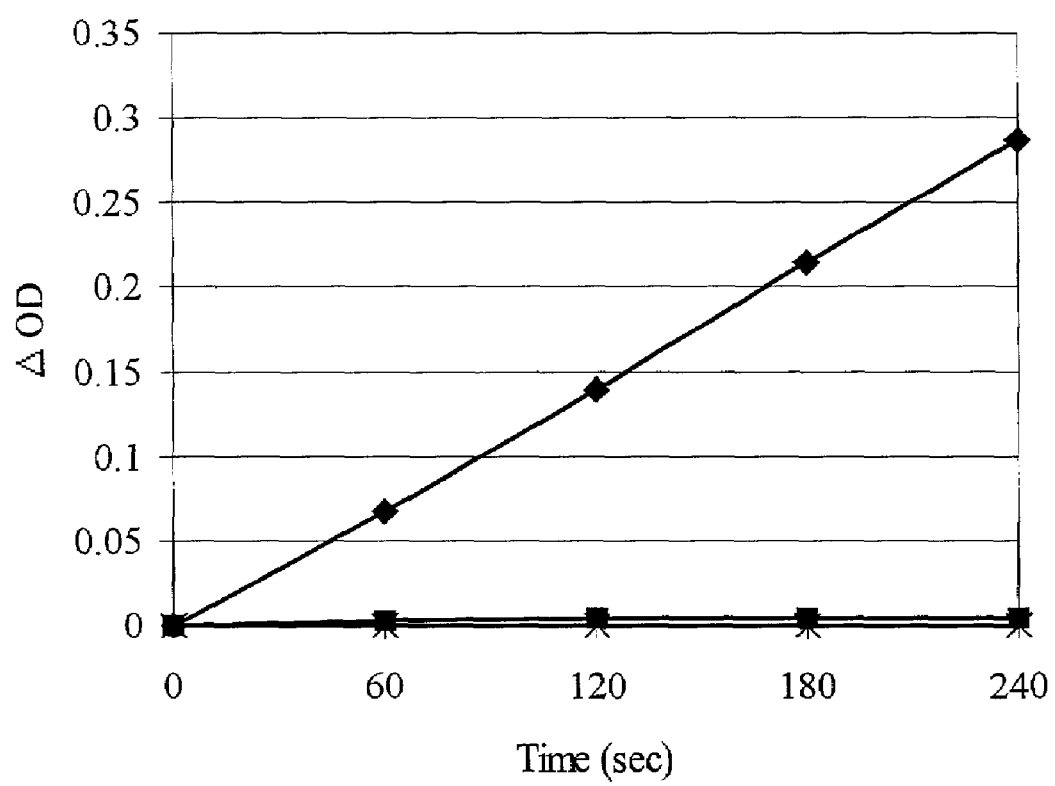

FIG. 55 shows the experimental determination of 6-Phospho-β-galactosidase enzyme activity as measured by substrate utilisation using crude lysates of strains transformed with pGex-6P-3 encoding A05 (♦), pGex-6P-3 encoding an irrelevant protein (■), or using lysis buffer only (X).

Figure 56:
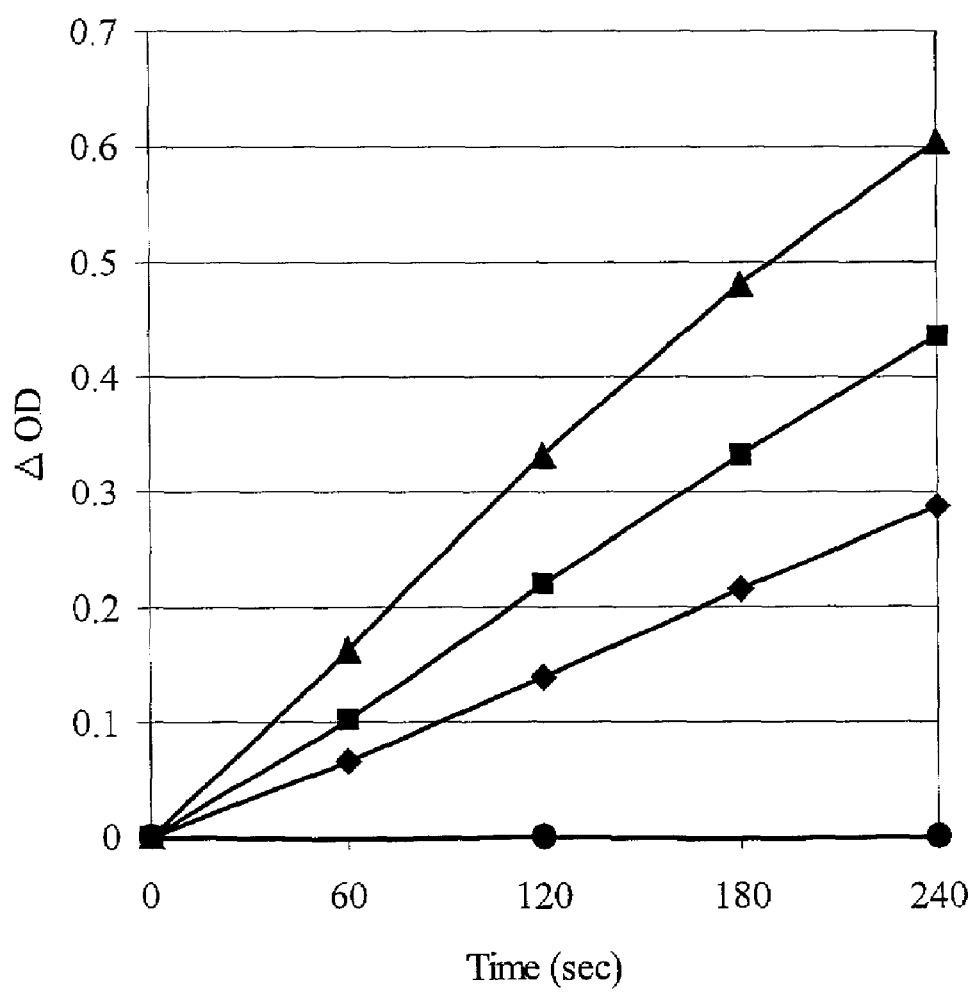

FIG. 56 shows the experimentally determined 6-Phospho-β-galactosidase enzyme activity as measured experimentally by substrate utilisation using increasing amounts of crude lysate from strains transformed with pGex-6P-3 encoding A05-GST fusion protein. ♦, 50 µl lysate; ■, 100 µl lysate; ●, 200 µl lysate; ♦, 200 µl lysis buffer only.

FIG. 57 shows the nucleotide sequence containing the *L. rhamnosus* strain HN001 aromatic aminotransferase gene AH7 (SEQ ID NO: 11) showing ATG initiation and translation stop codons (boxed).

FIG. 58 shows the amino acid sequence of HN001 aromatic aminotransferase AH7 (SEQ ID NO: 53).

FIG. 59 shows the nucleotide sequence containing the *L. rhamnosus* strain HN001 acetate kinase gene AP5 (SEQ ID NO: 33) showing ATG initiation and translation stop codons (boxed).

FIG. 60 shows the amino acid sequence of HN001 acetate kinase AP5 (SEQ ID NO: 75).

FIG. 61 shows the nucleotide sequence containing the *L. rhamnosus* strain HN001 basic surface protein gene AC9 (SEQ ID NO: 6) showing ATG initiation and translation stop codons (boxed).

FIG. 62 shows the amino acid sequence of HN001 basic surface protein AC9 (SEQ ID NO: 47).

FIG. 63 show the nucleotide sequence containing the *L. rhamnosus* strain HN001 aromatic outer membrane protein A AL8 (SEQ ID NO: 27) showing ATG initiation and translation stop codons (boxed).

FIG. 64 shows the amino acid sequence of HN001 outer membrane protein AL8 (SEQ ID NO: 69).

FIG. 65 show the nucleotide sequence containing the *L. rhamnosus* strain HN001 aromatic extracellular matrix binding protein AM4 (SEQ ID NO: 28) showing ATG initiation and translation stop codons (boxed).

FIGS. 66 show the amino acid sequence of HN001 extracellular matrix binding protein AM4 (SEQ ID NO: 70).

FIGS. 67 show the nucleotide sequence containing the *L. rhamnosus* strain HN001 aromatic high-molecular-weight adhesion protein AL7 (SEQ ID NO: 26) showing ATG initiation and translation stop codons (boxed).

FIG. 68 shows the amino acid sequence of HN001 high-molecular-weight adhesion protein AL7 (SEQ ID NO: 68).

FIG. 69 shows the nucleotide sequence containing the *L. rhamnosus* strain HN001 aromatic PEB1 AJ4 (SEQ ID NO: 16) showing ATG initiation and translation stop codons (boxed).

FIG. 70 shows the amino acid sequence of HN001 PEB1 AJ4 (SEQ ID NO: 58).

Figure 71:
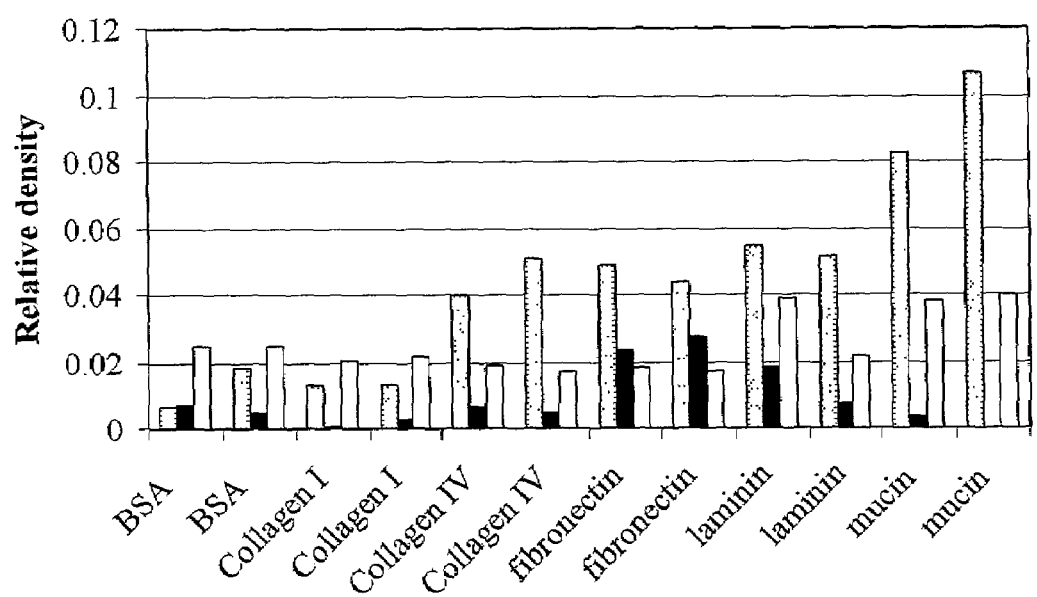

FIG. 71 shows the experimentally determined relative density of autoradiographic signals from AJ4 protein (grey bars) to dot blots of intestinal proteins, compared to a positive control (mapA, white bars) and negative control (irrelevant HN001 protein, black bars). Results for each dot (duplicates) are shown.

FIG. 72 shows the nucleotide sequence containing the *L. rhamnosus* strain HN001 dihydrodipicolinate reductase AI3 (SEQ ID NO: 14) showing ATG initiation and translation stop codons (boxed).

FIG. 73 shows the amino acid sequence of HN001 dihydrodipicolinate reductase AI3 (SEQ ID NO: 56).

FIG. 74 shows the nucleotide sequence containing the *L. rhamnosus* strain HN001 Fructose-bisphosphate aldolase AM8 (SEQ ID NO: 29) showing ATG initiation and translation stop codons (boxed).

FIG. 75 shows the amino acid sequence of HN001 Fructose-bisphosphate aldolase AM8 (SEQ ID NO: 71).

FIG. 76 shows the nucleotide sequence containing the *L. rhamnosus* strain HN001 chaperone protein dnaK AM9 (SEQ ID NO: 30) showing ATG initiation and translation stop codons (boxed).

FIG. 77 shows the amino acid sequence of HN001 chaperone protein dnaK AM9 (SEQ ID NO: 72).

FIG. 78 shows the nucleotide sequence containing the *L. rhamnosus* strain HN001 6-phospho-β-galactosidase gene AO5 (SEQ ID NO: 31) showing translation stop codon (boxed).

FIG. 79 shows the amino acid sequence of HN001 6-phospho-β-galactosidase AO5 (SEQ ID NO: 73).

FIG. 80 show the nucleotide sequence containing the *L. rhamnosus* strain HN001 peptidase pepO (SEQ ID NO: 1) showing ATG initiation and translation stop codons (boxed).

FIG. 81 shows the amino acid sequence of HN001 peptidase pepO (SEQ ID NO: 42).

DETAILED DESCRIPTION

The polynucleotides disclosed herein were isolated by high throughput sequencing of DNA libraries from the lactic acid bacteria *Lactobacillus rhamnosus* as described in Example 1. Cell wall, cell surface and secreted components of lactic acid bacteria are identified, the polynucleotides and polypeptides of the present invention including cell components selected from the group consisting of: peptidoglycans, teichoic acids, lipoteichoic acids, polysaccharides, adhesion proteins, secreted proteins, surface layer or S-layer proteins, collagen binding proteins and other cell surface proteins, and antibacterial substances such as bacteriocins and organic acids produced by these bacteria. Such bacterial cell components are known to mediate immune modulation, cell adhesion and antibacterial activities, producing many beneficial effects including: resistance to enteric pathogens: modulation of cancer, including colon cancer: anti-mutagenesis effects; reduction of small bowel bacterial overgrowth; modulation of auto-immune disorders; reduction in allergic disorders; modulation of urogenital infections, inflammatory bowel disorder, irritable bowel syndrome, *Helicobacter pylori* infection and hepatic encephalopathy; reduction of infection with pathogens; regulation of colonocyte proliferation and differentiation; reduction of mucosal permeability; and relief of constipation and diarrhea. Polynucleotides involved in the synthesis of these proteins and in the synthesis, modification, regulation, transport, synthesis and/or accumulation of precursor molecules for these proteins are used to modulate the immune effects, antibacterial, cell adhesion and competitive exclusion effects of the bacteria or of components that might be produced by these bacteria.

In order to function effectively as probiotic bacteria, *L. rhamnosus* HN001 survives environmental stress conditions in the gastrointestinal tract, as well as commercial and industrial processes. Modification of particular polynucleotides or regulatory processes have been shown to be effective against a number of stresses including oxidative stress, pH, osmotic stress, dehydration, carbon starvation, phosphate starvation, nitrogen starvation, amino acid starvation, heat or cold shock and mutagenic stress. Polynucleotides involved in stress resistance often confer multistress resistance, i.e., when exposed to one stress, surviving cells are resistant to several non-related stresses. Bacterial genes and/or processes shown to be involved in multistress resistance include:

Intracellular phosphate pools—inorganic phosphate starvation leads to the induction of pho regulon genes, and is linked to the bacterial stringent response. Gene knockouts involving phosphate receptor genes appear to lead to multistress resistance.

Intracellular guanosine pools—purine biosynthesis and scavenger pathways involve the production of phosphate-guanosine compounds that act as signal molecules in the bacterial stringent response. Gene knockouts involving purine scavenger pathway genes appear to confer multistress resistance.

Osmoregulatory molecules—small choline-based molecules, such as glycine-betaine, and sugars, such as trehalose, are protective against osmotic shock and are rapidly imported and/or synthesized in response to increasing osmolarity.

Acid resistance—*lactobacilli* naturally acidify their environment through the excretion of lactic acid, mainly through the cit operon genes responsible for citrate uptake and utilization.

Stress response genes—a number of genes appear to be induced or repressed by heat shock, cold shock, and increasing salt through the action of specific promoters.

The isolated polynucleotides of the present invention, and genetic constructs comprising such polynucleotides may be employed to produce bacteria having desired phenotypes, including increased resistance to stress and improved fermentation properties. Such genetic constructs may be used to increase production of selected polypeptides of the present invention in modified bacteria, or to produce modified levels and/or compositions of polypeptides related to polypeptides of the present invention in modified bacteria. Bacteria having desired phenotypes may also be produced by modulating the transcription and/or expression of polynucleotides of the present invention and incorporating modified regulatory elements in modified bacteria. Additionally, production of selected polypeptides of the present invention may be reduced or blocked in modified bacteria using techniques, such as antisense or gene silencing techniques, that are well known in the art. Such modified bacteria are also encompassed in the present invention.

Many enzymes are known to influence dairy product flavor, functional and textural characteristics, as well as general fermentation characteristics such as speed of growth, acid production and survival. These enzymes include those involved in the metabolism of lipids, polysaccharides, amino acids and carbohydrates, as well as those involved in the lysis of the bacterial cells.

The isolated polynucleotides and polypeptides of the present invention have been demonstrated to have the identities, functions and utilities described throughout this application and in the Examples. The polynucleotide and polypeptide SEQ ID NOS. of the present invention, and corresponding identification and functional information is provided below in Table 1A.

TABLE 1A

| SEQ ID NO Polynucleotide | SEQ ID NO Polypeptide | Category | Identification and Description |
|---|---|---|---|
| 1 | 42 | Flavor, nutrition | Peptidases are enzymes that break the peptide bonds linking the amino group of one amino acid with the carboxy group (acid group) of an adjacent amino acid in a peptide chain. Peptidases are important in the process of cheese ripening and the development of cheese flavor. |

TABLE 1A-continued

| SEQ ID NO Poly-nucleotide | SEQ ID NO Poly-peptide | Category | Identification and Description |
|---|---|---|---|
| 2 | 43 | Flavor, carbohydrate metabolism | Homolog isolated from *L. rhamnosus* of citM malic enzyme that catalyzes L-malate oxidative decarboxylation and pyruvate reductive carboxylation. It is part of the noncyclic, branched pathway "tricarboxylic acid cycle" that is characteristic of anaerobic citrate metabolism and is part of the pathway that converts L-malate to L-lactate. |
| 3 | 44 | Flavor | Homolog isolated from *L. rhamnosus* of her esterase that catalyzes the lipolysis of milk fat in dairy products such that the triglycerides are hydrolyzed to free fatty acids and glycerol or mono- and diglycerides. The protein plays an essential role in the development of flavor in cheese |
| 4 | 45 | Survival | Homolog isolated from *L. rhamnosus* of JP28/pbH phosphoryl carrier protein HPR, involved in the phosphoenolpyruvate: carbohydrate phosphotransferase system (PTS) that is responsible for the uptake and phosphorylation of a number of carbohydrates. The gene is up-regulated on heatshock |
| 5 | 46 | Amino acid metabolism, flavor | Homolog isolated from *L. rhamnosus* of metC cystathione beta-lyase (EC 4.4.1.8) that is involved in metabolism of sulpher-containing compounds with important flavor impacts. |
| 6 | 47 | Adhesion | Homolog isolated from *L. rhamnosus* of basic surface protein bspA (1) that is involved in adhesion to intestinal epithelial cells and binds mucin. |
| 7 | 48 | Amino acid metabolism, flavor | Homolog isolated from *L. rhamnosus* of serine dehydratase sdhB, beta subunit that is involved in the production of pyruvate from serine. It plays a role in metabolism, flavor and survival in carbohydrate poor media (including milk). |
| 7 | 49 | Amino acid metabolism, flavor | Homolog isolated from *L. rhamnosus* of the serine dehydratse alpha subunit sdhA that is involved in the production of pyruvate from serine. It plays a role in metabolism, flavor and survival in carbohydrate poor media (including milk). |
| 8 | 50 | Amino acid metabolism, flavor | Homolog isolated from *L. rhamnosus* of Aminotransferase HisC that is involved in histidine biosynthesis. It plays a role in the development flavor and biogenic amines. |
| 9 | 51 | Flavor, carbohydrate metabolism | Homolog isolated from *L. rhamnosus* of malate dehydrogenase citH that is involved in amino acid biosynthesis as well as L-malate utilization pathways. It is important for carbohydrate metabolism and production of flavor intermediates. |
| 10 | 52 | Adhesion | Homolog isolated from *L. rhamnosus* of autoaggregation protein aggH that plays a role in colonization of intestinal surface by excluding other bacteria from binding sites. |
| 11 | 53 | Amino acid metabolism, flavor | Homolog isolated from *L. rhamnosus* of aromatic amino acid transferase araT (1) that is involved in production of flavor compounds. |
| 12 | 54 | Amino acid metabolism, flavor | Homolog isolated from *L. rhamnosus* of aspartate aminotransferase aspB that produces alpha-ketoglutarate using L-glutamate as an amino donor. It is involved in production of important flavor determinants. |
| 13 | 55 | Amino acid metabolism, flavor | Homolog isolated from *L. rhamnosus* of dihydrodipicolinate synthase dapA (EC 4.2.1.52) that converts L-aspartate 4-semialdehyde and pyruvate to 1-2,3-dihydrodipicolinate as part of the lysine biosynthesis pathway. L-aspartate 4-semialdehyde is also the first step of the glycine, serine and threonine metabolic pathways. It is involved in production of important flavor determinants |

TABLE 1A-continued

| SEQ ID NO Poly-nucleotide | SEQ ID NO Poly-peptide | Category | Identification and Description |
|---|---|---|---|
| 14 | 56 | Amino acid metabolism, flavor | Homolog isolated from *L. rhamnosus* of dihydrodipicolinate reductase dapB (EC 1.3.1.26) that converts L-2,3-dihydrodipicolinate to L-tetrahydropicolinate as part of the lysine biosynthesis pathway. L-aspartate 4-semialdehyde is also the first step of the glycine, serine and threonine metabolic pathways. It is involved in production of important flavor determinants. |
| 15 | 57 | Health | Homolog isolated from *L. rhamnosus* of Aflatoxin B1 aldehyde reductase afar that metabolizes the carcinogen aflatoxin B1 (AFB1) and that is associated with AFB1-resistance. Afar is active against particular ketones, aromatic and aliphatic aldehydes and is an antocarcinogenic. It is also useful for the production of flavor compounds. |
| 16 | 58 | Adhesion | Homolog isolated from *L. rhamnosus* of pebB that mediates binding to epithelial cells, excludes binding of other bacteria and prevents pathogenic infection. It is involved in colonization of intestinal surfaces. |
| 17 | 59 | Amino acid metabolism, flavor | Homolog isolated from *L. rhamnosus* of Pyridoxal-5'-phosphate-dependent aminotransferase patB (1) that has both aminotransferase and regulatory activities, including the transamination of methionine and regulation of maltose utilization. It plays a role in production of flavor intermediates and growth on particular sugars. |
| 18 | 60 | Amino acid metabolism, flavor | Homolog isolated from *L. rhamnosus* of Pyridoxal-5'-phosphate-dependent aminotransferase patB (2) that has both aminotransferase and regulatory activities, including the transamination of methionine and regulation of maltose utilization. It plays a role in production of flavor intermediates and growth on particular sugars. |
| 19 | 61 | Survival | Homolog isolated from *L. rhamnosus* of Tagatose 1,6-diphosphate aldolase lacD (EC 4.1.2.40), a glycolytic enzyme that is up-regulated by stress conditions and is involved in stress resistance and carbohydrate utilization. |
| 20 | 62 | Survival | Homolog isolated from *L. rhamnosus* of Phosphoenolpyruvate hydratase eno (EC 4.2.1.11), a glycolytic enzyme up-regulated by stress conditions. It is involved in stress resistance and carbohydrate utilization. |
| 21 | 63 | Survival | Homolog isolated from *L. rhamnosus* of triosephosphate isomerase tpi (EC 5.3.1.1), a glycolytic enzyme up-regulated by stress conditions. It is involved in stress resistance and carbohydrate utilization. |
| 22 | 64 | Survival | Homolog isolated from *L. rhamnosus* of phosphoglycerate kinase pgk (EC 2.7.2.3), a glycolytic enzyme up-regulated by stress conditions. It is involved in stress resistance and carbohydrate utilization. |
| 23 | 65 | Cell wall structure and function | Homolog isolated from *L. rhamnosus* of Glyceraldehyde-3-phosphate dehydrogenase gapdh (EC 1.2.1.12), a glycolytic enzyme up-regulated by stress conditions. It is involved in stress resistance and carbohydrate utilization and is also a major cell wall component. |
| 24 | 66 | Regulation | Homolog isolated from *L. rhamnosus* of the positive regulator sorR in the sorbose operon. It is important in the control of carbohydrate metabolism and useful for inducible promoter for novel vectors. |

TABLE 1A-continued

| SEQ ID NO Poly-nucleotide | SEQ ID NO Poly-peptide | Category | Identification and Description |
|---|---|---|---|
| 25 | 67 | Survival | Homolog isolated from *L. rhamnosus* of Formamidopyrimidine-DNA-glycosylase fpg that is important in protecting bacterial DNA against oxidative free radicals. It removes oxidized purine residues present in DNA, including the highly mutagenic C8-oxo-guanine (8-oxoG) generated in DNA by active oxygen during metabolism. It plays an important role in stress resistance. |
| 26 | 68 | Adhesion | Homolog isolated from *L. rhamnosus* of hia, that mediates binding to epithelial cells and excludes binding of other bacteria. It is involved in colonization of intestinal surfaces. |
| 27 | 69 | Adhesion | Homolog isolated from *L. rhamnosus* of Outer membrane protein rompA, a surface bound molecule required for adhesion. |
| 28 | 70 | Adhesion | Homolog isolated from *L. rhamnosus* of MLC36 / emb that mediates binding to epithelial cells, excludes binding of other bacteria and prevents pathogenic infection. It is involved in colonization of intestinal surfaces and is involved in plasminogen binding. It plays a role in immune impacts. |
| 29 | 71 | Survival | Homolog isolated from *L. rhamnosus* of Fructose-bisphosphate aldolase fba (EC 4.1.2.13), a glycolytic enzyme that catalyzes the elimination reaction of D-Fructose 1,6-bisphosphate to glycerone phosphate and D-glyceraldehyde 3-phosphate. It is Up-regulatedby shock and is involved in metabolism, as a flavor intermediates and in stress resistance. |
| 30 | 72 | Stress resistance | Homolog isolated from *L. rhamnosus* of chaperone protein dnaK that plays a role in enhanced bacterial survival in industrial processes, improved colonization of human intestinal environment, altered protein translation characteristics and control of plasmid stability. |
| 31 | 73 | Bacterial growth, nutrition, flavor development | Homolog isolated from *L. rhamnosus* of 6-phospho-β-galactosidase (EC 3.2.1.85) that catalyzes the hydrolysis of O-glycosyl bonds of 6-phospho-beta-D-galactosides to give alcohols and 6-phospho-D-galactose, and is involved in lactose utilization. It is useful for flavor and aroma enhancement, nutritional enhancement, altered bacterial metabolic/growth characteristics and removal of bitter or undesirable flavors. |
| 32 | 74 | Flavor | Homolog isolated from *L. rhamnosus* of Acetoin dehydrogenase butA (EC 1.1.1.5) that catalyzes the reduction of diacetyl to acetoin, and acetoin to 2,3-butanediol as part of the pyruvate to 2,3-butanediol pathway. Diacetyl is an important dairy flavor component. |
| 33 | 75 | Flavor | Homolog isolated from *L. rhamnosus* of Acetyl kinase ackA (EC 2.7.2.1) that catalyzes the phosphotransfer between ADP and acetyl phosphate to yield ATP and acetate. |

Isolated polynucleotides of the present invention include the polynucleotides identified herein as SEQ ID NOS: 1–33; isolated polynucleotides comprising a polynucleotide sequence selected from the group consisting of SEQ ID NOS: 1–33; isolated polynucleotides comprising at least a specified number of contiguous residues (x-mers) of any of the polynucleotides identified as SEQ ID NOS: 1–33; isolated polynucleotides comprising a polynucleotide sequence that is complementary to any of the above polynucleotides; isolated polynucleotides comprising a polynucleotide sequence that is a reverse sequence or a reverse complement of any of the above polynucleotides; antisense sequences corresponding to any of the above polynucleotides; and variants of any of the above polynucleotides, as that term is described in this specification.

The word "polynucleotide(s)," as used herein, means a single or double stranded polymer of deoxyribonucleotide or ribonucleotide bases and includes DNA and corresponding RNA molecules, including mRNA molecules, both sense and antisense strands of DNA and RNA molecules, and comprehends cDNA, genomic DNA and recombinant DNA, as well as wholly or partially synthesized polynucleotides. A polynucleotide of the present invention may be an entire gene, or any portion thereof A gene is a DNA sequence which codes for a functional protein or RNA molecule. Operable antisense polynucleotides may comprise a fragment of the corresponding polynucleotide, and the definition of "polynucleotide" therefore includes all operable antisense fragments. Antisense polynucleotides and techniques involving antisense polynucleotides are well known in the art and are described, for example, in Robinson-Benion, et al., "Antisense techniques," *Methods in Enzymol.* 254(23): 363–375, 1995; and Kawasaki, et al., *Artific. Organs* 20 (8): 836–848, 1996.

The definitions of the terms "complement," "reverse complement," and "reverse sequence," as used herein, are best illustrated by the following examples. For the sequence 5' AGGACC 3', the complement, reverse complement, and reverse sequences are as follows:

```
complement              3' TCCTGG 5' reverse complement      3' GGTCCT 5' reverse sequence        5' CCAGGA 3'
```

Identification of genomic DNA and heterologous species DNA can be accomplished by standard DNA/DNA hybridization techniques, under appropriately stringent conditions, using all or part of a DNA sequence as a probe to screen an appropriate library. Alternatively, PCR techniques using oligonucleotide primers that are designed based on known DNA and protein sequences can be used to amplify and identify other identical or similar DNA sequences. Synthetic DNA corresponding to the identified sequences or variants thereof may be produced by conventional synthesis methods. All of the polynucleotides described herein are isolated and purified, as those terms are commonly used in the art.

The polynucleotides identified as SEQ ID NOS: 1–33 contain open reading frames ("ORFs"), or partial open reading frames, encoding polypeptides. The open reading frames are specifically identified in Example 1. Additionally, polynucleotides identified as SEQ ID NOS: 1–33 may contain non-coding sequences such as promoters and terminators that may be useful as control elements. The open reading frames contained in polynucleotides of the present invention may be isolated and/or synthesized. Expressible genetic constructs comprising the open reading frames and suitable promoters, initiators, terminators, etc., which are well known in the art, may then be constructed. Such genetic constructs may be introduced into a host cell to express the polypeptide encoded by the open reading frame. Expression of quantities of a polypeptide of the present invention using recombinant methodologies is useful, for example, when polynucleotides of the present invention are used as nutritional supplements, as flavor and/or texture enhancers, or the like.

Genetic constructs may be also designed and constructed, as is known in the art, to enhance or silence expression of an identified polypeptide. Antisense and gene silencing genetic constructs may be designed and constructed, for example, to reduce or silence expression of polypeptides of the present invention. Genetic constructs of the present invention may thus be assembled using techniques known in the art to enhance or reduce expression of polypeptides of the present invention encoded by polynucleotides of the present invention. Suitable host cells may include various prokaryotic and eukaryotic cells. In vitro expression of polypeptides is also possible, as well known in the art.

As used herein, the term "oligonucleotide" refers to a relatively short segment of a polynucleotide sequence, generally comprising between 6 and 60 nucleotides, and comprehends both probes for use in hybridization assays and primers for use in the amplification of DNA by polymerase chain reaction.

As used herein, the term "x-mer," with reference to a specific value of "x," refers to a polynucleotide or polypeptide comprising at least a specified number ("x") of contiguous residues of any of the polynucleotides and polypeptides identified as SEQ ID NOS: 1–33 and 42–75. The value of x may be from about 20 to about 600, depending upon the specific sequence.

In another aspect, the present invention provides isolated polypeptides encoded, or partially encoded, by the above polynucleotides, including the polypeptides identified as SEQ ID NOS: 42–75. As used herein, the term "polypeptide" encompasses amino acid chains of any length, including full-length proteins, wherein the amino acid residues are linked by covalent peptide bonds. The term "polypeptide encoded by a polynucleotide" as used herein, includes polypeptides encoded by a polynucleotide which comprises an isolated polynucleotide sequence or variant provided herein. Polypeptides of the present invention may be naturally purified products, or may be produced partially or wholly using recombinant techniques. Such polypeptides may be glycosylated with bacterial, fungal, mammalian or other eukaryotic carbohydrates or may be non-glycosylated.

Polypeptides of the present invention may be produced recombinantly by inserting a polynucleotide that encodes the polypeptide into an expression vector and expressing the polypeptide in an appropriate host. Any of a variety of expression vectors known to those of ordinary skill in the art may be employed. Expression may be achieved in any appropriate host cell that has been transformed or transfected with an expression vector containing a polynucleotide encoding a recombinant polypeptide. Suitable host cells include prokaryotes, yeast and higher eukaryotic cells. Preferably, the host cells employed are *Escherichia coli, Lactococcus lactis, Lactobacillus*, insect, yeast or mammalian cell lines, such as COS and CHO. The polynucleotide(s) expressed in this manner may encode naturally occurring polypeptides, portions of naturally occurring polypeptides, or other variants thereof.

In a related aspect, polypeptides are provided that comprise at least a functional portion of a polypeptide having an amino acid sequence encoded by a polynucleotide of the present invention. As used herein, a "functional portion" of a polypeptide is that portion which contains the active site essential for affecting the function of the polypeptide, for example, the portion of the molecule that is capable of binding one or more reactants. The active site may be made up of separate portions present on one or more polypeptide chains and will generally exhibit high binding affinity.

Functional portions of a polypeptide may be identified by first preparing fragments of the polypeptide by either chemical or enzymatic digestion of the polypeptide, or by mutation analysis of the polynucleotide that encodes the polypeptide and subsequent expression of the resulting mutant polypeptides. The polypeptide fragments or mutant polypeptides are then tested to determine which portions retain biological activity, using, for example, the representative assays provided below.

Portions and other variants of the inventive polypeptides may be generated by synthetic or recombinant means. Synthetic polypeptides having fewer than about 100 amino acids, and generally fewer than about 50 amino acids, may be generated using techniques that are well known to those of ordinary skill in the art. For example, such polypeptides may be synthesized using any of the commercially available solid-phase techniques, such as the Merrifield solid-phase synthesis method, where amino acids are sequentially added to a growing amino acid chain (See Merrifield, *J. Am. Chem. Soc.* 85:2149–2154, 1963). Equipment for automated synthesis of polypeptides is commercially available from suppliers such as Perkin Elmer/Applied Biosystems, Inc. (Foster City, Calif.), and may be operated according to the manufacturer's instructions. Variants of a native polypeptide may be prepared using standard mutagenesis techniques, such as oligonucleotide-directed site-specific mutagenesis (Kunkel, *Proc. Natl. Acad. Sci. USA* 82: 488–492, 1985). Sections of DNA sequences may also be removed using standard techniques to permit preparation of truncated polypeptides.

In general, the polypeptides disclosed herein are prepared in an isolated, substantially pure form. Preferably, the polypeptides are at least about 80% pure; more preferably at least about 90% pure; and most preferably at least about 99% pure.

As used herein, the term "variant" comprehends polynucleotide or polypeptide sequences different from the specifically identified sequences, wherein one or more nucleotides or amino acid residues is deleted, substituted, or added. Variants may be naturally occurring allelic variants, or non-naturally occurring variants. Variant polynucleotide sequences preferably exhibit at least 40%, more preferably at least 60%, more preferably yet at least 75%, and most preferably at least 90% or 95% identity to a sequence of the present invention. Variant polypeptide sequences preferably exhibit at least 50%, more preferably at least 75%, more preferably yet at least 90%, and most preferably at least 95% identity to a sequence of the present invention. The percentage identity is determined by aligning the two sequences to be compared as described below, determining the number of identical residues in the aligned portion, dividing that number by the total number of residues in the inventive (queried) sequence, and multiplying the result by 100.

Polynucleotide and polypeptide sequences may be aligned, and the percentage of identical residues in a specified region may be determined against another polynucleotide or polypeptide, using computer algorithms that are publicly available. Two exemplary algorithms for aligning and identifying the similarity of polynucleotide sequences are the BLASTN and FASTA algorithms. Polynucleotides may also be analyzed using the BLASTX algorithm, which compares the six-frame conceptual translation products of a nucleotide query sequence (both strands) against a protein sequence database. The percentage identity of polypeptide sequences may be examined using the BLASTP algorithm. The BLASTN, BLASTX and BLASTP programs are available on the NCBI anonymous FTP server from the National Center for Biotechnology Information (NCBI), National Library of Medicine, Building 38A, Room 8N805, Bethesda, Md. 20894, USA. The BLASTN algorithm Version 2.0.11 [Jan. 20, 2000], set to the parameters described below, is preferred for use in the determination of polynucleotide variants according to the present invention. The BLASTP algorithm, set to the parameters described below, is preferred for use in the determination of polypeptide variants according to the present invention. The use of the BLAST family of algorithms, including BLASTN, BLASTP and BLASTX, is described at NCBI's website and in the publication of Altschul, et al., *Nucleic Acids Res.* 25: 3389–3402, 1997.

The computer algorithm FASTA is available on the Internet at the ftp site ftp://ftp.virginia.edu/pub/fasta/, and from the University of Virginia by contacting David Hudson, Vice Provost for Research, University of Virginia, P.O. Box 9025, Charlottesville, Va. 22906-9025, USA. FASTA Version 2.0u4 [February 1996], set to the default parameters described in the documentation and distributed with the algorithm, may be used in the determination of variants according to the present invention. The use of the FASTA algorithm is described in Pearson and Lipman, *Proc. Natl. Acad. Sci. USA* 85:2444–2448, 1988; and Pearson, *Methods in Enzymol.* 183: 63–98, 1990.

The following running parameters are preferred for determination of alignments and similarities using BLASTN that contribute to the E values and percentage identity for polynucleotide sequences: Unix running command: blastall -p blastn -d embldb -e 10 -G0 -E0 -r 1 -v 30 -b 30 -i queryseq -o results; the parameters are: -p ProgramName [String]; -d Database [String]; -e Expectation value (E) [Real]; -G Cost to open a gap (zero invokes default behavior) [Integer]; -E Cost to extend a gap (zero invokes default behavior) [Integer]; -r Reward for a nucleotide match (BLASTN only) [Integer]; -v Number of one-line descriptions (V) [Integer]; -b Number of alignments to show (B) [Integer]; -i Query File [File In]; and -o BLAST report Output File [File Out] Optional.

The following running parameters are preferred for determination of alignments and similarities using BLASTP that contribute to the E values and percentage identity of polypeptide sequences: blastall -p blastp -d swissprotdb -e 10 -G 0 -E 0 -v 30 -b 30 -i queryseq -o results; the parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -v Number of one-line descriptions (v) [Integer]; -b Number of alignments to show (b) [Integer]; -I Query File [File In]; -o BLAST report Output File [File Out] Optional. The "hits" to one or more database sequences by a queried sequence produced by BLASTN, FASTA, BLASTP or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, FASTA, and BLASTP algorithms also produce "Expect" values for alignments. The Expect value (E) indicates the number of hits one can "expect" to see over a certain number of contiguous sequences by chance when searching a database of a certain size. The Expect value is used as a significance threshold for determining whether the hit to a database, such as the preferred EMBL database, indicates true similarity. For example, an E value of 0.1 assigned to a polynucleotide hit is interpreted as meaning that in a database of the size of the EMBL database, one might expect to see 0.1 matches over the aligned portion of the sequence with a similar score simply by chance. By this criterion, the aligned and matched portions of the polynucleotide sequences then have a probability of 90% of being the same. For sequences having an E value of 0.01 or less over aligned and matched portions, the probability of finding a match by chance in the EMBL database is 1% or less using the BLASTN or FASTA algorithm.

According to one embodiment, "variant" polynucleotides and polypeptides, with reference to each of the polynucleotides and polypeptides of the present invention, preferably comprise sequences producing an E value of 0.01 or less using the BLASTN, FASTA, or BLASTP algorithms set at parameters described above when compared to the polynucleotide or polypeptide of the present invention. According to a preferred embodiment, a variant polynucleotide is a sequence having an E value of 0.01 or less using the BLASTN or FASTA algorithms set at parameters described above when analyzed against a polynucleotide of the present invention. Similarly, according to a preferred embodiment, a variant polypeptide is a sequence having an E value of 0.01 or less using the BLASTP algorithm set at the parameters described above when analyzed against a polynucleotide of the present invention.

As noted above, the percentage identity is determined by aligning sequences using one of the BLASTN, FASTA, or BLASTP algorithms, set at the running parameters described above, and identifying the number of identical nucleic or amino acids over the aligned portions; dividing the number of identical nucleic or amino acids by the total number of nucleic or amino acids of the polynucleotide or polypeptide sequence of the present invention; and then multiplying by 100 to determine the percentage identity. For example, a polynucleotide of the present invention having 220 nucleic acids has a hit to a polynucleotide sequence in the EMBL database having 520 nucleic acids over a stretch of 23 nucleotides in the alignment produced by the BLASTN algorithm using the parameters described above. The 23 nucleotide hit includes 21 identical nucleotides, one gap and one different nucleotide. The percentage identity of the polynucleotide of the present invention to the hit in the EMBL library is thus $21/220$ times 100, or 9.5%. The polynucleotide sequence in the EMBL database is thus not a variant of a polynucleotide of the present invention.

In addition to having a specified percentage identity to an inventive polynucleotide or polypeptide sequence, variant polynucleotides and polypeptides preferably have additional structure and/or functional features in common with the inventive polynucleotide or polypeptide. Polypeptides having a specified degree of identity to a polypeptide of the present invention share a high degree of similarity in their primary structure and have substantially similar functional properties. In addition to sharing a high degree of similarity in their primary structure to polynucleotides of the present invention, polynucleotides having a specified degree of identity to, or capable of hybridizing to an inventive polynucleotide preferably have at least one of the following features: (i) they contain an open reading frame or partial open reading frame encoding a polypeptide having substantially the same functional properties as the polypeptide encoded by the inventive polynucleotide; or (ii) they contain identifiable domains in common.

Alternatively, variant polynucleotides of the present invention hybridize to the polynucleotide sequences recited in SEQ ID NOS: 1–33, or complements, reverse sequences, or reverse complements of those sequences under stringent conditions. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

The present invention also encompasses polynucleotides that differ from the disclosed sequences but that, as a consequence of the discrepancy of the genetic code, encode a polypeptide having similar enzymatic activity as a polypeptide encoded by a polynucleotide of the present invention. Thus, polynucleotides comprising sequences that differ from the polynucleotide sequences recited in SEQ ID NOS: 1–33, or complements, reverse sequences, or reverse complements of those sequences as a result of conservative substitutions are encompassed within the present invention. Additionally, polynucleotides comprising sequences that differ from the inventive polynucleotide sequences or complements, reverse complements, or reverse sequences as a result of deletions and/or insertions totaling less than 10% of the total sequence length are also contemplated by and encompassed within the present invention. Similarly, polypeptides comprising sequences that differ from the inventive polypeptide sequences as a result of amino acid substitutions, insertions, and/or deletions totaling less than 15% of the total sequence length are contemplated by and encompassed within the present invention, provided the variant polypeptide has similar activity to the inventive polypeptide.

The polynucleotides of the present invention may be isolated from various libraries, or may be synthesized using techniques that are well known in the art. The polynucleotides may be synthesized, for example, using automated oligonucleotide synthesizers (e.g., Beckman Oligo 1000M DNA Synthesizer) to obtain polynucleotide segments of up to 50 or more nucleic acids. A plurality of such polynucleotide segments may then be ligated using standard DNA manipulation techniques that are well known in the art of molecular biology. One conventional and exemplary polynucleotide synthesis technique involves synthesis of a single stranded polynucleotide segment having, for example, 80 nucleic acids, and hybridizing that segment to a synthesized complementary 85 nucleic acid segment to produce a 5-nucleotide overhang. The next segment may then be synthesized in a similar fashion, with a 5-nucleotide overhang on the opposite strand. The "sticky" ends ensure proper ligation when the two portions are hybridized. In this way, a complete polynucleotide of the present invention may be synthesized entirely in vitro.

Polynucleotides and polypeptides of the present invention comprehend polynucleotides and polypeptides comprising at least a specified number of contiguous residues (x-mers) of any of the polynucleotides and polypeptides identified as SEQ ID NOS: 1–33 and 42–75 or their variants. According to preferred embodiments, the value of x is preferably at least 20, more preferably at least 40, more preferably yet at least 60, and most preferably at least 80. Thus, polynucleotides and polypeptides of the present invention include polynucleotides comprising a 20-mer, a 40-mer, a 60-mer, an 80-mer, a 100-mer, a 120-mer, a 150-mer, a 180-mer, a 220-mer a 250-mer, or a 300-mer, 400-mer, 500-mer or 600-mer of a polynucleotide or polypeptide identified as SEQ ID NOS: 1–75 or a variant of one of the polynucleotides or polypeptides identified as SEQ ID NOS: 1–33 and 42–75.

Oligonucleotide probes and primers complementary to and/or corresponding to SEQ ID NOS: 1–33, and variants of those sequences, are also comprehended by the present invention. Such oligonucleotide probes and primers are substantially complementary to the polynucleotide of interest. An oligonucleotide probe or primer is described as "corresponding to" a polynucleotide of the present invention, including one of the sequences set out as SEQ ID NOS: 1–33 or a variant, if the oligonucleotide probe or primer, or its complement, is contained within one of the sequences set out as SEQ ID NOS: 1–33 or a variant of one of the specified sequences.

Two single stranded sequences are said to be substantially complementary when the nucleotides of one strand, optimally aligned and compared, with the appropriate nucleotide insertions and/or deletions, pair with at least 80%, preferably at least 90% to 95%, and more preferably at least 98% to 100%, of the nucleotides of the other strand. Alternatively, substantial complementarity exists when a first DNA strand will selectively hybridize to a second DNA strand under stringent hybridization conditions. Stringent hybridization conditions for determining complementarity include salt conditions of less than about 1 M, more usually less than about 500 mM and preferably less than about 200 mM. Hybridization temperatures can be as low as 5° C., but are generally greater than about 22° C., more preferably greater than about 30° C. and most preferably greater than about 37° C. Longer DNA fragments may require higher hybridization temperatures for specific hybridization. Since the stringency of hybridization may be affected by other factors such as probe composition, presence of organic solvents and extent of base mismatching, the combination of parameters is more important than the absolute measure of any one alone. DNA-DNA hybridization studies may performed using either genomic DNA or DNA derived by preparing cDNA from the RNA present in a sample to be tested.

In addition to DNA-DNA hybridization, DNA-RNA or RNA-RNA hybridization assays are also possible. In the first case, the mRNA from expressed genes would then be detected instead of genomic DNA or cDNA derived from mRNA of the sample. In the second case, RNA probes could be used. In addition, artificial analogs of DNA hybridizing specifically to target sequences could also be used.

In specific embodiments, the oligonucleotide probes and/or primers comprise at least about 6 contiguous residues, more preferably at least about 10 contiguous residues, and most preferably at least about 20 contiguous residues complementary to a polynucleotide sequence of the present invention. Probes and primers of the present invention may be from about 8 to 100 base pairs in length or, preferably from about 10 to 50 base pairs in length or, more preferably from about 15 to 40 base pairs in length. The primers and probes may be readily selected using procedures well known in the art, taking into account DNA-DNA hybridization stringencies, annealing and melting temperatures, potential for formation of loops and other factors, which are well known in the art. Tools and software suitable for designing probes, and especially suitable for designing PCR primers, are available on the Internet. In addition, a software program suitable for designing probes, and especially for designing PCR primers, is available from Premier Biosoft International, 3786 Corina Way, Palo Alto. Calif. 94303-4504. Preferred techniques for designing PCR primers are also disclosed in Dieffenbach and Dyksler, *PCR primer: a laboratory manual*, CSHL Press: Cold Spring Harbor, N.Y., 1995.

A plurality of oligonucleotide probes or primers corresponding to a polynucleotide of the present invention may be provided in a kit form. Such kits generally comprise multiple DNA or oligonucleotide probes, each probe being specific for a polynucleotide sequence. Kits of the present invention may comprise one or more probes or primers corresponding to a polynucleotide of the present invention, including a polynucleotide sequence identified in SEQ ID NOS: 1–33.

In one embodiment useful for high-throughput assays, the oligonucleotide probe kits of the present invention comprise multiple probes in an array format, wherein each probe is immobilized in a predefined, spatially addressable location on the surface of a solid substrate. Array formats which may be usefully employed in the present invention are disclosed, for example, in U.S. Pat. Nos. 5,412,087, 5,545,531, and PCT Publication No. WO 95/00530, the disclosures of which are hereby incorporated by reference.

Oligonucleotide probes for use in the present invention may be constructed synthetically prior to immobilization on an array, using techniques well known in the art (See, for example, Gait, ed., *Oligonucleotide synthesis a practical approach*, IRL Press: Oxford, England, 1984). Automated equipment for the synthesis of oligonucleotides is available commercially from such companies as Perkin Elmer/Applied Biosystems Division (Foster City, Calif.) and may be operated according to the manufacturer's instructions. Alternatively, the probes may be constructed directly on the surface of the array using techniques taught, for example, in PCT Publication No. WO 95/00530.

The solid substrate and the surface thereof preferably form a rigid support and are generally formed from the same material. Examples of materials from which the solid substrate may be constructed include polymers, plastics, resins, membranes, polysaccharides, silica or silica-based materials, carbon, metals and inorganic glasses. Synthetically prepared probes may be immobilized on the surface of the solid substrate using techniques well known in the art, such as those disclosed in U.S. Pat. No. 5,412,087.

In one such technique, compounds having protected functional groups, such as thiols protected with photochemically removable protecting groups, are attached to the surface of the substrate. Selected regions of the surface are then irradiated with a light source, preferably a laser, to provide reactive thiol groups. This irradiation step is generally performed using a mask having apertures at predefined locations using photolithographic techniques well known in the art of semiconductors. The reactive thiol groups are then incubated with the oligonucleotide probe to be immobilized. The precise conditions for incubation, such as temperature, time and pH, depend on the specific probe and can be easily determined by one of skill in the art. The surface of the substrate is washed free of unbound probe and the irradiation step is repeated using a second mask having a different pattern of apertures. The surface is subsequently incubated with a second, different, probe. Each oligonucleotide probe is typically immobilized in a discrete area of less than about 1 $mm^2$. Preferably each discrete area is less than about 10,000 $mm^2$, more preferably less than about 100 $mm^2$. In this manner, a multitude of oligonucleotide probes may be immobilized at predefined locations on the array.

The resulting array may be employed to screen for differences in organisms or samples or products containing genetic material as follows. Genomic or cDNA libraries are prepared using techniques well known in the art. The resulting target DNA is then labeled with a suitable marker, such as a radiolabel, chromophore, fluorophore or chemiluminescent agent, using protocols well known for those skilled in the art. A solution of the labeled target DNA is contacted with the surface of the array and incubated for a suitable period of time.

The surface of the array is then washed free of unbound target DNA and the probes to which the target DNA hybridized are determined by identifying those regions of the array to which the markers are attached. When the marker is a radiolabel, such as $^{32}P$, autoradiography is employed as the detection method. In one embodiment, the marker is a fluorophore, such as fluorescein, and the location of bound target DNA is determined by means of fluorescence spectroscopy. Automated equipment for use in fluorescence scanning of oligonucleotide probe arrays is available from Affymetrix, Inc. (Santa Clara, Calif.) and may be operated according to the manufacturer's instructions. Such equipment may be employed to determine the intensity of fluorescence at each predefined location on the array, thereby providing a measure of the amount of target DNA bound at each location. Such an assay would be able to indicate not only the absence and presence of the marker probe in the target, but also the quantitative amount as well.

The significance of such a high-throughput screening system is apparent for applications such as microbial selection and quality control operations in which there is a need to identify large numbers of samples or products for unwanted materials, to identify microbes or samples or products containing microbial material for quarantine purposes, etc., or to ascertain the true origin of samples or products containing microbes. Screening for the presence or absence of polynucleotides of the present invention used as identifiers for tagging microbes and microbial products can be valuable for later detecting the genetic composition of food, fermentation and industrial microbes or microbes in human or animal digestive system after consumption of probiotics, etc.

In this manner, oligonucleotide probe kits of the present invention may be employed to examine the presence/absence (or relative amounts in case of mixtures) of polynucleotides in different samples or products containing different materials rapidly and in a cost-effective manner. Examples of microbial species which may be examined using the present invention, include lactic acid bacteria, such as *Lactobacillus rhamnosus*, and other microbial species.

Another aspect of the present invention involves collections of a plurality of polynucleotides of the present invention. A collection of a plurality of the polynucleotides of the present invention, particularly the polynucleotides identified as SEQ ID NOS: 1–33, may be recorded and/or stored on a storage medium and subsequently accessed for purposes of analysis, comparison, etc. Suitable storage media include magnetic media such as magnetic diskettes, magnetic tapes, CD-ROM storage media, optical storage media, and the like. Suitable storage media and methods for recording and storing information, as well as accessing information such as polynucleotide sequences recorded on such media, are well known in the art. The polynucleotide information stored on the storage medium is preferably computer-readable and may be used for analysis and comparison of the polynucleotide information.

Another aspect of the present invention thus involves storage medium on which are recorded a collection of the polynucleotides of the present invention, particularly a collection of the polynucleotides identified as SEQ ID NOS: 1–33. According to one embodiment, the storage medium includes a collection of at least 20, of the polynucleotides of the present invention, preferably at least 20 of the polynucleotides identified as SEQ ID NOS: 1–33, including variants of those polynucleotides.

Another aspect of the present invention involves a combination of polynucleotides, the combination containing at least 5, preferably at least 10, more preferably at least 20 different polynucleotides of the present invention, including polynucleotides selected from SEQ ID NOS: 1–33, and variants of these polynucleotides.

In another aspect, the present invention provides genetic constructs comprising, in the 5'-3' direction, a gene promoter sequence and an open reading frame coding for at least a functional portion of a polypeptide encoded by a polynucleotide of the present invention. In certain embodiments, the genetic constructs of the present invention also comprise a gene termination sequence. The open reading frame may be oriented in either a sense or antisense direction. Genetic constructs comprising a non-coding region of a gene coding for a polypeptide encoded by the above polynucleotides or a nucleotide sequence complementary to a non-coding region, together with a gene promoter sequence, are also provided. A terminator sequence may form part of this construct. Preferably, the gene promoter and termination sequences are functional in a host organism. More preferably, the gene promoter and termination sequences are common to those of the polynucleotide being introduced. The genetic construct may further include a marker for the identification of transformed cells.

Techniques for operatively linking the components of the genetic constructs are well known in the art and include the use of synthetic linkers containing one or more restriction endonuclease sites as described, for example, by Sambrook et al., in *Molecular cloning: a laboratory manual*, Cold Spring Harbor Laboratories Press: Cold Spring Harbor, N.Y., 1989. The genetic constructs of the present invention may be linked to a vector having at least one replication system, for example, *E. coli*, whereby after each manipulation, the resulting construct can be cloned and sequenced and the correctness of the manipulation determined.

Transgenic microbial cells comprising the genetic constructs of the present invention are also provided by the present invention, together with microbes comprising such transgenic cells, products and progeny of such microbes, and materials including such microbes. Techniques for stably incorporating genetic constructs into the genome of target microbes, such as *Lactobacillus* species, *Lactococcus lactis* or *E. coli*, are well known in the art of bacterial transformation and are exemplified by the transformation of *E. coli* for sequencing in Example 1, as well as the transformations described in numerous of the examples provided below.

Transgenic, non-microbial, cells comprising the genetic constructs of the present invention are also provided, together with organisms comprising such transgenic cells, and products and progeny of such organisms. Genetic constructs of the present invention may be stably incorporated into the genomes of non-microbial target organisms, such as fungi, using techniques well known in the art.

In preferred embodiments, the genetic constructs of the present invention are employed to transform microbes used in the production of food products, ingredients, processing aids, additives or supplements and for the production of microbial products for pharmaceutical uses, particularly for modulating immune system function and immunological effects; and in the production of chemoprotectants providing beneficial effects, probiotics and health supplements. The inventive genetic constructs may also be employed to transform bacteria that are used to produce enzymes or substances such as polysaccharides, flavor compounds, and bioactive substances, and to enhance resistance to industrial processes such as drying and to adverse stimuli in the human digestive system. The genes involved in antibiotic production, and phage uptake and resistance in *Lactobacillus rhamnosus* are considered to be especially useful. The target microbe to be used for transformation with one or more polynucleotides or genetic constructs of the present invention is preferably selected from the group consisting of bacterial genera *Lactococcus, Lactobacillus, Streptococcus, Oenococcus, Lactosphaera, Trichococcus, Pediococcus* and others potentially useful in various fermentation industries selected, most preferably, from the group consisting of *Lactobacillus* species in the following list: *Lactobacillus acetotolerans, Lactobacillus acidophilus, Lactobacillus agilis, Lactobacillus alimentarius, Lactobacillus amylolyticus, Lactobacillus amylophilus, Lactobacillus amylovorus, Lactobacillus animalis, Lactobacillus arizonae, Lactobacillus aviarius, Lactobacillus bavaricus, Lactobacillus bifermen-

*tans, Lactobacillus brevis, Lactobacillus buchneri, Lactobacillus bulgaricus, Lactobacillus casei, Lactobacillus collinoides, Lactobacillus coryniformis, Lactobacillus crispatus, Lactobacillus curvatus, Lactobacillus delbrueckii, Lactobacillus delbrueckii* subsp. *bulgaricus, Lactobacillus delbrueckii* subsp. *lactis, Lactobacillus farciminis, Lactobacillus fermentum, Lactobacillus fructivorans, Lactobacillus gallinarum, Lactobacillus gasseri, Lactobacillus graminis, Lactobacillus hamsteri, Lactobacillus helveticus, Lactobacillus helveticus* subsp. *jugurti, Lactobacillus hetero, Lactobacillus hilgardii, Lactobacillus homohiochii, Lactobacillus japonicus, Lactobacillus johnsonii, Lactobacillus kefiri, Lactobacillus lactis, Lactobacillus leichmannii, Lactobacillus lindneri, Lactobacillus mali, Lactobacillus maltaromicus, Lactobacillus manihotivorans, Lactobacillus mucosae, Lactobacillus murinus, Lactobacillus oris, Lactobacillus panis, Lactobacillus paracasei, Lactobacillus paracasei* subsp. *pseudoplantarum, Lactobacillus paraplantarum, Lactobacillus pentosus, Lactobacillus plantarum, Lactobacillus pontis, Lactobacillus reuteri, Lactobacillus rhamnosus, Lactobacillus ruminis, Lactobacillus sake, Lactobacillus salivarius, Lactobacillus salivarius* subsp. *salicinius, Lactobacillus salivarius* subsp. *salivarius, Lactobacillus sanfranciscensis, Lactobacillus sharpeae, Lactobacillus thermophilus, Lactobacillus vaginalis, Lactobacillus venniforme, Lactobacillus zeae.*

In yet a further aspect, the present invention provides methods for modifying the concentration, composition and/or activity of a polypeptide in a host organism, such as a microbe, comprising stably incorporating a genetic construct of the present invention into the genome of the host organism by transforming the host organism with such a genetic construct. The genetic constructs of the present invention may be used to transform a variety of organisms. Organisms which may be transformed with the inventive constructs include plants, such as monocotyledonous angiosperms (e.g., grasses, corn, grains, oat, wheat and barley); dicotyledonous angiosperms (e.g., *Arabidopsis*, tobacco, legumes, alfalfa, oaks, eucalyptus, maple); gymnosperms, (e.g., Scots pine (Aronen, *Finnish Forest Res. Papers*, Vol. 595, 1996); white spruce (Ellis et al., *Biotechnology* 11:84–89, 1993); and larch (Huang et al., *In Vitro Cell* 27:201–207, 1991); and any kind of plant amenable to genetic engineering.

Thus, in yet another aspect, transgenic plant cells comprising the genetic constructs of the present invention are provided, together with plants comprising such transgenic cells, and fruits, seeds, products and progeny of such plants. Techniques for stably incorporating genetic constructs into the genome of target organisms, such as plants, are well known in the art and include *Agrobacterium tumefaciens* mediated introduction, electroporation, protoplast fusion, injection into reproductive organs, injection into immature embryos, high velocity projectile introduction and the like. The choice of technique will depend upon the target plant to be transformed. For example, dicotyledonous plants and certain monocots and gymnosperms may be transformed by *Agrobacterium* Ti plasmid technology, as described, for example by Bevan, *Nucleic Acids Res.* 12:8711–8721, 1984. Targets for the introduction of the genetic constructs include tissues, such as leaf tissue, disseminated cells, protoplasts, seeds, embryos, meristematic regions; cotyledons, hypocotyls, and the like.

Once the cells are transformed, cells having the genetic construct incorporated in their genome are selected. Transgenic cells may then be cultured in an appropriate medium, using techniques well known in the art. In the case of protoplasts, the cell wall is allowed to reform under appropriate osmotic conditions. In the case of seeds or embryos, an appropriate germination or callus initiation medium is employed. For explants, an appropriate regeneration medium is used. Regeneration of plants is well established for many species. For a review of regeneration of forest trees, see Dunstan et al., "Somatic embryogenesis in woody plants," in Thorpe, T. A., ed., *In vitro embryogenesis of plants*, (*Current Plant Science and Biotechnology in Agriculture*), 20(12):471–540, 1995. Specific protocols for the regeneration of spruce are discussed by Roberts et al. ("Somatic embryogenesis of Spruce," in Redenbaugh K., ed., *Synseed: applications of synthetic seed to crop improvement*, CRC Press: Ch. 23:427–449, 1993). The resulting transformed plants may be reproduced sexually or asexually, using methods well known in the art, to give successive generations of transgenic plants and practically unlimited amounts of tagged plant-derived products.

Polynucleotides of the present invention may also be used to specifically suppress gene expression by methods such as RNA interference (RNAi), which may also include cosuppression and quelling. This and other techniques of gene suppression are well known in the art. A review of this technique is found in *Science* 288:1370–1372, 2000. Traditional methods of gene suppression, employing antisense RNA or DNA, operate by binding to the reverse sequence of a gene of interest such that binding interferes with subsequent cellular processes and thereby blocks synthesis of the corresponding protein. RNAi also operates on a post-transcriptional level and is sequence specific, but suppresses gene expression more efficiently.

Studies have demonstrated that one or more ribonucleases specifically bind to and cleave double-stranded RNA into short fragments. The ribonuclease(s) remains associated with these fragments, which in turn specifically bind to complementary mRNA, i.e. specifically bind to the transcribed mRNA strand for the gene of interest. The mRNA for the gene is also degraded by the ribonuclease(s) into short fragments, thereby obviating translation and expression of the gene. Additionally, an RNA polymerase may act to facilitate the synthesis of numerous copies of the short fragments, which exponentially increases the efficiency of the system. A unique feature of this gene suppression pathway is that silencing is not limited to the cells where it is initiated. The gene-silencing effects may be disseminated to other parts of an organism and even transmitted through the germ line to several generations.

Specifically, polynucleotides of the present invention are useful for generating gene constructs for silencing specific genes. Polynucleotides of the present invention may be used to generate genetic constructs that encode a single self-complementary RNA sequence specific for one or more genes of interest. Genetic constructs and/or gene-specific self-complementary RNA sequences may be delivered by any conventional method known in the art. Within genetic constructs, sense and antisense sequences flank an intron sequence arranged in proper splicing orientation making use of donor and acceptor splicing sites. Alternative methods may employ spacer sequences of various lengths rather than discrete intron sequences to create an operable and efficient construct. During post-transcriptional processing of the gene construct product, intron sequences are spliced-out, allowing sense and antisense sequences, as well as splice junction sequences, to bind forming double-stranded RNA. Select ribonucleases bind to and cleave the double-stranded RNA, thereby initiating the cascade of events leading to degradation of specific mRNA gene sequences, and silencing specific genes. Alternatively, rather than using a gene construct to express the self-complementary RNA sequences, the gene-specific double-stranded RNA segments are delivered to one or more targeted areas to be internalized into the cell cytoplasm to exert a gene silencing effect.

Using this cellular pathway of gene suppression, gene function may be studied and high-throughput screening of sequences may be employed to discover sequences affecting gene expression. Additionally, genetically modified microbes and higher order organisms may be generated.

The following examples are offered by way of illustration and not by way of limitation.

EXAMPLE 1

Isolation and Characterization of DNA Sequences from *Lactobacillus rhamnosus* Strain HN001

*Lactobacillus rhamnosus* strain HN001 DNA libraries were constructed and screened as follows.

DNA was prepared in large scale by cultivating the bacteria in 2×100 ml cultures with 100 ml MRS broth (Difco Laboratories, Detroit Mich.) and 1 ml *Lactobacillus* glycerol stock as inoculum, placed into 500 ml culture flasks and incubated at 37 ° C. for approx. 16 hours with shaking (220 rpm).

The cultures were centrifuged at 3500 rpm for 10 min to pellet the cells. The supernatant was removed and the cell pellet resuspended in 40 ml fresh MRS broth and transferred to clean 500 ml culture flasks. Fresh MRS broth (60 ml) was added to bring the volume back to 100 ml and flasks were incubated for a further 2 hrs at 37° C. with shaking (220 rpm). The cells were pelleted by centrifugation (3500 rpm for 10 min) and supernatant removed. Cell pellets were washed twice in 20 ml buffer A (50 mM NaCl, 30 mM Tris pH 8.0, 0.5 mM EDTA).

Cells were resuspended in 2.5 ml buffer B (25% sucrose (w/v), 50 mM Tris pH 8.0, 1 mM EDTA, 20 mg/ml lysozyme, 20 µg/ml mutanolysin) and incubated at 37° C. for 45 min. Equal volumes of EDTA (0.25 M) was added to each tube and allowed to incubate at room temperature for 5 min. 20% SDS (1 ml) solution was added, mixed and incubated at 65° C. for 90 min. 50 µl Proteinase K (Gibco BRL, Gaithersburg, Md.) from a stock solution of 20 mg/ml was added and tubes incubated at 65° C. for 15 min.

DNA was extracted with equal volumes of phenol:chloroform:isoamylalcohol (25:24:1). Tubes were centrifuged at 3500 rpm for 40 min. The aqueous phase was removed to clean sterile Oak Ridge centrifuge tubes (30 ml). Crude DNA was precipitated with an equal volume of cold isopropanol and incubated at −20° C. overnight.

After resuspension in 500 µl TE buffer, DNase-free RNase was added to a final concentraion of 100 µg/ml and incubated at 37° C. for 30 min. The incubation was extended for a further 30 min after adding 100 µl Proteinase K from a stock solution of 20 mg/ml. DNA was precipitated with ethanol after a phenol:chloroform:isoamylalcohol (25:24:1) and a chloroform:isoamylalcohol (24:1) extraction and dissolved in 250 µl TE buffer.

DNA was digested with Sau3AI at a concentration of 0.004 U/µg in a total volume of 1480 µl, with 996 µl DNA, 138.75 µl 10× REACT 4 buffer and 252.75 µl H$_2$O. Following incubation for 1 hour at 37° C., DNA was divided into two tubes. 31 µl 0.5 M EDTA was added to stop the digestion and 17 µl samples were taken for agarose gel analysis. Samples were put into 15 ml Falcon tubes and diluted to 3 ml for loading onto sucrose gradient tubes.

Sucrose gradient size fractionation was conducted as follows. 100 ml of 50% sucrose (w/v) was made in TEN buffer (1M NaCl, 20 mM Tris pH 8.0, 5 mM EDTA) and sterile filtered. Dilutions of 5, 10, 15, 20, 25, 30, 35 and 40% sucrose were prepared and overlaid carefully in Beckman Polyallomer tubes, and kept overnight at 4° C. TEN buffer (4 ml) was loaded onto the gradient, with 3 ml of DNA solution on top. The gradients were centrifuged at 26K for 18 hours at 4° C. in a Centricon T-2060 centrifuge using a Kontron TST 28-38 rotor. After deceleration without braking (approx. 1 hour), the gradients were removed and fractions collected using an auto Densi-Flow (Haake-Buchler Instruments). Agarose gel was used to analyse the fractions. The best two pairs of fractions were pooled and diluted to contain less than 10% sucrose. TEN buffer (4 ml) was added and DNA precipitated with 2 volumes of 100% ice cold ethanol and an overnight incubation at −20° C.

DNA pellets were resuspended in 300 µl TE buffer and re-precipitated for approx. 6 hours at −20° C. after adding 1/10 volume 3 M NaOAC pH 5.2 and 2 volumes of ethanol. DNA was pelleted at top speed in a microcentrifuge for 15 min, washed with 70% ethanol and pelleted again, dried and resuspended in 10 µl TE buffer.

DNA was ligated into dephosphorylated BamHI-digested pBluescript SK II$^+$ and dephosphorylated BamHI-digested lambda ZAP Express using standard protocols. Packaging of the DNA was done using Gigapack III Gold packaging extract (Stratagene, La Jolla, Calif.) following the manufacturer's protocols. Packaged libraries were stored at 4° C.

Mass excision from the primary packaged phage library was done using XL1-Blue MRF' cells and ExAssist Helper Phage (Stratagene). The excised phagemids were diluted with NZY broth (Gibco BRL, Gaithersburg, Md.) and plated out onto LB-kanamycin agar plates containing 5-bromo-4-chloro-3-indolyl-β-D-galactoside (X-gal) and isopropylthio-beta-galactoside (IPTG). After incubation, single colonies were picked for PCR size determination before the most suitable libraries were selected for sequencing.

Of the colonies picked for DNA minipreps and subsequent sequencing, the large majority contained an insert suitable for sequencing. Positive colonies were cultured in LB broth with kanamycin or ampicillin depending on the vector used, and DNA was purified by means of rapid alkaline lysis minipreps (solutions: Qiagen, Venlo, The Netherlands; clearing plates, Millipore, Bedford, Mass.). Agarose gels at 1% were used to screen sequencing templates for chromosomal contamination and concentration. Dye terminator sequencing reactions were prepared using a Biomek 2000 robot (Beckman Coulter, Inc., Fullerton, Calif.) and Hydra 96 (Robbins Scientific, Sunnyvale, Calif.) for liquid handling. DNA amplification was done in a 9700 PCR machine (Perkin Elmer/Applied Biosystems, Foster City, Calif.) according to the manufacturer's protocol.

The sequence of the genomic DNA fragments were determined using a Perkin Elmer/Applied Biosystems Division Prism 377 sequencer. The DNA clones were sequenced from the 5' and/ or 3' end, and are identified as SEQ ID NOS: 1–33.

This example not only shows how the sequences were obtained, but also that a bacterium (*E. coli*) can be stably transformed with any desired DNA fragment of the present invention for permanent marking for stable inheritance.

The determined DNA sequences were compared to and aligned with known sequences in the public databases. Specifically, the polynucleotides identified in SEQ ID NO: 1–33 were compared to polynucleotides in the EMBL database as of the end of July 2001, using BLASTN algorithm Version 2.0.11 [Jan. 20, 2000], set to the following running parameters: Unix running command: blastall -p blastn -d embldb -e 10 -G 0 -E 0 -r 1 -v 30 -b 30 -i queryseq -o results. Multiple alignments of redundant sequences were used to build up reliable consensus sequences. Based on similarity to known sequences, the isolated polynucleotides of the present invention identified as SEQ ID NOS: 1–33 were identified as encoding polypeptides.

Numerous of the sequences provided in SEQ ID NO: 1–33 were found to be "full-length" and to contain open reading frames (ORFs). These full-length sequences, the location of ORFs (by nucleotide position) contained within these sequences, and the corresponding amino acid sequences are provided in Table 2 below.

TABLE 2

| Polynucleotide SEQ ID NO: | ORF | Polypeptide SEQ ID NO: |
|---|---|---|
| 1 | 1,128–3,026 | 42 |
| 2 | 196–924 | 43 |
| 3 | 145–1,098 | 44 |
| 4 | 82–348 | 45 |
| 5 | 103–1,239 | 46 |
| 6 | 122–934 | 47 |
| 7 | 94–759 | 48 |
| 7 | 807–1,676 | 49 |
| 8 | 126–1,232 | 50 |
| 9 | 181–1,086 | 51 |
| 10 | 23–1,510 | 52 |
| 11 | 209–1,381 | 53 |
| 12 | 1–1,179 | 54 |
| 13 | 1–650 | 55 |
| 14 | 1–768 | 56 |
| 15 | 163–1,167 | 57 |
| 16 | 64–888 | 58 |
| 17 | 47–1,219 | 59 |
| 18 | 45–1,295 | 60 |
| 19 | 175–1,173 | 61 |
| 20 | 48–1,352 | 62 |
| 21 | 1,705–2,280 | 63 |
| 22 | 60–1,250 | 64 |
| 23 | 71–1,093 | 65 |
| 24 | 120–1,074 | 66 |
| 25 | 86–934 | 67 |
| 26 | 2,209–7,434 | 68 |
| 27 | 74–4,465 | 69 |
| 28 | 821–6,460 | 70 |
| 29 | 141–1,022 | 71 |
| 30 | 83–607 | 72 |
| 31 | 27–875 | 73 |
| 32 | 96–881 | 74 |
| 33 | 1–1,191 | 75 |

The polynucleotide and polypeptide sequences of SEQ ID NOS: 1–33 and 42–75 were compared to sequences in the EMBL and SwissProt databases using the BLAST computer algorithms version 2.0.11 [Jan. 20, 2000]. Comparisons of polynucleotide sequences provided in SEQ ID NOS: 1–33 to sequences in the EMBL database were made as of August 2001. Comparisons of amino acid sequences provided in SEQ ID NOS: 42–75 to sequences in the SwissProt database were made as of August 2000. Analysis of six-frame translations of the polynucleotides of SEQ ID NOS: 1–33 were also compared to and aligned with the six-frame translations of polynucleotides in the SwissProt database using the BLASTX program BLASTN Polynucleotide Analysis The polynucleotide sequences of SEQ ID NOS: 1–3, 5–23 and 25–33 were determined to have less than 50% identity, determined as described above, to sequences in the EMBL database using the computer algorithm BLASTN, as described above. The polynucleotide sequence of SEQ ID NO: 24 was determined to have less than 90% identity, determined as described above, to sequences in the EMBL database using BLASTN, as described above. The polynucleotide sequence of SEQ ID NO: 4 was determined to have less than 98% identity, determined as described above, to sequences in the EMBL database using BLASTN, as described above.

BLASTP Amino Acid Analysis

The amino acid sequences of SEQ ID NOS: 43, 45–47, 51–53, 58, 60, 61, 63, 67, 68, 70, 71, 73 and 74 were determined to have less than 50% identity, determined as described above, to sequences in the SwissProt database using the BLASTP computer algorithm as described above. The amino acid sequences of SEQ ID NOS: 48–50, 55–56, 62, 64, 66, 69, 72 and 75 were determined to have less than 75% identity, determined as described above, to sequences in the SwissProt database using the BLASTP computer algorithm as described above. The amino acid sequences of SEQ ID NOS: 57 and 65 were determined to have less than 90% identity, determined as described above, to sequences in the SwissProt database using the computer algorithm BLASTP, as described above. The amino acid sequence of SEQ ID NO: 54 and 59 was determined to have less than 98% identity, determined as described above, to sequences in the SwissProt database using the computer algorithm BLASTP, as described above.

BLASTX Analysis

The six-frame translations of the polynucleotide sequences of SEQ ID NOS: 1–33 were compared to and aligned with six-frame translations of polynucleotides in the EMBL database using the BLASTX program version 2.0.11 [Jan. 20, 2000] set to the following running parameters: Unix running command: blastall -p blastn -d embldb -e 10 -G 0 -E 0 -v 30 -b 30 -i queryseq -o results. The translations of the polynucleotides of SEQ ID NOS: 1, 3, 5–9, 11–19, 21 and 25–32 were determined to have less than 50% identity, determined as described above, to translations of polynucleotides in the EMBL database using the computer algorithm BLASTX. The translations of the polynucleotides of SEQ ID NOS: 2, 4, 10, 20, 22, 23 and 33 were determined to have less than 75% identity, determined as described above, to translations of polynucleotides in the EMBL database using the computer algorithm BLASTX. The translations of the polynucleotide sequence of SEQ ID NO: 24 was determined to have less than 90% identity, determined as described above, to translations of polynucleotides in the EMBL database using the computer algorithm BLASTX.

EXAMPLE 2

Isolation and Characterization of Peptidase from *L. rhamnosus*

The full-length gene sequence of a peptidase believed to be related to pepO, and referred to herein as "pepO" from *L. rhamnosus* strain HN001 (given in SEQ ID NO: 1 and shown in FIG. 80) was isolated essentially as described in Example 1. Primers were designed to this sequence and employed to amplify pepO from *L. rhamnosus* HN001 using standard PCR methodology. PepO was cloned in the vector pTRKH2 (obtained from Dr Todd Klaenhammer, North Carolina State University, North Carolina, USA) and transformed into *E. coli*. Competent cells of *L. rhamnosus* HN001 were transformed with the pTRKH2+pepO construct to overexpress the gene in strain HN001. The amino acid sequence of the expressed protein is provided in SEQ ID NO: 42 and shown in FIG. 81.

Cell extracts of the HN001 strain constructs with enhanced levels of the peptidase enzyme showed enhanced enzyme activity on the casein peptide, $\alpha_{S1}$-casein(1–17). Specifically, $\alpha_{S1}$-casein(1–17) was incubated with non-transformed strain HN001 (referred to as DR20 WT) and strain HN001 transformed with the pepO construct described above (referred to as DR20 PepO:1 and DR20 PepO:4) HPLC separation of the resulting peptide products was performed using a Vydac reverse phase C18 column, 4.6 mm×250 mm. The solvent system was solvent A, 0.1% TFA in water, solvent B, 0.08% TFA in acetonitrile and the gradient employed was 15–40% solvent B over 20 minutes. A major peak was observed at 11 minutes, together with other non-identified minor peaks corresponding to hydrolysis products of the original substrate.

With non-transformed HN001 (DR 20 WT), the major peak of unhydrolysed $\alpha_{s1}$-casein(1–17) had a height of approximately 250 mAU. With each of the two transformed strains of HN001 (DR 20 PepO:1 and DR 20 PepO:4) the major peak of unhydrolysed $\alpha_{s1}$-casein(1–17) had a height of approximately 150 mAU, demonstrating that HN001 transformed with the pepO construct has enhanced peptidase activity compared to non-transformed HN001.

The peptidase of SEQ ID NO: 42, encoded by the polynucleotide of SEQ ID NO: 1, isolated from strain HN001, was not active on bradykinin, a standard substrate for measuring pepO activity (Pritchard et al., *Microbiol.* 140:923–30,1994). The enzyme of SEQ ID NO: 42 thus has a specificity that is significantly different from the homologous enzyme from *Lactococcus*.

The polypeptide of SEQ ID NO: 42, and the polynucleotide of SEQ ID NO: 1 have utility for processing food products to develop new characteristics in food products, and as supplements and additives to food products, including cheese and hydrolyzed milk protein products. This enzyme may also be used to develop non-food products. The attributes conferred by this enzyme, and the applications for use of this enzyme, include:

flavor and aroma enhancement;
removal of bitter peptides and undesirable flavors;
nutritional enhancement;
enhanced texture and functionality;
production of bioactive peptides; and
removal of allergenic peptides or proteins.

These attributes may be produced in food, such as dairy products, (including milk protein hydrolysates and cheese) by directed activity of the enzyme, introduced in a bacterial strain (including strain HN001, or starter cultures) comprising a polynucleitide of SEQ ID NO: 1, or a variant, or as an enzyme preparation comprising a polypeptide of SEQ ID NO: 42, or a variant.

EXAMPLE 3

Isolation and Characterisation of an Esterase from *L. rhamnosus* HN001

The full-length polynucleotide sequence of an esterase gene, given in SEQ ID NO: 3, was used to amplify the AA7 esterase gene from *L. rhamnosus* HN001 using standard PCR methodology. FIG. 1 shows the nucleotide sequence containing *L. rhamnosus* strain HN001 esterase gene AA7, with the ATG initiation and translation stop codons shown boxed.

The AA7 esterase gene sequence was then cloned into the pUniBlunt/V5-HisTopo vector (Invitrogen, Auckland, NZ) and transformed into the *E. coli* strain PIR1 OneShot competent cells (Invitrogen). To construct an expression plasmid, the pUniBlunt/V5-HisTopo vector construct was recombined with the pBad/Thio-E vector (Invitrogen) and transformed into the *E. coli* strain TOP10 competent cells (Invitrogen) according to the manufacturer's instructions. The gene product was therefore cloned as a fusion protein tagged with a His-patch polypeptide and thioredoxin protein. The esterase fusion protein was expressed and purified using a Ni-NTA column (Qiagen, Auckland, NZ) according to the manufacturer's instructions and protein expression checked by SDS-PAGE. The amino acid sequence of the esterase AA7 polypeptide is given in SEQ ID NO: 44 and shown in FIG. 2.

Esterase activity was assessed using the para-nitrophenyl butyrate assay as described in Lee and Lee, *Biotech. Appl. Biochem.* 11:552–563, 1989, with some modifications. Briefly, esterase activity was measured spectrophotometrically using p-nitrophenyl butyrate (Sigma Chemical Co., St Louis, Mo.) as substrate. Substrate was prepared by sonicating 1 ml of 50 mM methanolic p-nitrophenyl butyrate in 18 ml 50 mM sodium phosphate buffer (pH 7.5). Aliquots of 1.9 ml were placed in cuvettes, allowed to stabilize at 30° C., and between 5 and 20 µl of purified AA7 esterase added. Changes in optical density (OD) 410 nm were determined. Based on the results, enzyme activity was calculated, with one unit (U) of enzyme defined as the amount required to hydrolyze 1 µmol substrate per minute.

Esterase activity of the AA7 fusion protein was compared to the activity of a known esterase enzyme from *Streptococcus thermophilus* (ST1, as described in Liu et al., *Int. Dairy J.* 11:27–35, 2001), a non-esterase HN001 enzyme also expressed as a His-patch/Thioredoxin fusion protein and buffer-only.

Figure 3:
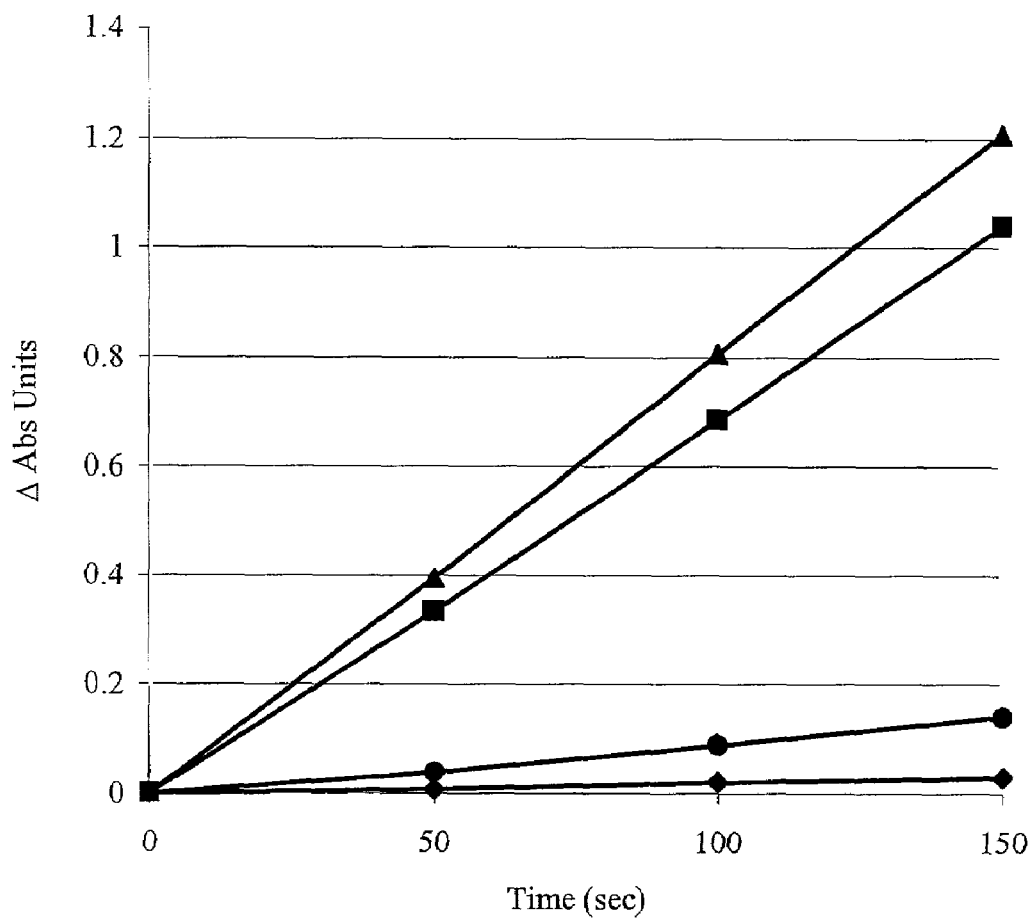
FIG. 3 demonstrates the esterase activity of the AA7 fusion protein. Production of ethyl butyrate from para-nitrophenyl butyrate substrate was measured by change in OD at 410 nm. While buffer only (♦) and the HN001 non-esterase fusion protein (●) showed minimal esterase activity, the ST1 esterase from *Streptococcus thermophilus* (▲) and the AA7 esterase fusion protein (■) showed strong activity.

The results are shown in FIG. 3 and the enzyme activities are given in Table 1B. FIG. 3 demonstrates the production of ethyl butyrate from para-nitrophenyl butyrate substrate as measured by change in OD at 410 nm. As shown in FIG. 3, while buffer only (♦) and the HN001 non-esterase fusion protein (●) showed minimal esterase activity, the ST1 esterase from *Streptococcus thermophilus* (σ) and the AA7 esterase fusion protein (v) showed strong activity. Thus, the AA7 esterase fusion protein showed strong esterase activity, compared to the positive control, and negligible amounts of esterase was produced by the two negative controls (buffer-only and the non-esterase fusion protein).

TABLE 1B

Esterase activity of the AA7 fusion protein

| Protein | Δ $OD_{410}$/min | Enzyme activity (µmol/min/ml) |
|---|---|---|
| AA7 fusion protein | 0.41 | 3.7 |
| ST1 esterase control | 0.49 | 4.0 |
| Non-esterase control | 0.05 | 0.4 |
| Buffer-only control | 0.02 | 0.2 |

The esterase activity exhibited by the AA7 fusion protein was not due to background hydrolysis of the substrate as the buffer-only control showed little or no activity. The specific enzyme activity of the His-patch/Thio/AA7 fusion protein was 1.42 µmol/min/mg protein compared with 0.03 µmol/min/mg for the non-esterase fusion protein showing an almost 50-fold difference in esterase activity. Therefore, AA7 esterase activity was due not due to the His-patch/Thioredoxin fusion protein tag.

Figure 4:
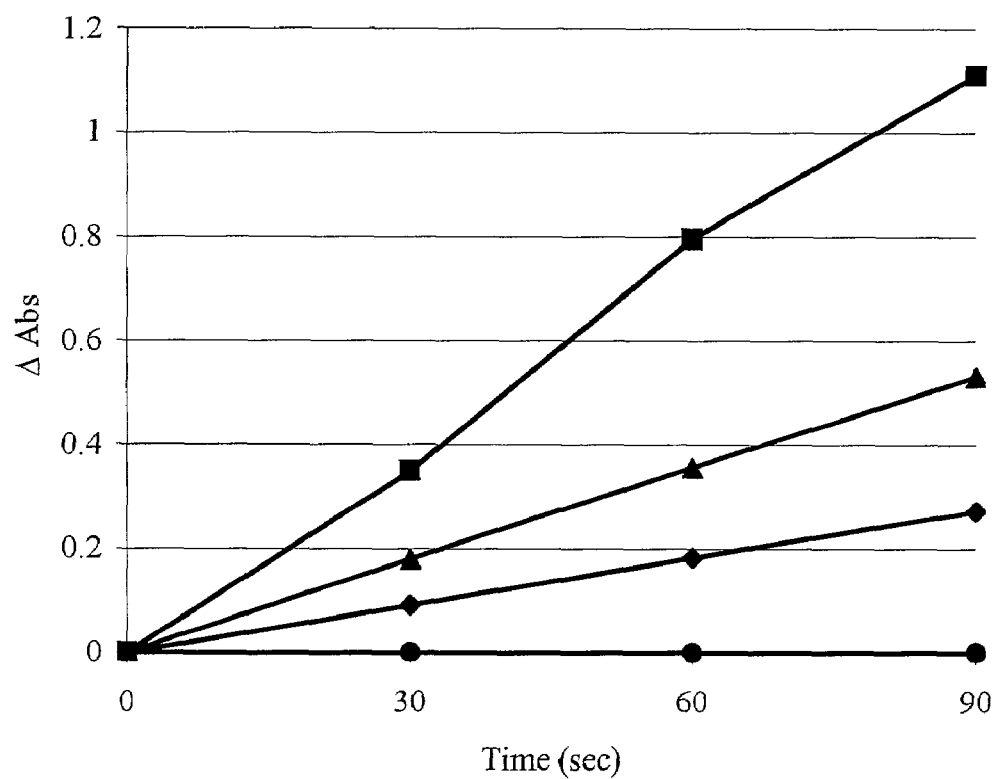
FIG. 4 shows the dose-response of the AA7 fusion protein. While buffer-only (●) showed no esterase activity, increasing amounts of His-patch/Thio/AA7 fusion protein; 5 μl (♦), 10 μl (▲) and 20 μl (■) purified protein showed increasing rates of substrate hydrolysis. The increase in substrate hydrolysis was proportional to amount of AA7 fusion protein added.

The dose-response of the AA7 fusion protein was determined by comparing the esterase activity in a series of three two-fold dilutions of the purified enzyme. Results are shown in FIG. 4 and the rate of change in optical density at 410 nm and enzyme activities given in Table 2. As shown in FIG. 4, while buffer-only (●) showed no esterase activity, increasing amounts of His-patch/Thio/AA7 fusion protein; 5 μl (♦), 10 μl (▲) and 20 μl (■) purified protein showed increasing rates of substrate hydrolysis. The increase in substrate hydrolysis was proportional to amount of AA7 fusion protein added.

TABLE 2

Esterase activity for increasing amounts of AA7 fusion protein

| Protein | Δ $OD_{410}$/min | Enzyme activity (μmol/min/ml) |
|---|---|---|
| 5 μl His-patch/Thio/AA7 | 0.18 | 5.9 |
| 10 μl His-patch/Thio/AA7 | 0.40 | 6.7 |
| 20 μl His-patch/Thio/AA7 | 0.68 | 5.6 |
| 1. Buffer-only | 0.00 | 0.0 |

Results indicated the rate of change in OD at 410 nm was proportional to the amount of enzyme added, whilst enzyme activity remained relatively constant. Therefore, esterase activity was dependent on the amount of esterase AA7 fusion protein present.

Figure 5:
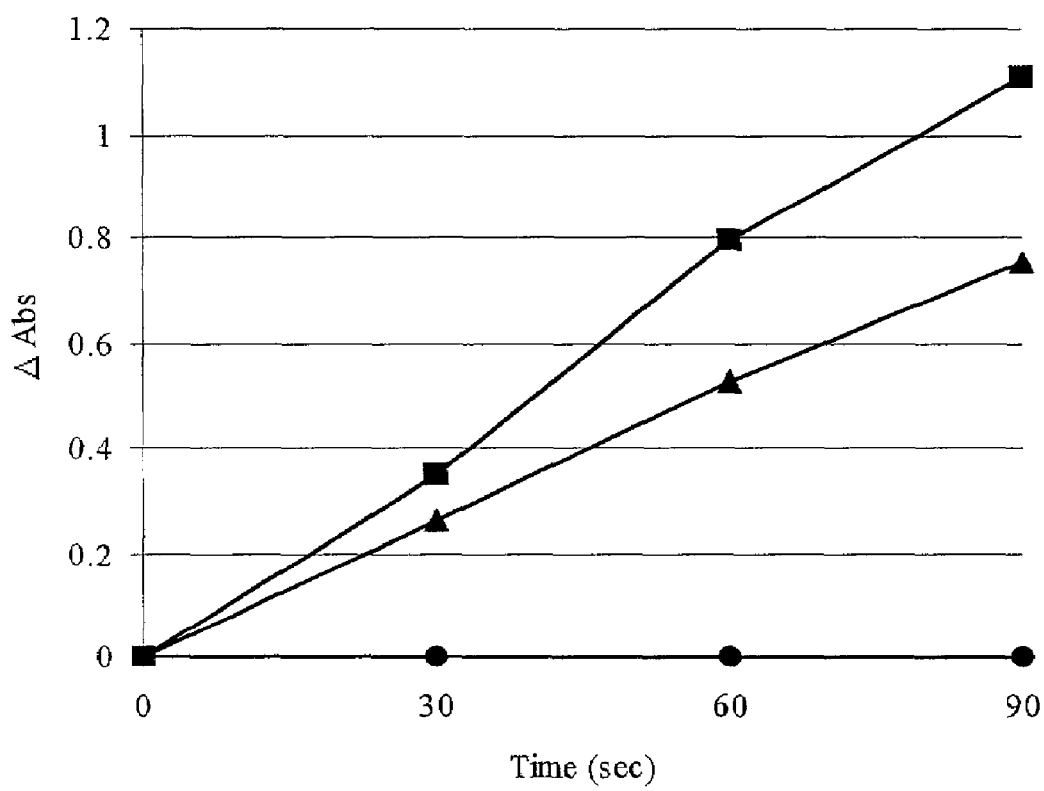
FIG. 5 shows the effect of the serine esterase inhibitor PMSF on esterase AA7 activity. Esterase activity of the His-patch/Thio/AA7 fusion protein was assessed in the absence (■) and presence (▲) of 10 mM PMSF. A buffer-only reaction (●) was used as a negative control. The presence of PMSF reduced HN001 esterase AA7 enzyme activity.

The effect of the serine esterase inhibitor PMSF was determined using the p-nitrophenyl butyrate assay. Esterase activity of the AA7 fusion protein was assessed in the presence and absence of 10 mM PMSF. Results are shown in FIG. 5, and the rate of change in OD at 410 nm and enzyme activities given in Table 3. Results in FIG. 5 and Table 3 indicate that the PMSF inhibitor caused a 17.9% reduction in the esterase activity of the AA7 fusion protein. Therefore, AA7 esterase activity was inhibited by the serine esterase-specific inhibitor PMSF.

TABLE 3

Effect of PMSF inhibitor on AA7 fusion protein esterase activity

| Protein | Δ $OD_{410}$/min | Enzyme activity (μmol/min/ml) |
|---|---|---|
| AA7 | 0.68 | 5.6 |
| AA7 + 10 mM PMSF | 0.50 | 4.1 |
| 2. Buffer-only | 0.00 | 0.0 |

The enzymatic breakdown of milk fat plays an essential role in the development of flavor in cheese. Esterases and lipases catalyze the lipolysis of milk fat in dairy products such that the triglycerides are hydrolyzed to free fatty acids and glycerol or mono- and diglycerides. Although exogenous esterases and lipases of mammalian and fungal origins are often used to encourage extensive lipolysis in cheeses, esterases and lipases from cheese microorganisms may also contribute to lipolysis (reviewed in Fox and Wallace, *Adv. Appl. Microbiol.* 45:17–85, 1997 and McSweeney and Wallace, *Lait* 80:293–324, 2000).

The polypeptide of SEQ ID NO: 44, and the polynucleotide of SEQ ID NO: 3 have utility for processing food products and as supplements and additives to food products. This esterase may also be used to develop non-food products. The attributes conferred by this enzyme include:
enhanced flavor and aroma
removal of off-flavors
altered levels of butyric acid
altered metabolic characteristics These attributes may be produced in food, such as dairy products, by directed activity of the enzyme, introduced in a bacterial strain (including strain HN001, or starter cultures) comprising a polynucleotide of SEQ ID NO: 3 or a variant, or as an enzyme preparation comprising a polypeptide of SEQ ID NO: 44 or a variant.

EXAMPLE 4

Isolation and Characterisation of Autoaggregation Protein AG5 from *L. rhamnosus* HN001

The full-length polynucleotide sequence of an autoaggregation protein from *L. rhamnosus* strain HN001, given in SEQ ID NO: 10, was used to amplify the AG5 autoaggregation gene from *L. rhamnosus* HN001 DNA using standard PCR methodology. The full-length polynucleotide sequence containing *L. rhamnosus* strain HN001 autoaggregation gene AG5, showing ATG initiation and translation stop codons (boxed) is shown in FIG. 6.

AG5 was then cloned into the EcoRI and SalI sites of the pGEX-6P-3 expression vector (Pharmacia Biotech, Auckland, NZ) and transformed into the *E. coli* strain K12 XL-1Blue competent cells according to standard laboratory protocols. The amino acid sequence is given in SEQ ID NO: 52. The amino acid sequence of the autoaggregation protein AG5 is shown in FIG. 7.

The autoaggregation AG5 protein was expressed as a fusion protein with glutathione S-transferase (GST), isolated and purified using Glutathione Sepharose 4B resin (Pharmacia Biotech) according to the manufacturer's instructions and protein expression checked by SDS-PAGE.

An assay for aggregation was adapted from Roos et al., *Mol Microbiol.* 32:427–436, 1999 with modifications. A 10 ml overnight culture of *L. rhamnosus* strain HN001 was grown in Man-Rogosa-Sharpe (MRS) broth (Oxoid) with glucose at a final concentration of 1%. The bacteria were washed five times in sterile deionized water resulting in loss of endogenous aggregation. Bacteria were suspended in 1 ml PBS, and 5 μl of the purified the HN001 autoaggregation protein AG5 fusion protein or an irrelevant (ie. non-adhesion) GST-fusion protein were added to 20 μl aliquots of the bacterial suspension, and placed on microscope slides. The slides were rocked gently for 13 min, and aggregation monitored by light microscopy.

As shown in FIG. 8A, in the presence of the AG5 autoaggregation GST-fusion protein, *L. rhamnosus* strain HN001 cells readily aggregated. FIG. 8A illustrates an image of a phase-contrast photomicrograph (exposure ⅛ sec, final magnification×240) showing obvious clumping of washed *L. rhamnosus* strain HN001 cells in the presence of AG5 autoaggregation protein tagged with GST. If an irrelevant (ie. non-adhesion) GST-fusion protein was used, no aggregation occurred. FIG. 8B illustrates an image of a phase-contrast photomicrograph (exposure ⅛ sec, final magnification×240) showing no clumping of washed *L. rhamnosus* strain HN001 cells in the presence of an irrelevant (non-adhesion) HN001 protein tagged with GST, as a negative control. The GST-tagged HN001 autoaggregation protein AG5 did not form observable clumps in the absence of bacterial cells (data not shown). Thus, the HN001 autoaggregation protein AG5 mediated the autoaggregation of *L. rhamnosus* strain HN001 cells.

The *L. rhamnosus* strain HN001 is known to have probiotic properties (see Tannock et al., *Appl. Environ. Microbiol.* 66:2,578–2,588, 2000; Gill et al., *Br. J. Nutr.* 83:167–176, 2000; Prasad et al., *Int. Dairy J.* 8:993–1002, 1998). In order to function effectively as probiotic bacteria,

*L. rhamnosus* HN001 must colonize (at least transiently) the gut environment, as well as exert positive health benefits, possibly through the exclusion of pathogenic bacteria from intestinal surfaces. The ability to form aggregates may be important for both and survival in the gut environment and functionality of *L. rhamnosus* HN001. The ability to auto-aggregate may assist in the formation of biofilms of *L. rhamnosus* HN001 and/or related species, improving the chances of colonization in the highly competitive gut environment, and then exclusion of competing bacteria, including pathogens.

The polypeptide of SEQ ID NO: 52, and the polynucleotide of SEQ ID NO: 10 have utility for processing food products and as supplements and additives to food products. This autoaggregation protein may also be used to develop non-food products. The attributes conferred by this enzyme include:

- as a prebiotic to enhance the growth of *L. rhamnosus* HN001 or other *Lactobacillus* species in the gut;
- as an agent to promote clumping of *L. rhamnosus* HN001 in media to improve survival in industrial processes; and
- as an agent to help prevent pathogenic colonization of mucosal surfaces.

These attributes may be produced in food, such as dairy products, by directed activity of the autoaggregation protein, introduced in a bacterial strain (including strain HN001, or starter cultures) comprising a polynucleotide of SEQ ID NO: 10 or a variant, or as an enzyme preparation comprising a polypeptide of SEQ ID NO: 52 or a variant.

EXAMPLE 5

Isolation and Characterisation of Malic Enzyme from *L. rhamnosus* HN001

The full-length polynucleotide sequence of malic enzyme AA5, given in SEQ ID NO: 2, was amplified from *L. rhamnosus* HN001 DNA using standard PCR methodology. The polynucleotide sequence containing *L. rhamnosus* strain HN001 malic enzyme gene AA5 showing ATG initiation and translation stop codons (boxed) is shown in FIG. 9. The upstream and downstream primers were tagged with EcoRI and BamHI restriction endonuclease recognition sequences to facilitate cloning.

The AA5 gene was then cloned into the EcoRI and BamHI sites of the pGEX-6P-3 expression vector (Pharmacia Biotech) and transformed into the *E. coli* strain DH-5α competent cells according to standard laboratory protocols. Cells were lysed by sonication and the AA5 protein, expressed as a GST fusion protein, was checked by SDS-PAGE analysis. The polypeptide sequence is given in SEQ ID NO: 43 and shown in FIG. 10.

Malic enzyme activity was assessed determining the rate of pyruvate reduction in transformed strains of an *E. coli* mutant. The *E. coli* strain EJ1321 contains multiple mutations that affect both NAD- and NADP-dependent malic enzyme activity, as well as malic enzyme regulation (Hansen and Juni, *Biochem. Biophys. Res. Comm.* 65:559–566, 1975). The strain was obtained from the *E. coli* Genetic Stock Centre (Yale University, USA), and transformed with the pGEX-6P-3 vector construct encoding the HN001 malic enzyme AA5. Transformants were selected by resistance to 100 μg/ml ampicillin on M9 plates supplemented with 0.5% glucose (ie. permissive growth conditions). Ampicillin resistant EJ132 colonies were picked and grown overnight at 37° C. in 10 ml LB broth with 100 μg/ml ampicillin and 2 ml then used to inoculate 100 ml LB broth with 100 μg/ml ampicillin. Cultures were incubated at 37° C. with shaking until OD at 600 nm reached approximately 0.4 whereupon expression of the AA5 protein was induced by the addition of 100 μl of 1 M IPTG. After a further 4 hours culture at 37° C. with shaking, 10 ml aliquots were taken, spun at 4000 rpm for 5 min, supernatants removed and cells resuspended in 5 ml PBS. Cultures were then sonicated to produce crude lysates. Malic enzyme activity in the crude lysates was measured according to Kobayashi et al., *J. Biol. Chem.* 264:3200–3205, 1989, with modifications. Briefly, total protein contents of the lysates were quantitated using the BCA Protein Assay Reagent kit (Pierce, Rockford, Ill., USA) according to the manufacturer's instructions, and 3.5 mg total protein added to 990 μl reaction solution containing 100 μM MOPS buffer (pH 6.1), 100 μM $Na_2CO_3$, 50 μM NADH and 5 μM $MgCl_2$ (Sigma). Lastly, 10 μl of 1 M sodium pyruvate was added as substrate and utilization of NADH measured as change in OD at 340 nm.

Malic enzyme activity was compared between PBS buffer only (20 μl), crude lysate from wild type EJ1321 cells (ie. non-transformed), EJ1321 cells transformed with pGEX-6P-3 encoding an irrelevant protein (AD5), and EJ1321 cells transformed with pGEX-6P-3 encoding HN001 malic enzyme AA5 (FIG. 11). Specific activities are given in Table 4, with a unit of enzyme was defined as μmole NADH used per min per mg protein.

Results in FIG. 11 and Table 4 indicate that although NADH was stable (ie. no change in OD in the presence of NADH and substrate), some background NADH reduction occurred when crude lysates from wild-type EJ1321 cells or EJ1321 cells expressing an irrelevant protein. Nonetheless, clear malic enzyme activity was observed when crude lysate from EJ1321 cells expressing AA5 protein was used, with over 6-fold more enzyme activity compared to background. Therefore, AA5 encodes a malic enzyme.

FIG. 11 shows malate enzyme activity measured as rate of pyruvate reduction by crude lysate preparations of EJ1321 cell transformants. ■ PBS buffer-only; ▲ 3.5 μg wild-type EJ1321 cell lysate; ◆ 3.5 μg cell lysate of EJ1321 transformed with pGEX-6P-3 construct encoding an irrelevant HN001 protein (AD5); ● 3.5 μg cell lysate of EJ1321 transformed with pGEX-6P-3 construct encoding HN001 malic enzyme AA5.

TABLE 4

Malic enzyme activity in crude lysates of transformed and non-transformed EJ1321 cells

| Lysate | Δ $OD_{340}$/min | Enzyme activity (μmol/min/ml) |
|---|---|---|
| Buffer-only | 0.00 | 0.00 |
| Wild-type EJ1321 | 0.01 | $2.0 \times 10^2$ |
| 3.EJ1321 with pGEX-6P-3 encoding an irrelevant protein | 0.02 | $4.2 \times 10^2$ |
| 4.EJ1321 with pGEX-6P-3 encoding AA5 | 0.12 | $26.8 \times 10^2$ |

The malic enzyme assay was repeated with increasing amounts of crude lysate from EJ1321 cells expressing AA5 protein to determine whether malic enzyme activity was proportional to amount of AA5 protein present (FIG. 12 and Table 5).

Results from FIG. 12 and Table 5 indicate that increased amounts of crude lysate of EJ1321 *E. coli* strain transformed with HN001 malic enzyme AA5 led to increased malic enzyme activity. However, as the amount of substrate became limiting at higher amounts of lysate, the increases in activity were not strictly proportional. Nonetheless, these results support the evidence that AA5 encodes the HN001 malic enzyme.

FIG. 12 shows data illustrating the effect of increasing amounts of EJ1321 crude lysate on malic enzyme activity. ■ 5 μl wild-type EJ1321 cell lysate; ▲ 5 μl cell lysate of EJ1321 transformed with pGex-6P-3 encoding AA5; ◆ 50 μl cell lysate of EJ1321 transformed with pGex-6P-3 encoding AA5; ● 200 μl cell lysate of EJ1321 transformed with pGex-6P-3 encoding AA5.

TABLE 5

Malic enzyme activity with increasing amounts of cell lysate

| Lysate | Δ OD$_{340}$/min | Enzyme activity (μmol/min/ml) |
|---|---|---|
| 5 μl wild-type EJ1321 | 0.004 | $3.2 \times 10^2$ |
| 5 μl EJ1321 with pGEX-6P-3 encoding AA5 | 0.032 | $25.8 \times 10^2$ |
| 5.50 μl EJ1321 with pGEX-6P-3 encoding AA5 | 0.216 | $17.3 \times 10^2$ |
| 6.200 μl EJ1321 with pGEX-6P-3 encoding AA5 | 0.232 | $4.6 \times 10^2$ |

The NAD-dependent malic enzyme (EC 1.1.1.38) catalyzes L-malate oxidative decarboxylation and pyruvate reductive carboxylation (Murai, T. et al,. *Biochem. Biophys. Res. Comm.* 43:875–881, 1971) and is central to citrate metabolism.

The polypeptide of SEQ ID NO: 43, and the polynucleotide of SEQ ID NO: 2 have utility for processing food products and as supplements and additives to food products, as well as in industrial processing. This malic enzyme may also be used to develop non-food products and in non-food processing systems. The attributes conferred by this enzyme include:

manipulation of energy production and growth in particular media;

altered survival characteristics in industrial processes;

formation of common intermediates of various flavor compounds; and lactic acid production, important for antibacterial effects and acid tolerance These attributes may be produced in food or in other environments by directed activity of the enzyme, introduced in a bacterial strain (including strain HN001, or starter cultures) comprising a polynucleotide of SEQ ID NO: 2 or a variant, or as an enzyme preparation comprising a polypeptide of SEQ ID NO: 43 or a variant.

EXAMPLE 6

Isolation and Characterisation of Malate Dehydrogenase from *L. rhamnosus* HN001

The full-length polynucleotide sequence of malic enzyme, given in SEQ ID NO: 9, was amplified from the AG3 malate dehydrogenase gene from *L. rhamnosus* HN001 DNA using standard PCR methodology. FIG. 13 shows the polynucleotide sequence containing *L. rhamnosus* strain HN001 malate dehydrogenase gene AG3 showing the TTG initiation and translation stop codons (boxed).

AG3 was then cloned into the pUniBlunt/V5-HisTopo vector (Invitrogen) and transformed into the *E. coli* strain PIR1 OneShot competent cells (Invitrogen) according to the manufacturer's instructions. To construct an expression plasmid, the pUniBlunt/V5-HisTopo vector construct was recombined with the pBad/Thio-E Echo vector (Invitrogen) and transformed into the *E. coli* strain TOP10 competent cells (Invitrogen) according to the manufacturer's instructions. The AG3 gene product was therefore cloned as a fusion protein tagged with a His-patch polypeptide and thioredoxin protein. The fusion protein was expressed and purified using a Ni-NTA column (Qiagen, Auckland, NZ) according to the manufacturer's instructions and protein expression checked by SDS-PAGE. The polypeptide sequence is given in SEQ ID NO: 51 and shown in FIG. 14.

Malate dehydrogenase activity was assessed by gene complementation of the mutant *E. coli* strain UTH4606 that lacks a functional malate dehydrogenase gene (Heard et al., *J. Bacteriol.* 122:329–331, 1975; Shaw et al., *Mutation Res.*, 18:247–250, 1973), provided by the *E. coli* Genetic Stock Centre (Yale University, USA). UTH4606 strain cells cannot utilize malate as a carbon source, in contrast to wild-type *E. coli*. pBAD-Thio-E construct containing the HN001 malate dehydrogenase AG3 gene or empty pBAD-Thio-E vector was transformed into the UTH4606 *E. coli* strain and plated onto M9 media plates containing 100 μg/ml kanamycin and 0.5% glucose. Transformant colonies were picked, and plated out onto a series of selective M9 agar plates containing 100 μg/ml Kanamycin and/or 0.5% glucose or 0.5% malate. Growth of the UTH4606 transformed with pBAD-Thio-E encoding the AG3 protein was compared with wild-type UTH4606 cells and UTH4606 cells transformed with empty pBAD-Thio-E vector. Plates were incubated aerobically at 37° C. overnight. Growth was assessed for malate dehydrogenase complementation.

Results are shown in Table 6 and indicate that wild-type UTH780 cells grew on M9 media supplemented with glucose, but not on M9 media supplemented with malate, or on media containing Kanamycin. This confirmed the phenotype of the UTH780 strain of being unable to utilize malate as a carbon source due to the loss of malate dehydrogenase function. Transformation with empty pBAD/Thio-E vector allowed growth on media containing Kanamycin, but did not complement the malate dehydrogenase mutation. Transformation with pBAD/Thio-E encoding the HN001 malate dehydrogenase AG3 allowed growth on Kanamycin, indicating the presence of the plasmid, and on malate, indication that the AG3 protein complemented the *E. coli* malate dehydrogenase deficiency. Therefore, the HN001 protein AG3 has malate dehydrogenase activity.

TABLE 6

Results of LB agar plate assay for malate dehydrogenase gene complementation

| E. coli UTH780 transformed with: | 0.5% Glucose | 0.5% Glucose + Kanamycin | 0.5% Malate + Kanamycin | 0.5% Malate |
|---|---|---|---|---|
| — | + | — | — | — |
| pBAD/Thio-E | + | + | — | — |
| pBAD/Thio-E encoding AG3 | + | + | + | + |

+: growth; −: no growth

Malate dehydrogenase (EC 1.1.1.37) catalyzes the reversible oxidation of malate to oxaloacetate with the concomitant reduction of NAD. As *lactobacilli* appear not to have a functioning Krebs cycle, the enzyme may be involved in amino acid biosynthesis or L-malate utilization pathways.

The polypeptide of SEQ ID NO: 51, and the polynucleotide of SEQ ID NO: 9 have utility for processing food and other products and as supplements and additives to food products and in industrial processing. The attributes conferred by this enzyme include:
- manipulation of energy production and growth in particular media;
- altered survival characteristics in industrial processes; and
- formation of common intermediates of various flavor compounds.

These attributes may be produced in food products, or in industrial processing, by directed activity of the enzyme, introduced in a bacterial strain (including strain HN001, or starter cultures) comprising a polynucleotide of SEQ ID NO: 9 or a variant, or as an enzyme preparation comprising a polypeptide of SEQ ID NO: 51 or a variant.

EXAMPLE 7

Isolation and Characterisation of Dihydrodipicolinate Synthase from *L. rhamnosus* HN001

The full-length polynucleotide sequence of dihydrodipicolinate synthase from *L. rhamnosus* HN001, given in SEQ ID NO: 13 and shown in FIG. 15 with ATG initiation and translation stop codons (boxed), was used to amplify the AI2 dihydrodipicolinate synthase gene from *L. rhamnosus* HN001 DNA using standard PCR methodology. The upstream and downstream primers were tagged with EcoRI and SalI restriction endonuclease recognition sequences to facilitate cloning.

AI2 was then cloned into the EcoRI and SalI sites of the pGEX-6P-3 expression vector (Pharmacia Biotech) and transformed into the *E. coli* strain K12 XL-1Blue competent cells according to standard laboratory protocols. The dihydrodipicolinate synthase AI2 protein was expressed as a fusion protein with glutathione S-transferase (GST), bound to Glutathione Sepharose 4B resin (Pharmacia Biotech), and PreScission protease used to cleave off dihydrodipicolinate synthase AI2 protein, according to the manufacturer's instructions. An aliquot of the purified AI2 protein was checked by SDS-PAGE analysis. The polypeptide sequence is given in SEQ ID NO: 55 and is shown in FIG. 16.

Dihydrodipicolinate synthase activity was assessed by gene complementation of the mutant *E. coli* strain AT997 deficient in dihydrodipicolinate synthase gene function (Bukhari and Taylor, *J. Bacteriol.* 105:844–854, 1971), provided by the *E. coli* Genetic Stock Centre (Yale University, USA). AT997 cells require diaminopimelic acid (DAP) for growth, in contrast to wild-type *E. coli* that is DAP-independent. pGEX-6P-3 construct containing the HN001 dihydrodipicolinate synthase AI2 gene or empty pGEX-6P-3 vector was transformed into the AT997 *E. coli* strain. Transformed AT997 cells were plated onto LB agar plates containing ampicillin (100 µg/ml) only or ampicillin and 45 µg/ml DAP, at dilutions designed to allow the visualization of distinct colonies (ie. <200 colonies/plate). Plates were incubated aerobically at 37° C. overnight and growth assessed as the presence of distinct colonies.

Results in Table 7 indicate that while AT997 cells transformed with either empty pGEX-6P-3 or pGEX-6P-3 containing the HN001 dihydrodipicolinate synthase AI2 grew in the presence of DAP, only cells transformed with vector containing AI2 grew without DAP. Therefore, the HN001 dihydrodipicolinate synthase protein AI2 complemented the dihydrodipicolinate synthase gene mutation in *E. coli* strain AT997.

TABLE 7

Results of LB agar plate assay for dihydrodipicolinate synthase gene complementation.

| | LB agar plates containing: | |
|---|---|---|
| *E. coli* AT997 transformed with: | Ampicillin and DAP | Ampicillin only |
| pGEX-6P-3 | + | − |
| pGEX-6P-3 with AI2 | + | + |

+: growth; −: no growth

Dihydrodipicolinate synthase (EC 4.2.1.52) converts L-aspartate 4-semialdehyde and pyruvate to 1-2,3-dihydrodipicolinate as part of the lysine biosynthesis pathway. L-aspartate 4-semialdehyde is also the first step of the glycine, serine and threonine metabolic pathways.

The polypeptide of SEQ ID NO: 55, and the polynucleotide of SEQ ID NO: 13 have utility for processing food products, as additives for industrial processing, and in the commercial production of lysine or intermediates. The attributes conferred by this enzyme include:
- altered amino acid content, with important flavor and metabolic impacts;
- commercial production of lysine or intermediates;
- manipulation of energy production and growth in particular media; and
- altered survival characteristics in industrial processes .

These attributes may be produced in food products and used in food and other types of industrial processing, by directed activity of the enzyme, introduced in a bacterial strain (including strain HN001, or starter cultures) comprising a polynucleotide of SEQ ID NO: 13 or a variant, or as an enzyme preparation comprising a polypeptide of SEQ ID NO: 55 or a variant.

EXAMPLE 8

Isolation and Characterisation of Dihydrodipicolinate Reductase from *L. rhamnosus* HN001

The full-length polynucleotide sequence of dihydrodipicolinate reductase from *L. rhamnosus* strain HN001, given in SEQ ID NO: 14 and shown in FIG. 72 with ATG initiation and translation stop codons (boxed), was used amplify the AI3 dihydrodipicolinate reductase gene from *L. rhamnosus* HN001 DNA using standard PCR methodology. The upstream and downstream primers were tagged with EcoRI and SalI restriction endonuclease recognition sequences to facilitate cloning.

AI3 was then cloned into the EcoRI and SalI sites of the pGEX-6P-3 expression vector (Pharmacia Biotech) and transformed into the *E. coli* strain K12 XL-1Blue competent cells according to standard laboratory protocols. The polypeptide sequence of dihydrodipicolinate reductase AI3 is given in SEQ ID NO: 56 and is shown in FIG. 73. The dihydrodipicolinate reductase AI3 protein was expressed as a fusion protein with glutathione S-transferase (GST), bound to Glutathione Sepharose 4B resin (Pharmacia Biotech), and PreScission protease used to cleave off dihydrodipicolinate reductase AI3 protein, according to the manufacturer's instructions. An aliquot of the purified AI3 protein was checked by SDS-PAGE analysis.

Dihydrodipicolinate reductase activity was assessed by gene complementation of the mutant *E. coli* strain AT999 deficient in dihydrodipicolinate reductase gene function (Bukhari and Taylor, *J. Bacteriol.* 105:844–854, 1971), provided by the *E. coli* Genetic Stock Centre (Yale University, USA). AT999 cells require diaminopimelic acid (DAP) for growth, in contrast to wild-type *E. coli* that is DAP-independent. pGEX-6P-3 construct containing the HN001 dihydrodipicolinate reductase AI3 gene or empty pGEX-6P-3 vector was transformed into the AT999 *E. coli* strain. Transformed AT999 cells were plated onto LB agar plates containing ampicillin (100 µg/ml) only or ampicillin and 45 µg/ml DAP, at dilutions designed to allow the visualization of distinct colonies (ie. <200 colonies/plate). Plates were incubated aerobically at 37° C. overnight and growth assessed as the presence of distinct colonies (Table 8).

Results in Table 8 indicate that while AT999 cells transformed with either empty pGEX-6P-3 or pGEX-6P-3 containing the HN001 dihydrodipicolinate reductase AI3 grew in the presence of DAP, only cells transformed with vector containing AI3 grew without DAP. Therefore, the HN001 dihydrodipicolinate reductase protein AI3 complemented the dihydrodipicolinate Reductase gene mutation in *E. coli* strain AT999.

TABLE 8

Results of LB agar plate assay for dihydrodipicolinate reductase gene complementation.

| E. coli AT999 transformed with: | LB agar plates containing: | |
|---|---|---|
|  | Ampicillin and DAP | Ampicillin only |
| pGEX-6P-3 | + | − |
| pGEX-6P-3 with AI3 | + | + |

+: growth; −: no growth

Dihydrodipicolinate reductase (EC 1.3.1.26) converts L-2,3-dihydrodipicolinate to L-tetrahydropicolinate as part of the lysine biosynthesis pathway.

The polypeptide of SEQ ID NO: 56, and the polynucleotide of SEQ ID NO: 14 have utility for processing food products, as additives for industrial processing, and in the commercial production of lysine or intermediates. The attributes conferred by this enzyme include:

altered amino acid content, with important flavor and metabolic impacts;

commercial production of lysine or intermediates;

manipulation of energy production and growth in particular media; and altered survival characteristics in industrial processes.

These attributes may be produced in food products and used in food and other types of industrial processing, by directed activity of the enzyme, introduced in a bacterial strain (including strain HN001, or starter cultures) comprising a polynucleotide of SEQ ID NO: 14 or a variant, or as an enzyme preparation comprising a polypeptide of SEQ ID NO: 56 or a variant.

EXAMPLE 9

Isolation and Characterisation of Aspartate Aminotransferase from *L. rhamnosus* HN001

The full-length gene sequence of aspartate aminotransferase from *L. rhamnosus* strain HN001, given in SEQ ID NO: 12 and shown in FIG. 17 with GTG initiation and translation stop codons (boxed), was used to amplify the AH9 aspartate aminotransferase gene from *L. rhamnosus* HN001 DNA using standard PCR methodology. The upstream and downstream primers were tagged with EcoRI and SalI restriction endonuclease recognition sequences to facilitate cloning.

AH9 was then cloned into the EcoRI and SalI sites of the pGEX-6P-3 expression vector (Pharmacia Biotech) and transformed into the *E. coli* strain K12 XL-1Blue competent cells according to standard laboratory protocols. The aspartate aminotransferase AH9 protein was expressed as a fusion protein with glutathione S-transferase (GST), bound to Glutathione Sepharose 4B resin (Pharmacia Biotech), and PreScission protease used to cleave off the aspartate aminotransferase AH9 protein, according to the manufacturer's instructions. An aliquot of the purified AH9 protein was checked by SDS-PAGE analysis. The polypeptide sequence is given in SEQ ID NO: 54 and is shown in FIG. 18.

AH9 activity was assayed according to the previously published malate dehydrogenase-coupled method (Karmen, *J. Clin. Invest.* 34:131–133, 1955) with modifications. Briefly, 1 ml reaction mixtures containing 100 µmol Tris hydrochloride buffer (pH 8.0), 100 µmol L-aspartate, 10 µmol of α-ketoglutarate, 0.2 µmol NADH, 0.015 µmol pyrodoxal 5'-phosphate (PLP), and 3 µg (3.6 U) malate dehydrogenase (all chemicals from Sigma Chemical Co.) were incubated at 37° C. with increasing amounts (0 to 142.5 ng) of the purified HN001 aspartate aminotransferase AH9 protein. The rationale of the assay is that aspartate aminotransferase converts α-ketoglutarate and L-aspartate to oxaloacetate and L-glutamate. The oxaloacetate is then substrate for the malate dehydrogenase, which oxidizes one molecule of NADH to $NAD^+$ for every molecule of oxaloacetate converted to L-malate. As the first step is rate limiting, the amount of NADH oxidized in the second step is directly proportional to the aspartate aminotransferase-dependent production of oxaloacetate from α-ketoglutarate in the first step. The reaction was monitored by the decrease in absorbance at 340 nm, and results used to calculate the 1 mol NADH oxidized per minute. One unit of enzyme was defined as the amount of enzyme that catalyzed the production of 1 µmol of oxaloacetate per minute at 37° C.

Results in Table 9 indicate that while in the absence of purified HN001 aspartate aminotransferase AH9 protein, there was some background oxidation of NADH, the addition of AH9 protein led to increased rates of aspartate aminotransferase-dependent NADH oxidation. Increased amounts of AH9 increased NADH oxidation in a dose-dependent manner. A similar background rate observed in reaction mixtures without the addition of AH9 protein was also observed in reaction mixtures without both AH9 protein and α-ketoglutarate substrate (data not shown), indicating that the background NADH oxidation was not aspartate aminotransferase-dependent. The addition of 142.5 ng of AH9 protein led to an over 19-fold increase in NADH oxidation. The activity of the purified HN001 aspartate aminotransferase AH9 protein was calculated to be 31 U/mg protein. Therefore, HN001 protein AH9 is an aspartate aminotransferase.

TABLE 9

Results of the malate dehydrogenase-coupled aspartate aminotransferase assay.

| Concentration of purified HN001 aspartate aminotransferase AH9 (ng/ml) | NADH oxidized (μmol/min/ml) |
|---|---|
| 0 | $0.20 \times 10^{-3}$ |
| 23.8 | $0.80 \times 10^{-3}$ |
| 47.5 | $1.13 \times 10^{-3}$ |
| 71.2 | $1.61 \times 10^{-3}$ |
| 95.0 | $1.95 \times 10^{-3}$ |
| 118.8 | $2.57 \times 10^{-3}$ |
| 142.5 | $3.82 \times 10^{-3}$ |

α-ketoglutarate is an important chemical mediator in lactic acid bacteria, and the addition of this compound to cheese curd has positive impacts on cheese flavor (Yvon et al., *Int. Dairy J.* 8:889–898, 1998). The formation of α-ketoglutarate using L-glutamate as an amino donor, catalysed by aspartate aminotransferase, is an important pathway in maintaining intracellular α-ketoglutarate levels.

The polypeptide of SEQ ID NO: 54, and the polynucleotide of SEQ ID NO: 12 have utility for processing food products and as supplements and additives to food products. This esterase may also be used to develop non-food products. The attributes conferred by this enzyme include:

altered amino acid content, with important flavor and metabolic impacts;
  manipulation of energy production and growth in particular media; and
  altered survival characteristics in industrial processes, including food processing These attributes may be produced in food, such as dairy products, and in other industrial processes, by directed activity of the enzyme, introduced in a bacterial strain (including strain HN001, or starter cultures) comprising a polynucleotide of SEQ ID NO: 12 or a variant, or as an enzyme preparation comprising a polypeptide of SEQ ID NO: 54 or a variant.

EXAMPLE 10

Isolation and Characterisation of Serine Dehydratase Subunits α and β from *L. rhamnosus* HN001

The full-length polynucleotide sequence of serine dehydratase subunits α and β, given in SEQ ID NO: 7 was used to amplify the AF8 serine dehydratase α subunit and AF7 serine dehydratase β subunit from *L. rhamnosus* HN001 DNA as a single operon using standard PCR methodology. The polynucleotide sequence containing *L. rhamnosus* strain HN001 serine dehydratase subunits α (AF8) and β (AF7) is shown in FIG. 19, with ATG translation initiation codons and termination codons shown boxed for AF8 and shaded for AF7.

The AF8 serine dehydratase α subunit and AF7 serine dehydratase β subunit were amplified from *L. rhamnosus* HN001 DNA as a single operon using standard PCR methodology. The AF8 and AF7 genes were cloned in the vector pTRKH2 (obtained from Dr Todd Klaenhammer, North Carolina State University, North Carolina, USA) and transformed into *E. coli* DH5α cells. Positive transformants were selected, grown overnight and the plasmid isolated by standard laboratory techniques. Competent *L. rhamnosus* HN001 cells were then transformed with the pTRKH2 construct containing the HN001 serine dehydratase subunits α and β to overexpress the genes in strain HN001. The amino acid sequences of the expressed proteins AF8 serine dehydratase α and AF7 serine dehydratase β are given in SEQ ID NOS: 49 and 48, respectively, and shown in FIGS. 22A and 22B, respectively.

Serine dehydratase enzyme activity was assessed by comparing serine utilization in liquid cultures of HN001 strain cells transformed with either the pTRKH2 construct containing the HN001 serine dehydratase or empty pTRKH2 vector only.

The results shown in FIGS. 20 and 21 indicate that the presence of the expression plasmid encoding HN001 serine dehydratase subunits α (AF8) and β (AF7) significantly increased the utilization of serine by HN001 strain cells, compared to cells transformed with empty expression vector only. Therefore the HN001 genes AF7 and AF8 encode the serine dehydratase enzyme. FIG. 20 shows the percentage serine utilization by HN001 strain in liquid culture with 5 mM initial serine concentration. ■ HN001 transformed with vector only; ♦ pTRKH2 construct containing HN001 serine dehydratase. FIG. 21 shows the percentage serine utilization by HN001 strain in liquid culture with 12 mM initial serine concentration. ■ HN001 transformed with vector only, ♦ pTRKH2 construct containing HN001 serine dehydratase.

Serine dehydratase (EC 4.2.1.13), comprising α and β subunits, catalyzes the irreversible deamination of serine to pyruvate and ammonia (Ogawa et al., *J. Biol. Chem.* 264: 15818–15822, 1989; Grabowski et al., *Trends in Biochem. Sci.* 18:297–300, 1993).

The polypeptides of SEQ ID NOS: 48 and 49, and the polynucleotide of SEQ ID NO: 7 have utility for processing food products and in other types of industrial processing, and in the production of ammonia. Applications for the HN001 serine dehydratase subunits AF7 and AF8 of the present invention include:

energy supply from amino acids present in growth media or environment;
  production of ammonia, regarded as a flavor compound;
  altered pyruvate levels—pyruvate is a highly reactive compound, and is important in a number of flavor pathways; and
  altered survival characteristics in industrial processes.

These applications may be implemented by directed activity of the enzyme, introduced in a bacterial strain (including strain HN001, or starter cultures) comprising a polynucleotide of SEQ ID NO: 7 or a variant, or as an enzyme preparation comprising a polypeptide of SEQ ID NOS: 48 and/or 49, or variants.

EXAMPLE 11

Isolation and Characterisation of Histidinol-Phosphate Aminotransferase from *L. rhamnosus* HN001

The full-length polynucleotide sequence of histidinol-phosphate aminotransferase from *L. rhamnosus* strain HN001, given in SEQ ID NO: 8 and shown in FIG. 23 with ATG initiation and translation stop codons (boxed), was used to amplify the AG2 histidinol-phosphate aminotransferase gene from *L. rhamnosus* HN001 DNA using standard PCR methodology. The upstream and downstream primers were tagged with EcoRI and BamHI restriction endonuclease recognition sequences to facilitate cloning.

AG2 was then cloned into the EcoRI and BamHI sites of the pGEX-6P-3 expression vector (Pharmacia Biotech) and transformed into *E. coli* strain DH-5α competent cells according to standard laboratory protocols. Cells were lysed by sonication and the presence of AG2 protein, expressed as a GST fusion protein, checked by SDS-PAGE analysis. The polypeptide sequence of AG2 is given in SEQ ID NO: 50 and shown in FIG. 24.

Histidinol-phosphate aminotransferase activity was assessed by gene complementation of the mutant *E. coli* strain UTH780 that lacks a functional hisC gene that encodes histidinol-phosphate aminotransferase (Goldschmidt et al., *Genetics*, 66:219–229, 1970), provided by the *E. coli* Genetic Stock Centre (Yale University, USA). UTH780 cells require L-histidine for growth, in contrast to wild-type *E. coli* that is L-histidine-independent. pGEX-6P-3 construct encoding HN001 histidinol-phosphate aminotransferase AG2 was transformed into the UTH780 *E. coli* strain and plated onto LB agar plates containing 100 µg/ml ampicillin. Ampicillin-resistant transformant colonies were picked and plated out onto selective media (ie. M9 media plates with and without 100 µg/ml L-histidine, with and without 100 µg/ml ampicillin). Growth of UTH780 transformed with AG2 was compared with the growth of wild-type UTH780 cells and UTH780 cells transformed with a pGex-6P-3 construct encoding a non-histidinol-phosphate aminotransferase (AE8). Plates were incubated aerobically at 37° C. overnight and growth assessed as the presence of distinct colonies.

Results in Table 10 indicate that while wild-type UTH780 cells grew in the presence of histidine, no growth was observed when ampicillin was added to the media. Therefore, ampicillin resistance in transformed UTH780 was due to the presence of pGEX-6P-3 vector. UTH780 cells transformed with either empty pGEX-6P-3 or pGEX-6P-3 encoding an irrelevant protein (AE9) grew in the presence of histidine and ampicillin, but remained auxotrophic for hisitidine, indicating that the HisC⁻ phenotype was not complemented. UTH780 cells transformed with pGEX-6P-3 encoding HN001 histidinol-phosphate aminotransferase AG2 grew in on M9 media without histidine. Therefore, the AG2 protein complemented the hisC mutation of UTH780 strain *E. coli* cells.

TABLE 10

Results of M9 agar plate assay for histidinol-phosphate aminotransferase gene complementation.

| *E. coli* UTH780 transformed with: | M9 agar plates containing: | | |
|---|---|---|---|
| | L-histidine only | Ampicillin and L-histidine | Ampicillin only |
| — | + | − | − |
| pGEX-6P-3 | + | + | − |
| pGEX-6P-3 encoding AE9 | + | + | − |
| pGEX-6P-3 encoding AG2 | + | + | + |

+: growth; −: no growth

Histidinol-phosphate aminotransferase (EC 2.6.1.9) catalyzes the transamination of histidinol phosphate and 2-oxoglutarate to 3-(Imidazol-4-yl)-2-oxopropyl phosphate and glutamate, as the eighth step in histidine biosynthesis (Martin et al., *J. Bio. Chem.* 242:1168–1174, 1967). Some lactic acid bacteria are known to decarboxylate amino acids, such that histidine can be converted to histamine, which has undesirable physiological effects (Lonvaud-Funel, *FEMS Microb. Lett.* 199:9–13, 2001).

The polypeptide of SEQ ID NO: 50, and the polynucleotide of SEQ ID NO: 8 have utility for processing food products and as supplements and additives to food products. This histidinol-phosphate aminotransferase may also be used to develop non-food products. The attributes conferred by this enzyme include:

- altered levels of particular amino acids, leading to flavor and metabolic changes;
- affect aromatic amino acid metabolism, a source of important flavor compounds; and
- modulate production of biogenic amines.

These attributes may be produced in food, and other products, by directed activity of the enzyme, introduced in a bacterial strain (including strain HN001, or starter cultures) comprising a polynucleotide of SEQ ID NO: 8 or a variant, or as an enzyme preparation comprising a polypeptide of SEQ ID NO: 50 or a variant.

EXAMPLE 12

Isolation and Characterisation of malY-Aminotransferase from *L. rhamnosus* HN001

The full-length polynucleotide sequence of malY aminotransferase from *L. rhamnosus* strain HN001, given in SEQ ID NO: 17 and shown in FIG. 25 with ATG initiation and translation stop codons (boxed), was used to amplify the AJ6 aminotransferase gene from *L. rhamnosus* HN001 DNA using standard PCR methodology. The upstream and downstream primers were tagged with EcoRI and BamHI restriction endonuclease recognition sequences to facilitate cloning.

AJ6 was then cloned into the EcoRI and BamHI sites of the pGEX-6P-3 expression vector (Pharmacia Biotech) and transformed into *E. coli* strain DH-5α competent cells according to standard laboratory protocols. Cells were lysed by sonication and the presence of AJ6 protein, expressed as a GST fusion protein, checked by SDS-PAGE analysis. The polypeptide sequence of AJ6 is given in SEQ ID NO: 59 and shown in FIG. 26.

A feature of malY-aminotransferases is the ability to complement mutations of the *E. coli* cystathione β-lyase protein metC (Zdych et al., *J. Bacteriol.* 177:5035–5039, 1995). Therefore, AJ6 activity was assessed by suppression of the metC⁻ phenotype in the *E. coli* strain CAG18527 (Singer et al., *Microbiol. Rev.* 53:1–24, 1989) provided by the *E. coli* Genetic Stock Centre (Yale University, USA). CAG1 8527 cells require L-methionine for growth, in contrast to wild-type *E. coli* that is L-methionine-independent. A pGEX-6P-3 construct encoding the HN001 aminotransferase AJ6 was transformed into the CAG18527 *E. coli* strain and plated onto LB agar plates containing 100 µg/ml ampicillin. Ampicillin-resistant transformant colonies were picked and plated out onto selective media (M9 plates with and without 1 mM L-methionine, with and without 5 µg/ml ampicillin). Growth of the CAG18527 transformed with AJ6 was compared with the growth of wild-type CAG18527 cells and CAG18527 cells transformed with a pGEX-6P-3 construct encoding a non-aminotransferase irrelevant protein. Plates were incubated aerobically at 37° C. for 48 hrs and growth assessed.

Results in Table 11 indicate that while wild-type CAG18527 cells grew in the presence of methionine, no growth was observed in the presence of ampicillin. This confirmed the ampicillin-sensitive, methionine-auxotrophic phenotype of the CAG18527 strain. CAG18527 cells transformed with either empty pGEX-6P-3 or pGEX-6P-3 encoding an irrelevant HN001 protein (AC9) grew in the presence of methionine and ampicillin, but not in the absence of methionine, indicating that the metC-phenotype was not suppressed. CAG18527 cells transformed with pGEX-6P-3 encoding HN001 aminotransferase AJ6 were ampicillin resistant and grew on M9 media without methionine. Therefore, the AJ6 protein suppressed the metC⁻ mutation of CAG18527 strain E. coli cells.

TABLE 11

Results of M9 agar plate assay for suppression of the metC⁻ phenotype.

| E. coli CAG18527 transformed with: | M9 agar plates containing: | | |
|---|---|---|---|
| | L-methionine only | Ampicillin and L-methionine | Ampicillin only |
| — | + | − | − |
| pGEX-6P-3 | + | + | − |
| pGEX-6P-3 encoding AC9 | + | + | − |
| pGEX-6P-3 encoding AJ6 | + | + | + |

+: growth; −: no growth

The malY/PatB pyridoxal-5'-phosphate-dependent aminotransferase family (EC 2.6.1.-) appear to have both aminotransferase and regulatory activities (Mehta and Christen, Eur. J. Biochem. 203 :373–376, 1993), including the transamination of methionine and regulation of maltose utilisation (Reidl and Boos, J. Bacteriol. 173:4862–4876, 1991), as well as other activities (Chu et al., Infect. Imm. 63: 4448–4455,1995).

The polypeptide of SEQ ID NO: 59, and the polynucleotide of SEQ ID NO: 17 have utility for processing food products and as supplements and additives to food products. This aminotransferase may also be used to develop non-food products. The attributes conferred by this enzyme include:
- altered levels of particular amino acids, leading to flavor and metabolic changes
- altered expression of catabolite or other regulons
- modulation of hemolytic activity
- probiotic effects These attributes may be produced in food products by directed activity of the enzyme, introduced in a bacterial strain (including strain HN001, or starter cultures) comprising a polynucleotide of SEQ ID NO: 17 or a variant, or as an enzyme preparation comprising a polypeptide of SEQ ID NO: 59 or a variant.

EXAMPLE 13

Isolation and Characterisation of malY-Aminotransferase from L. rhamnosus HN001

The fill-length polynucleotide sequence of a second malY-aminotransferase from L. rhamnosus strain HN001, given in SEQ ID NO: 18 and shown in FIG. 27 with ATG initiation and translation stop codons (boxed), was used to amplify the AJ7 aminotransferase gene from L. rhamnosus HN001 DNA using standard PCR methodology. The upstream and downstream primers were tagged with EcoRI and BamHI restriction endonuclease recognition sequences to facilitate cloning.

AJ7 was then cloned into the EcoRI and BamHI sites of the pGEX-6P-3 expression vector (Pharmacia Biotech) and transformed into E. coli strain DH-5α competent cells according to standard laboratory protocols. Cells were lysed by sonication and the presence of AJ7 protein, expressed as a GST fusion protein, checked by SDS-PAGE analysis. The polypeptide sequence of AJ7 is given in SEQ ID NO: 60 and shown in FIG. 28.

A feature of malY-aminotransferases is the ability to complement mutations of the E. coli cystathione β-lyase protein metC (Zdych et al., J. Bacteriol. 177:5035–5039, 1995). Therefore, AJ7 activity was assessed by suppression of the metC phenotype in the E. coli strain CAG18527 (Singer et al., Microbiol. Rev. 53:1–24, 1989) provided by the E. coli Genetic Stock Centre (Yale University, USA). CAG18527 cells require L-methionine for growth, in contrast to wild-type E. coli that is L-methionine-independent. pGEX-6P-3 construct encoding the HN001 aminotransferase AJ7 was transformed into the CAG18527 E. coli strain and plated onto LB agar plates containing 100 μg/ml ampicillin. Ampicillin-resistant transformant colonies were picked and plated out onto selective media (M9 plates with and without 1 mM L-methionine, with and without 5 μg/ml ampicillin). Growth of the CAG18527 transformed with AJ7 was compared with the growth of wild-type CAG18527 cells and CAG18527 cells transformed with a pGEX-6P-3 construct encoding a irrelevant protein. Plates were incubated aerobically at 37° C. for 48 hrs and growth assessed.

Results in Table 12 indicate that while wild-type CAG18527 cells grew in the presence of methionine, no growth was observed in the presence of ampicillin. This confirmed the ampicillin-sensitive, methionine-auxotrophic phenotype of the CAG18527 strain. CAG18527 cells transformed with either empty pGEX-6P-3 or pGEX-6P-3 encoding an irrelevant HN001 protein (AC9) grew in the presence of methionine and ampicillin, but not in the absence of methionine, indicating that the metC-phenotype was not suppressed. CAG18527 cells transformed with pGEX-6P-3 encoding HN001 aminotransferase AJ7 were ampicillin resistant and grew on M9 media without methionine. Therefore, the AJ7 protein suppressed the metC⁺ mutation of CAG18527 strain E. coli cells.

TABLE 12

Results of M9 agar plate assay for suppression of the metC⁻ phenotype.

| E. coil CAG18527 transformed with: | M9 agar plates containing: | | |
|---|---|---|---|
| | L-methionine only | Ampicillin and L-methionine | Ampicillin only |
| — | + | − | − |
| pGEX-6P-3 | + | + | − |
| pGEX-6P-3 encoding AC9 | + | + | − |
| pGEX-6P-3 encoding AJ7 | + | + | + |

+: growth; −: no growth

The malY/PatB pyridoxal-5'-phosphate-dependent aminotransferase family (EC 2.6.1.-) appear to have both aminotransferase and regulatory activities (Mehta and Christen, Eur. J. Biochem. 203 :373–376, 1993), including the transamination of methionine and regulation of maltose utilization (Reidl and Boos, J. Bacteriol. 173:4862–4876, 1991), as well as other activities (Chu et al., Infect. Imm. 63: 4448–4455, 1995).

The polypeptide of SEQ ID NO: 60, and the polynucleotide of SEQ ID NO: 18 have utility for processing food products and as supplements and additives to food products. This aminotransferase may also be used to develop non-food products. The attributes conferred by this enzyme include:

altered levels of particular amino acids, leading to flavor and metabolic changes;
  altered expression of catabolite or other regulons;
  modulation of hemolytic activity; and
  probiotic effects These attributes may be produced in food, such as dairy products, by directed activity of the enzyme, introduced in a bacterial strain (including strain HN001, or starter cultures) comprising a polynucleotide of SEQ ID NO: 18 or a variant, or as an enzyme preparation comprising a polypeptide of SEQ ID NO: 60 or a variant.

EXAMPLE 14

Isolation and Characterisation of Cystathione β-Lyase from *L. rhamnosus* HN001

The full-length polynucleotide sequence of cystathione β-lyase from *L. rhamnosus* strain HN001, given in SEQ ID NO: 5 and shown in FIG. 29 with ATG initiation and translation stop codons (boxed), was used to amplify the AC8 cystathione β-lyase gene from *L. rhamnosus* HN001 DNA using standard PCR methodology.

AC8 was cloned into the pUniBlunt/V5-HisTopo vector (Invitrogen) and transformed into the *E. coli* strain PIR1 OneShot competent cells (Invitrogen). To construct an expression plasmid, the pUniBlunt/V5-HisTopo vector construct was recombined with the pBad/Thio-E vector (Invitrogen) and transformed into the *E. coli* strain TOP10 competent cells (Invitrogen) according to the manufacturer's instructions. The AC gene product was therefore cloned as a fusion protein tagged with a His-patch polypeptide and thioredoxin protein. The AC8 fusion protein was expressed and purified using a Ni-NTA column (Qiagen, Auckland, NZ) according to the manufacturer's instructions and protein expression checked by SDS-PAGE. The polypeptide sequence of AC8 is given in SEQ ID NO: 46 and shown in FIG. 30.

Cystathione β-lyase activity was assessed according to the method of Uren, *Methods in Enzymol.* 143:483–496, 1987, with modifications. Briefly, aliquots of the purified AC8-GST fusion protein were added to 1 ml cuvettes containing 780 μl of 0.1 M Tris-HCl pH 9.0, 200 μl of 10 mM L-cystathionine, and 20 μl of 0.1M potassium phosphate, with pyridoxal-5'-phosphate added to a final concentration of 20 μM, on ice. Change in OD was measured at 412 nm over time, and one unit of enzyme defined as the formation of 1 μmol of mercaptide per minute at 37° C. Cystathione μ-lyase activity of the AC8 fusion protein was compared with activity of an irrelevant protein (pBAD/Thio-E/Uni-CAT expression control vector, Invitrogen), and reactions containing water or Ni-NTA column elution buffer. Results are shown in FIG. 31, with rates of change of OD and enzyme activity given in Table 13.

Results in FIG. 31 and Table 13 indicate that similar background rates of mercaptide formation were observed in reactions containing water only, elution buffer only or 10 μl purified CAT fusion protein. Significantly greater mercaptide formation was observed in reactions containing 10 μl purified HN001 cystathione β-lyase AC8 fusion protein. Therefore, AC8 protein has cystathione β-lyase activity. FIG. 31 shows cystathione β-lyase activity measured as rate of mercaptide formation. ♦ 10 μl purified HN001 cystathione β-lyase AC8 fusion protein; ■ 10 μl purified CAT fusion protein; ▲ 10 μl $H_2O$ only; ● 10 μl elution buffer only.

TABLE 13

Cystathione β-lyase activity of AC8 compared with irrelevant protein, $H_2O$ and elution buffer controls.

| Protein | Δ $OD_{412}$/min | Enzyme activity (μmol/min/ml) |
| --- | --- | --- |
| AC8 fusion protein | 0.00328 | 16.31 |
| CAT fusion protein | 0.00242 | 12.03 |
| $H_2O$ only | 0.00232 | 11.53 |
| Elution buffer-only | 0.00233 | 11.58 |

The dose-response of the HN001 cystathione β-lyase activity AC8 was determined by comparing mercaptide formation in a series of dilutions of the purified enzyme. Results are shown in FIG. 32, and the rate of change in optical density and enzyme activities given in Table 14.

Results in FIG. 32 and Table 14 indicate that the increased rate of mercaptide peptide was proportional to the amount of AC8 fusion protein, supporting that AC8 encodes HN001 cystathionine β-lyase. FIG. 32 shows the experimentally determined dose-response of the AC8 fusion protein. Cystathione β-lyase activity of increasing amounts of His-patch/Thio/AC8 fusion protein; 10 μl(♦), 25 μl (■) and 50 μl (▲) purified protein showed increasing rates of mercaptide formation. The increase in mercaptide formation was proportional to amount of AC8 fusion protein added.

TABLE 14

Cystathione β-lyase activity in increasing amounts of AC8 protein

| Amount of purified AC8 fusion protein | Δ $OD_{410}$/min | Enzyme activity (μmol/min/ml) |
| --- | --- | --- |
| 10 μl | 0.00319 | 15.8 |
| 25 μl | 0.00378 | 18.8 |
| 50 μl | 0.00496 | 24.7 |

Cystathionine β-lyase (EC 4.4.1.8) deaminates cystathionine to L-homocysteine, ammonia and pyruvate (Dwivedi et al., *Biochem.* 21:3064–3069, 1982), and may also have active on L-cystine and related substrates (Uren, *Methods in Enzymol.* 143:483–486, 1987; Alting et al., *Appl. Environ. Microbiol.* 61:4037–4042,1995). Thus, cystathionine β-lyase is involved in a number of pathways including methionine metabolism and catabolism of sulphur-containing compounds. L-homocysteine has been shown to have important health impacts in humans (Nittynen et al., *Ann. Med.* 31:318–326, 1999; Giles et al., *Am. Heart J.* 139: 446–453, 2000).

The polypeptide of SEQ ID NO: 46, and the polynucleotide of SEQ ID NO: 5 have utility for processing food products and as supplements and additives to food products. This lyase may also be used to develop non-food products. The attributes conferred by this enzyme include:

altered flavor and metabolic characteristics through changes in levels of particular amino acids;
  altered levels of important sulphur-containing flavor compounds; and
  health impacts through the modulation of L-homocysteine levels These attributes may be produced in food products by directed activity of the enzyme, introduced in a bacterial strain (including strain HN001, or starter cultures) comprising a polynucleotide of SEQ ID NO: 5 or a variant, or as an enzyme preparation comprising a polypeptide of SEQ ID NO: 46 or a variant.

EXAMPLE 15

Isolation and Characterisation of Phosphoenolpyruvate Hydratase from *L. rhamnosus* HN001

HN001 phosphoenolpyruvate hydratase AK4 was isolated by a series of experiments designed to identify HN001 strain proteins that were up-regulated in response to physiological stresses encountered during industrial processes. Cells were subjected to heat or osmotic shock, proteins radiolabeled with [$^{35}$S]-methionine and [$^{35}$S]-cysteine (Amersham, USA), and cell-free extracts from shocked and non-shocked HN001 cultures compared by 2-D analysis and N-terminal sequencing as below.

Shock proteins were radiolabeled according to standard laboratory methods. Heat shock was performed by incubation at 50° C. on both log phase and stationary phase HN001 strain cultures, and salt (osmotic) shock on late log phase by HN001 strain cultures by transfer into MRS broth containing 0.6 M sodium chloride. Immediately after heat or osmotic shock, approximately 5 µCi ml$^{-1}$ each of L-[$^{35}$S]-methionine and L-[$^{35}$S]-cysteine were added to the culture medium and incubated for 30 min, followed by the addition of excess of cold 1 mM L-cysteine hydrochloride and 1 mM L-methionine, and cultures then placed on ice. Radiolabeled cells were collected by centrifugation washed twice in washing buffer (0.1 M Tris-HCl, 1 mM EDTA, pH 7.5) and resuspended in resuspension buffer (10 MM Tris-HCl, 5 mM MgCl$_2$, 2 mM PMSF, pH 7.5). About 0.5 ml cell suspension was mixed with 0.5 g of 0.17–0.18 mm glass beads and homogenized using Shake-it-Baby (Biospec products). After homogenization for 25 min, the suspension was centrifuged and the supernatant was collected.

2-D Gel electrophoresis was performed on the cell free extract containing 50–75 µg of protein. Excess chilled methanol was added and kept at −80° C. for 1 hr followed by centrifugation at 13,000 rpm to collect the pellet. The pellet was vacuum-dried and resuspended in rehydration buffer (8M urea, 2% Triton X 100, 0.5% (v/v) IPG buffer (Amersham Pharmacia Biotech, USA) and few grains of bromophenol blue). Endonuclease (Sigma) was added (150 U) to the rehydrated sample and incubated at room temperature for 20 min. The solution was then added to IPG strips and rehydrated overnight at 20° C. The rehydrated IPG strips were placed on a flat bed electrophoresis unit (Amersham Pharmacia Biotech, USA) and focused at 300 Volts for 30 min followed by 3,000 volts for 4 hrs. The focused strips were equilibrated (15 min) in equilibration buffer (50 mM Tris-HCl, pH 8.8, 6 M Urea, 30% (v/v) glycerol, 2% (w/v) SDS and few grains bromophenol blue) containing either dithioerythritol (1.0% w/v) or iodoacetamide (2.5% w/v). After equilibration, the strips were placed on the second dimensional (vertical SDS-PAGE homogeneous) gels a using PROTEAN II xi cell (Bio-Rad). The second dimension was carried out at 20 mA per plate for 15 min and 40 mA per plate for 4 hrs.

Gels were then equilibrated in protein transfer buffer (24.8 mM Tris, pH 8.3, 192 mM Glycine and 10% (v/v) methanol) and blotted on a PVDF membrane using a Trans-blot apparatus (Bio-Rad) at 24 volts overnight at 4° C. PVDF membranes were exposed to Hyperfilm-βmax (Amersham Pharmacia Biotech, USA) for up to two weeks using standard procedures. Resultant autoradiograms were scanned using the Fluor-S Multimager system (Bio-Rad) and patterns compared using PDQuest software. For N-terminal sequencing, membranes were stained with Coommassie Brilliant Blue R-250. The desired spots were excised and N-terminal sequencing carried out using a protein sequencer (Applied BioSystems, Model 476A) according to standard methods.

A protein up-regulated by heat and osmotic shock was N-terminal sequenced and the amino acid sequence is given in SEQ ID NO: 83. This sequence was used to search an HN001 sequence database using the TBLASTN program (NCBI) and the corresponding polynucleotide and polypeptide sequences are given in SEQ ID NOS: 20 and 62, and shown in FIGS. 33 and 34, respectively. Similarity searching using BLAST software revealed closest amino acid sequence similarity to phosphoenolpyruvate hydratase sequences but with significant differences.

Phosphoenolpyruvate hydratase (EC 4.2.1.11) is a glycolytic pathway enzyme that hydrolyzes 2-phospho-D-glycerate to give phosphoenolpyruvate (Malmstroem, B. G, *The Enzymes,* 2nd. Ed., Boyer, P. D., Lardy, H., Myrbäck, K., eds., 5:471–494, 1961).

The polypeptide of SEQ ID NO: 62, and the polynucleotide of SEQ ID NO: 20 have utility for processing food products and as supplements and additives to food products. This hydratase may also be used to develop non-food products. The attributes conferred by this enzyme include:
  enhanced bacterial survival in industrial processes;
  improved colonization of human intestinal environment; and
  altered metabolic characteristics through changes in carbohydrate utilization These attributes may be produced in food products by directed activity of the enzyme, introduced in a bacterial strain (including strain HN001, or starter cultures) comprising a polynucleotide of SEQ ID NO: 20 or a variant, or as an enzyme preparation comprising a polypeptide of SEQ ID NO: 62 or a variant.

EXAMPLE 16

Isolation and Characterisation of Tagatose Bisphosphate Aldolase from *L. rhamnosus* HN001

HN001 tagatose bisphosphate aldolase AK1 was isolated by a series of experiments designed to identify HN001 strain proteins that were up-regulated in response to physiological stresses encountered during industrial processes. Cells were subjected to heat or osmotic shock, proteins radiolabeled with [$^{35}$S]-methionine and [$^{35}$S]-cysteine (Amersham, USA), and cell-free extracts from shocked and non-shocked HN001 cultures compared by 2-D analysis and N-terminal sequencing as described for Example 15 (HN001 phosphoenolpyruvate hydratase AK4).

A protein up-regulated by heat and osmotic shock was N-terminal sequenced and the polypeptide sequence is given in SEQ ID NO: 81. This was used to search an HN001 sequence database using the TBLASTN program (NCBI) and the corresponding polynucleotide and polypeptide sequences are given in SEQ ID NOS: 19 and 61, and shown in FIGS. 35 and 36, respectively. Similarity searching using BLAST software revealed closest amino acid sequence similarity to tagatose bisphosphate aldolase sequences but with significant differences.

Tagatose bisphosphate aldolase (EC 4.1.2.40) is involved in the tagatose 6-phosphate pathway of lactose catabolism, and converts D-tagatose 1,6-bisphosphate to glycerone phosphate and D-glyceraldehyde 3-phosphate (Anderson and Markwell, *Methods in Enzymol.* 90:232–234, 1982).

The polypeptide of SEQ ID NO: 61, and the polynucleotide of SEQ ID NO: 19 have utility for processing food and other products and as supplements and additives to food products. This aldolase may also be used to develop non-food products. The attributes conferred by this enzyme include:
  enhanced bacterial survival in industrial processes;
  improved colonization of human intestinal environment; and
  altered metabolic characteristics through changes in carbohydrate utilization These attributes may be produced in food products or in supplements, by directed activity of the enzyme, introduced in a bacterial strain (including strain HN001, or starter cultures) comprising a polynucleotide of SEQ ID NO: 19 or a variant, or as an enzyme preparation comprising a polypeptide of SEQ ID NO: 61 or a variant.

EXAMPLE 17

Isolation and Characterisation of Phosphoglycerate Kinase from *L. rhamnosus* HN001

HN001 phosphoglycerate kinase AK6 was isolated by a series of experiments designed to identify HN001 strain proteins that were up-regulated in response to physiological stresses encountered during industrial processes. Cells were subjected to heat or osmotic shock, proteins radiolabeled with [$^{35}$S]-methionine and [$^{35}$S] cysteine (Amersharm USA), and cell-free extracts from shocked and non-shocked HN001 cultures compared by 2-D analysis and N-terminal sequencing as described for Example 15 (HN001 phosphoenolpyruvate hydratase AK4).

A protein up-regulated by heat and osmotic shock was N-terminal sequenced and the polypeptide sequence is given in SEQ ID NO: 82. This was used to search an HN001 sequence database using the TBLASTN program (NCBI) and the corresponding polynucleotide and polypeptide sequences are given in SEQ ID NOS: 22 and 64, and shown in FIGS. 37 and 38, respectively. Similarity searching using BLAST software revealed closest amino acid sequence similarity to phosphoglycerate kinase sequences but with significant differences.

Phosphoglycerate kinase (EC 2.7.2.3) is involved in the glycolysis pathway, and catalyzes the phospho-transfer reaction of ATP and 3-phospho-D-glycerate to ADP and 3-phospho-D-glyceroyl phosphate (bacterial enzyme reviewed in Suzuki and Imahori, *Methods in Enzymol.* 90:126–130, 1982).

The polypeptide of SEQ ID NO: 64, and the polynucleotide of SEQ ID NO: 22 have utility for processing food products and as supplements and additives to food products. This kinase may also be used to develop non-food products. The attributes conferred by this enzyme include:
  enhanced bacterial survival in industrial processes;
  improved colonization of human intestinal environment; and
  altered metabolic characteristics through changes in carbohydrate utilization These attributes may be produced in food products and supplements by directed activity of the enzyme, introduced in a bacterial strain (including strain HN001, or starter cultures) comprising a polynucleotide of SEQ ID NO: 22 or a variant, or as an enzyme preparation comprising a polypeptide of SEQ ID NO: 64 or a variant.

EXAMPLE 18

Isolation and Characterisation of Triosephosphate Isomerase from *L. rhamnosus* HN001

HN001 triosephosphate isomerase AK5 was isolated by a series of experiments designed to identify HN001 strain proteins that were up-regulated in response to physiological stresses encountered during industrial processes. Cells were subjected to heat or osmotic shock, proteins radiolabeled with [$^{35}$S]-methionine and [$^{35}$S]-cysteine (Amersham, USA), and cell-free extracts from shocked and non-shocked HN001 cultures compared by 2-D analysis and N-terminal sequencing as described for Example 15 (HN001 phosphoenolpyruvate hydratase AK4).

A protein up-regulated by heat and osmotic shock was N-terminal sequenced and the polypeptide sequence is given in SEQ ID NO: 76. This sequence was used to search an HN001 sequence database using the TBLASTN program (NCBI) and the corresponding polynucleotide and polypeptide sequences are given in SEQ ID NOS: 21 and 63 and shown in FIGS. 39 and 40, respectively. Similarity searching using BLAST software revealed closest amino acid sequence similarity to triosephosphate isomerase sequences but with significant differences. FIG. 39 shows the nucleotide sequence containing *L. rhamnosus* strain HN001 triosephosphate isomerase AK5 showing ATG initiation and translation stop codons (boxed).

Triosephosphate isomerase (EC 5.3.1.1) is involved in the glycolysis pathway, and catalyzes the isomerisation reaction of D-glyceraldehyde 3-phosphate to glycerone phosphate (bacterial enzyme: Fahey et al., *Biochem. J.* 124:77P, 1971).

The polypeptide of SEQ ID NO: 63, and the polynucleotide of SEQ ID NO: 21 have utility for processing food and other products and as supplements and additives to food products. This isomerase may also be used to develop non-food products. The attributes conferred by this enzyme include:
  enhanced bacterial survival in industrial processes, including food processing;
  improved colonization of human intestinal environment; and
  altered metabolic characteristics through changes in carbohydrate utilization These attributes may be produced in food products or supplements by directed activity of the enzyme, introduced in a bacterial strain (including strain HN001, or starter cultures) comprising a polynucleotide of SEQ ID NO: 21 or a variant, or as an enzyme preparation comprising a polypeptide of SEQ ID NO: 63 or a variant.

EXAMPLE 19

Isolation and Characterisation of Fructose-bisphosphate Aldolase from *L. rhamnosus* HN001

HN001 fructose-bisphosphate aldolase AM8 was isolated by a series of experiments designed to identify HN001 strain proteins that were up-regulated in response to physiological stresses encountered during industrial processes. Cells were subjected to heat or osmotic shock, proteins radiolabeled with [$^{35}$S]-methionine and [$^{35}$S]-cysteine (Amersham, USA), and cell-free extracts from shocked and non-shocked HN001 cultures compared by 2-D analysis and N-terminal sequencing as described for Example 15 (HN001 phosphoenolpyruvate hydratase AK4).

A protein upregulated by heat and osmotic shock was N-terminal sequenced and the amino acid is given in SEQ ID NO: 77. This was used to search an HN001 sequence database using the TBLASTN program (NCBI) and and the corresponding polynucleotide and polypeptide sequences are given in SEQ ID NOS: 29 and 71 and shown in FIGS. 74 and 75, respectively.

Fructose-bisphosphate aldolase (EC 4.1.2.13) is involved in the glycolysis pathway, and catalyzes the elimination reaction of D-Fructose 1,6-bisphosphate to glycerone phosphate and D-glyceraldehyde 3-phosphate (bacterial enzyme reviewed in: Ujita and Kimura, *Methods in Enzymol.* 90: 235–241, 1982).

The polypeptide of SEQ ID NO: 71, and the polynucleotide of SEQ ID NO: 29 have utility for processing food and other products and as supplements and additives to food and other products. This aldolase may also be used to develop non-food products. The attributes conferred by this enzyme include:

enhanced bacterial survival of industrial processes;
  improved colonization of human intestinal environment; and
  altered metabolic characteristics through changes in carbohydrate utilization These attributes may be produced in food products and supplements by directed activity of the enzyme, introduced in a bacterial strain (including strain HN001, or starter cultures) comprising a polynucleotide of SEQ ID NO: 29 or a variant, or as an enzyme preparation comprising a polypeptide of SEQ ID NO: 71 or a variant.

EXAMPLE 20

Isolation and Characterisation Phosphoryl Carrier Protein HPR from *L. rhamnosus* HN001

HN001 phosphoryl carrier protein HPR AA9 was isolated by a series of experiments designed to identify HN001 strain proteins that were up-regulated in response to physiological stresses encountered during industrial processes. Cells were subjected to heat or osmotic shock, proteins radiolabeled with [$^{35}$S]-methionine and [$^{35}$S]-cysteine (Amersham, USA), and cell-free extracts from shocked and non-shocked HN001 cultures compared by 2-D analysis and N-terminal sequencing as described for Example 15 (HN001 phosphoenolpyruvate hydratase AK4).

A protein upregulated by heat and osmotic shock was N-terminal sequenced and the determined amino acid sequence is given in SEQ ID NO: 78. This sequence was used to search an HN001 sequence database using the TBLASTN program (NCBI) and the corresponding polynucleotide and polypeptide sequences are given in SEQ ID NOS: 4 and 45 and shown in FIGS. 41 and 42, respectively. Similarity searching using BLAST software revealed closest amino acid sequence similarity to phosphoryl carrier protein HPR sequences but with significant differences.

Phosphoryl carrier protein HPR is involved in the phosphoenolpyruvate:carbohydrate phosphotransferase system (PTS) responsible for the uptake and phosphorylation of a number of carbohydrates (De Reuse et al., *Gene* 35:199–207, 1985; Gonzy-Treboul et al., *Mol. Microbiol.* 3:103–112, 1989). PTS is also involved in the regulation of various bacterial functions by various mechanisms, including catabolite repression, inducer exclusion, and inducer expulsion (reviewed in Postma et al., *Microbiol. Rev.* 57:543–594, 1993; Reizer et al., *Crit. Rev. Microbiol.* 15:297–338, 1988; Saier et al., *Microbiol.* 142:217–230, 1996).

The polypeptide of SEQ ID NO: 45, and the polynucleotide of SEQ ID NO: 4 have utility for processing food products and as supplements and additives to food products. This aldolase may also be used to develop non-food products. The attributes conferred by this enzyme include:

enhanced bacterial survival in industrial processes;
  improved colonization of human intestinal environment;
  altered metabolic characteristics through changes in carbohydrate utilization; and
  control of catabolite regulation.

These attributes may be produced in food, such as dairy products, by directed activity of the enzyme, introduced in a bacterial strain (including strain HN001, or starter cultures) comprising a polynucleotide of SEQ ID NO: 4 or a variant, or as an enzyme preparation comprising a polypeptide of SEQ ID NO: 45 or a variant.

EXAMPLE 21

Isolation and Characterisation of Chaperone Protein dnaK from *L. rhamnosus* HN001

HN001 dnaK chaperone protein AM9 was isolated by a series of experiments designed to identify HN001 strain proteins that were up-regulated in response to physiological stresses encountered during industrial processes. Cells were subjected to heat or osmotic shock, proteins radiolabeled with [$^{35}$S]-methionine and [35S]cysteine (Amersham, USA), and cell-free extracts from shocked and non-shocked HN001 cultures compared by 2-D analysis and N-terminal sequencing as described for Example 15 (HN001 phosphoenolpyruvate hydratase AK4).

A protein up-regulated by heat and osmotic shock was N-terminal sequenced and the determined amino acid sequence is given in SEQ ID NO: 79. This sequence was used to search an HN001 sequence database using the TBLASTN program (NCBI) and the corresponding polynucleotide and polypeptide sequences are given in SEQ ID NOS: 30 and 72 and shown in FIGS. 76 and 77, respectively. Similarity searching using BLAST software revealed closest amino acid sequence similarity to chaperone protein dnaK sequences but with significant differences.

Chaperone protein dnaK is a 70 kDa heat shock protein (HSP). DnaK chaperones act by binding and protecting exposed regions on unfolded or partially folded protein chains, and are involved in reactivating proteins that become aggregated after heat shock (reviewed in Lund, *Adv. Microbial Physiol.* 44:93–140, 2001). Overexpression may contribute to plasmid instability (Lobacz and Wolska, *Acta Microbiol. Pol.* 46:393–397, 1977).

The polypeptide of SEQ ID NO: 72, and the polynucleotide of SEQ ID NO: 30 have utility for processing food products and as supplements and additives to food products. This chaperone protein may also be used to develop non-food products. The attributes conferred by this protein include:

enhanced bacterial survival in industrial processes;
  improved colonization of human intestinal environment;
  altered protein translation characteristics; and
  methods to control plasmid stability.

These attributes may be produced in food, such as dairy products, by directed activity of the enzyme, introduced in a bacterial strain (including strain HN001, or starter cultures) comprising a polynucleotide of SEQ ID NO: 30 or a variant, or as an enzyme preparation comprising a polypeptide of SEQ ID NO: 72 or a variant.

EXAMPLE 22

Isolation and Characterisation of
Glyceraldehyde-3-phosphate Dehydrogenase from
L. rhamnosus HN001

HN001 glyceraldehyde-3-phosphate dehydrogenase AK7 was isolated by a series of experiments designed to identify HN001 strain proteins that were up-regulated in response to physiological stresses encountered during industrial processes. Cells were subjected to heat or osmotic shock, proteins radiolabeled with [$^{35}$S]-methionine and [$^{35}$S]-cysteine (Amersham, USA), and cell-free extracts from shocked and non-shocked HN001 cultures compared by 2-D analysis and N-terminal sequencing as described for Example 15 (HN001 phosphoenolpyruvate hydratase AK4).

A protein up-regulated by heat and osmotic shock was N-terminal sequenced and the determined amino acid sequence is given in SEQ ID NO: 80. This sequence was used to search an HN001 sequence database using the TBLASTN program (NCBI) and the corresponding polynucleotide and polypeptide sequences are given in SEQ ID NOS: 23 and 65, and shown in FIGS. 43 and 44, respectively. Similarity searching using BLAST software revealed the closest amino acid sequence similarity to glyceraldehyde-3-phosphate dehydrogenase sequences but with significant differences.

A second experiment was also performed to identify surface layer proteins extracted from Lactobacillus rhamnosus HN001 strain. Surface layer proteins from were extracted using the method of Turner et al., J. Bacteriol. 179:3310–3316, 1997. Briefly, 100 ml stationary phase HN001 culture was pelleted by centrifugation, washed with an equal volume of 0. 15M NaCl, resuspended in 1 ml of 5M LiCl$_2$ and kept on ice for 15 min. The crude lysate was centrifuged at 13,000 rpm using a microcentrifuge and analyzed by SDS-PAGE on a 12.5% gel. To facilitate better extraction of surface layer proteins, freeze-dried DR20 was extracted with 0.2% SDS and 5M LiCl$_2$ as described by Brennan et al., Infect. Imm. 52:840–845, 1986 and Toba et al., J. Imm. Methods 182:193–207, 1995. After 1-D electrophoresis according to standard laboratory methods, gels were blotted on a PVDF membrane using a Semi-dry blotting apparatus (Bio-Rad). A major surface protein with molecular weight between 30 and 46 kDa was excised and N-terminal sequencing performed using a protein sequencer (Applied BioSystems, Model 476A). The determined N-terminal sequence was identical to that obtained from the heat and osmotic shock experiments as described above. Therefore, HN001 gene AK7 encodes glyceraldehyde-3-phosphate dehydrogenase, which is up-regulated by shock and is a major cell surface protein.

Glyceraldehyde-3-phosphate dehydrogenase (EC 1.2.1.12) is part of the glycolytic pathway and catalyzes the redox reaction of D-Glyceraldehyde 3-phosphate, phosphate and NAD$^+$ to 3-phospho-D-glyceroyl phosphate and NADH (for bacterial enzyme see Amelunxen, Methods in Enzymol. 41:268–273, 1975; D'Alessio and Josse, J. Biol. Chem. 246:4326–4333, 1971). The enzyme has also been found to be a major cell-surface component of several bacterial species including Saccharomyces cerevisiae (Delgado et al., Microbiol. 147:411–417, 2001), Candida albicans (Gil-Navarro et al., J. Bacteriol. 179: 4992–4999, 1997) and group A Streptococci (Pancholi and Fischetti, Proc. Natl. Acad. Sci. USA 90:8154–8158, 1993).

The polypeptide of SEQ ID NO: 65, and the polynucleotide of SEQ ID NO: 23 have utility for processing food products and as supplements and additives to food products. This dehydrogenase may also be used to develop non-food products. The attributes conferred by this enzyme include:
flavor and aroma enhancement;
enhanced bacterial survival in industrial processes;
prolonged survival in storage;
improved colonization of human intestinal environment;
enhanced textural properties;
enhanced adhesion to intestinal cell surfaces; and
altered metabolic characteristics These attributes may be produced in food, such as dairy products, by directed activity of the enzyme, introduced in a bacterial strain (including strain HN001, or starter cultures) comprising a polynucleotide of SEQ ID NO: 23 or a variant, or as an enzyme preparation comprising a polypeptide of SEQ ID NO: 65 or a variant.

EXAMPLE 23

Isolation and Characterisation of Transcription
Regulator sorR from L. rhamnosus HN001

The full-length polynucleotide sequence of a transcription regulator sorR, given in SEQ ID NO: 24 and shown in FIG. 45, was used to amplify the AL3 transcription regulator sorR gene from L. rhamnosus HN001 DNA using standard PCR methodology. The upstream and downstream primers were tagged with BamHI and PstI restriction endonuclease recognition sequences to facilitate cloning. The polypeptide sequence of AL3 is given in SEQ ID NO: 66 and shown in FIG. 46.

Full-length HN001 sorR transcription regulator AL3 was cloned into BamHI and PstI cut pFX3 vector (an in-house E. coli/Lactococcus lactis shuttle vector as used in Xu et al., FEMS Microbiol. Lett. 61:55–59, 1991), and transformed into competent E. coli DH5α cells according to standard laboratory methods. Positive transformants were selected, grown overnight, and the plasmid construct isolated using a QIAprep Spin Miniprep Kit (Qiagen). The pFX3 construct encoding the HN001 sorR transcription regulator AL3 was digested using the restriction enzymes EcoRI and NruI, which released a 500 bp internal AL3 fragment that was cloned into the pBEry1 vector cut with EcoRI and SmaI. The 3.6 kb pBEry1 vector was constructed using the replicon and multiple cloning site (MCS) from the phagemid pBlueScript (pBS-SK+) (Stratagene, La Jolla Calif., USA). The ampicillin resistance gene in pBS-SK+ was removed by digestion with RcaI (Roche, Auckland, New Zealand) and the 1,953 bp fragment containing the ColE1 origin and multiple cloning site purified and treated with Klenow enzyme (Roche) to give a blunt-ended fragment. A gene encoding resistance to erythromycin (Em) was isolated on a 1.6 kb fragment obtained after cutting pVA891 (Macrina et al., Gene 25:145–50, 1983) with ClaI and HindIII and treatment with Klenow to give blunt ends. The 1.6 kb Em fragment was ligated to the 1,953 bp pBS-SK+ fragment, transformed into E. coli TG1 (Gibson T J, Studies on the Epstein-Barr virus genome. Ph.D. Thesis, University of Cambridge, Cambridge, England, 1984), and plated on LB agar plates containing 200 μg/ml Em. Maintenance of α-complementation for blue/white colour selection of recombinant pBEry1 clones was confirmed by growing E. coli colonies on agar plates containing IPTG/X-gal.

The resulting pBEryl construct encoding the HN001 sorR transcription regulator AL3 gene was transformed into competent HN001 cells and grown anaerobically for 48 hrs at 37° C. on MRS *lactobacilli* agar (Difco, Detroit Mich.) containing 2.5 μg/ml Em. Erythromycin-resistant HN001 were checked for integration of the plasmid construct into the sorR gene by PCR using vector-specific (T3 or T7) and AL3 internal fragment-specific primers. Colonies giving PCR patterns consistent with the insertional inactivation of the endogenous HN001 sorR transcription regulator AL3 gene were assessed for sorbose auxotrophy.

Auxotrophy of selected HN001 mutants for metabolism of sorbose was tested by growing pure cultures (1% inoculum) overnight at 37° C. on MRS agar in the presence of 1% sorbose or 1% glucose, compared to wild-type HN001 and undefined mutant HN001 (Em-resistant cultures with intact sorR transcription regulator AL3 gene, the result of a random integration event) cultures.

Results in Table 15 indicate that the AL3⁻ HN001 mutant strain failed to utilize sorbose as a carbon source in contrast to wild type HN001 and undefined mutant HN001 strain. This result was confirmed by growing pure cultures (1% inoculum) overnight at 37° C. in liquid MRS broth with 1% sorbose or 1% glucose and measuring absorbance at 600 nm. Again, results showed a clear difference in growth between the AL3⁻ mutant strain, and the wild-type and undefined mutant HN001 strains containing intact the AL3 gene. Thus, the AL3 gene is required for sorbose metabolism in HN001, and encodes the sorR transcriptional regulator.

TABLE 15

Results of assessment of sorbose auxotrophy.

| MRS plates with: | Wild type HN001 | Undefined HN001 mutant | AL3⁻ mutant HN001 |
| --- | --- | --- | --- |
| 1% glucose | + | + | + |
| 1% sorbose | + | + | − |

+: growth; −: no growth

The sorR transcriptional regulator is required for the transcription of the sorbose operon, so regulating the utilization of L-sorbose as a carbon source, and its expression is induced by sorbose (Yebra et al., *J. Bacteriol.* 182:155–163, 2000; Sprenger and Lengeler, *Mol. Gen. Genetics* 209: 352–359, 1987).

The polypeptide of SEQ ID NO: 66, and the polynucleotide of SEQ ID NO: 24 have utility as transcriptional regulators in *L. rhamnosus* and other bacterial species. Specifically, applications for the HN001 sorR transcriptional regulator include:

Reagents for the control or modification of metabolic processes; and

Construction of sorbose-inducible HN001 expression vectors using the sorR gene promoter

EXAMPLE 24

Isolation and Characterisation of Formamidopyrimidine-DNA-Glycosylase from *L. rhamnosus* HN001

The full-length polynucleotide sequence of formamidopyrimidine-DNA-glycosylase (fpg) from *L. rhamnosus* strain HN001, given in SEQ ID NO: 25 and shown in FIG. 47 with ATG initiation and translation stop codons (boxed), was used to amplify the AL4 fpg gene from *L. rhamnosus* HN001 DNA using standard PCR methodology. The upstream and downstream primers were tagged with EcoRI and SalI restriction endonuclease recognition sequences to facilitate cloning.

AL4 was then cloned into the EcoRI and SalI sites of the pKK223-3 expression vector (Pharmacia Biotech) and transformed into the *E. coli* strain DH5α competent cells according to standard laboratory protocols. The polypeptide sequence of AL4 is given in SEQ ID NO: 67 and shown in FIG. 48. Expression of the fpg AL4 protein was confirmed by SDS-PAGE analysis.

AL4 fpg activity was assayed according to the previously published methods (Duwat et al., *Microbiol.* 141:411–417, 1995; Zhang et al., *Nucleic Acids Res.* 26:4669–4675, 1998) that examined the ability of fpg to suppress the spontaneous mutator phenotype of fpg or mutY mutants of *E. coli*. The *E. coli* strain CSH117 (Miller, in: *A short course in Bacterial Genetics*, Cold Spring Harbor Press, Cold Spring Harbor, N.Y., 1992) that contained a mutated mutY gene was obtained from the *E. coli* Genetic Stock Centre (Yale University, USA) and transformed with the pKK223-3 construct encoding the HN001 fpg AL4 gene according to standard laboratory methods. Positive transformants were selected according to ampicillin resistance, and used to innoculate 7 μml LB broth cultures containing 100 μg/ml ampicillin and incubated aerobically at 37° C. with shaking. Cultures containing pKK223-3 constructs encoding AL4 or empty pKK223-3 vector were grown to similar OD at 600 nm, serially diluted, and plated in triplicate on LB plates with and without 100 μg/ml rifampicin (Sigma). Plates were incubated overnight at 37° C. and colonies counted. Results are shown in Table 16 as mean plate counts from three independent experiments.

Results in Table 16 indicate there was a significant difference in the frequency of mutations leading to rifampicin resistance in *E. coli* CSH117 transformed with pKK223-3 encoding HN001 fpg AL4 and empty pKK22-3 vector ($p<0.001$ by paired Student's t-test (1-tailed)). Becuase the presence of AL4 suppressed the spontaneous mutation rate, it was concluded that AL4 encoded the HN001 fpg protein.

TABLE 16

Spontaneous mutagenesis in *E. coli* CHS117 expressing the HN001 fpg AL4 gene.

| Expt: | *E. coil* CSH117 transformed with pKK223-3 encoding: | Counts on LB plates (no rifampicin) ($10^8$/ml) | Counts on LB plates with rifampicin ($10^1$/ml) | Mutation frequency* |
| --- | --- | --- | --- | --- |
| 1 | Empty | 13.8 | 20.0 | 14.5 |
|   | AL4 | 11.0 | 3.7 | 3.4 |
| 2 | Empty | 13.0 | 25.8 | 20 |
|   | AL4 | 10.3 | 9.5 | 9.3 |
| 3 | Empty | 12.1 | 24.4 | 20.1 |
|   | AL4 | 11.6 | 8.6 | 7.7 |

*expressed as the number of rifampicin-resistant mutants per $10^8$ cells

The fpg protein (EC 3.2.2.23) is a DNA glycosylase/AP lyase that removes oxidized purine residues present in DNA, including the highly mutagenic C8-oxo-guanine (8-oxoG) generated in DNA by active oxygen during metabolism (Laval et al., *Mutation Res.* 233:73–79, 1990; Boiteux et al., *EMBO J.* 6: 3177–3183, 1987). The fpg protein exhibits three catalytic activities in vitro (Olga et al., *J. Biol. Chem.* 275:9924–9929, 2000): a DNA glycosylase that excises modified nucleotide bases (Laval et al., *Mutation Res.* 402:

93–102, 1998), an AP lyase that incises DNA at abasic sites by an elimination mechanism, and a deoxyribophosphodiesterase that removes 5'-terminal deoxyribose phosphate residues.

The polypeptide of SEQ ID NO: 67, and the polynucleotide of SEQ ID NO: 25 have utility for processing food products and as supplements and additives to food products. This glycosylase may also be used to develop non-food products. The applications for and attributes conferred by this enzyme include:

Reagents or techniques to improve the survival of HN001 in aerobic conditions;
Enhanced bacterial survival in industrial processes; and
Enhanced bacterial survival in the intestinal environment These attributes may be produced in food, such as dairy products, by directed activity of the enzyme, introduced in a bacterial strain (including strain HN001, or starter cultures) comprising a polynucleotide of SEQ ID NO: 25 or a variant, or as an enzyme preparation comprising a polypeptide of SEQ ID NO: 67 or a variant.

EXAMPLE 25

Isolation and Characterisation of Acetoin Dehydrogenase from L. rhamnosus HN001

The full-length polynucleotide sequence of acetoin dehydrogenase from L. rhamnosis strain HN001, given in SEQ ID NO: 32 and shown in FIG. 49 with ATG initiation and translation stop codons (boxed), was used to amplify the AP1 acetoin dehydrogenase gene from L. rhamnosus HN001 DNA using standard PCR methodology. The upstream and downstream primers were tagged with EcoRI and SalI restriction endonuclease recognition sequences to facilitate cloning.

AP1 was then cloned into the EcoRI and SalI sites of the pGEX-6P-3 expression vector (Pharmacia Biotech) and transformed into the E. coli strain K12 XL-1Blue competent cells according to standard laboratory protocols. The polypeptide sequence of acetoin dehydrogenase AP1 is given in SEQ ID NO: 74 and shown in FIG. 50. The acetoin dehydrogenase AP1 protein was expressed as a fusion protein with glutathione S-transferase (GST), and purified using Glutathione Sepharose 4B resin (Pharmacia Biotech) according to the manufacturer's instructions. An aliquot of purified AP1-GST fusion protein was confirmed by SDS-PAGE analysis.

Acetoin dehydrogenase activity was assayed according to published methods (Rattray et al., Int. Dairy J. 10:781–789, 2000) with some modifications. Briefly, acetoin dehydrogenase activity was measured spectrophotometrically by monitoring the change in absorbance of the cofactor NADH at 340 nm. Aliquots of the purified AP4-GST fusion protein solution were added to reaction mixtures containing 50 mM 2[N-morpholino]ethanesulphonic acid (MES, Sigma) buffer pH 5.5 at 30° C. and the reactions started by the addition of 0.5 mM NADH and 37 mM diacetyl (Sigma) in a total volume of 1 ml. The change in optical density at 340 mn was measured, and rates of NADH utilization measured as an indicator of acetoin dehydrogenase activity. Enzyme activity was calculated as the amount of protein required to convert 1 µmol diacetyl and NADH to acetoin and $NAD^+$ per minute at pH 5.5 at 30° C. Enzyme activity of AP1-GST fusion protein was compared to that of an irrelevant GST-fusion protein, GST protein and elution buffer only.

Results presented in FIG. 51 and Table 17 indicate significant background utilization of NADH in the reactions. Similar rates were observed for elution buffer, GST protein and irrelevant fusion protein, indicating that the GST fusion protein did not exhibit acetoin reductase activity. Nonetheless, presence of the AP1-GST fusion protein gave significantly greater acetoin dehydrogenase activity than background, indicating that HN001 AP1 protein encodes acetoin dehydrogenase. FIG. 51 shows the results of an acetoin reductase assay as measured by oxidation of NADH cofactor by OD at 340 nm in the presence of acetoin substrate. ●, elution buffer only; ■, purified irrelevant GST-fusion protein; ▲, purified GST protein; ♦, purified AP1 -GST fusion protein.

TABLE 17

Acetoin reductase activity of AP1 GST-fusion protein compared to elution buffer, GST protein, and irrelevant GST-fusion protein controls.

|  | Δ OD/min | Enzyme activity (µmol/min/ml) |
|---|---|---|
| AP1 -GST fusion protein | $3.54 \times 10^{-3}$ | 14.07 |
| Irrelevant GST-fusion protein | $2.77 \times 10^{-3}$ | 11.13 |
| GST protein | $2.68 \times 10^{-3}$ | 10.77 |
| Elution buffer only | $2.38 \times 10^{-3}$ | 9.56 |

Acetoin dehydrogenase (EC 1.1.1.5) catalyzes the reduction of diacetyl to acetoin, and acetoin to 2,3-butanediol as part of the pyruvate to 2,3-butanediol pathway (reviewed in Sarmiento and Burgos, Methods in Enzymol. 89:516–523, 1982). Diacetyl is an important flavor component in a variety of dairy products including butter, buttermilk, sour cream, fermented cream and cheese. Like its metabolites or related compounds acetoin, acetaldehyde and 2,3-butanediol, diacetyl plays a role in flavor when present in trace amounts (reviewed in Escamilla-Hurtado et al., Rev. Latinoamerican Microbiol. 38:129–37, 1996). A mixture of all these compounds is produced during lactic acid fermentation, and particular proportions of these compounds lead to characteristic flavors in dairy products.

The polypeptide of SEQ ID NO: 74, and the polynucleotide of SEQ ID NO: 32 have utility for processing food products and as supplements and additives to food products. This dehydrogenase may also be used to develop non-food products. The attributes conferred by and applications for use of this enzyme include:

Modulation of the production of important flavor compounds;
Modification of pyruvate metabolic pathways;
Industrial production of flavor compounds; and
control of diacetyl levels in dairy products These attributes may be produced in food, such as dairy products, and the applications implemented by directed activity of the enzyme, introduced in a bacterial strain (including strain HN001, or starter cultures) comprising a polynucleotide of SEQ ID NO: 32 or a variant, or as an enzyme preparation comprising a polypeptide of SEQ ID NO: 74 or a variant.

EXAMPLE 26

Isolation and Characterisation of Aflatoxin $B_1$ Aldehyde Reductase from *L. rhamnosus* HN001

The full-length polynucleotide sequence of aflatoxin $B_1$ aldehyde reductase from *L. rhamnosus* strain HN001, given in SEQ ID NO: 15 and shown with ATG initiation and translation stop codons (boxed) in FIG. 52, was used to amplify the AI7 aflatoxin $B_1$ aldehyde reductase gene from *L. rhamnosus* HN001 DNA using standard PCR methodology. The upstream and downstream primers were tagged with EcoRI and SalI restriction endonuclease recognition sequences to facilitate cloning.

AI7 was then cloned into the EcoRI and SalI sites of the pGEX-6P-3 expression vector (Pharmacia Biotech) and transformed into the *E. coli* strain DH5α competent cells according to standard laboratory protocols. The polypeptide sequence of aflatoxin $B_1$ aldehyde reductase AI7 is given in SEQ ID NO: 57 and shown in FIG. 53. The aflatoxin $B_1$ aldehyde reductase AI7 protein was expressed as a fusion protein with glutathione S-transferase (GST) and purified using Glutathione Sepharose 4B resin (Pharmacia Biotech) according to the manufacturer's instructions. An aliquot of the purified AI7 protein was checked by SDS-PAGE analysis.

AI7 activity was assayed by the previously published method of Ellis and Hayes, *Biochem. J.* 312:535–541, 1995 with some modifications. Briefly, the aldehyde- and ketone reducing activity of aflatoxin $B_1$ aldehyde reductase was assayed using 4-nitrobenzyl alcohol as substrate and NADPH as a cofactor. Enzyme activity was assessed spectrophotometrically by monitoring the utilization of NADPH at an OD of 340 nm. Reaction volumes of 1 ml containing 100 mM sodium phosphate pH 6.6 and 0.2 mM NADPH were prepared, aliquots of purified AI7 protein added, and the changes in OD measured. Enzyme activity was compared between reactions containing AI7-GST fusion protein, irrelevant GST-fusion protein, elution buffer used during protein purification and water only. Enzyme activity was calculated as μmol NADP used/min/ml.

Results presented in FIG. 54 and Table 18 indicate that HN001 AI7 protein fused with GST exhibited significant aldehyde reductase activity, while the irrelevant GST-fusion protein, as well as the water and elution buffer controls, showed no activity whatsoever. Therefore, the aflatoxin $B_1$ aldehyde reductase activity of the AP4-GST fusion protein was due to the AI7 moiety rather than the GST. Also, the results showed increased rate of substrate utilization proportional to the amount of AI7 protein added, indicating that aflatoxin $B_1$ aldehyde reductase activity of AI7 was dose dependent. Therefore, AI7 encodes HN001 aflatoxin $B_1$ aldehyde reductase.

FIG. 54 shows the experimental results of aflatoxin $B_1$ aldehyde reductase assay according to oxidation of the NADPH co-factor in the presence of acetoin substrate. X, water only; +, Sepharose column elution buffer only; ●, irrelevant GST-fusion protein; ■, 10 μl purified AP4-GST fusion protein; ▲ 20 μl purified AP4-GST fusion protein.

TABLE 18 aflatoxin $B_1$ aldehyde reductase activity of AI7 GST-fusion protein compared to elution buffer, water and irrelevant GST-fusion protein controls.

| | Δ OD/min at 340 nm | Enzyme activity (μmol/min/ml) |
|---|---|---|
| Elution buffer only | 0.00 | 0 |
| Water only | 0.00 | 0 |
| 10 μl Irrelevant protein | 0.00 | 0 |
| 10 μl AI7 | 0.038 | 606 |
| 20 μl AI7 | 0.087 | 690 |

Aflatoxin $B_1$ aldehyde reductase metabolizes the carcinogen aflatoxin $B_1$ ($AFB_1$) by converting the protein-binding dialdehyde form of $AFB_1$-dihydrodiol to the non-binding di-alcohol metabolite, and is associated with $AFB_1$-resistance in animal studies (Ellis et al., *Proc. Natl. Acad. Sci. USA* 90:10350–10354, 1993; Hayes et al., *Cancer Res.* 53:3887–3894, 1993). The enzyme is also active against other substrates including a particular class of ketone (ketone groups on adjacent carbon atoms, eg. 9,10-phenanthrenequinone), as well as aromatic and aliphatic aldehydes (Ellis and Hayes, *Biochem. J.* 312:535–541, 1995).

The polypeptide of SEQ ID NO: 57, and the polynucleotide of SEQ ID NO: 15 have utility for processing food products and as supplements and additives to food products. This reductase also has applications. The attributes conferred by and applications for use of this enzyme include:

Anti-carcinogenic or chemoprotectant reagents;
Probiotic bacterial strains with anti-cancer effects;
Research tools for cancer research;
Enhanced flavor or aroma characteristics;
Removal of undesirable flavors; and
Description and application of novel metabolic pathways These attributes may be produced and applications implemented by directed activity of the enzyme, introduced in a bacterial strain (including strain HN001, or starter cultures) comprising a polynucleotide of SEQ ID NO: 15 or a variant, or as an enzyme preparation comprising a polypeptide of SEQ ID NO: 57 or a variant.

EXAMPLE 27

Isolation and Characterisation of 6-Phospho-β-galactosidase from *L. rhamnosus* HN001

The full-length polynucleotide sequence of 6-phospho-β-galactosidase, given in SEQ ID NO: 31 and shown with the translation stop codon (boxed) in FIG. 78, was used to amplify the A05 6-phospho-β-galactosidase gene from *L. rhamnosus* HN001 DNA using standard PCR methodology. The upstream and downstream primers were tagged with EcoRI and SalI restriction endonuclease recognition sequences to facilitate cloning.

A05 was then cloned into the EcoRI and SalI sites of the pGEX-6P-3 expression vector (Pharmacia Biotech) and transformed into the *E. coli* strain DH5α competent cells according to standard laboratory protocols. The polypeptide sequence of aflatoxin $B_1$ aldehyde reductase AO5 is given in SEQ ID NO: 73 and shown in FIG. 79. The 6-phospho-β-galactosidase AO5 protein was expressed as a fusion protein with glutathione S-transferase (GST) and purified using Glutathione Sepharose 4B resin (Pharmacia Biotech) according to the manufacturer's instructions. An aliquot of the purified AO5 protein was checked by SDS-PAGE analysis.

A05 activity was assayed using standard laboratory methods as follows. Briefly, crude cell lysates were prepared by resuspending a 10 ml overnight culture of *E. coli* DH5α cells in 1 ml lysis buffer (50 mM potassium phosphate pH 7.8, 400 mM NaCl, 100 mM KCl, 10% glycerol, 0.5% Triton X-100, 10 mM imidazole). Cells were sonicated and spun to sediment cell debris according to standard laboratory methods. Aliquots of 50 μl of cell lysate were added to 900 μl reaction buffer (100 mM $KH_2PO_4$ pH 7.0, 2 mM $MgCl_2$) and 50 μl substrate O-nitrophenyl β-D-glycopyranoside (ONPG) (Sigma). Utilization of OPNG was measured spectrophotometrically by monitoring change in absorbance at 420 nm and enzyme activity calculated as μmol OPNG used/min/ml.

6-Phospho-β-galactosidase enzyme activity was compared in crude lysates from *E. coli* DH5α transformed with pGEX-6P-3 encoding A05, pGEX-6P-3 encoding an irrelevant protein, and lysis buffer only.

Experimental results presented in FIG. 55 and Table 19 indicate that while reactions containing crude lysates from cells transformed with an irrelevant GST-fusion protein or lysis buffer only exhibited little or no enzyme activity, crude lysate from *E. coli* expressing AO5-GST fusion protein showed significant enzyme activity. FIG. 55 shows the experimental determination of 6-Phospho-β-galactosidase enzyme activity as measured by substrate utilisation using crude lysates of strains transformed with pGex-6P-3 encoding A05 (♦), pGex-6P-3 encoding an irrelevant protein (■), or using lysis buffer only (X).

TABLE 19

6-Phospho-β-galactosidase enzyme activity in crude cell lysates

| Crude cell lysate expressing: | Δ OD/min at 420 nm | Enzyme activity (μmol/min/ml) |
|---|---|---|
| AO5-GST fusion protein | 0.074 | 0.60 |
| Irrelevant GST-fusion protein | 0.001 | 0.01 |
| Lysis buffer only | 0.000 | 0.00 |

Enzyme activity was also measured in increasing amounts of crude cell lysates to assess dose-dependency. Results shown in FIG. 56 and Table 20 indicate that increasing amounts of cell lysates from cell expressing the AO5-GST fusion protein led to proportional increases in 6-phospho-β-galactosidase enzyme activity. Therefore, A05 encodes HN001 6-phospho-β-galactosidase. FIG. 56 shows 6-Phospho-β-galactosidase enzyme activity as measured experimentally by substrate utilisation using increasing amounts of crude lysate from strains transformed with pGex-6P-3 encoding A05-GST fusion protein. ♦, 50 μl lysate; ■, 100 μl lysate; ▼, 200 μl lysate; ●, 200 μl lysis buffer only.

TABLE 20

6-Phospho-β-galactosidase enzyme activity in increasing amounts of crude cell lysates.

| Crude cell lysate expressing AO5-GST fusion protein | Δ OD/min at 420 nm | Enzyme activity (μmol/min/ml) |
|---|---|---|
| 50 μl | 0.074 | 0.60 |
| 100 μl | 0.113 | 0.92 |
| 200 μl | 0.169 | 1.38 |
| 200 μl Lysis buffer only | 0.000 | 0.00 |

6-Phospho-β-galactosidase (EC 3.2.1.85) catalyzes the hydrolysis of O-glycosyl bonds of 6-phospho-beta-D-galactosides to give alcohols and 6-phospho-D-galactose, and is involved in lactose utilization (Hengstenberg and Morse, *Methods in Enzymol.* 42:491–494, 1975).

The polypeptide of SEQ ID NO: 73, and the polynucleotide of SEQ ID NO: 31 have utility for processing food products and as supplements and additives to food products. This galactosidase may also be used to develop non-food products. The attributes conferred by this enzyme include:

flavor and aroma enhancement;

nutritional enhancement;

altered bacterial metabolic/growth characteristics; and removal of bitter or undesirable flavors These attributes may be produced in food, such as dairy products, by directed activity of the enzyme, introduced in a bacterial strain (including strain HN001, or starter cultures) comprising a polynucleotide of SEQ ID NO: 31 or a variant, or as an enzyme preparation comprising a polypeptide of SEQ ID NO: 73 or a variant.

EXAMPLE 28

Isolation and Characterisation of Aromatic Aminotransferase from *L. rhamnosus* HN001

The full-length polynucleotide sequence of aromatic aminotransferase of *L. rhamnosus* strain HN001, given in SEQ ID NO: 11 and shown in FIG. 57 with ATG initiation and translation stop codons (boxed), was used to amplify the AH7 aromatic aminotransferase gene from *L. rhamnosus* HN001 DNA using standard PCR methodology. The upstream and downstream primers were tagged with EcoRI and SalI restriction endonuclease recognition sequences to facilitate cloning.

AH7 was then cloned into the EcoRI and SalI sites of the pGEX-6P-3 expression vector (Pharmacia Biotech) and transformed into *E. coli* strain DH5α competent cells according to standard laboratory protocols. The polypeptide sequence of aflatoxin $B_1$ aldehyde reductase AI7 is given in SEQ ID NO: 53 and shown in FIG. 58. The aflatoxin $B_1$ aldehyde reductase AI7 protein was expressed as a fusion protein with glutathione S-transferase (GST) and purified using Glutathione Sepharose 4B resin (Pharmacia Biotech) according to the manufacturer's instructions. An aliquot of the purified AI7 protein was checked by SDS-PAGE analysis.

Aromatic aminotransferase activity was assayed according to previously published methods (Yvon et al., *Appl. Environ. Microbiol.* 63:414–419, 1997) with modifications. The assay is composed of two parts: the first is an aminotransferase reaction using the aromatic amino acid phenylalanine as substrate and results in the production of glutamate from α-ketoglutarate. The second part of the assay is the calorimetric determination of the glutamate. For the phenylalanine transamination, 250 μl reaction mixtures containing 70 mM Tris-HCl pH 8.0, 3 mM L-phenylalanine, 10 mM α-ketoglutarate and 0.05 μM pyridoxal 5' phosphate were incubated with purified proteins or elution buffer at 37° C. for 15 min. Aliquots of 20 μl were then taken and glutamate levels determined by adding to a reaction mixture containing 65 mM Tris pH 9.0, 1.3 mM EDTA, 40 mM hydrazine, 19.5 mM $NAD^+$, 65 mM ADP, with and without 2.4 U glutamate dehydrogenase in a total volume of 250 μl in the wells of a microtitre plate. Reactions were incubated at 37° C. for 40 min and absorbance at 340 nm measured using a plate reader (Molecular Devices, Sunnyvale Calif.). Enzyme activity of the purified AH7-His-Thio fusion protein was compared a purified irrelevant His-Thio-fusion protein, elution buffer used to elute the purified proteins from the Ni-NTA columns and water only and results are shown in Table 21. Glutamate concentrations were calculated using a standard curve, and assays on all samples and standards were performed in triplicate. Enzyme activities were calculated as μmol glutamate produced/min/ml and specific activities calculated using protein concentrations obtained using the BCA protein assay kit (Pierce) according to the manufacturer's instructions. Results indicate that while the irrelevant fusion protein, elution buffer and water resulted in little glutamate production, AP5 fusion protein exhibited significant aminotransferase activity using phenylalanine as substrate. Therefore, HN001 AP5 encodes an aromatic amino acid transferase.

TABLE 21

Aromatic amino acid transferase activity in HN001 AH7 purified protein as measured by glutamate production.

| | mM glutamate per reaction | Enzyme activity (μmol/min/ml) | Specific activity (μmol/min/μg) |
|---|---|---|---|
| Water only | 0.044 | 146 | — |
| 10 μl elution buffer | 0.031 | 103 | — |
| 10 μl irrelevant His-Thio-fusion protein solution | 0.030 | 100 | 0.52 |
| 10 μl His-Thio-AH7 fusion protein solution | 1.120 | 3733 | 17.7 |

Aromatic amino acid transferase (EC 2.6.1.57) catalyzes the transfer of amino groups between an aromatic amino acid and α-ketoglutarate to its aromatic oxo-acid and L-glutamate (Mavrides and Orr, *J. Biol. Chem.* 250:4128–4133, 1975). The products of enzymatic amino acid degradation play a major role in cheese flavor development. Degradation products from aromatic amino acids have both positive and negative impacts on cheese flavor (Dunn and Lindsay, *J. Dairy Sci.* 68:2859–2874, 1985; Engels et al., *Int. Dairy J.* 7:225–263, 1997).

The polypeptide of SEQ ID NO: 53, and the polynucleotide of SEQ ID NO: 11 have utility for processing food products and as supplements and additives to food products. This aminotransferase may also be used to develop non-food products. The attributes conferred by this enzyme include:

flavor and aroma enhancement;
removal of off-flavors;
altered levels of biogenic amines; and
altered metabolic characteristics.

These attributes may be produced in food, such as dairy products, by directed activity of the enzyme, introduced in a bacterial strain (including strain HN001, or starter cultures) comprising a polynucleotide of SEQ ID NO: 11 or a variant, or as an enzyme preparation comprising a polypeptide of SEQ ID NO: 53 or a variant.

EXAMPLE 29

Isolation and Characterisation of Acetate Kinase from *L. rhamnosus* HN001

The full-length polynucleotide sequence of acetate kinase, given in SEQ ID NO: 33 and shown in FIG. 59 with ATG initiation and translation stop codons (boxed), was used to amplify the AP5 acetate kinase gene from *L. rhamnosus* strain. The upstream and downstream primers were tagged with EcoRI and SalI restriction endonuclease recognition sequences to facilitate cloning.

AP5 was then cloned into the EcoRI and SalI sites of the pGEX-6P-3 expression vector (Pharmacia Biotech) and transformed into the *E. coli* strain K12 XL-1Blue competent cells according to standard laboratory protocols. The polypeptide sequence of the acetate kinase AP5 polypeptide is given in SEQ ID NO: 75 and shown in FIG. 60 and was expressed as a fusion protein with glutathione S-transferase (GST) and purified using Glutathione Sepharose 4B resin (Pharmacia Biotech) according to the manufacturer's instructions. An aliquot of the purified AP5 protein was checked by SDS-PAGE analysis.

AP5 activity was assayed based on a published method for analysis of the related carbamate kinase (Crow and Thomas, *J. Bacteriol.* 150:1024–1032, 1982) with modifications. Briefly, the assay uses a couple reaction such that acetyl phosphate and ADP is converted to $CO_2$, $NH_3$ and ATP in the presence of acetate kinase. The produced ATP is then combined with glucose by the enzyme hexokinase to give glucose-6-phosphate, which in turn is reduced by glucose-6-phosphate dehydrogenase using the $NADP^+$ cofactor. Because the hexokinase glucose-6-phosphate dehydrogenase enzymes are provided in excess, acetate kinase activity can be assessed spectrophotometrically by monitoring NADPH production at an OD of 340 nm. Reaction mixtures of 730 μl 200 mM Tris-HCL pH 7.9, 73 μl 200 mM acetyl phosphate, 36.5 μl 200 mM ADP, 36.5 μl 200 mM $MgCl_2$, 73 μl 500 mM glucose, 7 μl 100 mM $NADP^+$ and 7 μl hexokinase glucose-6-phosphate dehydrogenase were prepared and allowed to equilibrate at 37° C. Purified AP5-GST fusion protein and sterile milliQ water was added to a final volume of 1 ml, and changes in OD at 340 nm measured. Enzyme activity was compared between purified AP5-GST fusion protein, irrelevant fusion protein, and elution buffer used to elute the purified proteins off the Sepharose column and the results is shown in Table 22. Enzyme activities were calculated as μmol NAPDH produced/min/ml, and specific activities calculated using protein concentrations obtained using the BCA protein assay kit (Pierce) according to the manufacturer's instructions. Results in Table 22 indicate that while elution buffer and irrelevant GST-fusion protein showed little or no enzyme activity, the AP5-GST fusion protein exhibited significant activity. Therefore, AP5 encodes HN001 acetate kinase.

TABLE 22

Acetate kinase activity of HN001 protein AP5.

| | Δ OD/min at 340 nm | Enzyme activity (μmol/min/μl) | Specific activity (μmol/min/μg) |
|---|---|---|---|
| 20 μl elution buffer | 0.0 | 0.0 | — |
| 1 μl irrelevant GST-fusion protein solution | 0.13 | 0.05 | 0.025 |
| 2 μl AP5-GST fusion protein solution | 1.72 | 0.35 | 0.172 |

Acetyl kinase (EC 2.7.2.1) catalyzes the phosphotransfer between ADP and acetyl phosphate to give ATP and acetate (Nishimura and Griffith, *Methods in Enzymol.* 71:311–316, 1981). Acetate, a flavor compound in its own right, can give ammonia and carbon dioxide, both of which have important flavor and texture impacts in cheese (Fox et al., *Crit. Rev. Food Sci. Nutr.* 29:237–53, 1990).

The polypeptide of SEQ ID NO: 75, and the polynucleotide of SEQ ID NO: 33 have utility for processing food products and as supplements and additives to food products. This kinase may also be used to develop non-food products. The attributes conferred by this enzyme include:

flavor and aroma enhancement;
removal of off-flavors;
altered texture characteristics; and
altered metabolic characteristics These attributes may be produced in food, such as dairy products, by directed activity of the enzyme, introduced in a bacterial strain (including strain HN001, or starter cultures) comprising a polynucleotide of SEQ ID NO: 33 or a variant, or as an enzyme preparation comprising a polypeptide of SEQ ID NO: 75 or a variant.

EXAMPLE 30

Isolation and Characterisation of Basic Surface Protein from *L. rhamnosus* HN001

The full-length polynucleotide sequence of basic surface protein from *L. rhamnosus* strain HN001, given in SEQ ID NO: 6 and shown in FIG. 61 with ATG initiation and translation stop codons (boxed), was used to amplify the AC9 basic surface protein gene, but excluding the predicted N-terminal Type II signal sequence. The primer sequences used are given in SEQ ID NOS: 34 and 35 and were tagged with EcoRI and BamHI restriction endonuclease recognition sequences, respectively, to facilitate cloning. AC9 sequence was then amplified from HN001 strain genomic DNA, purified, cloned into EcoRI/BamHI-cut pGEX-6P-3 expression vector, and transformed into *E. coli* DH5α cells according to standard laboratory methods. The polypeptide sequence of basic surface protein AC9 is given in SEQ ID NO: 47 and shown in FIG. 62. The basic surface protein AC9 was expressed as a fusion protein with glutathione S-transferase (GST), bound to Glutathione Sepharose 4B resin (Pharmacia Biotech), and PreScission protease used to cleave off the basic surface protein AC9 protein, according to the manufacturer's instructions. An aliquot of the purified AC9 protein was checked by SDS-PAGE analysis.

Purified AC9 protein (14 μg) was labeled by radio-iodination with 0.1 mCi iodine-125 (Amersham Pharmacia) using IODO-BEADS iodination reagent (Pierce) following the manufacturer's instructions. The radio-iodinated protein was separated from unincorporated iodine-125 and excess sodium iodide-125 using a PD-10 desalting column (Amersham-Pharmacia) according to the manufacturer's instructions, except that the elution was performed in phosphate buffered saline in twelve 500 μl aliquots. Radioactivity in eluted fractions was quantitated on a Bioscan Quick Count QC-4000/XER Benchtop Radioisotope Counter (Bioscan, Inc.) and fractions containing the first peak of radioactivity (corresponding to labeled AC9 protein) were pooled and bovine serum albumin added to a final concentration of 10 mg/ml.

To analyze the binding of polypeptide AC9 to proteins associated with intestinal surface proteins known to act as ligands for bacterial adhesins, different intestinal protein ligands were dot blotted onto a nitrocellulose membrane using a Convertible Filtration Manifold System (Life Technologies) following the manufacturer's instructions. Duplicate dots of approximately 1 μg of type I collagen from calf skin, type IV collagen from human placenta, fibronectin from human plasma, laminin from the basement membrane of Engelbreth-Holm-Swarm mouse sarcoma and type III mucin partially purified from porcine stomach and bovine serum albumin included as a negative control (all proteins were obtained from Sigma) were blotted. The blot was incubated at room temperature on an orbital shaker in 10 ml phosphate buffered saline, pH 7.4, containing 0.1% Tween 20 and 5 mg/ml bovine serum albumin for 1 hour. Radio-iodinated AC9 protein was then added to a final concentration of approximately 500 ng/ml, and incubated at room temperature for a further hour. The blot was washed three times in approximately 40 ml phosphate buffered saline, pH 7.4, containing 0.1% Tween 20 at room temperature for 10 minutes, then autoradiographed against X-ray film at −80° C. overnight. The autoradiograph was developed and the resulting image digitized with a FluorS MultiImager (Bio-Rad). Binding by AC9 protein to the intestinal protein ligands was quantitated using Bio-Rad Quantity One software by measuring the density of the signal on the autoradiograph resulting from radiolabeled AC9 protein binding to the different ligands and subtracting the background density of blank film. To quantitate relative amounts of protein ligands blotted, blots were stained with Ponceau S using standard procedures (Ausubel et al., Current Protocols in Molecular Biology, John Wiley & Sons, 2001), and quantitated as for the autoradiograhs. The density corresponding to AC9 protein binding to individual ligands was divided by the average density of Ponceau S staining of the ligand to give the relative AC9 bound to each ligand. Binding of iodinated AC9 ($1.50 \times 10^7$ dpm) was compared to binding of iodinated mucus adhesion promoting (mapA) protein of *Lactobacillus reuteri* (GenBank accession number AJ293860) as a positive control, and iodinated irrelevant HN001 protein ($7.00 \times 10^6$ dpm) as a negative control.

Results in Table 23 indicate that while the irrelevant HN001 protein did not bind to any of the intestinal adhesin ligands, both the AC9 protein and the positive control protein mapA showed significant binding to mucin. Therefore, AC9 encodes the HN001 basic surface protein.

TABLE 23

Density of autoradiographic signals from AC9 basic surface protein binding to dot blots of intestinal proteins, compared to a positive control (mapA) and negative control (irrelevant HN001 protein). Results represent mean of relative density of two dots.

| Intestinal Protein | Relative AC9 Binding | Relative mapA Binding | Relative Irrelevant protein Binding |
|---|---|---|---|
| BSA | 0.25 | 0.76 | 0.06 |
| Collagen I | 0.44 | 1.02 | 0.26 |
| Collagen IV | 0.34 | 0.78 | 0.09 |
| Fibronectin | 0.35 | 0.67 | 0.09 |
| Laminin | 0.53 | 0.83 | 0.12 |
| Mucin | 2.20 | 2.57 | 0.68 |

The basic surface protein of *Lactobacillus fermentum* is a surface-bound molecule that belongs to a family of ATP-binding cassette (ABC) receptor solute binding proteins (Turner et al., *J. Bacteriol.* 179:3310–3316, 1997; Tam et al., *Microbiol. Rev.* 57:320–346, 1993). Basic surface protein has also been shown to be involved in cysteine uptake (Turner et al., *J. Bacteriol.* 181:2192–2198, 1999) and has been used as an attachment site for immunodominant proteins in the development of new vaccine strategies (Turner et al., *Infect. Imm.* 67:5486–5489, 1999).

The polypeptide of SEQ ID NO: 47, and the polynucleotide of SEQ ID NO: 6 have utility for processing food products and as supplements and additives. This basic surface protein may also be used to develop non-food products. The attributes conferred by this protein include:
enhanced adhesion to intestinal surface and cell lines;
enhanced bacterial survival in intestinal environment;
altered metabolic characteristics;
altered flavor or aroma characteristics;
enhanced probiotic effects;
reagents to block or modify adherence of bacteria to mucosal surfaces; and
development of vaccine carriers These attributes may be produced in food, such as dairy products, or in supplements by directed activity of the enzyme, introduced in a bacterial strain (including strain HN001, or starter cultures) comprising a polynucleotide of SEQ ID NO: 6 or a variant, or as an enzyme preparation comprising a polypeptide of SEQ ID NO: 47 or a variant.

EXAMPLE 31

Isolation and Characterisation of Outer Membrane Protein A from *L. rhamnosus* HN001

The full-length polynucleotide sequence of outer membrane protein A from *L. rhamnosus* strain HN001, given in SEQ ID NO: 27 and shown in FIG. 63 with ATG initiation and translation stop codons (boxed) was used to amplify the N-terminal region of AL8 outer membrane protein A gene. The primer sequences are given in SEQ ID NOS: 36 and 37, respectively, and were tagged with BamHI and XhoI restriction endonuclease recognition sequences, respectively, to facilitate cloning. AL8 sequence was then amplified from HN001 strain genomic DNA, purified, cloned into BamHI/ XhoI-cut pGEX-6P-3 expression vector, and transformed into *E. coli* DH5α cells according to standard laboratory methods. The polypeptide sequence of outer membrane protein A AL8 is given in SEQ ID NO: 69 and shown in FIG. 64. The outer membrane protein A AL8 was expressed as a fusion protein with glutathione S-transferase (GST), bound to Glutathione Sepharose 4B resin (Pharmacia Biotech), and PreScission protease used to cleave off the outer membrane protein A AL8 protein, according to the manufacturer's instructions. An aliquot of the purified AL8 protein was checked by SDS-PAGE analysis.

Purified AL8 protein (20 μg) was then labeled by radio-iodination with 0.1 mCi iodine-125 (Amersham Pharmacia) using IODO-BEADS iodination reagent (Pierce) following the manufacturer's instructions. Radio-iodinated protein was separated from unincorporated iodine-125 and excess sodium iodide-125 using a PD-10 desalting column (Amersham-Pharmacia) according to the manufacturer's instructions, except that the elution was performed in phosphate buffered saline in twelve 500 μl aliquots. Radioactivity in eluted fractions was quantitated on a Bioscan Quick Count QC-4000/XER Benchtop Radioisotope Counter (Bioscan, Inc.) and fractions containing the first peak of radioactivity (corresponding to labeled AL8 protein) were pooled and bovine serum albumin added to a final concentration of 10 mg/ml.

To analyze AL8 protein binding to proteins associated with intestinal surface proteins known to act as ligands for bacterial adhesins, different intestinal protein ligands were dot blotted onto a nitrocellulose membrane using a Convertible Filtration Manifold System (Life Technologies) following the manufacturer's instructions. Duplicate dots of approximately 1 μg of type I collagen from calf skin, type IV collagen from human placenta, fibronectin from human plasma, laminin from the basement membrane of Engelbreth-Holm-Swarm mouse sarcoma and type III mucin partially purified from porcine stomach and bovine serum albumin included as a negative control (all proteins were obtained from Sigma) were blotted. The blot was incubated at room temperature on an orbital shaker in 10 ml phosphate buffered saline, pH 7.4, containing 0.1% Tween 20 and 5 mg/ml bovine serum albumin for 1 hour. Radio-iodinated AL8 protein was then added to a final concentration of approximately 500 ng/ml, and incubated at room temperature for a further hour. The blot was then washed three times in approximately 40 ml phosphate buffered saline, pH 7.4, containing 0.1% Tween 20 at room temperature for 10 minutes, then autoradiographed against X-ray film at −80° C. overnight. The autoradiograph was developed and the resulting image digitised with a FluorS MultiImager (Bio-Rad). Binding by AL8 protein to the intestinal protein ligands was quantitated using Bio-Rad Quantity One software by measuring the density of the signal on the autoradiograph resulting from radio labelled AL8 protein binding to the different ligands and subtracting the background density of blank film. To quantitate relative amounts of protein ligands blotted, blots were stained with Ponceau S using standard procedures (Ausubel et al., Current Protocols in Molecular Biology, John Wiley & Sons, 2001), and quantitated as for the autoradiograhs. The density corresponding to AL8 protein binding to individual ligands was divided by the average density of Ponceau S staining of the ligand to give the relative AL8 bound to each ligand. Binding of iodinated AL8 ($3.2 \times 10^7$ DPM) was compared to binding of iodinated mucus adhesion promoting (mapA) protein of *Lactobacillus reuteri* (GenBank accession number AJ293860) ($6.6 \times 10^6$ dpm) as a positive control, and iodinated irrelevant HN001 protein ($7.0 \times 10^6$ DPM) as a negative control.

Results in Table 24 indicated that while the irrelevant HN001 protein did not bind to any of the intestinal adhesin ligands, both the AL8 protein and the positive control protein mapA showed significant binding to mucin. Therefore, AL8 encodes the HN001 outer membrane protein A.

TABLE 24

Density of autoradiographic signals from AL8 outer membrane protein A binding to dot blots of intestinal proteins, compared to a positive control (mapA) and negative control (irrelevant HN001 protein). Results represent mean of relative density of two dots.

| Intestinal Protein | Relative AL8 Binding | Relative mapA Binding | Relative Irrelevant protein Binding |
| --- | --- | --- | --- |
| BSA | 0.08 | 0.76 | 0.06 |
| Collagen I | 0.89 | 1.02 | 0.26 |
| Collagen IV | 0.16 | 0.78 | 0.09 |
| Fibronectin | 0.24 | 0.67 | 0.09 |
| Laminin | 0.47 | 0.83 | 0.12 |
| Mucin | 2.01 | 2.57 | 0.68 |

The outer membrane protein A of *Rickettsia* spp. is a 190 kDa surface bound molecule required for the adhesion of *Rickettsia* to host cells (Li and Walker, *Microbial Path.* 179:3310–3316, 1998). *Rickettsial* outer membrane protein A is also an immunodominant protein and has been used for the serotyping of *rickettsial* strains (Philip et al., *J. Imm.* 121:1961–1968, 1978).

The polypeptide of SEQ ID NO: 69, and the polynucleotide of SEQ ID NO: 27 have utility for processing food products and as supplements and additives. This outer membrane protein may also be used to develop non-food products. The attributes conferred by and applications for this protein include:

- enhanced adhesion to intestinal surface and cell lines;
- enhanced bacterial survival in intestinal environment;
- altered texture characteristics;
- enhanced probiotic effects;
- reagents to block or modify adherence of bacteria to mucosal surfaces; and
- development of vaccine carriers These attributes may be produced in food, such as dairy products, and the applications may be implemented by directed activity of the protein, introduced in a bacterial strain (including strain HN001, or starter cultures) comprising a polynucleotide of SEQ ID NO: 27 or a variant, or as an enzyme preparation comprising a polypeptide of SEQ ID NO: 69 or a variant.

EXAMPLE 32

Isolation and Characterisation of Extracellular Matrix Binding Protein from *L. rhamnosus* HN001

The full-length polynucleotide sequence of extracellular matrix binding protein, AM4, from *L. rhamnosus* strain HN001, given in SEQ ID NO: 28 and shown in FIG. 65, was used to amplify the N-terminal region of AM4 extracellular matrix binding protein gene. The primer sequences used are given in SEQ ID NOS: 38 and 39, respectively, and were tagged with EcoRI and NotI restriction endonuclease recognition sequences, respectively, to facilitate cloning. AM4 sequence was then amplified from HN001 strain genomic DNA, purified, cloned into EcoRI/NotI-cut pGEX-6P-3 expression vector, and transformed into *E. coli* DH5α cells according to standard laboratory methods. The polypeptide sequence of extracellular matrix binding protein AM4 is given in SEQ ID NO: 70 and shown in FIG. 66. The extracellular matrix binding protein AM4 was expressed as a fusion protein with glutathione S-transferase (GST) and purified using Glutathione Sepharose 4B resin (Pharmacia Biotech), according to the manufacturer's instructions. An aliquot of the purified AM4-GST fusion protein was checked by SDS-PAGE analysis.

Purified AM4 protein (10 µg) was labeled by radioiodination with 0.1 mCi iodine-125 (Amersham Pharmacia) using IODO-BEADS iodination reagent (Pierce) following the manufacturer's instructions. Radio-iodinated protein was separated from unincorporated iodine-125 and excess sodium iodide-125 using a PD-10 desalting column (Amersham-Pharmacia) according to the manufacturer's instructions, except that the elution was performed in phosphate buffered saline in twelve 500 µl aliquots. Radioactivity in eluted fractions was quantitated on a Bioscan Quick Count QC-4000/XER Benchtop Radioisotope Counter (Bioscan, Inc.) and fractions containing the first peak of radioactivity (corresponding to labeled AM4 protein) were pooled and bovine serum albumin added to a final concentration of 10 mg/ml.

To analyze binding of the AM4 protein proteins associated with intestinal surface proteins known to act as ligands for bacterial adhesins, different intestinal protein ligands were dot blotted onto a nitrocellulose membrane using a Convertible Filtration Manifold System (Life Technologies) following the manufacturer's instructions. Duplicate dots of approximately 1 µg of type I collagen from calf skin, type IV collagen from human placenta, fibronectin from human plasma, laminin from the basement membrane of Engelbreth-Holm-Swarm mouse sarcoma and type III mucin partially purified from porcine stomach and bovine serum albumin included as a negative control (all proteins were obtained from Sigma) were blotted. The blot was incubated at room temperature on an orbital shaker in 10 ml phosphate buffered saline, pH 7.4, containing 0.1% Tween 20 and 5 mg/ml bovine serum albumin for 1 hour. Radio-iodinated AM4 protein was then added to a final concentration of approximately 500 ng/ml, and incubated at room temperature for a further hour. The blot was then washed three times in approximately 40 ml phosphate buffered saline, pH 7.4, containing 0.1% Tween 20 at room temperature for 10 minutes, then autoradiographed against X-ray film at −80° C. overnight. The autoradiograph was developed and the resulting image digitised with a FluorS MultiImager (Bio-Rad). Binding by AM4 protein to the intestinal protein ligands was quantitated using Bio-Rad Quantity One software by measuring the density of the signal on the autoradiograph resulting from radiolabeled AM4 protein binding to the different ligands and subtracting the background density of blank film. To quantitate relative amounts of protein ligands blotted, blots were stained with Ponceau S using standard procedures (Ausubel et al., Current Protocols in Molecular Biology, John Wiley & Sons, 2001), and quantitated as for the autoradiograhs. The density corresponding to AM4 protein binding to individual ligands was divided by the average density of Ponceau S staining of the ligand to give the relative AM4 bound to each ligand. Binding of iodinated AM4-GST fusion protein ($3.3 \times 10^7$ DPM) was compared to binding of iodinated mucus adhesion promoting (mapA) protein of *Lactobacillus reuteri* (GenBank accession number AJ293860) ($6.6 \times 10^6$ DPM) as a positive control, and iodinated irrelevant HN001 protein ($7.0 \times 10^6$ dpm) as a negative control.

Results in Table 25 indicate that while the irrelevant HN001 protein did not bind to any of the intestinal adhesin ligands, the AM4 fusion protein gave a very similar binding pattern to the positive control protein mapA, with significant binding to mucin and collagen types I and IV. Therefore, AM4 encodes the HN001 extracellular matrix binding protein.

TABLE 25

Density of autoradiographic signals from AM4-GST fusion protein to dot blots of intestinal proteins, compared to a positive control (mapA) and negative control (irrelevant HN001 protein). Results represent mean of relative density of two dots.

| Intestinal Protein | Relative AM4-GST Binding | Relative mapA Binding | Relative Irrelevant Protein Binding |
|---|---|---|---|
| BSA | 0.37 | 0.76 | 0.06 |
| Collagen I | 1.43 | 1.02 | 0.26 |
| Collagen IV | 0.94 | 0.78 | 0.09 |
| Fibronectin | 0.53 | 0.67 | 0.09 |
| Laminin | 0.65 | 0.83 | 0.12 |
| Mucin | 1.48 | 2.57 | 0.68 |

The extracellular matrix binding protein is a surface bound molecule required for the adhesion of *Streptococcus* spp. to the extracellular matrix, exposed during tissue injury (Manganelli and van de Rijn, Infect. Imm. 67:50–56, 1999).

The polypeptide of SEQ ID NO: 70, and the polynucleotide of SEQ ID NO: 28 have utility for processing food products and as supplements and additives. This binding protein also has other applications. The attributes conferred by and applications for this enzyme include:

enhanced adhesion to intestinal surface and cell lines;

enhanced bacterial survival in intestinal environment;

altered texture characteristics;

enhanced probiotic effects;

reagents to block or modify adherence of bacteria to surfaces; and development of vaccine carriers These attributes may be produced in food, such as dairy products, and other applications may be implemented by directed activity of the binding protein, introduced in a bacterial strain (including strain HN001, or starter cultures) comprising a polynucleotide of SEQ ID NO: 28 or a variant, or as an enzyme preparation comprising a polypeptide of SEQ ID NO: 70 or a variant.

EXAMPLE 33

Isolation and Characterisation of High-Molecular-Weight Adhesion Protein from *L. rhamnosus* HN001

The full-length polynucleotide sequence of high-molecular-weight adhesion protein, AL7, from *L. rhamnosus* strain HN001 given in SEQ ID NO: 26 and shown in FIG. 67 with ATG initiation and translation stop codons (boxed), was used to amplify the N-terminal region of AL7 high-molecular-weight adhesion protein gene. The primer sequences used are given in SEQ ID NOS: 40 and 41, respectively, and were tagged with BamHI and EcoRI restriction endonuclease recognition sequences, respectively, to facilitate cloning. AL7 sequence was then amplified from HN001 strain genomic DNA, purified, cloned into BamHI/EcoRI-cut pGEX-6P-3 expression vector, and transformed into *E. coli* DH5α cells according to standard laboratory methods. The polypeptide sequence of high-molecular-weight adhesion protein AL7 is given in SEQ ID NO: 68 and shown in FIG. 68. The high-molecular-weight adhesion protein AL7 was expressed as a fusion protein with glutathione S-transferase (GST) and expression was checked by SDS-PAGE analysis.

Lysates of DH5α clones containing pGEX-6P-3 expressing AL7-GST fusion protein, lysates of DH5α clones containing pGEX-6P-3 expressing irrelevant HN001 GST-fusion protein, and crude cell wall cytoplasmic HN001 protein preparations (prepared by standard laboratory methods) were separated by SDS-PAGE. Proteins were blotted onto nitrocellulose membranes using a Trans-Blot SD Semi-Dry Electrophoretic Transfer Cell (Bio-Rad) according to the manufacturer's instructions. The nitrocellulose blot was then blocked overnight at 4° C. in phosphate buffered saline, pH 7.4, 0.1% Tween 20 (PBS-T), containing 5% non-fat dried milk. Rabbit anti-sera raised against HN001 cell wall proteins (supplied by Dr. Paul O'Toole, Institute of Molecular Biosciences, Massey University, Palmerston North, New Zealand) were diluted 1:5000 in PBS-T, 5% non-fat dried milk and incubated with the blot for 1 hr at room temperature. The blot was washed three times for 15 min each in PBS-T and incubated at room temperature in 50 ml PBS-T, 5% non-fat dried milk containing a 1:3000 dilution of a horseradish peroxidase-labeled antibody against rabbit Ig (Amersham Pharmacia) for 20 min. The blot was washed six times in PBS-T at room temperature for 15 min each, and binding visualized using the ECL Western blotting detection system (Amersham Pharmacia) according to the manufacturer's instructions.

Results of the Western blot revealed that the anti-sera detected a number of proteins from HN001 raised against the HN001 cell wall preparations. While several of these proteins were found in both the cell wall and cytoplasmic preparations of HN001, these proteins consisted of bands of approximately 66 kDa and less. In addition, a number of high molecular weight protein bands were detected in the HN001 cell wall protein preparations that were not present in the HN001 cytoplasmic protein preparations. These bands ranged from approx. 130 kDa to approx. 220 kDa or greater. Therefore the cell wall antisera specifically detected several large cell wall proteins from HN001. Of the *E. coli* extracts, the only signal came from the lysate of the DH5α clone containing pGEX-6P-3 expressing the N-terminal region of AL7. This strong band was approximately 97 kDa, the same size as the AL7-GST fusion protein. Lysates from *E. coli* clones expressing unrelated proteins showed no cross-reactivity with the HN001 cell wall anti-sera. This data indicates that AL7 encodes a high-molecular-weight adhesion protein at the cell surface.

The high-molecular-weight adhesion protein is a homologue of the surface-bound molecule of *Haemophilus influenzae* shown to be involved in adhesion to human cell lines (Barenkamp and St Geme, *Mol. Microbiol.* 19:1215–1223, 1996; St Geme et al., *Proc. Natl. Acad. Sci. USA* 90:2875–2879, 1993).

The polypeptide of SEQ ID NO: 68, and the polynucleotide of SEQ ID NO: 26 have utility for processing food products, as supplements and additives, and as reagents for several applications. The attributes conferred by and applications for use of this adhesion protein include:

enhanced adhesion to intestinal surfaces and cell lines;
enhanced bacterial survival in intestinal environment;
altered texture characteristics;
enhanced probiotic effects;
reagents to block or modify adherence of bacteria to surfaces; and
development of vaccine carriers.

These attributes may be produced products, and the applications may be implemented by directed activity of the adhesion protein, introduced in a bacterial strain (including strain HN001, or starter cultures) comprising a polynucleotide of SEQ ID NO: 26 or a variant, or as an enzyme preparation comprising a polypeptide of SEQ ID NO: 68 or a variant.

EXAMPLE 34

Isolation and Characterisation of Periplasmic Binding Protein 1 (PEB1) from *L. rhamnosus* HN001

The full-length polynucleotide sequence of a periplasmic binding protein 1 (PEB1), AJ4, from *L. rhamnosus* strain HN001, given in SEQ ID NO: 16 and shown in FIG. 69 with ATG initiation and translation stop codons (boxed), was used to amplify the AJ4 PEB1 gene from HN001 strain genomic DNA by PCR according to standard laboratory methods. Primers were tagged with BamHI and EcoRI to facilitate cloning. AJ4 PCR products were purified, cloned into BamHI/EcoRI-cut pGEX-6P-3 expression vector, and transformed into *E. coli* DH5α cells according to standard laboratory methods. The polypeptide sequence of PEB I AJ4 is given in SEQ ID NO: 58 and shown in FIG. 70. The PEB1 AJ4 was expressed as a fusion protein with glutathione S-transferase transferase (GST), bound to Glutathione Sepharose 4B resin (Pharmacia Biotech), and PreScission protease used to cleave off the PEB1 AJ4 protein, according to the manufacturer's instructions. An aliquot of the purified AJ4 protein was checked by SDS-PAGE analysis.

Purified AJ4 protein (10 μg) was then labeled by radioiodination with 0.1 mCi iodine-125 (Amersham Pharmacia) using IODO-BEADS iodination reagent (Pierce) following the manufacturer's instructions. Radio-iodinated protein was separated from unincorporated iodine-1 25 and excess sodium iodide-125 using a PD-10 desalting column (Amersham-Pharmacia) according to the manufacturer's instructions, except that the elution was performed in phosphate buffered saline in twelve 500 μl aliquots. Radioactivity in eluted fractions was quantitated on a Bioscan Quick Count QC-4000/XER Benchtop Radioisotope Counter (Bioscan, Inc.) and fractions containing the first peak of radioactivity (corresponding to labeled AJ4 protein) were pooled and bovine serum albumin added to a final concentration of 10 mg/ml.

To analyze the binding of the AJ4 protein proteins associated with intestinal surface proteins known to act as ligands for bacterial adhesins, different intestinal protein ligands were dot blotted onto a nitrocellulose membrane using a Convertible Filtration Manifold System (Life Technologies) following the manufacturer's instructions. Duplicate dots of approximately 1 µg of type I collagen from calf skin, type IV collagen from human placenta, fibronectin from human plasma, laminin from the basement membrane of Engelbreth-Holm-Swarm mouse sarcoma and type III mucin partially purified from porcine stomach and bovine serum albumin included as a negative control (all proteins were obtained from Sigma) were blotted. The blot was incubated at room temperature on an orbital shaker in 10 ml phosphate buffered saline, pH 7.4, containing 0.1% Tween 20 and 5 mg/ml bovine serum albumin for 1 hour. Radio-iodinated AJ4 protein was then added to a final concentration of approximately 500 ng/ml, and incubated at room temperature for a further hour. The blot was washed three times in approximately 40 ml phosphate buffered saline, pH 7.4, containing 0.1% Tween 20 at room temperature for 10 minutes, and autoradiographed against X-ray film at −80° C. overnight. The autoradiograph was developed and the resulting image digitized with a FluorS MultiImager (BioRad). Binding by AJ4 protein to the intestinal protein ligands was quantitated using Bio-Rad Quantity One software by measuring the density of the signal on the autoradiograph resulting from radio-labeled AJ4 protein binding to the different ligands and subtracting the background density of blank film. To quantitate relative amounts of protein ligands blotted, blots were stained with Ponceau S using standard procedures (Ausubel et al., Current Protocols in Molecular Biology, John Wiley & Sons, 2001), and quantitated as for the autoradiograhs. The density corresponding to AJ4 protein binding to individual ligands was divided by the average density of Ponceau S staining of the ligand to give the relative AJ4 bound to each ligand. Binding of iodinated AJ4 protein ($2.6 \times 10^6$ DPM) was compared to binding of iodinated mucus adhesion promoting (mapA) protein of *Lactobacillus reuteri* (GenBank accession number AJ293860) ($1.3 \times 10^6$ dpm) as a positive control, and iodinated irrelevant HN001 protein ($1.4 \times 10^6$ DPM) as a negative control.

Results shown in FIG. 71 demonstrate that while the irrelevant HN001 protein showed no significant binding to the intestinal proteins, AJ4 and the positive control protein mapA showed significant binding to mucin. AJ4 also showed some binding to laminin, fibronectin, and collagen type IV. Therefore, AJ4 encodes the HN001 PEB1. FIG. 71 shows the relative density of autoradiographic signals from AJ4 protein (grey bars) to dot blots of intestinal proteins, compared to a positive control (mapA, white bars) and negative control (irrelevant HN001 protein, black bars). Results for each dot (duplicates) are shown.

The PEB1 is a surface-bound molecule required for the adhesion of *Campylobacter* spp. to intestinal epithelial cells and is required for effective colonization of the gut environment (Pei et al., *Infect. Imm.* 66:938–943, 1998; Pei and Blaser, *J. Biol. Chem.* 268:18717–18725, 1993).

The polypeptide of SEQ ID NO: 58, and the polynucleotide of SEQ ID NO: 16 have utility for processing food products and as supplements and additives. This binding protein may also be used to develop non-food products. The attributes conferred by and applications for this protein include:

enhanced adhesion to intestinal surface and cell lines;
enhanced bacterial survival in intestinal environment;
altered texture characteristics;
enhanced probiotic effects;
reagents to block or modify adherence of bacteria to surfaces; and
development of vaccine carriers.

These attributes may be produced in food, such as dairy products, and implemented in other applications, by directed activity of the protein, introduced in a bacterial strain (including strain HN001, or starter cultures) comprising a polynucleotide of SEQ ID NO: 16 or a variant, or as an enzyme preparation comprising a polypeptide of SEQ ID NO: 58 or a variant.

SEQ ID NOS: 1–83 are set out in the attached Sequence Listing. The codes for nucleotide sequences used in the attached Sequence Listing, including the symbol "n," conform to WIPO Standard ST. 25 (1998), Appendix 2, Table 1.

All references cited herein, including all patent and literature references, are incorporated herein by reference in their entireties.

While in the foregoing specification this invention has been described in relation to certain preferred embodiments, and many details have been set forth for purposes of illustration, it will be apparent to those skilled in the art that the invention is susceptible to additional embodiments and that certain of the details described herein may be varied considerably without departing from the basic principles of the invention.

We claim:

1. An isolated polypeptide encoded by SEQ ID NO: 3.
2. An isolated polypeptide comprising SEQ ID NO: 44.
3. A fusion protein comprising at least one polypeptide according to claim 2.
4. A food product comprising an isolated polypeptide of claim 2.
5. The food product of claim 4, wherein the food product is derived from milk.
6. The food product of claim 5, wherein the food product is selected from the group consisting of: cheese; and yogurt.
7. The food product of claim 4, wherein the food product has enhanced flavor properties.
8. A method for modifying the flavor of a product, food, food additive, nutritional supplement, or probiotic supplement, wherein the product, food, food additive, nutritional supplement, or probiotic supplement is prepared from milk, the method comprising adding a polypeptide of claim 2 to the milk.
9. An isolated polypeptide comprising an amino acid sequence selected from the group consisting of:
    (a) sequences having at least 75% identity to SEQ ID NO: 44;
    (b) sequences having at least 90% identity to SEQ ID NO: 44; and
    (c) sequences having at least 95% identity to SEQ ID NO: 44,
   wherein the isolated polypeptide has esterase activity.
10. A fusion protein comprising an isolated polypeptide of claim 9.
11. A food product comprising an isolated polypeptide of claim 9.
12. The food product of claim 11, wherein the food product is derived from milk.
13. The food product of claim 12, wherein the food product is selected from the group consisting of: cheese; and yoghurt.
14. The food product of claim 11, wherein the food product has enhanced flavor properties.
15. A method for modifying the flavor of a product, food, food additive, nutritional supplement, or probiotic supplement, wherein the product, food, food additive, nutritional supplement, or probiotic supplement is prepared from milk, the method comprising adding a polypeptide of claim 9 to the milk.
16. An isolated polypeptide comprising an amino acid sequence selected from the group consisting of sequences differing from SEQ ID NO: 44 only by conservative amino acid substitutions, wherein the isolated polypeptide has esterase activity.
17. A fusion protein comprising an isolated polypeptide of claim 16.
18. A food product comprising an isolated polypeptide of claim 16.
19. The food product of claim 18, wherein the food product is derived from milk.
20. The food product of claim 19, wherein the food product is selected from the group consisting of: cheese; and yoghurt.
21. The food product of claim 18, wherein the food product has enhanced flavor properties.
22. A method for modifying the flavor of a product, food, food additive, nutritional supplement, or probiotic supplement, wherein the product, food, food additive, nutritional supplement, or probiotic supplement is prepared from milk, the method comprising adding a polypeptide of claim 16 to the milk.

* * * * *

SEQUENCE LISTING

```
<160> NUMBER OF SEQ ID NOS: 83

<210> SEQ ID NO 1
<211> LENGTH: 3215
<212> TYPE: DNA
<213> ORGANISM: Lactobacillus rhamnosus

<400> SEQUENCE: 1
gatcatgatg gggcagcagt cgccatcaag cagtatgcaa tgggtgaagg ttaataaaaa      60
agcgagtcga attcctgata atggaagtcg actcgctttt tatttttagcc gaaatagttt     120 cgtttaaatc taatctttta agtcaataat tgcctgttcc aactcctgtt tctgagctgc     180
```

-continued

```
agagatttcc ggatatttta gcggcaaagc ggtgacttcg cggttgatga tttgggacac    240
aaccagtcgg gagtaccact tatcgtctga cggaatcacg taccagggat ttgttttcgt    300
ggcggtgtgc tgaatggcat cttgataagc ttgctggtaa tcatcccaaa agcgccgttc    360
gtgaatatcc gccaatgaga acttccaatt cttttcggga atttcgattc gttttaagaa    420 gcgattttt tgttcggcct tggaaatgtg taagaagaac ttgagcagca agatgccatt     480
gcggtgcgca taggtttcta cgccttgat atcgttgaag cgtttggccc ataaatcgtc     540
atggacatca gcaacggtgt tgattcccgg caggttttct tttaatagca attcgggatg    600
aacccggtcg accagcactt cttcataatg ggagcgattg aacaccgtca gttcgccacc    660
agccgggaaa gcgttatgga tgcgccataa aaagtcatgg cctagttcaa gctcagtcgg    720
tactttaaac gacaccactg aggttccctg cggattgacg ccggacatga cgtgttcaat    780
catgctgtct tgccggctg catccatccc ttgaaagata atcaagacgc tgtattgttt     840
ctgtgccgcc aagtgttgct gaactttgga gagcaccttg atgttatgat caatgtctgc    900
tttgatctgc tcttttttat tttgaaaatg ttctggcggc gcggtcgcaa acgcttgaat    960
gttaaaggtg ccagtgccgt caaaacgata ttttttccaat gtcatcttat caccttcaat   1020
ttaagcttag tttcaacata gtagttacgc caaggatgtg caagcaattg acgccttggc    1080
ggattaaatc tatgctgaga ttcgacatg aaaacggagg caattgcatg acattaccaa     1140
gaattcaaga tgatttgtac ctagccgtca atggcgaatg gcaagcgaag acgccgattc    1200
cacctgacaa aagtgttgtg agtgcggata gtaatctgac cgatgatatt cgccaaaaac    1260
tagtggctga tctaagcacg atgacgaaaa cagccaaaac tttgccgctc cagtatgcag    1320
cgcggttgtt tgccaaagcc aatgaccaaa cccgccgtca gcagctaggc attgagccag    1380
ttcgtgatcg gataagcttt ttgatggcgc tcacgacgct tgatcaattt cgcagcgcta    1440
tgcccaaact ggttgctgat caatacgtct taccgatcag tccttacgtt gatgctgata    1500
tgcacgatgc cgagcataat attctgaatc ttggcgggcc agacacaatt ttacctgatg    1560
cggcgatgta ccaacatgaa gatgccgaaa atgcggcgga tctggcagcg tggtcgcaga    1620
tggcagctgc catgctggct gcggtaggat tcagtcagac tgatcaaaca gcatatgttg    1680
aagcggctaa acgatttgat cggcgttttgg ctgattatgt gccagcaaat gttgacttag    1740
cggtagatag cacgtatgac aatccattga gctggcaggc gtttgaagat gcggccggtt    1800
atttggggat cccacaagcc tttgcaactt acatgccgca aacaccggcg aaagtcaatg    1860
cggttgtacc ggcttatctt ccgcacttaa gcaaactact gacgccggac aattattcag    1920
aatggcacgc atggatggtg attaacgaat tgctaacctg cgccacttac ctcagtgatg    1980
atttacgtca attggccgga cagtatgatc ggttttttggc tggtcaacct gaggcgtcat    2040
cgtggacgaa acacgctttt gggattgcca acgagtattt tgacgatgtg attggtcagt    2100
attatgtcaa aacctacttt ggtgccgacg ctaaggcaga tgtgacggcc atggttaagc    2160
aaattcttgc gcaataccgc gtgcagctag aaaacaacac ttggctgagt ccggctacga    2220
agcaaaaggc gatgcgcaag ttagccacga tgcaagtcaa aatgggggtat ccggagcgac    2280 tcttttcctt gtatgatcac ttgagcgtgg atgttgacga tgatttgttg acggcaattc    2340
tgaaacttag cgcacagacg caggcctttt ggtttaaaca gttaggccag acggtggatc    2400
ggaatcaatg gaatatgccg ggacacttgg tgaatgccag ttatgatccg ctgaaaaatg    2460
acatcacttt tcccgctggt atcttgcagc cgccgtatta ctcactcaaa tggacccggg    2520
cggaaaacct cggagggaca ggcgcaacga tcggtcatga aatctcgcat tcgtttgata    2580
```

-continued

```
ataacggggc gctgtatgat gaatatggta atttgcataa ctggtggaca ccagcggata    2640
agcaggcatt tgatcagctg gtaaaagcga tggcggcaca gtttgatggc cgtgactatg    2700
aaggagtcaa ggtcaacggt acactgaccg ttagtgaaaa catggcggat aacgccggca    2760
tggatgtggc gttggcgtta ctaggcgatc agccggatgt taaggatctg caggcattct    2820
tcatcactta cgctcgttca tgggccacca aaatgcgacc ggagcgggct aaaactgttt    2880
tgcggcaaga tgttcatgcg ccggctacct tacgcgtgaa tgtgccggtg caaaactttc    2940
ctgcatggta ccaggcattt aatgttcagc cacaagatgg tatgtatcgg caaccacaga    3000
agcggctgac gatttggcat cagtaatatt taaataaaag agttttatgt gaaccttttt    3060
cgagaaccgc gagatcaact gtgtgtcaca ctgttcatgg ggaagcgtaa acaaaaaggc    3120
aacgattgcc gtgagacaat cgttgccttt tttcaatctt gggacaggtc gtggtaataa    3180
tgtagccagc cggtttcgcg ttcgccgatt tgatc                              3215

210> SEQ ID NO 2
<211> LENGTH 924
<212> TYPE: NA
<213> ORGAISM: Lactobacillus rhamnosus
<400> SEQUENCE: 2
acggctattg tgacggcttg tcagagtggg atgggcggta ctggcgacgt ggctattctc     60
agtacggcga atcggatgaa tctgatgcca tttgctcagg tggcaacacg cttgggtggc    120
gcgattaccg ttattaccat gacggcgatt ctgcggatga tctttttaaat cgactagttt    180 cgaaacttaa ggaggatgat tcacatggca aagaaggatt ttaatcaact agcgctagat    240
caagcaaaag taaatggcgg aaaattgagt gtggaaccga agtaccaat tgagacgcgc    300 gatgatttga gtattgcgta tactccaggc gtcggggcag tttcttctgc tattgccaag    360
gatcagtcgc tcgtttatga cttaaccact aagaaaaata cggttgcagt tgtcagtgac    420
ggttcggcgg ttttagggtt aggcaatatc ggtgccgagg ctgcgatgcc ggtgatggaa    480
ggaaaagccg ctttgttcaa acggtttgct aaggttgatg ccgtgccgat tgtgttggat    540
acgcaagaca ctgaagcaat cattgcggcg gttaaagcca ttgcaccaac atttggcggg    600
atcaatcttg aggatatcag tgcgccacga tgttttgaaa tcgaagcacg actcattgat    660
gagctcaaca tcccggtgtt ccacgatgat caacatggca ctgcgattgt ggtgctcgcc    720
gctttgtaca atgccttgaa agtagcggat aaaaagattg aagacattcg cgtggtggtt    780
aatggcggcg gctcagcggg gctatccgtt gcccggcgat tcttggcagc ggagtcaaa    840 cacgtcatgg tggtggataa ggtgggcatt ttagctaaaa agaacgctga tcaactgcca    900
ccacatcaag cgggattgcc ttaa                                          924

<210> SEQ ID NO 3
<211> LENGTH: 1218
<212> TYPE: DNA
<213> ORGANISM: Lactobacillus rhamnosus

<400> SEQUENCE: 3
gtgttaaatc caaggatcgt taaaaaacgg gcttaaaatc aaacgattag actgtcgggt     60
gacgcaccgg cagtcttttt tgcgttaatat aggaataacc ttttaacacg attcgttaac    120
acgaggaaat ggaggcattc gttaatggca gatgaagagg caatgttggc aaaggttcaa    180
gcgagctggg cgcaaacggc tgctcgggat aaggcacggt acgcggatga acgggtaccg    240
gaagatgttc attgggagac ggaatatcgg tacgaacagt cggctgatcc gcagcaaacc    300
```

-continued

```
ctgaacctgt actatccggc aaaagacgc aacgcaacca tgccgaccgt catcgatatt        360
catggtggcg ggtggtttta tggtgatcgt aatttgaatc gtaattattg ccgctatttg        420
gctagtcaag gatacgcagt gatgggtatg ggctatcggt tgttaccgga tgttgattta        480
cgcggccaga ttcaagacat ctttgctagt ctgcgctggt tatcgcattt tggccctcaa        540
cgcggatttg accttgacca tgtgcttttg accggggatt cagctggcgg ccacctggcg        600
tccttggttg cctgcatcca gcagagtgcg gagttacagg aactctttgg cgtgagtcgg        660
gttaatttca acttcaccct ggtggcgctg gtttgtccag tcgcagaacc aagtaagctt        720
cccgaagcag ccggtgacat gagcgatatg gccgcgtttt atctggacaa gttaagcggc        780
ggcgatcagg cactggccga tcacctgaat ttctcgcagg ttgtcaaggg tttggacctg        840
ccgccgttta tgctgattgg cgggcaaaat gacagctttt acttgcaaag ccaagccttg        900
ttgaaggtgt tcgatgctaa tcacgtcacc tatacaacga agctatgcc ggcaagtgcg        960 gggccacacc tcaagcatgt gtttaatgtt caacattggg aatggccgga agtattgag        1020 acgaacttgg agatgctgcg gacgtttgat gcgttaagca agcagcaaga tcaagctgaa        1080
gaaaacgaat tgaatagtc tgcggaagtg gcagtcatag cagccgctca tccggcgata        1140
gaaaaagact cagaggcgat ctgagtcttt ttagattaaa aaaccgcgc agtttgaagg        1200 ctacgcggag gaaatggc                                                     1218
```

<210> SEQ ID NO 4
<211> LENGTH: 491
<212> TYPE: DNA
<213> ORGANISM: Lactobacillus rhamnosus

<400> SEQUENCE: 4

```
ttgttttggg tacgagtacg cacacaaact attcggaaaa acactagaaa aatctagtta         60
atacgaagga gcagatcagt catggaaaaa cgcgaattta acattattgc agaaaccggg        120
attcacgcac gtccggcaac cttgttggta caagcagcta gcaagttcaa ctcagatatc        180
aacttggaat ataaaggtaa gagcgttaac ttgaagtcca tcatggggtgt tatgagtttg        240 ggcgttggtc aaggtgccga tgttacaatc tctgctgaag gcgctgacga agccgatgca        300
atcgctgcaa ttacggacac aatgaaaaag gaaggcttgg ctgaataatg gctgaacatt        360
tgaagggaat cgctgctagt gatgggatcg ccacagcgaa ggcctattta ctggttcaac        420
ctgatttatc atttgacaaa aagacggttg atgatccttc aaaggagatc gaccggctaa        480
agcaggcact t                                                              491
```

<210> SEQ ID NO 5
<211> LENGTH: 1276
<212> TYPE: DNA
<213> ORGANISM: Lactobacillus rhamnosus

<400> SEQUENCE: 5

```
ccaagtaatc atgccattca gctagcaaac attgcccgtc aacctgcttc attgacgggc         60
atacataaaa gaacactatt cattaaagga ggtcgggttt caatgaccca attcaatacc        120
aaactcgttc atggaccaca actaaatgtc gaccaagccg gtgccatcgt gccaccagta        180
taccaaagtg ccatgttccg ctttgctcct gatggtcagg aaacccactg ggactatgcg        240
cgcagtggta acccgacccg tgaatacctg gaacgtcaga ttgctacgct agaaaatggc        300
gatgctggct ttgcgttttc cagcggtgtt gcagcgattg caacggtgct cgcgattttc        360
```

```
cccgaccaca gtcacttcat tattggtgat tcgctctaca gtggcaccga tcgcctcatc    420
aaccagtatt tttctcaaca cggcctgacc tttacaccgg tggatacgcg tgatctggca    480
gcggtggaag ccgccatccg ccccgaaact aaagcaattt tctttgagac tttttccaat    540
ccgctcctca aagtcagcag cgtcaaggcc atcagtgccc tcgccaaaac ccatgatctg    600
ttaacgattg tcgacaacac gttcttaacc ccttattacc agcggccact tgacctcggt    660
gccgacatcg ttctacacag cgccaccaaa tacctcggtg ccacggtga cctcatcgcc    720 ggcctcgttg tctccgctca ccccgacctc agcgagaagc tcgcttttcct gcaaaacacg    780 atcggtgcca ttttaagccc gcttgactgt agcctcgtca cccgcggcat tgccaccctc    840
tccgttcgcc ttgatcgtga aactgcaaac gcccaagccg tcgccgaatt tctagcgcag    900
cacccagacg tcgcccacgt ttactacccc ggacttaaaa acgatcccgg ttacgcatta    960
gcccaaaaag aaaccacggg tgccagcgga ctcctgacga tcaaactagc cgacaacatt   1020
gatcccttaa agttcgttaa cagcaccaaa attttcgact tgccgactc acttggcacc   1080 gtctccagtc tagtcaaact accttggttt aagctcccgg aagacaaacg cgccgatttt   1140
ggtttgacac cgcaacatgt ccggattgca attggcttgg aggatcagca ggacttgatt   1200
gacgatctgc agcaggcact ggttgcagcg gaaaaatagt atccaaaata atatctatta   1260
cttttgctaa ataggc                                                   1276

<210> SEQ ID NO 6
<211> LENGTH: 1032
<212> TYPE: DNA
<213> ORGANISM: Lactobacillus rhamnosus

<400> SEQUENCE: 6
atgccattgt ctgcactttc ttagcttggg gtcagcggta tctcgaaaaa ttcacatcac     60
gctacaatgc caatgcacaa accacgcaat tataatccgc cattttgaaa ggaagaaagc    120
tatgttaaag aaaaagttgt ggttcctgtt gccgcttgtg gccttggtaa ccttcacgct    180
caccgcttgc accagcgcat catctgacac gtcaaaaaac agcgacgtca ccgccgaact    240
catcaacaaa aatgagctta ccatcggcct tgaaggtact tatgcgccat tttcttatcg    300
caaagatggc aaacttgaag gcttcgaagt ggaactgggg aaagccttag ccaagaaaat    360
cggggttaag gcaaaattcg tgcccaccca atgggattcg ctgattgcag gattaggcag    420
ccagaaattt gatctcgtac tgaatgatat tagtgaaacg cccgcacgca aaaaggtcta    480
caacttcacc actccgtaca tgtactcgcg ttatgcctta ataacccgca gcgataacac    540
caccatcaaa tcgcttgccg atattaaagg caaacatttt gtcgaaggca ccggtacacc    600
caatgccgct ttagccaaaa aatacggcgc taagatcacc ccgtctggcg actttaccgt    660
atcgcttagc cttgtgaaag aaaaacgcgc agacggaacc atcaacgcct cggctgcatg    720
gtatgccttt gccaagaata actcaaccgc gggcttaaag agtcaaaccc tcaaagatag    780
tgtcgttaaa cccgatgaag tagctggcat ggtcagcaaa aaatcgccta aactacaagc    840
cgcactttca aagggcattc aagaactacg caaagacggc acgttgaaaa aactgtcgca    900
aaaatatttt ggcaccgatt taaccaccaa gtaatcatgc cattcagcta gcaaacattg    960
cccgtcaacc tgcttcataa acgggcatac ataaagaac actattcatt aaaggaggtc   1020
gggtttcaat ga                                                      1032

<210> SEQ ID NO 7
<211> LENGTH: 1886
```

<212> TYPE: DNA
<213> ORGANISM: Lactobacillus rhamnosus

<400> SEQUENCE: 7

| | | | | |
|---|---|---|---|---|
| aacatcaggg | tggtaaaatc | acactgatta | aggaacgggt | tgtcggcttg | aacgactgaa | 60 |
| aacttcgact | tcggtcatct | aaaggagaaa | actatgccag | atgtacgttt | tcacagcgtc | 120 |
| tttgatatta | ttggaccggt | tatggtgggg | ccaagtagct | cacatacagc | cggggcagcg | 180 |
| cggattggta | aagtcgtgcg | cgacattttt | ggcgaacccc | cggagacgat | tacgatttac | 240 |
| ctttacgaat | catttgccaa | aacctatcgc | ggtcatggta | ccgatgtggc | gctagtagca | 300 |
| gggctgttgg | ggatggcacc | cgatgatccg | cggttgccgg | aatcgctgaa | gttggcctat | 360 |
| gaccaaggca | ttaaagtgag | ttttgtgccg | aaaagcgata | aggttgatca | tcctaacacg | 420 |
| gcacatattg | tcttgcaagc | cggtgatcac | cggttagcgg | tcactggggt | ttccattggt | 480 |
| ggcgggaata | ttcagatcac | ggaaatcaat | gggtttaaga | tatcgttgag | catgggtcag | 540 |
| ccgacttata | tcaccattca | tgacgatgtg | ccggggatga | ttgcacaggt | caccaagatt | 600 |
| ttctccgatg | ccggcattaa | tatcgggaca | atgacggtga | cccgcactgc | taaaggggaa | 660 |
| caggcaatta | tgatcattga | aacggatgat | tatcatgatg | atattttggc | caaattgaaa | 720 |
| ttattaccgc | atatgcgcaa | tgtcacttac | tttgagtgat | gacgcgctaa | caactggtta | 780 |
| cgaactggct | aataaaggag | cttatcatgt | tttataccgt | taaagaactt | gtagaacaaa | 840 |
| gtcatgcctt | ctcctcggtt | gccgaactca | tggtgcatac | ggaagtcgaa | aactcaacgc | 900 |
| ggactgaagc | acagatccgt | catttaatga | gccgtaatct | ggaagtgatg | gaacgctcgg | 960 |
| ttaaggaagg | cattgccggg | gtcaaaagtg | tcaccggggtt | aaccggcggc | gaggccaaaa | 1020 |
| agctgaacca | ttatattgct | gatgaccggt | tcatgagcgg | taaaccgatc | atggaggctg | 1080 |
| ttcgcaatgc | agtggcagtt | aatgaagtga | acgctaaaat | ggggctgatt | tgtgcgacgc | 1140 |
| cgactgcgga | tcggcagga | gttctggccg | gtgttttgtt | ggcgatgcgt | gatcgcctgc | 1200 |
| acctgacgca | tgatcagcag | cttgattttc | tttttaccgc | tggtgcattt | ggcttggtca | 1260 |
| ttgcaaataa | tgccgggatt | gccggagcag | aaggcgggtg | ccaggaagaa | gttggctcgg | 1320 |
| ccagtgcgat | ggctgcggcg | gcgttggttt | gtgctaatgg | cggcagtgcc | gaacaggcag | 1380 |
| ccaccgccgt | tgcgattacg | ttgcaaaaca | tgctggggtt | ggtttgtgac | ccagttgccg | 1440 |
| gcttggtgga | ggttccgtgt | gtgaagcgaa | atgcattggg | agcaagtcaa | gccatgattt | 1500 |
| ccgctgatat | ggcattggcc | ggttgcatca | gtgtgattcc | ggccgatgag | gtgattgaag | 1560 |
| cggttaaccg | cgtcggcatg | cagttgccag | caacattgcg | ggaaaccggc | gagggcggcc | 1620 |
| tagcaacgac | accaactggc | ttacggctga | agaacaaat | cttcggcaaa | agtaattgt | 1680 |
| gattcaatga | cggcacgaca | aatttttgcc | cggcatgagt | tttatttaaa | cggcgttact | 1740 |
| ggcaacaagg | tatttggaaa | gggtcaatcg | tgattaattt | atatattatt | cgacatggtg | 1800 |
| aaacagcagg | caatgtgcgc | cgcttaattc | aaggcgtgac | gaattcacac | ttgaatgcgc | 1860 |
| gcggacgtaa | acaggcgtat | gctttg | | | | 1886 |

210> SEQ ID NO 8
<211> LENGTH 1350
<212> TYPE: DA
<213> ORGANISM: Lactobacillus rhamnosus

<400> SEQUENCE: 8

| | | | | |
|---|---|---|---|---|
| gtgaaggaaa | aatgagtcgc | ttaaaagagc | gcgataaaat | caacaaatat | tgacaaccga | 60 |

-continued

```
ttgccagcca gcgctcacgt ttgaagctcg gccaaaccaa acaagatcac aaggaggcgt      120
tgtttatgtt taaacccacc attcatcaac ttcatcccta tacgccagaa aagcctcttg      180
ccgtattaaa agaagaactt ggcttgccac agctggtgcg gatgtcagca aacgaaaacc      240
cattcggtac cagcgtcaaa gttcagcagg ccgtgaccaa ctggaatttt acgcaaagtc      300
gtgattaccc cgatggctat gccagtcaac tacgcaccgc ggtggcaaaa catttagacg      360
ttgccgcaga gcagttggtt tttggcaatg gtctggatga agtcattgcc ttaattgccc      420
gcactttttt gagcccgggg gatgaagtca ttgaaccatg ccaacatttt ccgagtacc       480 gcttgcatgc ccaaattgaa ggggccaccg tgattgatgt gcccgtcact gaaactggca      540
attttgattt atctgcaatg gcgcaggcgc taaccgcgaa aacgaaactg atttgggtgt      600
gcaacccaaa taacccacg gcacgctgc tgtcaattgc gacactgacc gaatggctgc       660
gacagatacc aaaagacgtg ctggttttaa tggatgaggc ttatattgag ttcactgatg      720
actatccagc cacgagcgct atcagcttat tatcaaagtt tccaaacctc gtcgtgctgc      780
gaacattttc aaaaatctat ggactggcga atttccgggt cggcttcggt gttttcccta     840
aacaacttgt taactacttg caaaccgttc ggctgcctta caatttaagc agcattgccc     900
aagttagcgc acaggcggcc ttggctgatc aagattttgt cgcgatgaca cgcaagcgag     960
tgcagcaagc gcgcgatagt tgggaacgct tttaaccca aactggactg ccacacaccc    1020
ggagccaaac caactttcaa ttctttcagg ccccaaaaat gcaggcatcg gctttaaaaa   1080
agcgcctgct acaacaaggt tttccttgtcc gtgatggctt aaaacccggc tggctgcgcg   1140
tcacgtttgg cactgaggta caaaacacgg cggtacagcg catcattgaa acttttcagg   1200
cagaactcac tgggccaaat gcgctgaagt gattggaacc gccaccatgc aggcgtaaac   1260 taaggtgtg gttaatggct catctgaaag gaagcattta ttttgaaaat tgccaaatta   1320
aacaaccatc cctatctgat aacgtctgca                                    1350
```

<210> SEQ ID NO 9
<211> LENGTH: 1275
<212> TYPE: DNA
<213> ORGANISM: Lactobacillus rhamnosus

<400> SEQUENCE: 9

```
aaagcaatcg gttcgatcat catcgcattt gttgccatga ttttggcttt gctttggcca      60
ccgttaacga tcatactgga cttggtaatg ttactcttgt gggccatccc ggatcagcgg     120
gttgaacggc atttgctaca tggcccgaaa aactaaactt tgtgaaaagg ggttttatc     180 ttggcaagaa ccattggtat tatccggtatt ggacatgttg gggtgacaac agcatttaat    240
ctcgttagca agggattgc ggatcgtctg gtgctaattg accaaaaggc tgatttagct    300
gaaggcgaaa gttatgattt gaaggatgca cttggtggat tgccgactta taccgagatt    360
atcgtcaatg attacgatgc tttgaaagat gcagatgttg tcatttccgc ggttggcaat    420
atcggtgcga tttcaaacgg cgatcgaatt ggtgaaaccc aaacgtcaaa acaagcatta    480
gacgatgtgg caccaaagtt gaaagcgtcc ggattccatg gcgttttgct ggatatcacc    540
aatccttgtg atgctgtcac cagctattgg caatatttac ttgacctacc aaagtcccag    600
attattggca ccggcacctc gctggatact tatcggatgc ggcgcgcggt tgctgaatcg    660
ctaaatgtga atgtcgccga tgttcgcggt tataacatgg gtgagcatgg tgagtcacaa    720 tttacgcgt ggtcaacggt gcgggttaac aacgagccaa tcacggatta tgcgcaagta    780
gattatgatc aattagctga tgcggcgcgg gctggcggct ggaagattta tcaggccaaa    840
```

```
cattatacca gctacggtat tgccaccatt gctactgaaa tgacacaggc gattatcagt      900
gatgccaagc ggattttttcc gtgcgctaac tatgatcctg aattcggtat cgccatcggt    960
catccggcga cgattggcaa gctcggtgtt gttaacacgc taagttgaa gcttaccgat     1020 gaagagcgtg ctaagtatgt tcattccgcg ggcatcatta agctacagt ggaaaagatg    1080 aagtaagatt aatccagtag cattgatgtc atgcataaaa agacgccaaa ttgtgaccgg   1140
tattctctaa cgttttactc caacgttgag ggtgctgatc aaatcggcgc ctttttacta   1200
gagttaattt daatgttacg ccttaataag gagttttttcg ggtatggtta aaaaatatac  1260
gttggtgact gttga                                                    1275
```

<210> SEQ ID NO 10
<211> LENGTH: 1536
<212> TYPE: DNA
<213> ORGANISM: Lactobacillus rhamnosus

<400> SEQUENCE: 10

```
ttcgaagttt aaagaactag gtttggatca tgatctctta aaggcaatcg cccagtcagg      60
ttttgaggaa gcgacgccga ttcaagcgga gacgatccca ctggttctgg aaggcaaaga    120
tgtgatcggt caagcccaga ccggtaccgg gaaaacggca gcatttggct tgccaattct    180
gcaacacatc gataaagccg accggagtat ccaagcattg gtcatttccc caactcggga   240
attggcgatt cagacccaag aagagcttta ccgtttaggc cgcgacaaga agatcaaggt    300
tcaggctgtc tatggcggcg ctgatattcg ccgccagatt cgtcagcttg ctgaccatcc    360
gcaaattgtg gttgggacac ctggtcggat tcttgatcat attggtcgtc ataccttaaa    420 gttgaacacac cttgatacct tggtgttaga tgaagccgat gaaatgctcg atatgggctt    480
cattgacgat attgaaaaga ttgttgaaca aatgccgacc gagcgtcaaa cattactgtt    540
ctccgcgacg atgccggcag cgatcatgcg cttaaccaac aagttcatga agaacctgt     600 gattgtcaag attaaggcta aggaactgac agcagatacc gttgagcaat attatgttcg    660
ggccaaggac tatgaaaagt tcgatgtcat gacacgactg tttgacgttc aggatccgga    720
cttggcactg atttttggac ggaccaagcg tcgtgttgac gaactgacac ggggattaaa    780
ggcacgcggc tatcgggctg aaggtattca cggcgattta acccagcaaa agcgaatgag    840
cgttttgcgg cagttcaaga gcggccaatt ggattttctg gttgcaaccg atgtcgctgc    900 tcgtggggttg gacatttctg gtgtcaccca tgtttacaac tatgatatcc cgcaagatcc    960
ggattcctat gttcaccgta tcggtcggac gggacgcgcc ggacataaag gggtatccgt   1020 aaccttttgtc acgccaaatg aaattgaata tctgcacacc attgaagatc tcaccaagaa   1080
gcggatgtta cccatgaagc cgccgacagc tgaagaagca ttaatgggcc agatctccag   1140
cggcttagca accatcaagg aacaagttga agctaacgat accgaaaagt atgaagcaat   1200
ggctgaaacc ttgttggaaa actacacccc gttgcagctg gtttcggcgt atctcaaggc   1260
agtcagccct gacgatgcga gtgccgttcc ggttaaaatt acaccagaac gtccattacc   1320
acgccgcggc cgcaacaatc acggccatgg caacaatcgt ggcggttata aggcggcta    1380 caaaggcaag cgacgcgatg gcggctatca aggtaatcgc gatggcaagc gcagttacga   1440
caagaagcgc aactttggcg acaaacgtaa aaacgttaag cgtaatttca aaatccgtac   1500
gggtgaataa tcaccagtac gttaatagac cggtca                             1536
```

<210> SEQ ID NO 11

<211> LENGTH: 1409
<212> TYPE: DNA
<213> ORGANISM: Lactobacillus rhamnosus

<400> SEQUENCE: 11

| | | | | | | |
|---|---|---|---|---|---|---|
| tatgacgttg | cgtgtcgata | ggcaaatgga | ctatgctatt | tgcatgctat | tataacgcgt | 60 |
| ttgccagcgt | aaaagtcagt | taggcaatct | tttagttgta | gccgtctaac | tccgacttct | 120 |
| aactgcatcg | gttcgcgttt | acatcataat | gcgctctcct | gcccagaaat | cgggtttggc | 180 |
| tcgcgcttac | tttattaagg | agatttgtat | gacattgcaa | cctttaaacg | aacaactacc | 240 |
| tgccatcgag | gttagtgaga | ttcgacaatt | tgacgaaagt | gtcagtgata | ttcccggtat | 300 |
| tttgaaactg | acgctaggcg | aacctgattt | caacaccccg | aacatgttaa | gcaagccgg | 360 |
| gatcaaagcc | attcaggaaa | attactcgca | ttataccggg | atggttggtg | atccggagtt | 420 |
| acgcgaagcc | gcacaacatt | tttttaaaac | gaaatatgcc | actgactatc | gggctacaga | 480 |
| tgaaattctg | gtgacagtcg | gggccactga | agcactggca | accgccatta | cgacgatcag | 540 |
| tgatccgggt | gatgccatgc | tggttccgtc | accaatttat | ccgggctaca | ttccgcttct | 600 |
| gacgctgaat | cacgttacgc | cgctttatat | ggatacgagt | aaaaccgact | ttgtcttgac | 660 |
| ccccgaactc | attgaggcca | ccatcactgc | aaatcctgac | gctaaaatca | aaggcattat | 720 |
| ccttaactat | ccaagtaatc | ccaccggtgt | cacgtatcgg | gcggcagaag | ttaaagccat | 780 |
| tgcggacatc | gccgctaaac | ataacctcta | cattatctgt | gacgaaattt | attctgaact | 840 |
| gacttatggt | gagccgcatg | tttccatggg | acaatttgcc | tacgatcgta | catttattgt | 900 |
| caacggtctg | tctaaatcac | atgcaatgac | cggctggcga | atcggctttt | tgatgggtcc | 960 |
| ccagcagtta | atcgcgcaag | ccaaaaaggt | gcaccaatat | cttgtgactg | ccgcaacgac | 1020 |
| cattgcccag | cgcgctggta | ttgaagctct | gacgaacggt | gcagacgatg | ctcaggtgat | 1080 |
| gaaagcagct | tacgttaaac | gccgtgattt | tgtttatgcc | gccctcatcg | acatgggctt | 1140 |
| tagcgtggct | cgtcctgatg | gtgcctttta | tcttttgca | aaaattccga | cccaactgca | 1200 |
| tctaagctca | cgcgaattta | cgcacgcctt | ggcacatgaa | cagaagttag | ctctgatttc | 1260 |
| aggtaccgct | tttggccccg | gcggcgaagg | ttatatccga | atcagttacg | cggcatcaat | 1320 |
| gaccgatctt | caagaagccg | ttaagcgatt | gcgcgcgttc | atggccagcc | acatcggcta | 1380 |
| atcaagcgta | aacggaaaga | atccgcacg | | | | 1409 |

<210> SEQ ID NO 12
<211> LENGTH:1247
<212> TYPE: DA
<213> ORGANISM: Lactobacillus rhamnosus

<400> SEQUENCE: 12

| | | | | | | |
|---|---|---|---|---|---|---|
| gtgcatttag | caaaaagaat | cctcaacgtc | gcaccgtcag | cgacattggc | cttaagtaat | 60 |
| cagacgaaag | acttaaaggc | aaaaggtgcc | gacgtcattg | atttgtctat | tggccaacca | 120 |
| gatttttcaa | cccctaaggc | gattgatgac | gcagctattg | cggcgattca | ggctggtaat | 180 |
| gccagtttct | atacggcagc | aaccggtatt | ccggaattaa | agcaggcgat | tagtgaccgg | 240 |
| atatttgccc | aagacggtat | tcgttatgat | catcgtcaaa | tcgttgcaac | caccggcgct | 300 |
| aagtttgctt | tgtatgcctt | atttcaggtt | ttccttaaacc | caggcgatga | ggtgctgatt | 360 |
| cctgttccat | actgggtttc | ctacgaggaa | cagattaaat | tggcgagcgg | cgtgccacat | 420 |
| ctggtcatgc | cggcagtcgg | acataaagtc | agtgtcgatg | atcttgaggc | ggctcggacc | 480 |
| gataaaaccc | gggcattgat | tatcaattcg | ccacaaaacc | caagtggcgt | tgtctatgat | 540 |

-continued

| | |
|---|---|
| cgcacggaac tgaccttaat tggcaattgg gcgctgaagc atcatatttt ggtagtgact | 600 |
| gacgatattt accgagatct gatttataac ggtacgactt acacctcaat gattagtatc | 660 |
| gatcccgata tcgcagcgaa tactgtttta atttccggcg tctccaagtc atatgcgatg | 720 |
| acgggttggc ggattggtta tgcggccggt ccggaaaagc tgattcaggc catggcgacc | 780 |
| tttattagcc acacgacctc taatccggca gcagtttccg aatacgccgc ggtggcagct | 840 |
| ttaactggcg atcagcaggt tgttgaaaag atgcgccgtg cttttgaaga acggctgaat | 900 |
| cttttctatg atcttctggc agatattccc ggtttcgata tgggagataa accgcaaggc | 960 |
| gccttctatc ttttcccgaa tattaagcgt gccgctcaat tgagtcatta tggtacggtt | 1020 |
| gatgatttta tcagtgcact gttgaccgaa accggggttg ccattgttcg tgctggacgg | 1080 |
| gcgtttggca tgccggatca tgcgcggatt agttattgta aagatttggc cagtctgaaa | 1140 |
| gaggccgccc ggcgtatccg ggagtttgtt ggtaaataat tattgaagtg gggagttaac | 1200 |
| gcatgacgga aaagattcgc attattgatg caaaagaaca tgtgaac | 1247 |

<210> SEQ ID NO 13
<211> LENGTH:650
<212> TYPE: NA
<213> ORGAISM: Lactobacillus rhamnosus

<400> SEQUENCE: 13

| | |
|---|---|
| atgcaaagag cagaattaat caccgcgatt gtgacaccgt ttaacgaccg cgatgaaatt | 60 |
| gactatgata gtatgcaacg gttagtcgat catctcattg atcaaggcac tgacgggttt | 120 |
| gtggttggag ctcgacgggg tgaagggcct acgttgagtc atgatgaaaa gatcacccrt | 180 |
| tacacccgtt ttgtggccat ggttcacggg cgcgcactcg tcattgccaa ttcagggtct | 240 |
| aacaacaccc gcgaaaccac tgattttacg catgaagtcg gtggaattgc cggaattgat | 300 |
| gctactttgg ttgtggttcc gtattacaac aagccggatc aagatggcat gatcgcgcac | 360 |
| tataccacgg ttgcggcaag tgcgcaaaaa ccgatcatta tttacaacat tccagggcga | 420 |
| accggcgtaa acatgttacc ggaaaccgtg caacgctgg cacaaaaccc catgattcaa | 480 |
| gggatcaagc agtgcggcag tctggcagca ctcagcgata tcatcgaccg aaccaaacac | 540 |
| gatgccttca atgtctggac cggcgaagat gctcaagcgc tgacgatcaa acactgggc | 600 |
| gggatgggcg ttatttcagt tgcctcccac ctatatgccc atagcatccg | 650 |

<210> SEQ ID NO 14
<211> LENGTH: 768
<212> TYPE: DNA
<213> ORGANISM: Lactobacillus rhamnosus

<400> SEQUENCE: 14

| | |
|---|---|
| ctacaagaaa ttttccaacc ccacaaccaa atgatccgct gcctgaacct tgcgaatggc | 60 |
| aacggcgacc ccttgcatga agctttggcg atcgaaggag tcttggcgga tggtgagggc | 120 |
| ttcaccggga ccgccgaaga ggacttgttc gtgggcgatg taacctggta agcggacggc | 180 |
| gtggaccggg acgtcatcaa tgcgttggcc gcgggcgtcg ttgtcgatgg tggacaatgg | 240 |
| cttttgggtg cgtccggcgg cgattttgtg cgcagtggcg atggcggtac ctgatggcgc | 300 |
| atcggctttg tcctgatgat gcatctcgat aatttcggcg tcaggaagt aggcggcggc | 360 |
| ttcctgcgcg aacttcatta agagaaccgc ggaaaggccg aagtttgggg cgattagacc | 420 |
| gccgatatga cgggcttggg cgagttcgat taagcggttt tgatcggctt gcgtcatgcc | 480 |

| | |
|---|---|
| gcttgtgcca acgactgggt gaatgcctgc tttgatcgcg gcttcaatgt tggcagcgac | 540 |
| ggcagtggga ttggtaaaat caacccacac atcggcaatg tcgggattga gctgatcata | 600 |
| gctcgtgagc acttttgtat cagctggtag tccatatttt tgggcatcag cggcagttgc | 660 |
| tttgggatca aaacggcac ttaatgcgaa atcttttgt gactgaacca ttttgactgt | 720 |
| tttttgaccc atggcaccgc gaaaaccggc gacaagaacg tgaatcat | 768 |

<210> SEQ ID NO 15
<211> LENGTH: 1277
<212> TYPE: DNA
<213> ORGANISM: Lactobacillus rhamnosus

<400> SEQUENCE: 15

| | |
|---|---|
| actaatgtgg atgacggcgt ggcgaacttt ttaacggatt tttttgagaa gtgagctttt | 60 |
| tccgtaaaaa gtggggtttc tggttgattg ttagcgaaac gtttgccacc atagagatgg | 120 |
| taaacgtttt tattttgcgg tcgtttgagg agggctttaa tcatgtatca tgcagcagct | 180 |
| gatcgttatg agaaaatgcc ggttcgccat gctggtaaga cagggttgat gttgccggtt | 240 |
| atttcgttgg gattgtggca gcattatggc aacttggatc catttggccc gcgacgctcg | 300 |
| gtgattttgg atgcgtttga tcgtggcgtt tttcattttg atgtcgctaa tcattatggt | 360 |
| aatggtgatc gtgaaccggg atttggctct agtgaaaggt tactcgggca gattctggcc | 420 |
| acggatttaa aaccgtatcg agacgaattg gtgattagta ccaaggtggg ttatgagatt | 480 |
| caccctggtc catacggtgt cgggacgtcg cgtaaagcag ttattcaagg cttgaatgat | 540 |
| tcactcaagc gcttgcagtt ggattatgtc gatatttact atgcccaccg atttgacgat | 600 |
| accgtggcct tggaagagac ggttaatgcg ctggatcaaa cggtgcgtga cggtaaggcg | 660 |
| ttgtatattg gtatttccaa ctatgatacg aagcagacca agaagcaat tgcgatgttt | 720 |
| aaagatctgc acacgccttt tgtactgaat caatacagtt acaacatgtt taatcgcacc | 780 |
| gctgaaacgt ccggcttgat cgatgcatta aaagctgatg gtgccgggtt gattgcatac | 840 |
| ggaccgttat cagaaggctt gttatcagat cgctacctaa agggaattcc ggatactttc | 900 |
| aaaatccatc caaccaacaa ggccactttt gctaagggca agaggctgt ggttaagcaa | 960 |
| ctaaatgcgc ttaatgaaat tgcgcatgat cgtgaccaaa ccctgagtca atgggccttg | 1020 |
| gcgtggttgt tacgggatcc ggttgtcaca agtgtgatca ttgggacgac ctcagttgaa | 1080 |
| caccttcagg ataaccttaa agcaacggaa catctgacct ttactgctga agagattcaa | 1140 |
| caaattgatg atatttaaa tgcttagttg acgtttggct gtaaaaggct aagcgtaagt | 1200 |
| ataaaaaaac ggcttcggag tgttttttga ctccggagcc gttttattt tgaggaacaa | 1260 |
| tgcttgacag gtgctct | 1277 |

<210> SEQ ID NO 16
<211> LENGTH: 964
<212> TYPE: DNA
<213> ORGANISM: Lactobacillus rhamnosus

<400> SEQUENCE: 16

| | |
|---|---|
| gcaatgacca cacaatccgg cttctaccca cgctggctgg cgctcacgag gagggacatt | 60 |
| aaaatgcaa aaatgtggaa acgcatgctc ctgccactgg tgttgttact attgatgata | 120 |
| ccgttaagca gctgtggcaa agtgtggcg gatcgtgata ttttagcgaa cgccaaggca | 180 |
| accaatacga ttatttgggg cgtcaaggcc gataccegtc tgtttggctt gatgaacatt | 240 |
| aaaaccggta aaattgaagg ctttgatgtt gatatggcca aggcgattac caagcagatt | 300 |

```
ttaggcaaaa aagggaacgc ccagctggtt caggtgacca gtgatacccg cgtgccgatg    360
attaaaggtg ggaacctgga cgcggtgatc gctaccatga cgattacccc ggagcgccaa    420
aagattctgg acttttccga tgtttacttt aatgccgggc aaagtctttt agttaaaaaa    480
ggcagtccga ttaagtcagt gaaggatttg aagaaaggca ccaaagttat cggcgtgcaa    540
gggtccaatt cagttgataa tgttaaaaaa gctgctcccg acaccactgt tctgcagtta    600
gccgattatg cgcaggcgtt taccgctttg aaatcaggcc aaggtgatgc cttgaccact    660
gacaatggga ttttatacgg gatgtcagaa caggataaga actatattgt caccgggggc    720
accttcacta agagccata cgggattgcg attaacaaag gccagaagcc gtttgtcaac    780
gcggttaata aggcgatcaa acaactcaaa caaaacggga cttatgcaaa gctaatcaag    840
aagtggttcg gcgatgtgcc aggattcagt cttaaggagg tggaataaca tgtggtcaat    900
tcttaccaat aattggaaca ccttcctttc cggacttggt ttcacgttag cagcgagcat    960
ttag                                                                 964

<210> SEQ ID NO 17
<211> LENGTH: 1263
<212> TYPE: DNA
<213> ORGANISM: Lactobacillus rhamnosus

<400> SEQUENCE: 17
ggatggtgca ggggcttagg cttctgtgcc ttttagaaa gaagcgatga aattgacaat      60
ttatgacttt gatcatgtta tcgatcgccg gggtacgttt agcactcaat gggattatat    120
tgctgatagg tttggccgta acgatatcct gccctttttcg atctccgata cagattttcc    180
agtaccagtt gaagtgcaag atgcgctaaa agaacggtta acacatccaa tttatggcta    240
tacacgatgg aatcatgcta cttacaaaga cagtattgtt cactggttcg agcgtgatgg    300
tcatacaaag ataaacccgg attggattgt ttatagccct agcgttgttt ttacgattgc    360
tacactcatt cgaatgaaga gcgatcccgg ggacggagtg gctgtgttta cgcctatgta    420
tgatgccttc tatggtacga ttaaacagaa cgatcgagtg ttgatcccga ttcgattagc    480
agctgcagat gaaggctatg tgattgattg ggatagtttg gcaacggtac ttgctgaaaa    540
gcagacaaaa atattcttac taacaaatcc gcataaaccg acaggacatg ttttacaaa    600 atcggaatta gcacgccttt atgacttgtg tcaggcagcc catgttttct tgatctctga    660
tgatattcac cgcgatattg tttatccggg tcattcgtac gaaccaatga caaatgtcgg    720
cacaagtgat gttgcactct gctgctcagg gtcaaagaca tttaacacac caggcctgat    780
tggctcatat gccttcttac cagatcatga tgtaagggca caatttttga cggaattaaa    840
gcagaaaaat gctctgtctt ctgtaagcat ctttggcatg ctggcgcaaa ttgcggctta    900
taacggttca gaggattacg tggaacaact gactgcctat acaaaaaata atatggagtt    960
ggttgctagt tatttagagg aaaatttgcc ggaattgcag ttttcgttac cggatgccac   1020
gtacttagcc tggataaatg tgtctaaact gagattaacg tcagaggaac ttcaacatcg   1080
gttagtaaac ggcggccatg ttggcattat ggcgggcaaa acttatggtg ataccagata   1140
tctaaggatg aatattgcct gtccaaagaa gaagttagtg atggggctag aacgtttaaa   1200
gaagggaatt aggggataat atgctcttac tcagagaaat caaaatctta cgccgcctgt   1260
ccc                                                                 1263

<210> SEQ ID NO 18
```

<211> LENGTH: 1356
<212> TYPE: DNA
<213> ORGANISM: Lactobacillus rhamnosus

<400> SEQUENCE: 18

| | | | | | |
|---|---|---|---|---|---:|
| atgactgatt | gggtacttga | tgacggtgga | catggttcta | ctggatgcgt | acaatgacaa | 60 |
| caaaagcaag | aaagcaggga | tcattgatgg | aagatttgcc | aactgatatt | gcaacgtttg | 120 |
| tggacacgca | cttagttgat | cgccataata | gcaatgctgt | gaagtgggac | ggtctgaaag | 180 |
| aagaatttgg | ccgggctgac | ttgttgccta | tgtggattgc | cgacactgag | tttaaggcgc | 240 |
| ctcaagcagt | tttggatgca | ttgacagttc | gcgtcaagga | agggacgttt | ggctattcca | 300 |
| ttcgcccgca | gtcttattac | gaagccttca | ttaactggca | aaaggaacga | catggcatta | 360 |
| cggttgaacc | tgagtggatg | cgttttggcg | ttggcgttgt | caaatcactg | tatgcgatgg | 420 |
| tgaactggct | gacagaacct | ggtgatccgg | tcctcatcat | gcagccggtt | tattatccct | 480 |
| ttatgaatgc | cattaatgat | cttggacgta | aagtcgtatc | agttgacttg | caattaaccg | 540 |
| ctgatggttg | gcgcatggat | tttgaccaat | agaaaagac | cttggcggcg | aatgaaatta | 600 |
| aagcgatgat | tctgtgttca | ccgcacaatc | cggttggtcg | gatctggacc | cgagatgagt | 660 |
| tagaacaact | ttttgccatc | acaagtcggt | atgatgtgac | agtggtttct | gatgaaattc | 720 |
| acggtgatct | tgaagtgagt | gggccgaagt | ttacatccgc | tttacaggtc | gctgaaggta | 780 |
| aagctcgaaa | aaagcttgtt | gtgctcaatg | cgccgtcaaa | acatttaat | ttagccgcct | 840 |
| tgctgaattc | acacattatt | attcccgatc | aagcgttgcg | tacgagttat | gatgccttca | 900 |
| ttaagcagct | gcatccggtt | gatacgagct | tgatgggca | agtggccggt | gaagctgctt | 960 |
| atcggcatgg | cgctgcttgg | ttagatcagg | tcttacaagt | ggttcgctac | aattatcggc | 1020 |
| aactgcaagc | tggtttagcc | gcggcggccc | cacaagcgac | cctggccgac | ttacaaggga | 1080 |
| cttatttggc | ttatgttgat | atcggtgctt | atgttgcgcc | aagtcagatc | aaagactttg | 1140 |
| ttgaaggtgt | gtgcggattg | ctgttgatt | atggtgcatg | gttttcaccg | caaacggcaa | 1200 |
| cttatattcg | tttaaattta | gctactgatc | ctaagcttgt | tgccgaggcg | attaaccgac | 1260 |
| taaccactca | tttggcacag | cagccgcagc | ggtgatcggg | acaagaatta | aattgccttt | 1320 |
| ttcaagataa | aactcgaatt | caaagagacg | gaatgg | | | 1356 |

<210> SEQ ID NO 19
<211> LENGTH:1254
<212> TYPE: DNA
<213> ORGANISM: Lactobacillus rhamnosus

<400> SEQUENCE: 19

| | | | | | |
|---|---|---|---|---|---:|
| tatagcacgc | caagccaagc | agctcgcagg | tggtttttgg | gttaaagctt | ctattattga | 60 |
| ctgactttct | ttgagtttca | tgaaaatgat | cggcgaaaaa | tgtctattat | tgtcattttg | 120 |
| ttctatacta | atcgtgtact | gaacatttaa | ggattaccta | ggaggtattt | ttacatgtct | 180 |
| gttaaactta | ctgctggtca | gttagagcat | ttgaagcaat | tgtccaatga | caacaacgtc | 240 |
| atctcggctt | tagccattga | ccaacgcggt | tccctgaaga | agatgcttgc | agctgcagcg | 300 |
| aacaagccag | ctgacgaaac | cacgattgtt | gatttcaaga | agctgtttc | tgaagaatta | 360 |
| accaaatacg | ccagcgcgat | tctgcttgat | ccagaatacg | gcctgccagc | tgccaaggtt | 420 |
| cgcgatccta | gtccggcct | cttgctttcc | tatgaaaaga | ccggctacga | tgcgactgaa | 480 |
| cctggccgtt | tcccagattt | gattgataac | caaagtgctt | tgcgcatcaa | gaacgaaggc | 540 |
| ggcgatgcag | tcaagttctt | actgtacatt | gaccctgacg | aacctgatag | tatcaacgat | 600 |

```
cgtaaatatg cgtttgttga acggggttggt gctgaagcta aggctaatga tctgccactg    660
ttcttggaat tagtttccta cgatggcaag accaacgaaa ccggcaccgc tgcatgggca    720
aaagcaaagc ctgaaaaagt tatcaagatc actaaggaat tcagcaaggc gcaatacaac    780
gtttctgttt tgaagcttga agttccggtt gatcaaaagt ttgttgaagg ttacaccgat    840
gaaggcgtaa cgccggttta cagcaaggaa gaagctgcta agtactacaa ggctcaatcc    900
gatgcaaccg atttgccatt catcttcctg tccgctggtg tttccaacga attgttcctt    960
gaagaactca aatttgctaa ggaagccggt tcaaccttta cggtgtgct ttgcggccgg   1020 gcaacctgga agccaggcgt taagccattt gctgctgaag gcgaagctgc cggcaagaag   1080
tggctgcaaa cggaaggtaa agctaacatc gatcgtttga acaaggtttt ggctgacact   1140
gctactcctt ggacagacaa ggttgaaggc taattctttt taactaatta atcgttcaaa   1200
aaccagccac agatgcggct ggttttttat atggtgagcg tgagccagcc cgct         1254

<210> SEQ ID NO 20
<211> LENGTH:1482
<212> TYPE: DA
<213> ORGAISM: Lactobacillus rhamnosus

<400> SEQUENCE: 20
tctggtttca atattaaaca gccttctggc aaaaaggaga agaatatatg tctatcatta     60
ctgatgtatt ggcacgcgaa gttttagact cacgtggcaa ccctactgtt gaagttgaat    120
tgtataccga agatggcggt tcggccgcg cattagttcc atcaggtgct tcaaccggtg    180
aacatgaagc cgttgaattg cgtgatggcg ataaggatcg ttttggcggc aagggtgttt    240
tgaaggccgt tgaccacgta aacaatgaaa ttgctaaggc tgtgattggc cttgacgtca    300
ccgaacaacg cttgattgac caaaccatga tcgatcttga tggcacgcct aataaaggca    360
agctcggtgc caatgcgatt ttgggtgttt ccttggctgc tgcccgtgct gcggctgatg    420
aagttggtct gccattgtat caatatcttg gcggcccgaa tgctcatgtt ttgccaacgc    480
caatgatgaa cgttcttaat ggtggtgcac attcaactaa caccgttgac ttccaggaat    540
tcatgatcat gcctgttggt gccaagagtg ttcgtgaagc cgttcggatg ggttcagaaa    600
ccttccacgc attgcaggca ctgctcaaga gcaagggtga catcactgct gttggtgatg    660
aaggcggctt tgcacctaac ttgaaggata cgaagaagc tttcgaattg cttgttgaag    720
cgatcaagaa ggctggctac aagccgggtg atgacattgc tttggccttc gacgttgctg    780
cttcagaaat gtacgatgct gataccaaga cgtacacaac caagtggtcc aaccctgaca    840
agaagtacac aaccgaagaa tggaccaaca tgattgacgg ctacattaac aagtatccga    900
tcgtttctgt tgaagatcca atcgatgaaa acgactggga aggctggcag acattcaccg    960
agaagatggg cgacaaagtc caaatcgttg tgatgacct gtttgttacc aacaccgatt   1020
acctgaagaa gggtattgac atgggtgttg ctaactccat cctgatcaag ttgaaccaaa   1080
tcggtacatt gacagaaacc ttcgaagcaa tcgaaatggc caaagaagct ggttacacgg   1140
ctgttgtttc acatcgttca ggtgaaaccg aagataccac gattgctgac ttggttgttg   1200
caaccaacgc cggtgaaatc aagactggtt caatgagccg gactgaccgg attgccaagt   1260
acaatcagtt gatgcgcatc gaagatcaat taggtgctca atcacaatac aagggtcgca   1320
agtccttcta caacgttaaa gcaattgact aattaacgct tgacgttaac atgaaaagca   1380
cgtcacttca aatggtggcg tgtttttttct attcttagct taagcaaaag atgaacttgc   1440
```

```
tcacgctttg tgactgaggg ctgtctggtg ccggtgcaag ca              1482
```

<210> SEQ ID NO 21
<211> LENGTH: 2407
<212> TYPE: DNA
<213> ORGANISM: Lactobacillus rhamnosus

<400> SEQUENCE: 21

```
tgcttgcacc ggcaccagac agccctcagt cacaaagcgt gagcaagttc atcttttgct    60
taagctaaga atagaaaaaa cacgccacca tttgaagtga cgtgctttc atgttaacgt    120
caagcgttaa ttagtcaatt gctttaacgt tgtagaagga cttgcgaccc ttgtattgtg   180
attgagcacc taattgatct tcgatgcgca tcaactgatt gtacttggca atccggtcag   240
tccggctcat tgaaccagtc ttgatttcac cggcgttggt tgcaacaacc aagtcagcaa   300
tcgtggtatc ttcggtttca cctgaacgat gtgaaacaac agccgtgtaa ccagcttctt   360
tggccatttc gattgcttcg aaggtttctg tcaatgtacc gatttggttc aacttgatca   420
ggatggagtt agcaacaccc atgtcaatac ccttcttcag gtaatcggtg ttggtaacaa   480
acaggtcatc accaacgatt tggactttgt cgcccatctt ctcggtgaat gtctgccagc   540
cttcccagtc gttttcatcg attggatctt caacagaaac gatcggatac ttgttaatgt   600
agccgtcaat catgttggtc cattcttcgg ttgtgtactt cttgtcaggg ttggaccact   660
tggttgtgta cgtcttggta tcagcatcgt acatttctga agcagcaacg tcgaaggcca   720
aagcaatgtc atcacccggc ttgtagccag ccttcttgat cgcttcaaca agcaattcga   780
aagcttcttc gttatccttc aagttaggtg caaagccgcc ttcatcacca acagcagtga   840
tgtcacccct gctcttgagc agtgcctgca atgcgtggaa ggtttctgaa cccatccgaa   900
cggcttcacg aacactcttg gcaccaacag gcatgatcat gaattcctgg aagtcaacgg   960
tgttagttga atgtgcacca ccattaagaa cgttcatcat tggcgttggc aaaacatgag   1020
cattcgggcc gccaagatat tgatacaatg gcagaccaac ttcatcagcc gcagcacggg   1080
cagcagccaa ggaaacaccc aaaatcgcat tggcaccgag cttgcctta ttaggcgtgc    1140
catcaagatc gatcatggtt tggtcaatca agcgttgttc ggtgacgtca aggccaatca   1200
cagccttagc aatttcattg tttacgtggt caacggcctt caaaacaccc ttgccgccaa   1260
aacgatcctt atcgccatca cgcaattcaa cggcttcatg ttcaccggtt gaagcacctg   1320
atggaactaa tgcgcggccg aaaccgccat cttcggtata caattcaact tcaacagtag   1380
ggttgccacg tgagtctaaa acttcgcgtg ccaatacatc agtaatgata gacatatatt   1440
cttctccttt tgccagaaag gctgtttaat attgaaacca gattaatctt ggtagttagc   1500
caaggcgatg aaactgtcag gatccatcga agcgccacca actaaaccac catcaatatc   1560
aggcttagcc attaattcct tgacgttcgc tggtttaaca gagccgccgt aaagaatccg   1620
aacagcatct gccgtatctt tattatacaa cttctcaacg gttgcacgga tgtgagcaac   1680
aacttcttgt gcttgatctg cagttgctgt tttaccagtg ccgatagccc agattggttc   1740
ataagccaaa accgaaacct taacttggtc ggcacttaag cctgccaaag ctgcttcgat   1800
ttgagaagca acccagtctt cggtttgacc ggcttcacgc tgagccaaac tttcaccaca   1860
gcagataatc ggcaaaagat tgttcttaaa gatggcctta gccttcttgt tgatatcttc   1920
gtcggtttcg tggaaataac cgcgacgttc actgtgaccg ataatgacgt aatcaacgcc   1980
catttctttt aaggctttcg ggctggtttc gccggtaaaa gccttcgt cttcaaagta    2040
gcagttttcc gccgctgtct tcaaaggagt accttctgca ccggcaacca gtgtcgttag   2100
```

-continued

```
atcaatggca ggtgcgccaa tgactgtttc aactttgctt gcatcaggta acttacccTT    2160
aacagcatct aagaaggctt gcgtctcctt aggattctta ttcattttcc agttaccagc    2220
aatgaatggt gtccgcatga catccttcc tttcattatg taccgacatg catcatgcat    2280
gtcgataatg actgttagat cagcatcact aacaattact tgtcagaaat ggctgcaata    2340
cctggtaagg tcttgccttc aaggtattca aggctagcac cgccaccagt ggagatgtgg    2400
gtaatct                                                              2407
```

<210> SEQ ID NO 22
<211> LENGTH: 1407
<212> TYPE: DNA
<213> ORGANISM: Lactobacillus rhamnosus

<400> SEQUENCE: 22

```
tgttgatggt aagcttaatt gaaacatcat ctttaggaaa atgaaggagg tcatatcttt    60
tggctaaatt aatcgtttca gatttagacg ttaaagacaa aaaagtcttg attcgcgttg    120
acttcaacgt gccgatcaaa gacggcgtta tcggtgatga caatcggatc gtggcagcat    180
tgccaaccat ccaatatgtc attgatcacg gcggcaaggc aattctgctg tctcaccttg    240
gccgggttaa gaccgaagaa gataaggcaa agctgacctt gaagcctgtt gcagaacgcc    300
ttagtgaatt gctgaagaag ccagttacat ttgtaccagc tacccgtggt aaagaattgg    360
aagacgcgat cgcaaagtta aatgacggcg acgtactttt gatggaaaat acgcggtttg    420
aagatcttga cggtaaaaaa gaatccggca acgatcctga actcggcaag tactgggcaa    480
gcttaggcga cttgtttgtc aatgatgcct ttggtaccgc tcaccgtaag catgcttcaa    540
acgttggtat tgcctccaac atgaaacaaa ctgctgccgg cttcttgatg gaaaaagaaa    600
tcaagttctt gggtgacgct gtggacaatc caaagcatcc attcatcgca attttgggtg    660
gtgctaaggt ttccgataag atcggtgtga ttgaaaacct ggttcctaaa gctgacaaga    720
ttctcatcgg cggcggcatg acttatacct tctatgctgc caagggtatg agcatcggta    780
attcactggt tgaaaaggac aagatcgact tagctaagaa gatcatggac caagccggtg    840
acaagctgct tttgcctgtt gattctgtgg ttgccccaga ttttctaac gatgcaccgc    900 ataaggttgt tgaaggcgac attccggatg gctacatggc gttggatatc ggccctaaga    960
cgattcagga attcaaggat gcacttaagg gtgccaagac agttgtctgg aacggcccaa    1020
tgggtgtctt tgaaatgagt aactatgctg aaggcacact tgaagttggt cgtgctcttg    1080
gtgatttgaa ggatgcaact acgatcatcg gtggcggcga ctcaacagct gcagctaagc    1140
aacttggcat tgcacctaag attacccaca tctccactgg tggcggtgct agccttgaat    1200
accttgaagg caagaccttg ccaggtattg cagccatttc tgacaagtaa ttgttagtga    1260
tgctgatcta acagtcatta tcgacatgca tgatgcatgt cggtacataa tgaaaggaag    1320
gtatgtcatg cggacaccat tcattgctgg taactggaaa atgaataaga atcctaagga    1380
gacgcaagcc ttcttagatg ctgttaa                                        1407
```

<210> SEQ ID O 23
<211> LENGTH:1178
<212> TYPE DNA
<213> ORGANISM: Lactobacillus rhamnosus

<400> SEQUENCE: 23

```
ccacaaactc gattttaact ggggcaaccc gttagaataa accttatttc ctaaaggagg    60
```

| | |
|---|---|
| aaatttagc atgactgtta agattggtat taatggtttt ggccgtatcg gtcgtttggc | 120 |
| attccgtcgt atttacgaat tgggtgcaaa gagcaatgac attcaggttg ttgcgatcaa | 180 |
| cgatttgacc agcccaacca tgctggctca cttgctgaag tatgattcaa cccacggtac | 240 |
| tttccctggt gaagttagtg caaccgataa cggtattgtc gttgacggta agaataccg | 300 |
| tgtctacgca gaaccgcaag cccagaacat tccttgggtt aagaacgacg gcgttgacta | 360 |
| cgttcttgaa tgcacaggct tctatacttc tgctgaaaag tcacaagctc acttggatgc | 420 |
| aggcgcaaag cgtgttctga tttctgcccc agctggcaag attaagacta tcgtttataa | 480 |
| cgttaatgat gacaccttga atgcagacga caagatcgtt tctgcaggtt cttgcacgac | 540 |
| caactgcttg gcaccaatgg cttacttcct gaaccaggaa ttcggcattg aagttggtac | 600 |
| catgaccacc gttcatgcct acacctcaac tcagatgttg cttgacggcc cagttcgtgg | 660 |
| cggcaacctg cgtgctgcac gttcagctgc tgctaacacg attcctcaca gcactggtgc | 720 |
| tgctaaggct atcggtttgg ttatcccaga attgaacggc aagttacagg gtcatgcaca | 780 |
| gcgtgtttct gttgttgacg gttccttgac tgaattggtt tccatcttga agaccaagaa | 840 |
| cgttacggc gaccaagtca acgaagctat caagaagcac accgaaaaca accctagctt | 900 |
| tggctggaac gaagacgaaa tcgtatcttc cgatgttatc ggtacgacat acggttcaat | 960 |
| cttcgatcct actcagaccg aagttacaac tgccggtgac tatcaattag ttaagacggt | 1020 |
| tgcttggtac gataacgaat atggctttac ttgccagatg atccgtacct tgctgaaatt | 1080 |
| tgctactctc taatccggag taacgctttt ctaaccgcaa catccgaagc ggagggagct | 1140 |
| ttactccctc cgcttttttt ggaaagacca ttaaaagg | 1178 |

<210> SEQ ID NO 24
<211> LENGTH: 1074
<212> TYPE: DNA
<213> ORGANISM: Lactobacillus rhamnosus

<400> SEQUENCE: 24

| | |
|---|---|
| tcattcacaa atgttaaact taagttgtta ctaatttcac ttttgattat aattggaatg | 60 |
| taatcggtta caacgtgact gttgaataat ttcacatttg tgatttcgag gtgacatcaa | 120 |
| tgtcaaattt gcctaaacgg tatgatcgtg caactttagt caagatatcc gatctttact | 180 |
| acatgcacgg tctaactcaa caagaaatat ctaacattgc ccatattcac agaaccgaaa | 240 |
| taagtcgaat tctgaaggcg gctagggatg aaggcgtggt atctatcgca atcaatcccg | 300 |
| aaaccaccgc cgtcagccaa cttattgatt tttttaaaca aaaatacaat ttgcgagagg | 360 |
| ccgttatagt cccggcttct gaaaatggag gcaatgagtt aaacgctttg agtgttacg | 420 |
| catcaatgtt tttatcaaga atcattaaaa gtggtgacgt aattggggtta agttggggtt | 480 |
| caacgctttc aagtgttatc agtcaatttc aacagataa aggccttcgt gatattaaag | 540 |
| ttgttccgct ggtgggtggc ccaatgggaa gaataccttc gaactatcat gtgagctatc | 600 |
| tgacacaccg gctcgccaat cggctaaacg gaacagcgtt tgtcttggat tcccctgcct | 660 |
| ttgtcagatc aaaagcgctt cgtaaagagc ttctcgccaa ccccaacacg caagaaatct | 720 |
| taggattgtg gaatcgtgtc aatatcgcga tctttggcat cggaagttca ctaattacag | 780 |
| attctcctga ttggcaagcg ttctatgaga acacaaactt caagtcttat ttcagtgccg | 840 |
| atatggtcgg agatattctt tcacaccctt tcgacaagga tggaaaatta gctcgcgata | 900 |
| tcgactccat tcttgttgcc tttccttttt cggcattgcg aaaagtacca cactccgttg | 960 |
| gaattgcttt tggggaagaa aagtaaatg ctatccttgc cgctcttcga ggtggtctct | 1020 |

-continued

```
taaacacttt aattactacc gaagcaacag caaaggcaat caaagagttg tcct       1074

<210> SEQ ID NO 25
<211> LENGTH: 1025
<212> TYPE: DNA
<213> ORGANISM: Lactobacillus rhamnosus

<400> SEQUENCE: 25
gactcggctt gtttcacttg tggtaccttt gaaagtcgaa agtcattatg gaccgacctg     60
gtttgatgcg aaataaggag aactcatgcc tgaattacct gaagttgaaa cggttcgccg    120
ttccttgtta ccgttagtca aaataaaaa aatcaccgcg attagcacaa actgggagaa     180
aatcctaatt aatggtctgg caacctttca aaaacaggtt gtgggcgctg ctgtcaacac    240
gattgatcgc cgcggtaagt atttactgat tcggcttaac aacggcatga cgattgtcag    300
tcatttgcgc atggaaggcc gctattacgt tgtttcggat gccaaaacgc cgctggataa    360
gcatgatcat gtgacgttta cctttcagga tggcagccag ttgcgttacc gcgatctgcg    420
caagtttggc cggatgcggc tgattcacac gggtcaggag caattggtgc cagcgctggc    480
caagctagga ccggagccga ctgctgctac ttttagcgaa agtgactttg cccagaaact    540
aaaacggcat cataaagcca ttaaatcggt tttgctggat caaactgttg tggccggaat    600
tggtaatatt tacgcggatg aggtcttatg gctcagcaag ctcaatccgc tgcagccagc    660
taatacctta accaaggcgg aggttcacac gttacatgat gcgattatca aggaattgga    720
cgacgccatt gccgctggcg gtaccagtgc ccatacttac gttgatgcaa aaggcaaccg    780
cggttcgttt caggacgctt tgcatgtcta tgatcgtgaa gggacgcctt gtgatcgttg    840
cggcaccacg attgtcaaaa ttaaagtcgg tcaacgcggc acgcattatt gcccgcattg    900
ccagccgtta cgtcgaaggg ggcaactggc atgaccttt tgttagggct gacgggcggc    960
attgcgtcag gcaagtcaac ggtaagccgg acatttaaag cagctgggtt tccagtggtg   1020
gatgc                                                              1025

<210> SEQ ID NO 26
<211> LENGTH: 7755
<212> TYPE: DNA
<213> ORGANISM: Lactobacillus rhamnosus

<400> SEQUENCE: 26
gattcagcag caagcacgag tgatgcaacc gattcgaaat cgctagcgac agattcagca     60
gcagtcaaac cgcaaacggt gacccaagaa gaccgctcac ttgcatccgc agctgttcag    120
acaacttcgg ccgcagcatc atcggcggct tcatctgcat cgtcacaagc atccttagca    180
gcacaatcgg caacaacaac tcaggtcaac acgcaagctc cggccaatgc aacagctgct    240
gaaaatacgc agaccattgg cgactatacc tacagtcttg atacggcaaa cggtacagca    300
acggttaccg gccgcgccaa cgccaatgtc accgatatta cattggcgc gtctgttacc    360 tataatggcc aaacttttaa agtgacggcg attaacaatg cgcttttgc aacgcttaat    420 aatttgggta atgttaacgt ggctgatact gtcacgtcca ttgcgaaaaa tgcttttgca    480
tacagtcagt ttcgggcaa cattacaatt gaaaatgcag aaagtctcgg caaagccgca    540
tttgccggaa ttaaggcagg gtcagtcacg ctgaagaaga cggctaacat ttcagagcgc    600
gccttttatt ttgctaacgt gaaagatata acgattgcag acgctcagac tatagaggca    660
caggcattct ttagtcttac agcttcatct ttaaaaattg atggtcaagc cgatattggc    720
```

-continued

```
gagtctgctt ttgaatctgc caatattgct ggggatgtca ccgttaatcg tgcaaagacg    780
atcggaaaaa atgcattcgc cactttaaag gcgcattcgt tgacgttgga caatctaacg    840
acgcttgatg aaggtgcctt tggtggtgct gtattcactg gtaatcttac aattaatggc    900
gcaaaaacta ttggcaagtc cgcattcgct tatgacaaag taaccggaga tgtcacggtg    960
agcggctcac ctgccattgg tgaaattgcc ttttatggga ttcaggcggc gacaatcacg   1020
attgatggcg cccaaaccac tttcgataag accgcgtttg gatttgccac ggcggatcac   1080
gtaacagtca atgtagccac ccttgatcat gaggcatttt atcatcttta tactgaccaa   1140
ctaacccttg gtcctgatgt tcgagatatt acagatggcg cttttcagtt tattcaaaat   1200
accaaaaaaa cagagagtaa cgctgaaaat gatactacgg acgttcaaat agcagtgttg   1260
aacctgccag ctaatgtcaa aacaatcagc ggctcggctt tttatggttc gaaagttaaa   1320
acgatcgcag ttgcagaaaa cagtcaattg acaactctcg gatttcaggc gtttgcattt   1380
tccactgcta cggcgattaa cttacccgat tcgctggagc agattggtga tcaggcgttt   1440
tatggcggga agcttgtgaa agtagcgttt ggacccaaat tgcaatcaat tggtaatctg   1500
gcctttactg aatttggccc gttggaaaat gttgacttta ctcgggccac ggcgctcgaa   1560
acaattggtg atagtgcgtt tgcctacaat acgattaaca atgcgatcac gttaccacct   1620
aagctattaa cgatcggaaa tgcggccttt gtcgggaata aaattccaaa actggttctg   1680
gatgatcggt taaagacaat cggtgacact gcttttggct ataaccagat ccaggacgca   1740
ctcgatgttc ctgacagcgt gaccgacatc ggtaagtatg catttgttta caactctatc   1800
agtaatttaa cgttaggaaa tggactgaaa acgattggcc aggaagcatt tgaagccaat   1860
gttatttaa atgcgcaaac gataccaagc agtgttacga gtattggcgc caaggcattt   1920
aaggctaatt tgattcctaa agttgttgtt gagggcacgc caaccattgg caatgatgct   1980
ttttcgaata accggatcac tgtgctgaaa gcagcgacag ccaagccgac aaccccggat   2040
gctttggagc agaatgccga tgcctataca gactcggcgc acgtaagtct aagtgatttc   2100
tttgatgtgg ccatttccgg agtgacccac caaaacatcg ttgtttcaaa catcaaagga   2160
gttaatggcg ctacggtaac ttttgatacg gcaagtaagt cgtttaaaat gccagctaag   2220
acgcagggat ttaatttcga ttggtctttg aaagggcaag acggtgttac ctacacaggc   2280
cactacattg ttcatctcga tgatccagtg attcgtgccc atgacatcag cctatttact   2340
ggccaggtat ggaagccgga actgaatttt gaaaacgcga ttaaaagcga cggtactgag   2400
gttccattga gtgagttgac ttggtcagtg acggatgaaa aaggcaatgt ggtagcatct   2460
aaggataaaa atggggttgt caccggtcat gtggataata gccagccaac gacttatgtg   2520
gtcacctata cctatggtgc agaaagcggt tctgctaaaa tcaattacaa gcaacggtta   2580
gcggcttcat atgctttgac tggtactcag accgtcaccg caacaggaag tccgattacc   2640
gtcgatgtct cccaatttgc actgagtttg ggtgacggtt ttgatgcggg gaaattagaa   2700
ttaagtgatc ttaatttctt tgatgccgat ggtaagccgg tagccgcaga tgctctgatt   2760
aaaactggcg tctacagtgt ggaattatca gaagctgcgt gggcacggat cgccaaatta   2820
acaaatgatg aaggccagtc tgctgcgggt tatgatttta ccggaacaag tacggcacaa   2880
ttaatcatcg gtctaacggc tacaggtcat ttgagcgata gcggttttgt ttatgacggc   2940
aaaacaacag ccagtcagtc taaagatttg gcggtcacgg tgacattgag tgatggcact   3000
cagaaagaaa tgaacctgac ctcagaagac ttctcattag ttgaaaaaga ttcagctaac   3060
gttggcacgt accattattt gttaaacagc gttggtttcg ctcgtttaca agcgttacta   3120
```

-continued

```
ggtgataccg tgacgattga tcaaactgcc atcaatcaaa attccggaaa aatcaccatt    3180
acgccagcac cggctacagt taatagtaat agtacggatt ttgaatatga tggcaaaacc    3240
aaggccagtg aggctaaagg tattcaagct acagtcaaac taggcgaaac tggaaaaacg    3300
attgacctga cgtcagctga cattgttgtt gagaatgatg gtgtagatgc aggcaagtac    3360
agctatgagc tgagtgacgc tggtaaagct aaattgcaag ccgcaactgg aaataactat    3420
cagttgactg cagacgatct ggctaaagtc acgggagcta tcacgattac gccagctacc    3480
acctcagttg atagcaatga cgtttcattt gaatacgatg gtaagaccaa ggccagtgaa    3540
gctgcaggta ttcaagccac aatcaagctc gacactggta aagttgtaga cttgaccgcg    3600
gccgatatta tcgttaccaa tgatgacgta acgctggtc agtacagcta tcaactaagt    3660
gatgctggta aggctaagtt acaagccgca actggaaata actatcagtt gactgcagac    3720
gatttggcca aggttgctgg aactatcacg atcacgccag ccgttaccac agttgatagt    3780
agtgacgtat cattcgaata tgacggcaag accaaggcca gtgaagccaa gggtattcaa    3840
gctacaatca gctggacac tggtaaagtt gtagacttga ccgcggccga tattatcgtt    3900
accaacgatg acgtaaacgc tggtcagtac agctatcaac taagtgatgc tggtaaggct    3960
aagttacaag ccgcaaccgg aaataactac caactcacgg cagacgattt agctaaagtc    4020
atgggaacca tcacgatcac gccagccgct gtcacagcag acagcaatga cctttcgttc    4080
gaatatgatg gtaaaacgaa agccagtgaa gccaaggta ttcaagccat ggtaaaacta    4140
ggcgagactg aaaaaacggt tgacctgacg tcagctgaca ttgttgttgc caacgatgac    4200
gtaaacgccg gtcagtacag ctatcagcta agtgatgctg gtaaggctaa gctgcaagct    4260
gcaactggaa ataactatca gttgactgca gacggtttgg ctaaggttgc tggaacaatc    4320
acaatcacgc cagctaccac tacagcggat agcaatgacg tttcatttga atacgatggt    4380
aagaccaagg ccagtgaagc caagggtatt caagccacaa tcaaattagg cgaaattgaa    4440
aaaacggttg acctatcgtc agctgacatt atcgttgcca atgacggagt aatcgttggc    4500
aaatacactt acagtctgag cgacagcggc aaatctaaat acaggcggc aacaggaagt    4560 aattatcagt taacgacaga agttttggat aaggtttcag gaagcattac aatcacccct    4620
gctggagcaa tcgcaacagg caaggatgct cactttgagt acgatggaaa aacgaaagcc    4680
agtgaagcta aaggcattca agcgattttg accattgacg ggactgaaaa gactgttgac    4740
ctgaccgcgg ctgacattgt tgttgcggag gatggcgtag atgcaggcaa gtacagttat    4800
cgactgagcg atgctggtaa atctaagtta cagagggaag cagggagcga ccatcagcta    4860 accgcagacac acttggctga agtcacggga actatcacga tcacgccagc cattgccaca    4920
gcagatagta atgacgtttc atttgaatat aatggcaaga ccaaggccag tgaagctgaa    4980
ggtattcaag ccacggttat gctgggtgag tctggacaag ttgttgctct aacatcggct    5040
gatgttgttg ttgtgaatga tggtgtagat gcaggcaagt acagctatca gctgagtgat    5100
gctggtaaag ctaagctaca agccgcaacc ggaaataact accagctcac ggcagacgat    5160
ttagataaag tcacgggaac catcacgatc acgccagcta ccaccacagt tgatagcaat    5220
gacgtttcat tcgaatatga cggcaagacc aaggccggtg aagctaaggg tattcaagtt    5280
acagtcaaac taggcgaaac tgaaaaaacg gttgacctga cgtcagctga cattgttgtt    5340
gccaacgatg acgtaaacgc tggtcagtac agctatcagc taagtgatgc tggtaaggct    5400
aagttacaag ccgcaactgg aaataactac cagctaactg cagacgatct ggctaaagtc    5460
```

-continued

```
acgggaacca tcacgatcac gccagccgtt accacagcag atagcaatga cgtttcattc    5520
gaatatgacg gcaagaccaa ggccagtgaa gctaagggta ttcaagttat agtcaaacta    5580
ggcgaaactg aaaaaacggt tgacctgacg tcagctgaca ttgttgtagc caacgatgat    5640
gtaaacgctg gtcattacag ctatcagcta agtgatgctg gtaaggctaa gttgcaagcc    5700
gcaaccggaa ataactatca actaactgca gacgatttgg ccaagatcac tggaaccatc    5760
acgattaccc cagccgttgc cacagcagat agcaataacg tttcatttga atataacggc    5820
aagaccaagg ccagtgaagc tcggggcatt caagccacag tcaaactagg cgaaaatgga    5880
aaaaccgttg cgctaaccgc ggctgacatt gttgtcgtca atgacgggt caatgctggc     5940 cagtacgact ataagttaag tgctgctggt atgacaaagc tacgccaggc aacaggaact    6000
aattatcaat tcaaaaagga ggacttaacc aaacttggcg gcacggtcac gatcacgcca    6060
gctacggcat tagctgatct gaatgatgtt tcatttagtt atgatggaca aactaaggcg    6120
agtcaggcac acgacttaac tgccaacatc aaacttggta ctaaggttgt ttcggtacat    6180
ctgaacgcca cagacattct tgtaaccgat gatggtgtgg gcgtaggtca gtaccaatac    6240
aaattggatg ctaacgggat cgctaaatta cgtcaggcat caggtgataa ttaccaattt    6300
gatgccaaag tcttggcggg attgactggt acgattacaa tcaaaccggt taccggtgcg    6360
gtgacagtta atgacacatc ttttgtttat gatggtcata ctaaagcaag tgctgccgcg    6420
ggattacagg caagtctttaa cctgccgcaa gccgaggcca agcaacgat acaactgaca    6480 cgggaagata tccttgtgac aaatgacggc acagcagcag gtacgtatcg ttatcggttg    6540
agccaaaccg gtatcgccaa gttacagaag gctgttggca agaactacga gttagatcaa    6600
gatgaattgg cgggattgac cggcaccatt acgattacgc cgctgacggt gaatgccaca    6660
gttaatcatg gtcagttcca atacaacggt gtcactcgtg caagtcaagc aggcggatta    6720
gcgataactg tccaactgcc agaaaagtct caaaagatcg ccttgacgaa cacagatatt    6780
gcagttgaaa acgacagcgt caatgtcggg acgtacacgt atcatttgac agcaagcggg    6840
ctggctaaat tggccgtagc gattggtcct aattatcagg ttactgatca aacgttcagc    6900
ggcaccatca ccattacacc agcgcctata tctgcaacgc tcagtggtct tcaaaagaaa    6960
acttacgatg ccagccagg cgcttttgaat gacgactatt atcggttagt tttgggtgac    7020
ggaactgaaa ttcagcttca agccggcgat ctgatctttg tagacggtca agctcctgtt    7080
aatccgggaa gctatgcggt agctctcagc acatctggcc tgcaacgaat caaggcgtcg    7140
ttgccaaata atcgtgttgaa aaatgttaac acgcagcagg ctattttga gattgttgcc      7200 ttgccaagtc ctgatcccgg gaccggaaca acgccggata cgccggatca tcacttgccg    7260
aatacaggta ctggcaccca acagtccgag atttccacgc ataatggaac gaaacatcga    7320
cttccacaaa caggcgatac ccagtcacaa acactaagcc tcatgggatt gttgctggca    7380
acgatgagcg gcttattcgg attagctggc cggaaacgga aagcgcaccg ttaaacgttt    7440
tgttagaaat gtagtgatta aaaagatcct atcacgatga gttctgctca tgtggtggga    7500
tcttttgtta tggcaaaaac taggcgcaaa agcttacagt ggtaccgctg cgccttgggt    7560
taaccctgat ttgattttgg caaaagccgg gtctgttagg aaagcactga tgagttgccg    7620
catattgatg ttactatcct gaatctccgg catgtttggc gtaatgcttg tgcctgtcac    7680
agtaagattg tactggctgg cgagactggt gatagcttgc ttggactgat acatgttgta    7740
gagtttaacg gtttc                                                     7755
```

<210> SEQ ID NO 27
<211> LENGTH: 4645
<212> TYPE: DNA
<213> ORGANISM: Lactobacillus rhamnosus

<400> SEQUENCE: 27

```
tagggggtca aaaatgggaa ccaaaatagc cgttaaaatc aacaagtggc aagtgtagct        60
caagccagca gcagtgcgag cgatggtcaa gccaaagcaa gcagggggcta atgtggcaac      120
gaccactaat agtaaaattg gcggcagtca agtagtgcc aaggcagcca gtgcgtttaa       180
aagtagtgct agcgttgaaa gtagtggcca gatcaaaagc actagtttag ccagtgctgg      240
cagtaacggc gaaaagcga ccagcgctct aagcagtagt gcagttgatg ccagcgatgg       300
tcgtgcgagt cagggtgttg gcggcacgtc aagtggtagt tcagatacta cgagtcaggc      360
aaatgaaggc aacagcgccg ccagtgtaac aagtgcaagc gccaatagtg cctctgcaac      420
aaatacatct gaaggtcaaa ctccagttaa tgaagcggta tcaaacgatg cttctagcgc      480
cgatgtcagc accgcgtcag agtttgatgc agccatggcc gattcaacgg taagtgtcat      540
caacgtacag tccgactttg ttatggatgt tagtggtgat cgccaatcgt atgcttatcg      600
gccaaaccta attattaatg gcaataacca cacaattgat tttcaaaaga agtatttcga      660
agctgatcct acaagtagtc agaatgaatc atttaccatc aacgatttaa atatgtacgg      720
ttacagttgg tggggcccgg ttactatcaa gggcagtaag ccgaaagacg gcatcgatca      780
ttcggtagtg ttcaataatg tcacatacac aggtgcacaa ctgatgtatg catttatac       840
aaaagccttt attaagggga atacaaagat tcagtcagtg ggcagttatg tttccccgct      900
ggacggatca acccagacaa cccaaggctt aggcaaccag caaaactttc aaattagtta      960
tttagaggtt ttgcctggcg ctacttacac ggggacaact actggtggga ctaacgttga     1020
agtatatgat ggcggttcat ttattgttga caagggagca accgttaact acaacgcac      1080
ggatgcaagc aaatcgaatg aacgtggtac gaatgcattg attgatacac agggaggtaa     1140
cgttgagttt aaggatggat caaccgttat ccttaataaa aatgcacttg tgaaagatgg     1200
cttttgcacca atctatattg aagacggtgg taatctaacc gttgataaga atgcaacggt     1260
atccattacc ggtgcaactg gaaacatccc ggtaagaatt gacggtaccg gaactgtcaa     1320
cctcaacgaa ggatcgcaca tgacgatcac tcaaaatggt gcgcctaaac ttggctatgg     1380
cttatcaat attaaaggta ccggaggctt cttcgttgca gtggcagca ctttggatct      1440
taatgtaacg ggtacaggga caaagagtgt caatgcaatt aatgtagcaa atgacggtca     1500
actgagtttt gcacaggatg ctacggccaa cttaaccatt gacggtggca cgggcgaagc     1560
gcatttgttg aaagtcggtg acgatgccaa cattaacatc tatatgccga atccgttct      1620
ttttaagatt accgataacg atgacgcaga cagcagttta tttaaagtca gtggtaccgg     1680
cacgctaaca ggtcaatatg tgaaaatcat tccggatgac gggaatgcct atgggccata     1740
taagtccgct atctatacac taaagggaa tggctcttct tcagataccg ctacggttga     1800
aggtgagaca gcgaagatg aacaatccgg gaaagcactt gccgacacgt ttgcgactga     1860
caaaagcttg gagttcgtca gtgccagtga taatttatt aaggtaaatc cagttactga     1920
tgaaaccaca acgcttacag gtaaaaccac tgccggagcc tatgtaacga tttcaggttt     1980
aaagggggatt ccagaaggca gcttaactgc gaattcctat gatagtacaa aatatttggt     2040
acaggcggac aaggacggta attggagtta cgaactgccg actggggttt cgttacctgc     2100
caatgcttca tttgaagtta tttcgagtgc tggattcatt gtgaaaacag cgacggtagt     2160
```

-continued

```
gatcaacgat gccgaaacgc caaagcaggc atccagtgca gctggcagct taatcaacgc    2220
caatagtgct gctgatgtca cagcttcaca ggcaaaggct acaagtgctg ctgctagtga    2280
tgcggcgagt tatgcaagtg aagcgcaatc gattgctggc agtcatgctg ataatatgga    2340
aatcaagtct ctcgccagtg atgctgagaa gcaatcgcaa attgctttgg cagctagcaa    2400
gtctgctgcg gctagttcca gtgcggcagc gtccgcagca atcgtggcaa gtagcgcggc    2460
tagtgaagcg tcatctgcag ctgctgccgt aagtaacgct gatgcatcag caaactctgc    2520
agccgctgct tatgattcct acgcttctga ggccagtgcc gcttctgctg ctaatgatag    2580
ttcgggatat gccactgcat catttgcagc aagttccgct gcggctgcca tgagcgcagc    2640
gttatcgaca gcgcaagttg ctgccaaggt tgcagtgagt gatgcagcag cagcgggtag    2700
tgcagctgct gttgctagtg cagctcaaag cgactccaag aataaacaag cgactgcagc    2760
tacagcaaga agtcaagcac ttgatgattt gaataagatc aagtctctaa ctgattacgc    2820
aagtggcgca agctccagtg ccagcgaagc gggtcaagca tcgactgcaa catctgcgta    2880
tgctagtgct gcaagttcga gtgccagtga agccggttca tatgctcatc aggcaggctc    2940
cagcgccagt gacgctgtcg gtcagtccgg cagtgcagcc caacatgcca gcaccgctgc    3000
gagtgcggca tccagctatc cgaaggatag tgggattcag tcactagcca gtcaggctgc    3060
aagcgaggca gcaaaggcaa gcagtaacgc gagtgccgca accagcgccg cggccgttgg    3120
tttcagtgct gccagtgatg caagtgaaca ggcgaagacg gctgcaagtg ccgatgtggt    3180
ggcaagcagt gcggccagca cggctaacag taatgcgagt gccgcagcca gtgcgaccaa    3240
ggctggtgat agcaaagccg cagcaggatt ctcgagtgca gcgagtgctg cagcaagcag    3300
tgccaagggt gcagaagcag ttgccagcga agcggcgagt gccgcggcat ccgatgactc    3360
ggtagcttct agtgccgcca gtgcggctgc aggctttgac aaagctgcca gcgctgcgga    3420
aggcgcagct tcaagtgccg cgagcgcggc tgctagttca gcggcagctc aaggcacacg    3480
aggtggcgca agctccagtg ccagcgaagc gggtcaagca tcaaccgcaa catctgtgta    3540
tgctagtgct gcaagttcga gtgccagtga agccggttca tatgctcatc aggcaggctc    3600
cagtgccagt gaagcgactg ccatgcaagt agtgctaca agtcaagcaa gtgccgcatc    3660
cagtgctgcg tccaggtacc caagtgatag tgggatccag tcagatgtaa gtattgcgtc    3720
cagtgcagca agtactgcat ccagtgccgc tagtgccgca caaagtgagg cttcgacggc    3780
atcgtcggct gcaagtcatg ctagtgaaca agcaagtatt gcttccagtg aggatgttgt    3840
atcaagcagt gctgcgagtg tcgcgtccag cgcggccagt gccgcatcca gtgctgcaaa    3900
ggctggtaac agtagtgctg cgggtatata ctctcatgca gcaagtgcag ctgcaagcag    3960
tgctaagagc gctgaaagtc aagcaagcag tgccgccagt gctgctgctt ctgatgattc    4020
ggtagcttct agcgctgcca gtgccgcttt gtctgacgat gctaaggcaa gtagcgccgc    4080
cgatgtagca tccagcgcta caactgctgc cattagttcc gccacatcct ggctgatca    4140 gagtgccaca gggtcaaccg ctggctccca tattttgcca agtactggtg gagagacgac    4200
aggtagtata ccatcgggtc agacgccaac acagacgaag ccaacacaga cgaagccaac    4260
acaaacgaag ccaacacaag ccggtcaaac aacccagaca ggttcattac cgcaaacgga    4320
tcatgcaggg aggcatatgc taccgcagac cggtgatgat gctgaaagcg gtacttctgt    4380
tttgggtttg ctgattgtta gtctgatggg attgtttggt cttgcgggaa ccagacatca    4440
gaaggacaat aagccatcaa agtaatattg gatcactaat gtcgcccata cactggtgat    4500
aaaccaaaat ctgatggaaa tagctagtgg tgtaagagat gattattctc ttgcaccact    4560
```

-continued

```
tttttgttaa gcacgttttt ttatggattc tgtgtgccaa atgtttgaaa ttgatgtggt    4620
taaatttggt tttgcgggta atcta                                          4645

<210> SEQ ID NO 28
<211> LENGTH: 7639
<212> TYPE: DNA
<213> ORGANISM: Lactobacillus rhamnosus

<400> SEQUENCE: 28
ctgcttaatg gtcacccatt ccttgtcaag cagaaaacta atgatttcgt agtgcttgag      60
caggctactt tccaatagtt cttccataaa cttacctccc caagtaggtt gttactatca     120
aaacttgcct aacgttaggc aagctttgaa ctagaaccaa tcattgattt atttatacta     180
atgacatatt gcataagcat tgcttggttc accataaatt ataaagtgat aatgcttgtt     240
gtttcaatta ttaagaactc gcctttcaaa atgtaataat ttatatcaaa tattttgaga     300
atgggtaggg ttaacttaat tgtttgctgt tttgggttca ataaagggga ggcatgttga     360
agtgaaaaag gggagactga tattactatt agccacggga ctgatttcaa ttggtctttg     420
ggattcaagc ggtgtcgtat tggcagcgaa taagccccag gctggtgata tccatttggg     480
tggtgccgat ggttcgagct ataggaagct tataaatagc atcacattcc aatatagcaa     540
cgacgccgtg gtatatgacg aaggtacgga taccttcaaa attccaattc ggttcggctc     600
gcttgaatca gatggcttgg atcgtgtattt ggagtttggg tattcgttta acgatgcctt     660
agaaggaaaa atcaagcggg ttgtgatttc acctgatggc ctggtcccag cggttattac     720
aagtcttaac aagaacagag aatttgcacg gcgctgggat ggtagtgatg gtaaaagcgt     780
tagtcatcaa ctaggtggac gagcagatgc cgtcatctac atgcaggcgc ataagattat     840
gcccgaggat tggattgctg ttcggatgga accaatcggg attgaaggga acacccctat     900
tcatccagca tttcgatcca ctcgcattct tgagtacaac gattttggtc ctgcactcaa     960
cgccaaactt ttagaagcca tgaagaaaaa ggcgattgat gacacggcca aggatcctaa    1020
accggttcaa gaagaagtta agaaaaagt cgacccaatc acggttgacg aggactttga    1080
caagctcatt caggaaatcg ttttaaacgc gcataaggaa caggctaaac gagatattga    1140
tgccgaagcc gccaaagtca gcgctgaaat tgagcaggat ccgactttaa cggcaacgga    1200
aaaggcaaag caaaaagatg gcgttgcagc cgaagcaacc aaggccaagg cggcaatcga    1260
ccaagcgcaa accgaaacag gggttcagca ggcgcgagag gccggcattg cagcaatcga    1320
tgcccaacat cagcctggaa ccggactcaa cgtgcgccga aagaagcta agcaggcgat    1380 tgatgccgaa gcggctaaag tgactgctga gattgagcag gattcaacct tagctactag    1440
cgaaaaagcg gcccaaaagc aaggagttgc tgatgaagcc gcgaaagcca agacggcgat    1500
tgatcaggcc caaacgattg aagccatcga taaagctaaa gatgatggga ttaaagcaat    1560
tgatgcccaa cacaagcaag gcgctgactt cgatacgcgt aaagctcaag ctaaagacgc    1620
aattgatgcc gaagcggcca agtcaagga tgctattgat caagacccga ctctgacggc    1680
caaagacaag acggcccaga agcaaggcgt tggtgatgaa gcgaccaaag ctaagactgc    1740
cattgatcaa gcgaagacca ttgatggggt gatccaagcg aaagatgatg gcatcaaggc    1800
aattgatgcc caacatcagg caggtaccga tttggcgacc cgcaaagata gtgctaaaca    1860
agcgatcgat gccgaagcgg ccaaaataac cgatgccatc aaccaagatg acacgctaac    1920
cagtaccgaa aaggacgccc agaagcaggc agtagctgac gaagcggcta agccaaagc    1980
```

-continued

```
agcgattgac caggctcaaa acgcagatgc cattcttcag gcccaagctg atgggattaa    2040
agccattgat gcgaaacatc aaattggtgc agatttagat acccagaaaa ccaaggctaa    2100
gcaggcaatt gacaaggaag ccgccaaagt tttaacggca attgagcaag atccgacttt    2160
gaccagtgct gaaaaaaagg cgcaaaagca aggcgttgcc gatgaaactg ctaaagccaa    2220
gaccgcaatt gattcggcgc ggaatgctga tgaaatcgcc aaagcgcaag cagatgggat    2280
taaagccatc gatgcgcaac atcggctggg aatggattta gctaagcgta aaactgatgc    2340
acaagcggcc attgacgctg aagctgccaa agttggcgaa gcgattgatc aagatcctac    2400
tttaacgagc caagaaaagg cggcccaaaa gcagaccttt gctgctgaag caaccaaggc    2460
taaagatacc atcgccaaag cgcaggatgc cgatggtgtt attcaggctg aaaaagcagg    2520
cattcaagcc attgacgatg gcatcaatc aggtgcactt ttagatacgc gcaaagttga    2580
tgctaaaaaa gccattgatg ccgaagctgc taaaattaat gacgccattg accaagatgt    2640
cacgttaacc agcgctgaga aagccactca gaagcaaaaa gttacggatg aagcagtcaa    2700
agccaagaca gcgattgacg cagctaaaaa tgcggacacc gttgatcagg ctaaagcatc    2760
aggcatccaa gccattgatg ccgtccatca aagcggcacg cttttagaca ctcgcaaaca    2820
agatgccaaa aaggcgattg atgcggaagc agttaaagtc attgcagcta ttggccaaga    2880
tgtgaccttg acgcaagcgg aaaaactaac gcaacagcaa gcagtcgctg atgcagcaac    2940
gcaagctaag gctgctattg atgctgccaa gaatgccgat gcggtggacc aagccaaagc    3000
ggatggtatc aaggcgattg atgcccaaca ccaagccggg ttggcgttga acgaacgcaa    3060
agaagcagcc aaaaagctaa ttgcggaaac cgctgataag gtgcaggctg cgattggtca    3120
ggatgtgacg ctgactgcga cccagaaagc agtgcaaaga caggcgatta ccgtggaagt    3180
cactaaagcc aatcaagcca ttgatgcggc tggcaatgct gacgcggtcg atcaagctaa    3240
aaatgcggga gttaaagcaa tttatgacca gcatcaatcc ggtcaggcac tcgcagatcg    3300
gaagcgtgat gccaaacagg cgattgatgc cgaggcggca aaagaaacag ctgccattga    3360
tcaggatgca actttaaccg cgaatgaaaa ggcaagccaa aaacaggcgg ttgccgatga    3420
agcgactaaa gccaaagaag cgattgatgc ggctaagcag gctgatgcag tcgaccaggc    3480
caagaatgac gggatcagag cgattgacgc ccaacatcac gctggccaag cagttgccga    3540
tcgtaaagcc gctgctaagc aagccattga tgccgaagcg gctaaagtaa cgggcaacat    3600
tgatcaagat gaaaccctca cagcgacaga aaaagcggcg caaaaacagg cagttgcaac    3660
cgaagccgat aacgcgaagc aagcgatcga caaagggcaa aatgctgacg ccgtcgacaa    3720
agctaaaaca ggcggcatca aagcgattga cgctcagcac cagtctgggc aggcaattaa    3780
agcgcgccaa aatgacgcca agcaggctat tgatgctgaa gccgcaaaag taaccaaagc    3840
gattgaccaa gatccaactt taaccgccgc tgaaaaaaag gcacagaagc aagcagtcac    3900
agatgcggaa actaaagcta aagctgctat tgatgctacg ttagtggccg atgcgattga    3960
ccaagctctg gctgacggga ttaaaaccat cgatgcccaa taccaaactg gtatagcatt    4020
ggataagcaa aaggcggcgg ccaaacaaac aattgatgcc gaagcagcca aggttagtga    4080
agcaattgat caggatgtca ctttgacagc cgaccaaaag gctacacaaa agcaggcagt    4140
ggcagatgaa gcaacgaaag caaaagcggc cattgaccaa gcctctgacg ccgatgcggt    4200
gattcaagca acaattgatg gtattgaagc tattgacgcg caacaccagt ccgcaacggc    4260
acttgacaag caaaagcagc aagcaaaaca ggcattgat gctgaagcgg ccaaagtaag    4320
taaggcgatc gatcaagatg tgacgttaac ggcaacgcaa aaagctgacc agaagcaggc    4380
```

-continued

```
tgtgatcgct gaagcagaca aagccaaaaa gcttatcgat gcagctggca atgctgatgg    4440
tatcaagcaa gctgaaagtg atgggatcaa agcaatcgac gctcagcatc aatccagtca    4500
ggcactcgca gatcggaagc gtgatgctaa aactgccatt gatgccgaag cggcaaaaga    4560
aacagctgct attgatcacg atgccacctt aaccgcgaat gaaaaggcaa gccagaaaca    4620
ggcggttacg gatgaagcaa ctaaagccaa aaagcgatt gatgcggcta agcaggctga    4680
tgcagtcgac caggccaaga ctgacgggat caaagcgatt gacgcccaac atcactccgg    4740
gcaagctctt gacgatcgta aagccgatgc caagcaggtc attgatgctg aagcagccaa    4800
ggtgacggca gcgattgatc aggataacac gttgaccaaa gcccaaaaag ctgcccagaa    4860
acaaggggtt gcgacagaag ccgacaaagc taagcaagcc attgatgctg ccggggatgc    4920
cgatgctgta gatcaagcaa agacagccgg gattcaagcc atcgatgctc agcacaaagc    4980
cggtaaaacc attgatagcc gtcatgatga cgctaagcaa gcgattgatg aagaagcggc    5040
taaggtgatt aaagcgattg accaggatcc aactctgacc gctgcccaaa aagaagcaca    5100
aaagcaagcg gtagcaactg aagccgataa agctaaaaaa gcaattgacg ctgcaggcga    5160
tgcggatgct gtagatcagg caaaaacagc cggcatcaag gctatcgatg agcaacacaa    5220
gtcaggacaa acagttgatg cacgaaaaga agatgccaaa aaggccattg atgctgaagc    5280
cggtaaagtt actgatgcaa ttgatcacga cgccactttg acggctgctc aaaaagaagc    5340
gcagaagcag gcgttgctg atgaggctga taaagctaaa aaagcgattg atgcagctgg    5400
aaatgcggat gctattgatc aggcaaaatc tgctggtatc aaggcaattg acgaacaaca    5460
caagtcagga caaagcatcg atactcgtaa agatgacgct aagaaagcta ttgatggaga    5520
agttgctaag ataactgatg cgatcgatca tgacccaaca ctgaccgatg ctgaaaaggc    5580
aacacaaaag caggccgtca tcgctgaagc tgacaaggcc aagaaggcaa ttgatgcagc    5640
cggtgatgct gatgccgttg accaggcaca aaaggctggc atcaaggcga tcgaccagca    5700
acacaaatcc gggcaagcac tagcaatccg aaagatgct gctaagaaag ccattgatga    5760
agaagctgct aaagtaagcg aagccattga tcatgatgta acgttgacgg acagcgaaaa    5820
gggcactcag aagcaagctg ttgctgacga ggccaagaaa gctaagcagg cgattgatac    5880
tgccgacaat gctgatggcg ttgatcaagc agtgaccaaa gcattcaga tcattgacgc    5940 gcagcaccag tccggccaag cgctcaccga tcgtaaggct gctgcgaaaa aagccattga    6000
tgccgaagct gcaaaggtag gccaagctat tgagcaggat ccaacactga cggcaacaga    6060
aaagaagcgt caaaaacaag ccgttgcaga cgaagcaaca aaggccaaag cggcgattga    6120
tactgctgct aatgcttcag cggttgacca agcaaaaaat gccggtatta aggccattga    6180
tgctcaacac gtctctggta aagctttga cttaagcaag gacgaagcca agaaagcgat    6240
tgatgctgaa gctaccaaag ttcaaggtga aattgatcag gacccgactc tgaccgctac    6300
tgccaagaaa cagcaaaaag aagcagtgcc gacagaagcc ggtaaagcaa acaggcatt    6360 tgatcaggct aaaaatatcg aggaggtacg accgccaaag acgaaggcat caaagcgatt    6420
gatgcgcaac atcagtcagg acaagcagtt gcacacgtaa agacgatgca aagaaagcaa    6480
tcgacgacga agctgctaaa gtgaccgaag caattgatca tgattcgtca ttgactgatg    6540
ctgaaaagaa ggctcagaaa caaggcgttg taacagaagc tgacaaagcg aagaaagcga    6600
ttgatgcagc tggcagtgcc gatgcagtcg atcaggccaa agatgcaggc atcaaggcca    6660
tcgacgcgca acatcagtca ggacaagcag ttgcaacacg taaagacgat gcaaagaaag    6720
```

-continued

```
cgattgacga cgaagctgct aaagtcatca aggcaattga tcaagatccc aacattgact    6780
gacgcagaaa aaacggcgca aaagcaagca gttgcaacag aagctgacaa agcgaaaaaa    6840
gccattgatg cggcaaaagg tgccgatgca gtagacaaag ccaaagcagc tggtatcaag    6900
gcaattgatg cccagcaccg ctccggtcaa accatcgcgg cgcaaaaaga tgcggccaaa    6960
aaggcaattg acgacgaagc tgctaaagtc atcaaggcaa ttgatcaaga tccaacattg    7020
actgatgcag aaaaggcagc gcaaaagcaa gcagttgccg cagaagctga taaagcaaag    7080
aaagcgattg acgcagctgg taacgctgat gcggtgaacc aagccaaagt agctggcatt    7140
aaggcaatta acgaccaaca tcgtgccggc aagggacaaa aggtcaccaa agcaacacct    7200
ctgccaacga ctaaggcacc tgagacgcct gcagcaccta aaacaaaagt tatcacctca    7260
tcagaaggca accttccgaa acaggggag caacaatctc tgtggatggt ggtcctaggc    7320
gctttgttga gtctgttctc aggattgtgg ttcgccaaaa agaaagcgtc acattaggcg    7380
ttgagatcaa gattcttaag ctcaaaaagt tgcagttatg aatggtaggg aaacctcatc    7440
atagaaagct gattttcgg aaactgacag ccggcaagtg agacgtttta tctcatttgt    7500
cggctgtttt tctggctata cctgttgatg atttttaaat atttgattca tttttaaatt    7560
cagcggtcca gttgattgac atggtatagc ccaaccgcta cgcttaaagc atgacaaaga    7620
agggtgtgag cttatggca                                                7639

<210> SEQ ID NO 29
<211> LENGTH:1257
<212> TYPE: DA
<213> ORGANISM: Lactobacillus rhamnosus

<400> SEQUENCE: 29
atgtgttatc agcgtgaccg tttcctttca aaccggtcag caaaaccgtc acgttctcat      60
cattttctcg ccctttcttt ttgtcatta tggtagaata caacagttgt gaattgtata     120
tttcgtagga ggatatctac atgccattag ttaacgctgc agagcttgta aaagctgcac     180
ataaaggtca ctactgtatc ggtgccttca acaccaacaa cttggaatgg actcgtgcca     240
ttctcgccgg cgctcaagaa ttgaacgttc cggttatcat ccagacttcc atgggtgctg     300
ctaagtacat gggtggctat gaattctgcc aaaccatgat cgaagctgcc gttaaagcca     360
tggacatcac cgttcctgtt gtgattcact tggaccacgg taactatgaa gcagccaagg     420
aagctattgc tgctggctac aactcagtta tgtttgacgg ccacgacctc gactttgaag     480
ataacttgga aaagaccaag gaaatcgtta agctggccca cgccaagggc atttccgttg     540
aagctgaagt tggttccatc ggcgtgaag aagacggtgt tgtcggcgaa ggtgaattag     600
ctgacgttga agaagccaag actttggcag ctaccggat cgacttcctg gcagccggca     660
ttggtaacat ccacggccaa tatccagaca actggaaagg cctgcacttc gaccgcttac     720
aagaattgaa cgacgctgtt aagatgccgc tcgttctcca cggtggttcc ggtatccctc     780
aagaacaagt tcaaaaggcg atcaccatgg gcatttccaa gttgaacatc aacaccgaat     840
gccaacttgc ctttgctaag gcaacacgtg aatacatcga agctggtaag gatcaacaag     900
gcaagggctt tgaccctcgt aagatgctca agccaggcac cgatgcgatc accgatacct     960
tcaaggaaat caccggctgg attggcaaca agccagttaa gatggttcct gaagcacttt    1020
aattttttaa tcaaagacca tttaaagaac ccactcgctg aaattgcgag tgggttcttt    1080
tcgtctctcg tacttaagct gttaaggata agcgctgccg ctgtgactga atttaggatg    1140
acgtacgctt agtcctctac ctcatcccat gctcggtctt catcagtcac agcatctctg    1200
```

```
aatccttgcc aatcagcggc agtggcaaat aaatcagatc gcagcggtgt cagcaca      1257
```

<210> SEQ ID NO 30
<211> LENGTH:1153
<212> TYPE: DA
<213> ORGAISM: Lactobacillus rhamnosus

<400> SEQUENCE: 30

```
ccttcgtaca caaagtaatg gatattcgcc aaaggttgac agcactgtca aaacaccatc      60
acctaactgc acgatggaaa catcaaatgt gccgtcgaca aagtcgtaaa ccaaatcttt     120
tccgttgaac attcaaacca gcgatcttac cggcatcctt gtttgcctga cgctcactgt     240
cattaaagta aaccggaact gtgataaccg catctttaac cggttcgccc agatagtctt     300
cagaaaattt tttgatgtac tgtaaaatca tcgctgaaat ttcttgcggg gtgtattctt     360
tatcgccaac cttaacttta tagttagctt cgcccatgtg acgcttaatt gacacgatgg     420
tatccggatt agtgatcgcc tggcgttttg ccacttcacc aacttggatt tcaccatctt     480
taaatgcgac aacagatggc gtggtgcgat gccttccgg gttggtgatg attttttggct     540
gattgccttc caaaaccgca actgcagagt tggtggttcc taagtcaata ccaataactt     600
tactcatatt tttatacctt cttatttca gattaattat ttagcgacaa cgaccatagc     660
agggcgcaga acccgatcct tgagataata ccctttttgt aacacctgcg cgaccgtgtc     720
agcgggatgt ttgtcgtccg ccgccacggt ttgtactgcc tgttgggtat tcggatcaaa     780
cttgtcgcca gcaccatcaa tcgcagtgat gccattttcc ttcaaggcgc gttccagatg     840
atcgtaaacc atctgcacac cttttttgag tgaggccgca ctgtcatctt tggcttcggt     900
tgcaagcgca cgctctagat tgtcaactac cggcaaaatc gccttggcta acttctggcc     960
gtcatatttc aacatttttt gctgctcttt ttcgaaccgc gcattcatgt tttgaatctc    1020
tgcagctgcg cgcaaatact tgtcttcgaa tgcatcacgc tcttgcttca gttgttcacc    1080
atcatgcttg ctggttttca attgctcatt aagatcagca atgctttcct gcagcccggg    1140
ggatccacta gtt                                                       1153
```

<210> SEQ ID NO 31
<211> LENGTH:1724
<212> TYPE: DNA
<213> ORGANISM: Lactobacillus rhamnosus

<400> SEQUENCE: 31

```
tgcaaattgc cacggatacc cagacacaag tcattgcaga cggcgttgtt accaagtata      60
cgccagccaa tgccatgatc gttgccactc atcggcacac agccaaacag ttgctggccg     120
cagcaggaat accagttgca cgtggggcta agtttactaa atggccggat gccaaagcag     180
cttttgagca cagctttgcg cataaaagta ttgtggtgaa acccgaggca cgcagccaag     240
gcaaagcggt tgagcagttt tcgataccac cgactgaaaa gcagtttgac cgagcctttc     300
atgaagccaa tcgccatcat ggggtgctca ttgaaatgat ggcacgcggc acgacctacc     360
attttaccat catcgggcaa caagtgctca gcgtcttgga aacagcagca gctaatgttg     420
taggcgatgg gcgcaaagcc attaaggaat tgatcgcctt gaaaaatggt caccgcgcga     480
cttcccggca attgcagctt gacgccagtg cacggcgtca gttaaaggct caagcgttaa     540
cacccgagac tgtgcttcaa cgcgggcagc aggttttctt aaccactgcc gcgcatccgc     600
aaaccggtgg cgatttgtat gacgtgacgg acgagattga tgacagttac aagcaactgg     660
```

-continued

```
cgctaaaagc tgctgccacg cttgatttgc cggtagcagc tgtcgacatt gtgattgata      720
atctgtatgc accgtatgat ccggaggcag atgggcaggc aatcgtgatt agcctcaatc      780
cggtaccgga tctcgctgtg ccgttgcatc cggacatggg cgaatcacgc gcacttgccc      840
cggcattgct aaactggctg tttgctgtga gataagtaaa cgaggtcata ttaaaaccga      900
cctcagcatg gtaaatttgc tctaaggtcg gttggttaca ccgttcatga tcatgcttct      960
gcgcgttacg gtcacgatgc tgacatttag gtgcggccac actccattat attggttaag    1020
ttgcgccaaa cgtctttagc ggttgcttag ataggttaaa accactttt cttaggcttt     1080 tcttgcgtgt catcaagtgg cggtaaggtg atgttagcct gattgatggc agtggctgcc    1140
acaataagta gccctggcgc ggtatcggca gtttgcgccg tttcgttagc aaccaatgta    1200
aatggcacat tggcatcggt gaggagcttc atgtaaggac cggtaatggc attatcaagt    1260
ttgccgttga gtagggcttt atagttgcgg tcatggaaat cttttaataa tggggcaacc    1320
tgatgctgtc gtttgggatc agccagttcc tgattgctga tacataaagc gacccgttca    1380
cgtaacgagc ccatgtactt gcggcgttcg tcgggtttgg tttgcggtgg gccgtatagt    1440
gcactgttga gatgttcctg catattgtct tctgccatga tgaaaagcct ccttatgatg    1500
ggtttgatca ataacgatt taacgatcct tggtgaaccg tcttgttgtg tgaacgcgag     1560
tcgtaatgtt gaaacctgac aacgcgttgc aatatgacct cattgtaaca tgttctagcg    1620
taaagaaagg aatgacgaaa gggtgtttac cagtaacgac tttgcggttt ttgctgcgcc    1680
aacgctaagt gcgcggatgg ccttgatccg gcaacagttg gatc                     1724
```

<210> SEQ ID NO 32
<211> LENGTH: 1000
<212> TYPE: DNA
<213> ORGANISM: Lactobacillus rhamnosus

<400> SEQUENCE: 32

```
gcgtggtgta agattcggta aggctagagc aaagcggttg tgtgaagtgt gaatccagca      60
agctgaattc ctgaattgat gaaaggaaga cggatatgta tcgagatctg aatggtaagg     120
ttgcagtcgt gactggtggc tccaaaggca ttggcgcggg cattgcagaa cggtttggcc     180
aagagcatat ggccgttgtg attaattatt taggtgatca cgaaggcgcg cgaaaaacag     240
ccgatacagt gatcaaaaat ggcggtcagg cagtcagtat tcatgcagat gtttcgacag     300
aagcggggat agcgagtttg gttaaaactg ccgagtccga atttggccgc cttgatgtct     360
gggtcaataa tgcaggcatg gaaattaaag caccgacgca tgaagtgtct ctggatgact    420
ggaataaagt cattgcgatt aatcaaaccg gggtcttttt aggcgcccgg gctgctttga    480
attattttct cgaccatcac cagccaggca atattattaa catctcatcg gtccatgaac    540
agattccctg ccaacgtttt gccagttatg ctgcagctaa agggtcggtt aagcttttca    600
cggagacgat tgcgatggaa tacgctaacc gcggaattcg ggtcaacgct atcggccccg    660
gtgccattga gacgccgatt aatgcggaaa gtttgctgaa taaggcgcag tatgaccaaa    720
cagtcgccat gattccccaa ggacggctag gcaaaccgga agatgttgcc gccggagcag    780
cctggctggc atcgacagag tcaagttacg tcactggcac gaccctatt ttgacggcg     840 ggatgacatt atatcctgcg tttaaagacg gacagggctg atcaatgttg cgaagatgca    900
aaaagtcgcc atctcgatta tgaaatggcg acttttttgtg tacgggttag aattcgcgtt    960
ttttatacag cacggtgctt aaccaccaag agaagatgaa                          1000
```

<210> SEQ ID NO 33
<211> LENGTH: 1191
<212> TYPE: DNA
<213> ORGANISM: Lactobacillus rhamnosus

<400> SEQUENCE: 33

| | | | | | |
|---|---|---|---|---|---|
| atggcaaaga | ttctcgcagt | caatgcaggt | agttcgaccc | tgaagtggaa | gcttttgat | 60 |
| atgccggctg | aagtgcagtt | ggctgagggg | ttggtcgatc | gattgggcca | gccgcaatcg | 120 |
| aaggttaaaa | ttaaatatgg | cgacggtcag | aagtacgaga | gcgataccc | aattgcaaac | 180 |
| tatcaagaag | cagttgccag | cttgatgggt | aatattaagg | cgctagggtt | agtggagcat | 240 |
| ttgcacgaga | ttatcggggt | cggccatcga | gtggttgctg | gcggcgaaat | ttttgccgaa | 300 |
| tcagttgttg | ttgatgatga | gacgttgctg | cagattcaga | atctgcgcga | ctatgcaccg | 360 |
| ttgcataatc | ccgttgaagc | ggactatatt | tcggttttc | ggaaaatgat | gccttgggcg | 420 |
| aatgaagtgg | cagtttttga | cacggctttc | caccaaacaa | tgcaaccgga | gaacttttta | 480 |
| tatagcattc | catacgaata | ttatgagcaa | tatggtgcgc | ggaagtatgg | tgcgcatgga | 540 |
| acaagtgtcc | gttatgtgag | cgctcgtgct | gctgaaatgt | tgggcaagcc | gctagaagat | 600 |
| ctacgtatga | ttgtcatgca | cttagggtct | ggctctagca | tcaccgcggt | tcaaggcgga | 660 |
| cagtcaattg | atacgtccat | gggctttacg | ccattagcag | gtgtcaccat | gggcacgcga | 720 |
| tcaggtgata | ttgatccgtc | attggtaggc | tatctcatga | agaagttggc | gataccggat | 780 |
| gttggccaaa | tgattcatat | tctcaacaac | gattccggtc | tgctaggtat | ctccggactc | 840 |
| agcaatgata | tgcgtgactt | ggaagccgcc | gaggacacca | atacacgcgc | taagctggca | 900 |
| ctggatattt | ttgtgaaccg | cgttgtgaaa | tacgttggct | cttacgttgc | tttaatggat | 960 |
| ggcgtcgacg | tgctggtctt | caccgctggc | attggcgaaa | acggtgacga | gatccgtgat | 1020 |
| aagattatgc | ggtcgcttga | ttacctcggc | gccaaaatcg | acaatgatct | gaattacaag | 1080 |
| tcacatggcg | ttgaagcaga | tctaagcacg | gcagattcaa | ccgtgaaaac | gctgctggta | 1140 |
| ccgacaaatg | aagaacttat | gattgtacgc | gatgtgatgg | cactgagcta | a | 1191 |

<210> SEQ ID NO 34
<211> LENGTH:33
<212> TYPE: DNA
<213> ORGANISM: Artificial Sequence
<220> FEATURE:
<223> OTHER INFORMATION: Made in the lab

<400> SEQUENCE: 34
ccgccgccgg gatccaccag cgcatcatct gac          33

<210> SEQ ID NO 35
<211> LENGTH: 36
<212> TYPE: DNA
<213> ORGANISM: Artificial Sequence
<220> FEATURE:
<223> OTHER INFORMATION: Made in the lab

<400> SEQUENCE: 35
ccgccgccgg aattcttact tggtggttaa atcggt          36

<210> SEQ ID NO 36
<211> LENGTH: 39
<212> TYPE: DNA
<213> ORGANISM: Artificial Sequence
<220> FEATURE:
<223> OTHER INFORMATION: Made in the lab -continued

```
<400> SEQUENCE: 36
ccgccgccgg gatccctaag cagtagtgca gttgatgcc                                    39

<210> SEQ ID NO 37
<211> LENGTH: 39
<212> TYPE: DNA
<213> ORGANISM: Artificial Sequence
<220> FEATURE:
<223> OTHER INFORMATION: Made in the lab

<400> SEQUENCE: 37
ccgccgccgc tcgagttaat cgttgatcac taccgtcgc                                    39

<210> SEQ ID NO 38
<211> LENGTH: 35
<212> TYPE: DNA
<213> ORGANISM: Artificial Sequence
<220> FEATURE:
<223> OTHER INFORMATION: Made in the lab

<400> SEQUENCE: 38
ccgccgccgg aattcccttt gggattcaag cggtg                                        35

<210> SEQ ID NO 39
<211> LENGTH: 41
<212> TYPE: DNA
<213> ORGANISM: Artificial Sequence
<220> FEATURE:
<223> OTHER INFORMATION: Made in the lab

<400> SEQUENCE: 39
ccgccgccgg cggccgctca attcttggca gcatcaatag c                                 41

<210> SEQ ID NO 40
<211> LENGTH: 37
<212> TYPE: DNA
<213> ORGANISM: Artificial Sequence
<220> FEATURE:
<223> OTHER INFORMATION: Made in the lab

<400> SEQUENCE: 40
ccgccgccgg gatcccattc gttgacgttg gacaatc                                      37

<210> SEQ ID NO 41
<211> LENGTH: 42
<212> TYPE: DNA
<213> ORGANISM: Artificial Sequence
<220> FEATURE:
<223> OTHER INFORMATION: Made in the lab

<400> SEQUENCE: 41
ccgccgccgg aattcttaac ctagtaacgc ttgtaaacga gc                                 42

<210> SEQ ID NO 42
<211> LENGTH: 632
<212> TYPE: PRT
<213> ORGANISM: Lactobacillus rhamnosus

<400> SEQUENCE: 42

Met Thr Leu Pro Arg Ile Gln Asp Asp Leu Tyr Leu Ala Val Asn Gly
  1               5                  10                  15

Glu Trp Gln Ala Lys Thr Pro Ile Pro Pro Asp Lys Ser Val Val Ser
             20                  25                  30
```

-continued

```
Ala Asp Ser Asn Leu Thr Asp Asp Ile Arg Gln Lys Leu Val Ala Asp
         35                  40                  45
Leu Ser Thr Met Thr Lys Thr Ala Lys Thr Leu Pro Leu Gln Tyr Ala
     50                  55                  60
Ala Arg Leu Phe Ala Lys Ala Asn Asp Gln Thr Arg Arg Gln Gln Leu
 65                  70                  75                  80
Gly Ile Glu Pro Val Arg Asp Arg Ile Ser Phe Leu Met Ala Leu Thr
                 85                  90                  95
Thr Leu Asp Gln Phe Arg Ser Ala Met Pro Lys Leu Val Ala Asp Gln
            100                 105                 110
Tyr Val Leu Pro Ile Ser Pro Tyr Val Asp Ala Asp Met His Asp Ala
        115                 120                 125
Glu His Asn Ile Leu Asn Leu Gly Gly Pro Asp Thr Ile Leu Pro Asp
    130                 135                 140
Ala Ala Met Tyr Gln His Glu Asp Ala Glu Asn Ala Ala Asp Leu Ala
145                 150                 155                 160
Ala Trp Ser Gln Met Ala Ala Met Leu Ala Ala Val Gly Phe Ser
                165                 170                 175
Gln Thr Asp Gln Thr Ala Tyr Val Glu Ala Ala Lys Arg Phe Asp Arg
            180                 185                 190
Arg Leu Ala Asp Tyr Val Pro Ala Asn Val Asp Leu Ala Val Asp Ser
        195                 200                 205
Thr Tyr Asp Asn Pro Leu Ser Trp Gln Ala Phe Glu Asp Ala Ala Gly
    210                 215                 220
Tyr Leu Gly Ile Pro Gln Ala Phe Ala Thr Tyr Met Pro Gln Thr Pro
225                 230                 235                 240
Ala Lys Val Asn Ala Val Val Pro Ala Tyr Leu Pro His Leu Ser Lys
                245                 250                 255
Leu Leu Thr Pro Asp Asn Tyr Ser Glu Trp His Ala Trp Met Val Ile
            260                 265                 270
Asn Glu Leu Leu Thr Cys Ala Thr Tyr Leu Ser Asp Asp Leu Arg Gln
        275                 280                 285
Leu Ala Gly Gln Tyr Asp Arg Phe Leu Ala Gly Gln Pro Glu Ala Ser
    290                 295                 300
Ser Trp Thr Lys His Ala Phe Gly Ile Ala Asn Glu Tyr Phe Asp Asp
305                 310                 315                 320
Val Ile Gly Gln Tyr Tyr Gly Gln Thr Tyr Phe Gly Ala Asp Ala Lys
                325                 330                 335
Ala Asp Val Thr Ala Met Val Lys Gln Ile Leu Ala Gln Tyr Arg Val
            340                 345                 350
Gln Leu Glu Asn Asn Thr Trp Leu Ser Pro Ala Thr Lys Gln Lys Ala
        355                 360                 365
Met Arg Lys Leu Ala Thr Met Gln Val Lys Met Gly Tyr Pro Glu Arg
    370                 375                 380
Leu Phe Ser Leu Tyr Asp His Leu Ser Val Asp Val Asp Asp Leu
385                 390                 395                 400
Leu Thr Ala Ile Leu Lys Leu Ser Ala Gln Thr Gln Ala Phe Trp Phe
                405                 410                 415
Lys Gln Leu Gly Gln Thr Val Asp Arg Asn Gln Trp Asn Met Pro Gly
            420                 425                 430
His Leu Val Asn Ala Ser Tyr Asp Pro Leu Lys Asn Asp Ile Thr Phe
        435                 440                 445
Pro Ala Gly Ile Leu Gln Pro Pro Tyr Tyr Ser Leu Lys Trp Thr Arg
```

```
                450                 455                 460
Ala Glu Asn Leu Gly Gly Thr Gly Ala Thr Ile Gly His Glu Ile Ser
465                 470                 475                 480

His Ser Phe Asp Asn Asn Gly Ala Leu Tyr Asp Glu Tyr Gly Asn Leu
                485                 490                 495

His Asn Trp Trp Thr Pro Ala Asp Lys Gln Ala Phe Asp Gln Leu Val
            500                 505                 510

Lys Ala Met Ala Ala Gln Phe Asp Gly Arg Asp Tyr Glu Gly Val Lys
            515                 520                 525

Val Asn Gly Thr Leu Thr Val Ser Glu Asn Met Ala Asp Asn Ala Gly
530                 535                 540

Met Asp Val Ala Leu Ala Leu Leu Gly Asp Gln Pro Asp Val Lys Asp
545                 550                 555                 560

Leu Gln Ala Phe Phe Ile Thr Tyr Ala Arg Ser Trp Ala Thr Lys Met
                565                 570                 575

Arg Pro Glu Arg Ala Lys Thr Val Leu Arg Gln Asp Val His Ala Pro
            580                 585                 590

Ala Thr Leu Arg Val Asn Val Pro Val Gln Asn Phe Pro Ala Trp Tyr
            595                 600                 605

Gln Ala Phe Asn Val Gln Pro Gln Asp Gly Met Tyr Arg Gln Pro Gln
            610                 615                 620

Lys Arg Leu Thr Ile Trp His Gln
625                 630
```

<210> SEQ ID NO 43
<211> LENGTH: 242
<212> TYPE: PRT
<213> ORGANISM: Lactobacillus rhamnosus

<400> SEQUENCE: 43

```
Met Ile His Met Ala Lys Lys Asp Phe Asn Gln Leu Ala Leu Asp Gln
1               5                   10                  15

Ala Lys Val Asn Gly Gly Lys Leu Ser Val Glu Pro Lys Val Pro Ile
                20                  25                  30

Glu Thr Arg Asp Asp Leu Ser Ile Ala Tyr Thr Pro Gly Val Gly Ala
            35                  40                  45

Val Ser Ser Ala Ile Ala Lys Asp Gln Ser Leu Val Tyr Asp Leu Thr
        50                  55                  60

Thr Lys Lys Asn Thr Val Ala Val Val Ser Asp Gly Ser Ala Val Leu
65                  70                  75                  80

Gly Leu Gly Asn Ile Gly Ala Glu Ala Ala Met Pro Val Met Glu Gly
                85                  90                  95

Lys Ala Ala Leu Phe Lys Arg Phe Ala Lys Val Asp Ala Val Pro Ile
            100                 105                 110

Val Leu Asp Thr Gln Asp Thr Glu Ala Ile Ile Ala Ala Val Lys Ala
        115                 120                 125

Ile Ala Pro Thr Phe Gly Gly Ile Asn Leu Glu Asp Ile Ser Ala Pro
    130                 135                 140

Arg Cys Phe Glu Ile Glu Ala Arg Leu Ile Asp Glu Leu Asn Ile Pro
145                 150                 155                 160

Val Phe His Asp Asp Gln His Gly Thr Ala Ile Val Val Leu Ala Ala
                165                 170                 175

Leu Tyr Asn Ala Leu Lys Val Ala Asp Lys Lys Ile Glu Asp Ile Arg
            180                 185                 190
```

```
Val Val Val Asn Gly Gly Gly Ser Ala Gly Leu Ser Val Ala Arg Arg
        195                 200                 205

Phe Leu Ala Ala Gly Val Lys His Val Met Val Val Asp Lys Val Gly
    210                 215                 220

Ile Leu Ala Lys Lys Asn Ala Asp Gln Leu Pro Pro His Gln Ala Gly
225                 230                 235                 240

Leu Pro

<210> SEQ ID NO 44
<211> LENGTH: 317
<212> TYPE: PRT
<213> ORGANISM: Lactobacillus rhamnosus

<400> SEQUENCE: 44

Met Ala Asp Glu Glu Ala Met Leu Ala Lys Val Gln Ala Ser Trp Ala
 1               5                  10                  15

Gln Thr Ala Ala Arg Asp Lys Ala Arg Tyr Ala Asp Glu Arg Val Pro
            20                  25                  30

Glu Asp Val His Trp Glu Thr Glu Tyr Arg Tyr Glu Gln Ser Ala Asp
        35                  40                  45

Pro Gln Gln Thr Leu Asn Leu Tyr Tyr Pro Ala Lys Arg Arg Asn Ala
50                  55                  60

Thr Met Pro Thr Val Ile Asp Ile His Gly Gly Gly Trp Phe Tyr Gly
65                  70                  75                  80

Asp Arg Asn Leu Asn Arg Asn Tyr Cys Arg Tyr Leu Ala Ser Gln Gly
                85                  90                  95

Tyr Ala Val Met Gly Met Gly Tyr Arg Leu Leu Pro Asp Val Asp Leu
            100                 105                 110

Arg Gly Gln Ile Gln Asp Ile Phe Ala Ser Leu Arg Trp Leu Ser His
        115                 120                 125

Phe Gly Pro Gln Arg Gly Phe Asp Leu Asp His Val Leu Leu Thr Gly
    130                 135                 140

Asp Ser Ala Gly Gly His Leu Ala Ser Leu Val Ala Cys Ile Gln Gln
145                 150                 155                 160

Ser Ala Glu Leu Gln Glu Leu Phe Gly Val Ser Arg Val Asn Phe Asn
                165                 170                 175

Phe Thr Leu Val Ala Leu Val Cys Pro Val Ala Glu Pro Ser Lys Leu
            180                 185                 190

Pro Glu Ala Ala Gly Asp Met Ser Asp Met Ala Ala Phe Tyr Leu Asp
        195                 200                 205

Lys Leu Ser Gly Gly Asp Gln Ala Leu Ala Asp His Leu Asn Phe Ser
    210                 215                 220

Gln Val Val Lys Gly Leu Asp Leu Pro Pro Phe Met Leu Ile Gly Gly
225                 230                 235                 240

Gln Asn Asp Ser Phe Tyr Leu Gln Ser Gln Ala Leu Leu Lys Val Phe
                245                 250                 255

Asp Ala Asn His Val Thr Tyr Thr Thr Lys Leu Trp Pro Ala Ser Ala
            260                 265                 270

Gly Pro His Leu Lys His Val Phe Asn Val Gln His Trp Glu Trp Pro
        275                 280                 285

Glu Ser Ile Glu Thr Asn Leu Glu Met Leu Arg Thr Phe Asp Ala Leu
    290                 295                 300

Ser Lys Gln Gln Asp Gln Ala Glu Glu Asn Glu Phe Glu
305                 310                 315
```

```
<210> SEQ ID NO 45
<211> LENGTH: 88
<212> TYPE: PRT
<213> ORGANISM: Lactobacillus rhamnosus

<400> SEQUENCE: 45

Met Glu Lys Arg Glu Phe Asn Ile Ile Ala Glu Thr Gly Ile His Ala
  1               5                  10                  15

Arg Pro Ala Thr Leu Leu Val Gln Ala Ala Ser Lys Phe Asn Ser Asp
                 20                  25                  30

Ile Asn Leu Glu Tyr Lys Gly Lys Ser Val Asn Leu Lys Ser Ile Met
             35                  40                  45

Gly Val Met Ser Leu Gly Val Gly Gln Gly Ala Asp Val Thr Ile Ser
         50                  55                  60

Ala Glu Gly Ala Asp Glu Ala Asp Ala Ile Ala Ala Ile Thr Asp Thr
 65                  70                  75                  80

Met Lys Lys Glu Gly Leu Ala Glu
                 85

<210> SEQ ID NO 46
<211> LENGTH: 378
<212> TYPE: PRT
<213> ORGANISM: Lactobacillus rhamnosus

<400> SEQUENCE: 46

Met Thr Gln Phe Asn Thr Lys Leu Val His Gly Pro Gln Leu Asn Val
  1               5                  10                  15

Asp Gln Ala Gly Ala Ile Val Pro Val Tyr Gln Ser Ala Met Phe
                 20                  25                  30

Arg Phe Ala Pro Asp Gly Gln Glu Thr His Trp Asp Tyr Ala Arg Ser
             35                  40                  45

Gly Asn Pro Thr Arg Glu Tyr Leu Glu Arg Gln Ile Ala Thr Leu Glu
         50                  55                  60

Asn Gly Asp Ala Gly Phe Ala Phe Ser Ser Gly Val Ala Ala Ile Ala
 65                  70                  75                  80

Thr Val Leu Ala Ile Phe Pro Asp His Ser His Phe Ile Ile Gly Asp
                 85                  90                  95

Ser Leu Tyr Ser Gly Thr Asp Arg Leu Ile Asn Gln Tyr Phe Ser Gln
            100                 105                 110

His Gly Leu Thr Phe Thr Pro Val Asp Thr Arg Asp Leu Ala Ala Val
            115                 120                 125

Glu Ala Ala Ile Arg Pro Glu Thr Lys Ala Ile Phe Phe Glu Thr Phe
        130                 135                 140

Ser Asn Pro Leu Leu Lys Val Ser Ser Val Lys Ala Ile Ser Ala Leu
145                 150                 155                 160

Ala Lys Thr His Asp Leu Leu Thr Ile Val Asp Asn Thr Phe Leu Thr
                165                 170                 175

Pro Tyr Tyr Gln Arg Pro Leu Asp Leu Gly Ala Asp Ile Val Leu His
            180                 185                 190

Ser Ala Thr Lys Tyr Leu Gly Gly His Gly Asp Leu Ile Ala Gly Leu
            195                 200                 205

Val Val Ser Ala His Pro Asp Leu Ser Glu Lys Leu Ala Phe Leu Gln
        210                 215                 220

Asn Thr Ile Gly Ala Ile Leu Ser Pro Leu Asp Cys Ser Leu Val Thr
225                 230                 235                 240
```

```
Arg Gly Ile Ala Thr Leu Ser Val Arg Leu Asp Arg Glu Thr Ala Asn
                245                 250                 255

Ala Gln Ala Val Ala Glu Phe Leu Ala Gln His Pro Asp Val Ala His
            260                 265                 270

Val Tyr Tyr Pro Gly Leu Lys Asn Asp Pro Gly Tyr Ala Leu Ala Gln
            275                 280                 285

Lys Glu Thr Thr Gly Ala Ser Gly Leu Leu Thr Ile Lys Leu Ala Asp
            290                 295                 300

Asn Ile Asp Pro Leu Lys Phe Val Asn Ser Thr Lys Ile Phe Asp Phe
305                 310                 315                 320

Ala Asp Ser Leu Gly Thr Val Ser Ser Leu Val Lys Leu Pro Trp Phe
                325                 330                 335

Lys Leu Pro Glu Asp Lys Arg Ala Asp Phe Gly Leu Thr Pro Gln His
            340                 345                 350

Val Arg Ile Ala Ile Gly Leu Glu Asp Gln Gln Asp Leu Ile Asp Asp
            355                 360                 365

Leu Gln Gln Ala Leu Val Ala Ala Glu Lys
            370                 375

<210> SEQ ID NO 47
<211> LENGTH: 270
<212> TYPE: PRT
<213> ORGANISM: Lactobacillus rhamnosus

<400> SEQUENCE: 47

Met Leu Lys Lys Lys Leu Trp Phe Leu Leu Pro Leu Val Ala Leu Val
1               5                   10                  15

Thr Phe Thr Leu Thr Ala Cys Thr Ser Ala Ser Ser Asp Thr Ser Lys
            20                  25                  30

Asn Ser Asp Val Thr Ala Glu Leu Ile Asn Lys Asn Glu Leu Thr Ile
        35                  40                  45

Gly Leu Glu Gly Thr Tyr Ala Pro Phe Ser Tyr Arg Lys Asp Gly Lys
    50                  55                  60

Leu Glu Gly Phe Glu Val Glu Leu Gly Lys Ala Leu Ala Lys Lys Ile
65                  70                  75                  80

Gly Val Lys Ala Lys Phe Val Pro Thr Gln Trp Asp Ser Leu Ile Ala
                85                  90                  95

Gly Leu Gly Ser Gln Lys Phe Asp Leu Val Leu Asn Asp Ile Ser Glu
            100                 105                 110

Thr Pro Ala Arg Lys Lys Val Tyr Asn Phe Thr Thr Pro Tyr Met Tyr
            115                 120                 125

Ser Arg Tyr Ala Leu Ile Thr Arg Ser Asp Asn Thr Thr Ile Lys Ser
    130                 135                 140

Leu Ala Asp Ile Lys Gly Lys Thr Phe Val Glu Gly Thr Gly Thr Pro
145                 150                 155                 160

Asn Ala Ala Leu Ala Lys Lys Tyr Gly Ala Lys Ile Thr Pro Ser Gly
                165                 170                 175

Asp Phe Thr Val Ser Leu Ser Leu Val Lys Glu Lys Arg Ala Asp Gly
            180                 185                 190

Thr Ile Asn Ala Ser Ala Ala Trp Tyr Ala Phe Ala Lys Asn Asn Ser
            195                 200                 205

Thr Ala Gly Leu Lys Ser Gln Thr Leu Lys Asp Ser Val Val Lys Pro
    210                 215                 220

Asp Glu Val Ala Gly Met Val Ser Lys Lys Ser Pro Lys Leu Gln Ala
225                 230                 235                 240
```

-continued

```
Ala Leu Ser Lys Gly Ile Gln Glu Leu Arg Lys Asp Gly Thr Leu Lys
            245                 250                 255
Lys Leu Ser Gln Lys Tyr Phe Gly Thr Asp Leu Thr Thr Lys
        260                 265                 270

<210> SEQ ID NO 48
<211> LENGTH: 221
<212> TYPE: PRT
<213> ORGANISM: Lactobacillus rhamnosus

<400> SEQUENCE: 48

Met Pro Asp Val Arg Phe His Ser Val Phe Asp Ile Ile Gly Pro Val
 1               5                  10                  15
Met Val Gly Pro Ser Ser His Thr Ala Gly Ala Arg Ile Gly
            20                  25                  30
Lys Val Val Arg Asp Ile Phe Gly Glu Pro Glu Thr Ile Thr Ile
        35                  40                  45
Tyr Leu Tyr Glu Ser Phe Ala Lys Thr Tyr Arg Gly His Gly Thr Asp
 50                  55                  60
Val Ala Leu Val Ala Gly Leu Leu Gly Met Ala Pro Asp Asp Pro Arg
65                  70                  75                  80
Leu Pro Glu Ser Leu Lys Leu Ala Tyr Asp Gln Gly Ile Lys Val Ser
                85                  90                  95
Phe Val Pro Lys Ser Asp Lys Val Asp His Pro Asn Thr Ala His Ile
            100                 105                 110
Val Leu Gln Ala Gly Asp His Arg Leu Ala Val Thr Gly Val Ser Ile
        115                 120                 125
Gly Gly Gly Asn Ile Gln Ile Thr Glu Ile Asn Gly Phe Lys Ile Ser
    130                 135                 140
Leu Ser Met Gly Gln Pro Thr Tyr Ile Thr Ile His Asp Asp Val Pro
145                 150                 155                 160
Gly Met Ile Ala Gln Val Thr Lys Ile Phe Ser Asp Ala Gly Ile Asn
                165                 170                 175
Ile Gly Thr Met Thr Val Thr Arg Thr Ala Lys Gly Glu Gln Ala Ile
            180                 185                 190
Met Ile Ile Glu Thr Asp Asp Tyr His Asp Asp Ile Leu Ala Lys Leu
        195                 200                 205
Lys Leu Leu Pro His Met Arg Asn Val Thr Tyr Phe Glu
    210                 215                 220

<210> SEQ ID NO 49
<211> LENGTH: 289
<212> TYPE: PRT
<213> ORGANISM: Lactobacillus rhamnosus

<400> SEQUENCE: 49

Met Phe Tyr Thr Val Lys Glu Leu Val Glu Gln Ser His Ala Phe Ser
 1               5                  10                  15
Ser Val Ala Glu Leu Met Val His Thr Glu Val Glu Asn Ser Thr Arg
            20                  25                  30
Thr Glu Ala Gln Ile Arg His Leu Met Ser Arg Asn Leu Glu Val Met
        35                  40                  45
Glu Arg Ser Val Lys Glu Gly Ile Ala Gly Val Lys Ser Val Thr Gly
    50                  55                  60
Leu Thr Gly Gly Glu Ala Lys Lys Leu Asn His Tyr Ile Ala Asp Asp
65                  70                  75                  80
```

-continued

```
Arg Phe Met Ser Gly Lys Pro Ile Met Glu Ala Val Arg Asn Ala Val
                85                  90                  95
Ala Val Asn Glu Val Asn Ala Lys Met Gly Leu Ile Cys Ala Thr Pro
            100                 105                 110
Thr Ala Gly Ser Ala Gly Val Leu Ala Gly Val Leu Ala Met Arg
        115                 120                 125
Asp Arg Leu His Leu Thr His Asp Gln Gln Leu Asp Phe Leu Phe Thr
    130                 135                 140
Ala Gly Ala Phe Gly Leu Val Ile Ala Asn Asn Ala Gly Ile Ala Gly
145                 150                 155                 160
Ala Glu Gly Gly Cys Gln Glu Val Gly Ser Ala Ser Ala Met Ala
                165                 170                 175
Ala Ala Ala Leu Val Cys Ala Asn Gly Gly Ser Ala Glu Gln Ala Ala
                180                 185                 190
Thr Ala Val Ala Ile Thr Leu Gln Asn Met Leu Gly Leu Val Cys Asp
            195                 200                 205
Pro Val Ala Gly Leu Val Glu Val Pro Cys Val Lys Arg Asn Ala Leu
    210                 215                 220
Gly Ala Ser Gln Ala Met Ile Ser Ala Asp Met Ala Leu Ala Gly Cys
225                 230                 235                 240
Ile Ser Val Ile Pro Ala Asp Glu Val Ile Glu Ala Val Asn Arg Val
                245                 250                 255
Gly Met Gln Leu Pro Ala Thr Leu Arg Glu Thr Gly Glu Gly Gly Leu
            260                 265                 270
Ala Thr Thr Pro Thr Gly Leu Arg Leu Lys Glu Gln Ile Phe Gly Lys
        275                 280                 285
Lys

<210> SEQ ID NO 50
<211> LENGTH: 368
<212> TYPE: PRT
<213> ORGANISM: Lactobacillus rhamnosus

<400> SEQUENCE: 50

Met Phe Lys Pro Thr Ile His Gln Leu His Pro Tyr Thr Pro Glu Lys
 1               5                  10                  15
Pro Leu Ala Val Leu Lys Glu Glu Leu Gly Leu Pro Gln Leu Val Arg
                20                  25                  30
Met Ser Ala Asn Glu Asn Pro Phe Gly Thr Ser Val Lys Val Gln Gln
            35                  40                  45
Ala Val Thr Asn Trp Asn Phe Thr Gln Ser Arg Asp Tyr Pro Asp Gly
    50                  55                  60
Tyr Ala Ser Gln Leu Arg Thr Ala Val Ala Lys His Leu Asp Val Ala
65                  70                  75                  80
Ala Glu Gln Leu Val Phe Gly Asn Gly Leu Asp Glu Val Ile Ala Leu
                85                  90                  95
Ile Ala Arg Thr Phe Leu Ser Pro Gly Asp Glu Val Ile Glu Pro Trp
            100                 105                 110
Pro Thr Phe Ser Glu Tyr Arg Leu His Ala Gln Ile Glu Gly Ala Thr
        115                 120                 125
Val Ile Asp Val Pro Val Thr Glu Thr Gly Asn Phe Asp Leu Ser Ala
    130                 135                 140
Met Ala Gln Ala Leu Thr Ala Lys Thr Lys Leu Ile Trp Val Cys Asn
145                 150                 155                 160
```

-continued

```
Pro Asn Asn Pro Thr Gly Thr Leu Leu Ser Ile Ala Thr Leu Thr Glu
                165                 170                 175
Trp Leu Arg Gln Ile Pro Lys Asp Val Leu Val Leu Met Asp Glu Ala
            180                 185                 190
Tyr Ile Glu Phe Thr Asp Asp Tyr Pro Ala Thr Ser Ala Ile Ser Leu
        195                 200                 205
Leu Ser Lys Phe Pro Asn Leu Val Val Leu Arg Thr Phe Ser Lys Ile
    210                 215                 220
Tyr Gly Leu Ala Asn Phe Arg Val Gly Phe Gly Val Phe Pro Lys Gln
225                 230                 235                 240
Leu Val Asn Tyr Leu Gln Thr Val Arg Leu Pro Tyr Asn Leu Ser Ser
                245                 250                 255
Ile Ala Gln Val Ser Ala Gln Ala Ala Leu Ala Asp Gln Asp Phe Val
            260                 265                 270
Ala Met Thr Arg Lys Arg Val Gln Gln Ala Arg Asp Ser Trp Glu Arg
        275                 280                 285
Phe Leu Thr Gln Thr Gly Leu Pro His Thr Arg Ser Gln Thr Asn Phe
    290                 295                 300
Gln Phe Phe Gln Ala Pro Lys Met Gln Ala Ser Ala Leu Lys Lys Arg
305                 310                 315                 320
Leu Leu Gln Gln Gly Phe Leu Val Arg Asp Gly Leu Lys Pro Gly Trp
                325                 330                 335
Leu Arg Val Thr Phe Gly Thr Glu Val Gln Asn Thr Ala Val Gln Arg
            340                 345                 350
Ile Ile Glu Thr Phe Gln Ala Glu Leu Thr Gly Pro Asn Ala Leu Lys
        355                 360                 365

<210> SEQ ID NO 51
<211> LENGTH: 301
<212> TYPE: PRT
<213> ORGANISM: Lactobacillus rhamnosus

<400> SEQUENCE: 51

Leu Ala Arg Thr Ile Gly Ile Gly Ile Gly His Val Gly Val Thr
 1               5                  10                  15
Thr Ala Phe Asn Leu Val Ser Lys Gly Ile Ala Asp Arg Leu Val Leu
            20                  25                  30
Ile Asp Gln Lys Ala Asp Leu Ala Glu Gly Glu Ser Tyr Asp Leu Lys
        35                  40                  45
Asp Ala Leu Gly Gly Leu Pro Thr Tyr Thr Glu Ile Ile Val Asn Asp
    50                  55                  60
Tyr Asp Ala Leu Lys Asp Ala Asp Val Val Ile Ser Ala Val Gly Asn
65                  70                  75                  80
Ile Gly Ala Ile Ser Asn Gly Asp Arg Ile Gly Glu Thr Gln Thr Ser
                85                  90                  95
Lys Gln Ala Leu Asp Asp Val Ala Pro Lys Leu Lys Ala Ser Gly Phe
            100                 105                 110
His Gly Val Leu Leu Asp Ile Thr Asn Pro Cys Asp Ala Val Thr Ser
        115                 120                 125
Tyr Trp Gln Tyr Leu Leu Asp Leu Pro Lys Ser Gln Ile Ile Gly Thr
    130                 135                 140
Gly Thr Ser Leu Asp Thr Tyr Arg Met Arg Arg Ala Val Ala Glu Ser
145                 150                 155                 160
Leu Asn Val Asn Val Ala Asp Val Arg Gly Tyr Asn Met Gly Glu His
```

```
                      165                 170                 175

Gly Glu Ser Gln Phe Thr Ala Trp Ser Thr Val Arg Val Asn Asn Glu
            180                 185                 190

Pro Ile Thr Asp Tyr Ala Gln Val Asp Tyr Asp Gln Leu Ala Asp Ala
            195                 200                 205

Ala Arg Ala Gly Gly Trp Lys Ile Tyr Gln Ala Lys His Tyr Thr Ser
        210                 215                 220

Tyr Gly Ile Ala Thr Ile Ala Thr Glu Met Thr Gln Ala Ile Ile Ser
225                 230                 235                 240

Asp Ala Lys Arg Ile Phe Pro Cys Ala Asn Tyr Asp Pro Glu Phe Gly
                245                 250                 255

Ile Ala Ile Gly His Pro Ala Thr Ile Gly Lys Leu Gly Val Val Asn
            260                 265                 270

Thr Pro Lys Leu Lys Leu Thr Asp Glu Glu Arg Ala Lys Tyr Val His
        275                 280                 285

Ser Ala Gly Ile Ile Lys Ala Thr Val Glu Lys Met Lys
        290                 295                 300

<210> SEQ ID NO 52
<211> LENGTH: 495
<212> TYPE: PRT
<213> ORGANISM: Lactobacillus rhamnosus

<400> SEQUENCE: 52

Leu Asp His Asp Leu Leu Lys Ala Ile Ala Gln Ser Gly Phe Glu Glu
1               5                   10                  15

Ala Thr Pro Ile Gln Ala Glu Thr Ile Pro Leu Val Leu Glu Gly Lys
            20                  25                  30

Asp Val Ile Gly Gln Ala Gln Thr Gly Thr Gly Lys Thr Ala Ala Phe
        35                  40                  45

Gly Leu Pro Ile Leu Gln His Ile Asp Lys Ala Asp Arg Ser Ile Gln
    50                  55                  60

Ala Leu Val Ile Ser Pro Thr Arg Glu Leu Ala Ile Gln Thr Gln Glu
65                  70                  75                  80

Glu Leu Tyr Arg Leu Gly Arg Asp Lys Lys Ile Lys Val Gln Ala Val
                85                  90                  95

Tyr Gly Gly Ala Asp Ile Arg Arg Gln Ile Arg Gln Leu Ala Asp His
            100                 105                 110

Pro Gln Ile Val Val Gly Thr Pro Gly Arg Ile Leu Asp His Ile Gly
        115                 120                 125

Arg His Thr Leu Lys Leu Glu His Leu Asp Thr Leu Val Leu Asp Glu
    130                 135                 140

Ala Asp Glu Met Leu Asp Met Gly Phe Ile Asp Ile Glu Lys Ile
145                 150                 155                 160

Val Glu Gln Met Pro Thr Glu Arg Gln Thr Leu Leu Phe Ser Ala Thr
                165                 170                 175

Met Pro Ala Ala Ile Met Arg Leu Thr Asn Lys Phe Met Lys Glu Pro
            180                 185                 190

Val Ile Val Lys Ile Lys Ala Lys Glu Leu Thr Ala Asp Thr Val Glu
        195                 200                 205

Gln Tyr Tyr Val Arg Ala Lys Asp Tyr Glu Lys Phe Asp Val Met Thr
    210                 215                 220

Arg Leu Phe Asp Val Gln Asp Pro Asp Leu Ala Leu Ile Phe Gly Arg
225                 230                 235                 240
```

```
Thr Lys Arg Arg Val Asp Glu Leu Thr Arg Gly Leu Lys Ala Arg Gly
                245                 250                 255

Tyr Arg Ala Glu Gly Ile His Gly Asp Leu Thr Gln Gln Lys Arg Met
            260                 265                 270

Ser Val Leu Arg Gln Phe Lys Ser Gly Gln Leu Asp Phe Leu Val Ala
        275                 280                 285

Thr Asp Val Ala Ala Arg Gly Leu Asp Ile Ser Gly Val Thr His Val
    290                 295                 300

Tyr Asn Tyr Asp Ile Pro Gln Asp Pro Asp Ser Tyr Val His Arg Ile
305                 310                 315                 320

Gly Arg Thr Gly Arg Ala Gly His Lys Gly Val Ser Val Thr Phe Val
                325                 330                 335

Thr Pro Asn Glu Ile Glu Tyr Leu His Thr Ile Glu Asp Leu Thr Lys
            340                 345                 350

Lys Arg Met Leu Pro Met Lys Pro Pro Thr Ala Glu Glu Ala Leu Met
        355                 360                 365

Gly Gln Ile Ser Ser Gly Leu Ala Thr Ile Lys Glu Gln Val Glu Ala
    370                 375                 380

Asn Asp Thr Glu Lys Tyr Glu Ala Met Ala Glu Thr Leu Leu Glu Asn
385                 390                 395                 400

Tyr Thr Pro Leu Gln Leu Val Ser Ala Tyr Leu Lys Ala Val Ser Pro
                405                 410                 415

Asp Asp Ala Ser Ala Val Pro Val Lys Ile Thr Pro Glu Arg Pro Leu
            420                 425                 430

Pro Arg Gly Arg Asn Asn His Gly His Gly Asn Asn Arg Gly Gly
        435                 440                 445

Tyr Lys Gly Gly Tyr Lys Gly Lys Arg Arg Asp Gly Gly Tyr Gln Gly
    450                 455                 460

Asn Arg Asp Gly Lys Arg Ser Tyr Asp Lys Lys Arg Asn Phe Gly Asp
465                 470                 475                 480

Lys Arg Lys Asn Val Lys Arg Asn Phe Lys Ile Arg Thr Gly Glu
                485                 490                 495

<210> SEQ ID NO 53
<211> LENGTH: 390
<212> TYPE: PRT
<213> ORGANISM: Lactobacillus rhamnosus

<400> SEQUENCE: 53

Met Thr Leu Gln Pro Leu Asn Glu Gln Leu Pro Ala Ile Glu Val Ser
  1               5                  10                  15

Glu Ile Arg Gln Phe Asp Glu Ser Val Ser Asp Ile Pro Gly Ile Leu
             20                  25                  30

Lys Leu Thr Leu Gly Glu Pro Asp Phe Asn Thr Pro Glu His Val Lys
         35                  40                  45

Gln Ala Gly Ile Lys Ala Ile Gln Glu Asn Tyr Ser His Tyr Thr Gly
     50                  55                  60

Met Val Gly Asp Pro Glu Leu Arg Glu Ala Gln His Phe Lys
 65                  70                  75                  80

Thr Lys Tyr Ala Thr Asp Tyr Arg Ala Thr Asp Glu Ile Leu Val Thr
                 85                  90                  95

Val Gly Ala Thr Glu Ala Leu Ala Thr Ala Ile Thr Thr Ile Ser Asp
            100                 105                 110

Pro Gly Asp Ala Met Leu Val Pro Ser Pro Ile Tyr Pro Gly Tyr Ile
        115                 120                 125
```

```
Pro Leu Leu Thr Leu Asn His Val Thr Pro Leu Tyr Met Asp Thr Ser
            130                 135                 140

Lys Thr Asp Phe Val Leu Thr Pro Glu Leu Ile Glu Ala Thr Ile Thr
145                 150                 155                 160

Ala Asn Pro Asp Ala Lys Ile Lys Gly Ile Ile Leu Asn Tyr Pro Ser
                165                 170                 175

Asn Pro Thr Gly Val Thr Tyr Arg Ala Ala Glu Val Lys Ala Ile Ala
            180                 185                 190

Asp Ile Ala Ala Lys His Asn Leu Tyr Ile Ile Cys Asp Glu Ile Tyr
        195                 200                 205

Ser Glu Leu Thr Tyr Gly Glu Pro His Val Ser Met Gly Gln Phe Ala
    210                 215                 220

Tyr Asp Arg Thr Phe Ile Val Asn Gly Leu Ser Lys Ser His Ala Met
225                 230                 235                 240

Thr Gly Trp Arg Ile Gly Phe Leu Met Gly Pro Gln Gln Leu Ile Ala
                245                 250                 255

Gln Ala Lys Lys Val His Gln Tyr Leu Val Thr Ala Ala Thr Thr Ile
            260                 265                 270

Ala Gln Arg Ala Gly Ile Glu Ala Leu Thr Asn Gly Ala Asp Asp Ala
        275                 280                 285

Gln Val Met Lys Ala Ala Tyr Val Lys Arg Arg Asp Phe Val Tyr Ala
    290                 295                 300

Ala Leu Ile Asp Met Gly Phe Ser Val Ala Arg Pro Asp Gly Ala Phe
305                 310                 315                 320

Tyr Leu Phe Ala Lys Ile Pro Thr Gln Leu His Leu Ser Ser Arg Glu
                325                 330                 335

Phe Thr His Ala Leu Ala His Glu Gln Lys Leu Ala Leu Ile Ser Gly
            340                 345                 350

Thr Ala Phe Gly Pro Gly Gly Glu Gly Tyr Ile Arg Ile Ser Tyr Ala
        355                 360                 365

Ala Ser Met Thr Asp Leu Gln Glu Ala Val Lys Arg Leu Arg Ala Phe
    370                 375                 380

Met Ala Ser His Ile Gly
385                 390

<210> SEQ ID NO 54
<211> LENGTH: 391
<212> TYPE: PRT
<213> ORGANISM: Lactobacillus rhamnosus

<400> SEQUENCE: 54

Val His Leu Ala Lys Arg Ile Leu Asn Val Ala Pro Ser Ala Thr Leu
 1               5                  10                  15

Ala Leu Ser Asn Gln Thr Lys Asp Leu Lys Ala Lys Gly Ala Asp Val
                20                  25                  30

Ile Asp Leu Ser Ile Gly Gln Pro Asp Phe Ser Thr Pro Lys Ala Ile
            35                  40                  45

Asp Asp Ala Ala Ile Ala Ala Ile Gln Ala Gly Asn Ala Ser Phe Tyr
        50                  55                  60

Thr Ala Thr Gly Ile Pro Glu Leu Lys Gln Ala Ile Ser Asp Arg
65                  70                  75                  80

Ile Phe Ala Gln Asp Gly Ile Arg Tyr Asp His Arg Gln Ile Val Ala
                85                  90                  95

Thr Thr Gly Ala Lys Phe Ala Leu Tyr Ala Leu Phe Gln Val Phe Leu
```

```
                      100                 105                 110
Asn Pro Gly Asp Glu Val Leu Ile Pro Val Pro Tyr Trp Val Ser Tyr
            115                 120                 125

Glu Glu Gln Ile Lys Leu Ala Ser Gly Val Pro His Leu Val Met Pro
130                 135                 140

Ala Val Gly His Lys Val Ser Val Asp Asp Leu Glu Ala Ala Arg Thr
145                 150                 155                 160

Asp Lys Thr Arg Ala Leu Ile Ile Asn Ser Pro Gln Asn Pro Ser Gly
                165                 170                 175

Val Val Tyr Asp Arg Thr Glu Leu Thr Leu Ile Gly Asn Trp Ala Leu
            180                 185                 190

Lys His His Ile Leu Val Val Thr Asp Asp Ile Tyr Arg Asp Leu Ile
            195                 200                 205

Tyr Asn Gly Thr Thr Tyr Thr Ser Met Ile Ser Ile Asp Pro Asp Ile
            210                 215                 220

Ala Ala Asn Thr Val Leu Ile Ser Gly Val Ser Lys Ser Tyr Ala Met
225                 230                 235                 240

Thr Gly Trp Arg Ile Gly Tyr Ala Ala Gly Pro Glu Lys Leu Ile Gln
                245                 250                 255

Ala Met Ala Thr Phe Ile Ser His Thr Thr Ser Asn Pro Ala Ala Val
            260                 265                 270

Ser Glu Tyr Ala Ala Val Ala Ala Leu Thr Gly Asp Gln Gln Val Val
            275                 280                 285

Glu Lys Met Arg Arg Ala Phe Glu Glu Arg Leu Asn Leu Phe Tyr Asp
290                 295                 300

Leu Leu Ala Asp Ile Pro Gly Phe Asp Met Gly Asp Lys Pro Gln Gly
305                 310                 315                 320

Ala Phe Tyr Leu Phe Pro Asn Ile Lys Arg Ala Ala Gln Leu Ser His
                325                 330                 335

Tyr Gly Thr Val Asp Asp Phe Ile Ser Ala Leu Leu Thr Glu Thr Gly
            340                 345                 350

Val Ala Ile Val Pro Gly Arg Ala Phe Gly Met Pro Asp His Ala Arg
            355                 360                 365

Ile Ser Tyr Cys Lys Asp Leu Ala Ser Leu Lys Glu Ala Ala Arg Arg
370                 375                 380

Ile Arg Glu Phe Val Gly Lys
385                 390

<210> SEQ ID NO 55
<211> LENGTH: 301
<212> TYPE: PRT
<213> ORGANISM: Lactobacillus rhamnosus

<400> SEQUENCE: 55

Met Gln Arg Ala Glu Leu Ile Thr Ala Ile Val Thr Pro Phe Asn Asp
 1               5                  10                  15

Arg Asp Glu Ile Asp Tyr Asp Ser Met Gln Arg Leu Val Asp His Leu
                20                  25                  30

Ile Asp Gln Gly Thr Asp Gly Phe Val Val Gly Ala Thr Thr Gly Glu
            35                  40                  45

Gly Pro Thr Leu Ser His Asp Glu Lys Ile Thr Leu Tyr Thr Arg Phe
        50                  55                  60

Val Ala Met Val His Gly Arg Ala Leu Val Ile Ala Asn Ser Gly Ser
65                  70                  75                  80
```

```
Asn Asn Thr Arg Glu Thr Thr Asp Phe Thr His Glu Val Gly Gly Ile
                 85                  90                  95

Ala Gly Ile Asp Ala Thr Leu Val Val Pro Tyr Asn Lys Pro
            100                 105                 110

Asp Gln Asp Gly Met Ile Ala His Tyr Thr Thr Val Ala Ala Ser Ala
            115                 120                 125

Gln Lys Pro Ile Ile Ile Tyr Asn Ile Pro Gly Arg Thr Gly Val Asn
130                 135                 140

Met Leu Pro Glu Thr Val Ala Thr Leu Ala Gln Asn Pro Met Ile Gln
145                 150                 155                 160

Gly Ile Lys Gln Cys Gly Ser Leu Ala Ala Leu Ser Asp Ile Ile Asp
                165                 170                 175

Arg Thr Lys His Asp Ala Phe Asn Val Trp Thr Gly Glu Asp Ala Gln
                180                 185                 190

Ala Leu Thr Ile Lys Thr Leu Gly Gly Met Gly Val Ile Ser Val Ala
            195                 200                 205

Ser His Leu Tyr Ala His Ser Ile Arg Glu Met Tyr Arg Ala Leu Asp
        210                 215                 220

Arg Gly Asp Ile Thr Thr Val Ala Ala Leu Gln Arg Gln Leu Leu Pro
225                 230                 235                 240

Lys Met Ala Ala Leu Phe His Phe Pro Ser Pro Ala Pro Thr Lys Ala
                245                 250                 255

Ala Leu Asn Ala Leu Gly Phe Lys Val Gly Ser Pro Arg Leu Pro Leu
                260                 265                 270

Leu Pro Leu Thr Ala Ala Gln Gln Gln Glu Leu Ala His Leu Leu Gly
            275                 280                 285

Val Ser Glu Leu Ser Ala Ile Glu Ala Glu Val Leu Ala
            290                 295                 300

<210> SEQ ID NO 56
<211> LENGTH: 255
<212> TYPE: PRT
<213> ORGANISM: Lactobacillus rhamnosus

<400> SEQUENCE: 56

Met Ile His Val Leu Val Ala Gly Phe Arg Gly Ala Met Gly Gln Lys
1               5                   10                  15

Thr Val Lys Met Val Gln Ser Gln Lys Asp Phe Ala Leu Ser Ala Val
            20                  25                  30

Phe Asp Pro Lys Ala Thr Ala Ala Asp Ala Gln Lys Tyr Gly Leu Pro
        35                  40                  45

Ala Asp Thr Lys Val Leu Thr Ser Tyr Asp Gln Leu Asn Pro Asp Ile
50                  55                  60

Ala Asp Val Trp Val Asp Phe Thr Asn Pro Thr Ala Val Ala Ala Asn
65                  70                  75                  80

Ile Glu Ala Ala Ile Lys Ala Gly Ile His Pro Val Val Gly Thr Ser
                85                  90                  95

Gly Met Thr Gln Ala Asp Gln Asn Arg Leu Ile Glu Leu Ala Gln Ala
            100                 105                 110

Arg His Ile Gly Gly Leu Ile Ala Pro Asn Phe Gly Leu Ser Ala Val
        115                 120                 125

Leu Leu Met Lys Phe Ala Gln Glu Ala Ala Tyr Phe Pro Asp Ala
        130                 135                 140

Glu Ile Ile Glu Met His His Gln Asp Lys Ala Asp Ala Pro Ser Gly
145                 150                 155                 160
```

```
Thr Ala Ile Ala Thr Ala His Lys Ile Ala Ala Gly Arg Thr Gln Lys
                165                 170                 175
Pro Leu Ser Thr Ile Asp Asn Asp Ala Arg Gly Gln Arg Ile Asp Asp
            180                 185                 190
Val Pro Val His Ala Val Arg Leu Pro Gly Tyr Ile Ala His Glu Gln
        195                 200                 205
Val Leu Phe Gly Pro Gly Glu Ala Leu Thr Ile Arg Gln Asp Ser
    210                 215                 220
Phe Asp Arg Gln Ser Phe Met Gln Gly Val Ala Val Ala Ile Arg Lys
225                 230                 235                 240
Val Gln Ala Ala Asp His Leu Val Val Gly Leu Glu Asn Phe Leu
                245                 250                 255
```

<210> SEQ ID NO 57
<211> LENGTH: 334
<212> TYPE: PRT
<213> ORGANISM: Lactobacillus rhamnosus

<400> SEQUENCE: 57

```
Met Tyr His Ala Ala Ala Asp Arg Tyr Glu Lys Met Pro Val Arg His
1               5                   10                  15
Ala Gly Lys Thr Gly Leu Met Leu Pro Val Ile Ser Leu Gly Leu Trp
            20                  25                  30
Gln His Tyr Gly Asn Leu Asp Pro Phe Gly Pro Arg Arg Ser Val Ile
        35                  40                  45
Leu Asp Ala Phe Asp Arg Gly Val Phe His Phe Asp Val Ala Asn His
    50                  55                  60
Tyr Gly Asn Gly Asp Arg Glu Pro Gly Phe Gly Ser Ser Glu Arg Leu
65                  70                  75                  80
Leu Gly Gln Ile Leu Ala Thr Asp Leu Lys Pro Tyr Arg Asp Glu Leu
                85                  90                  95
Val Ile Ser Thr Lys Val Gly Tyr Glu Ile His Pro Gly Pro Tyr Gly
            100                 105                 110
Val Gly Thr Ser Arg Lys Ala Val Ile Gln Gly Leu Asn Asp Ser Leu
        115                 120                 125
Lys Arg Leu Gln Leu Asp Tyr Val Asp Ile Tyr Tyr Ala His Arg Phe
    130                 135                 140
Asp Asp Thr Val Ala Leu Glu Glu Thr Val Asn Ala Leu Asp Gln Thr
145                 150                 155                 160
Val Arg Asp Gly Lys Ala Leu Tyr Ile Gly Ile Ser Asn Tyr Asp Thr
                165                 170                 175
Lys Gln Thr Lys Glu Ala Ile Ala Met Phe Lys Asp Leu His Thr Pro
            180                 185                 190
Phe Val Leu Asn Gln Tyr Ser Tyr Asn Met Phe Asn Arg Thr Ala Glu
        195                 200                 205
Thr Ser Gly Leu Ile Asp Ala Leu Lys Ala Asp Gly Ala Gly Leu Ile
    210                 215                 220
Ala Tyr Gly Pro Leu Ser Glu Gly Leu Leu Ser Asp Arg Tyr Leu Lys
225                 230                 235                 240
Gly Ile Pro Asp Thr Phe Lys Ile His Pro Thr Asn Lys Ala Thr Phe
                245                 250                 255
Ala Lys Gly Lys Glu Ala Val Val Lys Gln Leu Asn Ala Leu Asn Glu
            260                 265                 270
Ile Ala His Asp Arg Asp Gln Thr Leu Ser Gln Met Ala Leu Ala Trp
```

```
              275                 280                 285
Leu Leu Arg Asp Pro Val Val Thr Ser Val Ile Ile Gly Thr Thr Ser
        290                 295                 300
Val Glu His Leu Gln Asp Asn Leu Lys Ala Thr Glu His Leu Thr Phe
305                 310                 315                 320
Thr Ala Glu Glu Ile Gln Gln Ile Asp Asp Ile Leu Asn Ala
                325                 330

<210> SEQ ID NO 58
<211> LENGTH: 274
<212> TYPE: PRT
<213> ORGANISM: Lactobacillus rhamnosus

<400> SEQUENCE: 58

Met Ala Lys Met Trp Lys Arg Met Leu Leu Pro Leu Val Leu Leu Leu
 1               5                  10                  15
Leu Met Ile Pro Leu Ser Ser Cys Gly Lys Ser Val Ala Asp Arg Asp
            20                  25                  30
Ile Leu Ala Asn Ala Lys Ala Thr Asn Thr Ile Ile Trp Gly Val Lys
        35                  40                  45
Ala Asp Thr Arg Leu Phe Gly Leu Met Asn Ile Lys Thr Gly Lys Ile
    50                  55                  60
Glu Gly Phe Asp Val Asp Met Ala Lys Ala Ile Thr Lys Gln Ile Leu
65                  70                  75                  80
Gly Lys Lys Gly Asn Ala Gln Leu Val Gln Val Thr Ser Asp Thr Arg
                85                  90                  95
Val Pro Met Ile Lys Gly Gly Asn Leu Asp Ala Val Ile Ala Thr Met
            100                 105                 110
Thr Ile Thr Pro Glu Arg Gln Lys Ile Leu Asp Phe Ser Asp Val Tyr
        115                 120                 125
Phe Asn Ala Gly Gln Ser Leu Leu Val Lys Lys Gly Ser Pro Ile Lys
    130                 135                 140
Ser Val Lys Asp Leu Lys Lys Gly Thr Lys Val Ile Gly Val Gln Gly
145                 150                 155                 160
Ser Asn Ser Val Asp Asn Val Lys Lys Ala Ala Pro Asp Thr Thr Val
                165                 170                 175
Leu Gln Leu Ala Asp Tyr Ala Gln Ala Phe Thr Ala Leu Lys Ser Gly
            180                 185                 190
Gln Gly Asp Ala Leu Thr Thr Asp Asn Gly Ile Leu Tyr Gly Met Ser
        195                 200                 205
Glu Gln Asp Lys Asn Tyr Ile Val Thr Gly Gly Thr Phe Thr Lys Glu
    210                 215                 220
Pro Tyr Gly Ile Ala Ile Asn Lys Gly Gln Lys Pro Phe Val Asn Ala
225                 230                 235                 240
Val Asn Lys Ala Ile Lys Gln Leu Lys Gln Asn Gly Thr Tyr Ala Lys
                245                 250                 255
Leu Ile Lys Lys Trp Phe Gly Asp Val Pro Gly Phe Ser Leu Lys Glu
            260                 265                 270
Val Glu

<210> SEQ ID NO 59
<211> LENGTH: 390
<212> TYPE: PRT
<213> ORGANISM: Lactobacillus rhamnosus

<400> SEQUENCE: 59
```

```
Met Lys Leu Thr Ile Tyr Asp Phe Asp His Val Ile Asp Arg Arg Gly
 1               5                  10                  15

Thr Phe Ser Thr Gln Trp Asp Tyr Ile Ala Asp Arg Phe Gly Arg Asn
             20                  25                  30

Asp Ile Leu Pro Phe Ser Ile Ser Asp Thr Asp Phe Pro Val Pro Val
             35                  40                  45

Glu Val Gln Asp Ala Leu Lys Glu Arg Leu Thr His Pro Ile Tyr Gly
 50                  55                  60

Tyr Thr Arg Trp Asn His Ala Thr Tyr Lys Asp Ser Ile Val His Trp
 65                  70                  75                  80

Phe Glu Arg Asp Gly His Thr Lys Ile Asn Pro Asp Trp Ile Val Tyr
                 85                  90                  95

Ser Pro Ser Val Val Phe Thr Ile Ala Thr Leu Ile Arg Met Lys Ser
                100                 105                 110

Asp Pro Gly Asp Gly Val Ala Val Phe Thr Pro Met Tyr Asp Ala Phe
            115                 120                 125

Tyr Gly Thr Ile Lys Gln Asn Asp Arg Val Leu Ile Pro Ile Arg Leu
130                 135                 140

Ala Ala Ala Asp Glu Gly Tyr Val Ile Asp Trp Asp Ser Leu Ala Thr
145                 150                 155                 160

Val Leu Ala Glu Lys Gln Thr Lys Ile Phe Leu Leu Thr Asn Pro His
                165                 170                 175

Asn Pro Thr Gly His Val Phe Thr Lys Ser Glu Leu Ala Arg Leu Tyr
            180                 185                 190

Asp Leu Cys Gln Ala Ala His Val Phe Leu Ile Ser Asp Asp Ile His
            195                 200                 205

Arg Asp Ile Val Tyr Pro Gly His Ser Tyr Glu Pro Met Thr Asn Val
210                 215                 220

Gly Thr Ser Asp Val Ala Leu Cys Cys Ser Gly Ser Lys Thr Phe Asn
225                 230                 235                 240

Thr Pro Gly Leu Ile Gly Ser Tyr Ala Phe Leu Pro Asp His Asp Val
                245                 250                 255

Arg Ala Gln Phe Leu Thr Glu Leu Lys Gln Lys Asn Ala Leu Ser Ser
            260                 265                 270

Val Ser Ile Phe Gly Met Leu Ala Gln Ile Ala Ala Tyr Asn Gly Ser
            275                 280                 285

Glu Asp Tyr Val Glu Gln Leu Thr Ala Tyr Thr Lys Asn Asn Met Glu
290                 295                 300

Leu Val Ala Ser Tyr Leu Glu Glu Asn Leu Pro Glu Leu Gln Phe Ser
305                 310                 315                 320

Leu Pro Asp Ala Thr Tyr Leu Ala Trp Ile Asn Val Ser Lys Leu Arg
                325                 330                 335

Leu Thr Ser Glu Glu Leu Gln His Arg Leu Val Asn Gly Gly His Val
            340                 345                 350

Gly Ile Met Ala Gly Lys Thr Tyr Gly Asp Thr Arg Tyr Leu Arg Met
            355                 360                 365

Asn Ile Ala Cys Pro Lys Lys Leu Val Met Gly Leu Glu Arg Leu
370                 375                 380

Lys Lys Gly Ile Arg Gly
385                 390

<210> SEQ ID NO 60
<211> LENGTH: 416
```

```
<212> TYPE: PRT
<213> ORGANISM: Lactobacillus rhamnosus

<400> SEQUENCE: 60

Met Arg Thr Met Thr Thr Lys Ala Arg Lys Gln Gly Ser Leu Met Glu
  1               5                  10                  15

Asp Leu Pro Thr Asp Ile Ala Thr Phe Val Asp Thr His Leu Val Asp
             20                  25                  30

Arg His Asn Ser Asn Ala Val Lys Trp Asp Gly Leu Lys Glu Glu Phe
         35                  40                  45

Gly Arg Ala Asp Leu Leu Pro Met Trp Ile Ala Asp Thr Glu Phe Lys
 50                  55                  60

Ala Pro Gln Ala Val Leu Asp Ala Leu Thr Val Arg Val Lys Glu Gly
 65                  70                  75                  80

Thr Phe Gly Tyr Ser Ile Arg Pro Gln Ser Tyr Tyr Glu Ala Phe Ile
                 85                  90                  95

Asn Trp Gln Lys Glu Arg His Gly Ile Thr Val Glu Pro Glu Trp Met
            100                 105                 110

Arg Phe Gly Val Gly Val Val Lys Ser Leu Tyr Ala Met Val Asn Trp
        115                 120                 125

Leu Thr Glu Pro Gly Asp Pro Val Leu Ile Met Gln Pro Val Tyr Tyr
    130                 135                 140

Pro Phe Met Asn Ala Ile Asn Asp Leu Gly Arg Lys Val Val Ser Val
145                 150                 155                 160

Asp Leu Gln Leu Thr Ala Asp Gly Trp Arg Met Asp Phe Asp Gln Leu
                165                 170                 175

Glu Lys Thr Leu Ala Ala Asn Glu Ile Lys Ala Met Ile Leu Cys Ser
            180                 185                 190

Pro His Asn Pro Val Gly Arg Ile Trp Thr Arg Asp Glu Leu Glu Gln
        195                 200                 205

Leu Phe Ala Ile Thr Ser Arg Tyr Asp Val Thr Val Val Ser Asp Glu
    210                 215                 220

Ile His Gly Asp Leu Glu Val Ser Gly Pro Lys Phe Thr Ser Ala Leu
225                 230                 235                 240

Gln Val Ala Glu Gly Lys Ala Arg Lys Lys Leu Val Val Leu Asn Ala
                245                 250                 255

Pro Ser Lys Thr Phe Asn Leu Ala Ala Leu Leu Asn Ser His Ile Ile
            260                 265                 270

Ile Pro Asp Gln Ala Leu Arg Thr Ser Tyr Asp Ala Phe Ile Lys Gln
        275                 280                 285

Leu His Pro Val Asp Thr Ser Leu Met Gly Gln Val Ala Gly Glu Ala
    290                 295                 300

Ala Tyr Arg His Gly Ala Ala Trp Leu Asp Gln Val Leu Gln Val Val
305                 310                 315                 320

Arg Tyr Asn Tyr Arg Gln Leu Gln Ala Gly Leu Ala Ala Ala Ala Pro
                325                 330                 335

Gln Ala Thr Leu Ala Asp Leu Gln Gly Thr Tyr Leu Ala Tyr Val Asp
            340                 345                 350

Ile Gly Ala Tyr Val Ala Pro Ser Gln Ile Lys Asp Phe Val Glu Gly
        355                 360                 365

Val Cys Gly Leu Ala Val Asp Tyr Gly Ala Trp Phe Ser Pro Gln Thr
    370                 375                 380

Ala Thr Tyr Ile Arg Leu Asn Leu Ala Thr Asp Pro Lys Leu Val Ala
385                 390                 395                 400
```

Glu Ala Ile Asn Arg Leu Thr Thr His Leu Ala Gln Gln Pro Gln Arg
                405                 410                 415

<210> SEQ ID NO 61
<211> LENGTH: 332
<212> TYPE: PRT
<213> ORGANISM: Lactobacillus rhamnosus

<400> SEQUENCE: 61

Met Ser Val Lys Leu Thr Ala Gly Gln Leu Glu His Leu Lys Gln Leu
1               5                   10                  15

Ser Asn Asp Asn Asn Val Ile Ser Ala Leu Ala Ile Asp Gln Arg Gly
                20                  25                  30

Ser Leu Lys Lys Met Leu Ala Ala Ala Asn Lys Pro Ala Asp Glu
            35                  40                  45

Thr Thr Ile Val Asp Phe Lys Lys Ala Val Ser Glu Glu Leu Thr Lys
    50                  55                  60

Tyr Ala Ser Ala Ile Leu Leu Asp Pro Glu Tyr Gly Leu Pro Ala Ala
65                  70                  75                  80

Lys Val Arg Asp Pro Lys Ser Gly Leu Leu Ser Tyr Glu Lys Thr
                85                  90                  95

Gly Tyr Asp Ala Thr Glu Pro Gly Arg Phe Pro Asp Leu Ile Asp Asn
            100                 105                 110

Gln Ser Ala Leu Arg Ile Lys Asn Glu Gly Gly Asp Ala Val Lys Phe
        115                 120                 125

Leu Leu Tyr Ile Asp Pro Asp Glu Pro Asp Ser Ile Asn Asp Arg Lys
    130                 135                 140

Tyr Ala Phe Val Glu Arg Val Gly Ala Glu Ala Lys Ala Asn Asp Leu
145                 150                 155                 160

Pro Leu Phe Leu Glu Leu Val Ser Tyr Asp Gly Lys Thr Asn Glu Thr
                165                 170                 175

Gly Thr Ala Ala Trp Ala Lys Ala Lys Pro Glu Lys Val Ile Lys Ile
            180                 185                 190

Thr Lys Glu Phe Ser Lys Ala Gln Tyr Asn Val Ser Val Leu Lys Leu
        195                 200                 205

Glu Val Pro Val Asp Gln Lys Phe Val Glu Gly Tyr Thr Asp Glu Gly
    210                 215                 220

Val Thr Pro Val Tyr Ser Lys Glu Ala Ala Lys Tyr Tyr Lys Ala
225                 230                 235                 240

Gln Ser Asp Ala Thr Asp Leu Pro Phe Ile Phe Leu Ser Ala Gly Val
                245                 250                 255

Ser Asn Glu Leu Phe Leu Glu Glu Leu Lys Phe Ala Lys Glu Ala Gly
            260                 265                 270

Ser Thr Phe Asn Gly Val Leu Cys Gly Arg Ala Thr Trp Lys Pro Gly
        275                 280                 285

Val Lys Pro Phe Ala Ala Glu Gly Glu Ala Ala Gly Lys Lys Trp Leu
    290                 295                 300

Gln Thr Glu Gly Lys Ala Asn Ile Asp Arg Leu Asn Lys Val Leu Ala
305                 310                 315                 320

Asp Thr Ala Thr Pro Trp Thr Asp Lys Val Glu Gly
                325                 330

<210> SEQ ID NO 62
<211> LENGTH: 434
<212> TYPE: PRT

-continued

<213> ORGANISM: Lactobacillus rhamnosus

<400> SEQUENCE: 62

```
Met Ser Ile Ile Thr Asp Val Leu Ala Arg Glu Val Leu Asp Ser Arg
 1               5                  10                  15
Gly Asn Pro Thr Val Glu Val Glu Leu Tyr Thr Glu Asp Gly Gly Phe
                20                  25                  30
Gly Arg Ala Leu Val Pro Ser Gly Ala Ser Thr Gly Glu His Glu Ala
            35                  40                  45
Val Glu Leu Arg Asp Gly Asp Lys Asp Arg Phe Gly Gly Lys Gly Val
        50                  55                  60
Leu Lys Ala Val Asp His Val Asn Asn Glu Ile Ala Lys Ala Val Ile
 65                  70                  75                  80
Gly Leu Asp Val Thr Glu Gln Arg Leu Ile Asp Gln Thr Met Ile Asp
                85                  90                  95
Leu Asp Gly Thr Pro Asn Lys Gly Lys Leu Gly Ala Asn Ala Ile Leu
            100                 105                 110
Gly Val Ser Leu Ala Ala Ala Arg Ala Ala Ala Asp Glu Val Gly Leu
        115                 120                 125
Pro Leu Tyr Gln Tyr Leu Gly Gly Pro Asn Ala His Val Leu Pro Thr
    130                 135                 140
Pro Met Met Asn Val Leu Asn Gly Gly Ala His Ser Thr Asn Thr Val
145                 150                 155                 160
Asp Phe Gln Glu Phe Met Ile Met Pro Val Gly Ala Lys Ser Val Arg
                165                 170                 175
Glu Ala Val Arg Met Gly Ser Glu Thr Phe His Ala Leu Gln Ala Leu
            180                 185                 190
Leu Lys Ser Lys Gly Asp Ile Thr Ala Val Gly Asp Glu Gly Gly Phe
        195                 200                 205
Ala Pro Asn Leu Lys Asp Asn Glu Glu Ala Phe Glu Leu Leu Val Glu
    210                 215                 220
Ala Ile Lys Lys Ala Gly Tyr Lys Pro Gly Asp Asp Ile Ala Leu Ala
225                 230                 235                 240
Phe Asp Val Ala Ala Ser Glu Met Tyr Asp Ala Asp Thr Lys Thr Tyr
                245                 250                 255
Thr Thr Lys Trp Ser Asn Pro Asp Lys Lys Tyr Thr Thr Glu Glu Trp
            260                 265                 270
Thr Asn Met Ile Asp Gly Tyr Ile Asn Lys Tyr Pro Ile Val Ser Val
        275                 280                 285
Glu Asp Pro Ile Asp Glu Asn Asp Trp Glu Gly Trp Gln Thr Phe Thr
    290                 295                 300
Glu Lys Met Gly Asp Lys Val Gln Ile Val Gly Asp Asp Leu Phe Val
305                 310                 315                 320
Thr Asn Thr Asp Tyr Leu Lys Lys Gly Ile Asp Met Gly Val Ala Asn
                325                 330                 335
Ser Ile Leu Ile Lys Leu Asn Gln Ile Gly Thr Leu Thr Glu Thr Phe
            340                 345                 350
Glu Ala Ile Glu Met Ala Lys Glu Ala Gly Tyr Thr Ala Val Val Ser
        355                 360                 365
His Arg Ser Gly Glu Thr Glu Asp Thr Thr Ile Ala Asp Leu Val Val
    370                 375                 380
Ala Thr Asn Ala Gly Glu Ile Lys Thr Gly Ser Met Ser Arg Thr Asp
385                 390                 395                 400
```

```
Arg Ile Ala Lys Tyr Asn Gln Leu Met Arg Ile Glu Asp Gln Leu Gly
                405                 410                 415

Ala Gln Ser Gln Tyr Lys Gly Arg Lys Ser Phe Tyr Asn Val Lys Ala
            420                 425                 430

Ile Asp

<210> SEQ ID NO 63
<211> LENGTH: 251
<212> TYPE: PRT
<213> ORGANISM: Lactobacillus rhamnosus

<400> SEQUENCE: 63

Met Arg Thr Pro Phe Ile Ala Gly Asn Trp Lys Met Asn Lys Asn Pro
 1               5                  10                  15

Lys Glu Thr Gln Ala Phe Leu Asp Ala Val Lys Gly Lys Leu Pro Asp
                20                  25                  30

Ala Ser Lys Val Glu Thr Val Ile Gly Ala Pro Ala Ile Asp Leu Thr
            35                  40                  45

Thr Leu Val Ala Gly Ala Glu Gly Thr Pro Leu Lys Thr Ala Ala Glu
        50                  55                  60

Asn Cys Tyr Phe Glu Asp Glu Gly Ala Phe Thr Gly Glu Thr Ser Pro
65                  70                  75                  80

Lys Ala Leu Lys Glu Met Gly Val Asp Tyr Val Ile Ile Gly His Ser
                85                  90                  95

Glu Arg Arg Gly Tyr Phe His Glu Thr Asp Glu Asp Ile Asn Lys Lys
            100                 105                 110

Ala Lys Ala Ile Phe Lys Asn Asn Leu Leu Pro Ile Ile Cys Cys Gly
        115                 120                 125

Glu Ser Leu Ala Gln Arg Glu Ala Gly Gln Thr Glu Asp Trp Val Ala
    130                 135                 140

Ser Gln Ile Glu Ala Ala Leu Ala Gly Leu Ser Ala Asp Gln Val Lys
145                 150                 155                 160

Val Ser Val Leu Ala Tyr Glu Pro Ile Trp Ala Ile Gly Thr Gly Lys
                165                 170                 175

Thr Ala Thr Ala Asp Gln Ala Gln Glu Val Val Ala His Ile Arg Ala
            180                 185                 190

Thr Val Glu Lys Leu Tyr Asn Lys Asp Thr Ala Asp Ala Val Arg Ile
        195                 200                 205

Leu Tyr Gly Gly Ser Val Lys Pro Ala Asn Val Lys Glu Leu Met Ala
    210                 215                 220

Lys Pro Asp Ile Asp Gly Gly Leu Val Gly Gly Ala Ser Met Asp Pro
225                 230                 235                 240

Asp Ser Phe Ile Ala Leu Ala Asn Tyr Gln Asp
                245                 250

<210> SEQ ID NO 64
<211> LENGTH: 396
<212> TYPE: PRT
<213> ORGANISM: Lactobacillus rhamnosus

<400> SEQUENCE: 64

Leu Ala Lys Leu Ile Val Ser Asp Leu Asp Val Lys Asp Lys Lys Val
 1               5                  10                  15

Leu Ile Arg Val Asp Phe Asn Val Pro Ile Lys Asp Gly Val Ile Gly
                20                  25                  30

Asp Asp Asn Arg Ile Val Ala Ala Leu Pro Thr Ile Gln Tyr Val Ile
```

35                  40                  45
Asp His Gly Gly Lys Ala Ile Leu Leu Ser His Leu Gly Arg Val Lys
 50                  55                  60

Thr Glu Asp Lys Ala Lys Leu Thr Leu Lys Pro Val Ala Glu Arg
 65                  70                  75                  80

Leu Ser Glu Leu Leu Lys Lys Pro Val Thr Phe Val Pro Ala Thr Arg
                 85                  90                  95

Gly Lys Glu Leu Glu Asp Ala Ile Ala Lys Leu Asn Asp Gly Asp Val
                100                 105                 110

Leu Leu Met Glu Asn Thr Arg Phe Glu Asp Leu Asp Gly Lys Lys Glu
            115                 120                 125

Ser Gly Asn Asp Pro Glu Leu Gly Lys Tyr Trp Ala Ser Leu Gly Asp
            130                 135                 140

Leu Phe Val Asn Asp Ala Phe Gly Thr Ala His Arg Lys His Ala Ser
145                 150                 155                 160

Asn Val Gly Ile Ala Ser Asn Met Lys Gln Thr Ala Ala Gly Phe Leu
                165                 170                 175

Met Glu Lys Glu Ile Lys Phe Leu Gly Asp Ala Val Asp Asn Pro Lys
            180                 185                 190

His Pro Phe Ile Ala Ile Leu Gly Gly Ala Lys Val Ser Asp Lys Ile
            195                 200                 205

Gly Val Ile Glu Asn Leu Val Pro Lys Ala Asp Lys Ile Leu Ile Gly
            210                 215                 220

Gly Gly Met Thr Tyr Thr Phe Tyr Ala Ala Lys Gly Met Ser Ile Gly
225                 230                 235                 240

Asn Ser Leu Val Glu Lys Asp Lys Ile Asp Leu Ala Lys Lys Ile Met
                245                 250                 255

Asp Gln Ala Gly Asp Lys Leu Leu Leu Pro Val Asp Ser Val Val Ala
            260                 265                 270

Pro Glu Phe Ser Asn Asp Ala Pro His Lys Val Val Glu Gly Asp Ile
            275                 280                 285

Pro Asp Gly Tyr Met Ala Leu Asp Ile Gly Pro Lys Thr Ile Gln Glu
            290                 295                 300

Phe Lys Asp Ala Leu Lys Gly Ala Lys Thr Val Val Trp Asn Gly Pro
305                 310                 315                 320

Met Gly Val Phe Glu Met Ser Asn Tyr Ala Glu Gly Thr Leu Glu Val
                325                 330                 335

Gly Arg Ala Leu Gly Asp Leu Lys Asp Ala Thr Thr Ile Ile Gly Gly
            340                 345                 350

Gly Asp Ser Thr Ala Ala Lys Gln Leu Gly Ile Ala Pro Lys Ile
            355                 360                 365

Thr His Ile Ser Thr Gly Gly Ala Ser Leu Glu Tyr Leu Glu Gly
            370                 375                 380

Lys Thr Leu Pro Gly Ile Ala Ala Ile Ser Asp Lys
385                 390                 395

<210> SEQ ID NO 65
<211> LENGTH: 340
<212> TYPE: PRT
<213> ORGANISM: Lactobacillus rhamnosus

<400> SEQUENCE: 65

Met Thr Val Lys Ile Gly Ile Asn Gly Phe Gly Arg Ile Gly Arg Leu
  1               5                  10                  15

```
Ala Phe Arg Arg Ile Tyr Glu Leu Gly Ala Lys Ser Asn Asp Ile Gln
            20                  25                  30

Val Val Ala Ile Asn Asp Leu Thr Ser Pro Thr Met Leu Ala His Leu
        35                  40                  45

Leu Lys Tyr Asp Ser Thr His Gly Thr Phe Pro Gly Glu Val Ser Ala
    50                  55                  60

Thr Asp Asn Gly Ile Val Val Asp Gly Lys Glu Tyr Arg Val Tyr Ala
65                  70                  75                  80

Glu Pro Gln Ala Gln Asn Ile Pro Trp Val Lys Asn Asp Gly Val Asp
                85                  90                  95

Tyr Val Leu Glu Cys Thr Gly Phe Tyr Thr Ser Ala Glu Lys Ser Gln
            100                 105                 110

Ala His Leu Asp Ala Gly Ala Lys Arg Val Leu Ile Ser Ala Pro Ala
        115                 120                 125

Gly Lys Ile Lys Thr Ile Val Tyr Asn Val Asn Asp Asp Thr Leu Asn
    130                 135                 140

Ala Asp Asp Lys Ile Val Ser Ala Gly Ser Cys Thr Thr Asn Cys Leu
145                 150                 155                 160

Ala Pro Met Ala Tyr Phe Leu Asn Gln Glu Phe Gly Ile Glu Val Gly
                165                 170                 175

Thr Met Thr Thr Val His Ala Tyr Thr Ser Thr Gln Met Leu Leu Asp
            180                 185                 190

Gly Pro Val Arg Gly Gly Asn Leu Arg Ala Ala Arg Ser Ala Ala Ala
        195                 200                 205

Asn Thr Ile Pro His Ser Thr Gly Ala Ala Lys Ala Ile Gly Leu Val
    210                 215                 220

Ile Pro Glu Leu Asn Gly Lys Leu Gln Gly His Ala Gln Arg Val Ser
225                 230                 235                 240

Val Val Asp Gly Ser Leu Thr Glu Leu Val Ser Ile Leu Lys Thr Lys
                245                 250                 255

Asn Val Thr Ala Asp Gln Val Asn Glu Ala Ile Lys Lys His Thr Glu
            260                 265                 270

Asn Asn Pro Ser Phe Gly Trp Asn Glu Asp Glu Ile Val Ser Ser Asp
        275                 280                 285

Val Ile Gly Thr Thr Tyr Gly Ser Ile Phe Asp Pro Thr Gln Thr Glu
    290                 295                 300

Val Thr Thr Ala Gly Asp Tyr Gln Leu Val Lys Thr Val Ala Trp Tyr
305                 310                 315                 320

Asp Asn Glu Tyr Gly Phe Thr Cys Gln Met Ile Arg Thr Leu Leu Lys
                325                 330                 335

Phe Ala Thr Leu
            340

<210> SEQ ID NO 66
<211> LENGTH: 318
<212> TYPE: PRT
<213> ORGANISM: Lactobacillus rhamnosus

<400> SEQUENCE: 66

Met Ser Asn Leu Pro Lys Arg Tyr Asp Arg Ala Thr Leu Val Lys Ile
1               5                   10                  15

Ser Asp Leu Tyr Tyr Met His Gly Leu Thr Gln Gln Glu Ile Ser Asn
            20                  25                  30

Ile Ala His Ile His Arg Thr Glu Ile Ser Arg Ile Leu Lys Ala Ala
        35                  40                  45
```

-continued

```
Arg Asp Glu Gly Val Val Ser Ile Ala Ile Asn Pro Glu Thr Thr Ala
 50                  55                  60
Val Ser Gln Leu Ile Asp Phe Phe Lys Gln Lys Tyr Asn Leu Arg Glu
 65                  70                  75                  80
Ala Val Ile Val Pro Ala Ser Glu Asn Gly Asn Glu Leu Asn Ala
                 85                  90                  95
Leu Ser Val Tyr Ala Ser Met Phe Leu Ser Arg Ile Ile Lys Ser Gly
                100                 105                 110
Asp Val Ile Gly Leu Ser Trp Gly Ser Thr Leu Ser Val Ile Ser
                115                 120                 125
Gln Phe Pro Thr Asp Lys Gly Leu Arg Asp Ile Lys Val Val Pro Leu
    130                 135                 140
Val Gly Gly Pro Met Gly Arg Ile Pro Ser Asn Tyr His Val Ser Tyr
145                 150                 155                 160
Leu Thr His Arg Leu Ala Asn Arg Leu Asn Gly Thr Ala Phe Val Leu
                165                 170                 175
Asp Ser Pro Ala Phe Val Arg Ser Lys Ala Leu Arg Lys Glu Leu Leu
                180                 185                 190
Ala Asn Pro Asn Thr Gln Glu Ile Leu Gly Leu Trp Asn Arg Val Asn
            195                 200                 205
Ile Ala Ile Phe Gly Ile Gly Ser Ser Leu Ile Thr Asp Ser Pro Asp
    210                 215                 220
Trp Gln Ala Phe Tyr Glu Asn Thr Asn Phe Lys Ser Tyr Phe Ser Ala
225                 230                 235                 240
Asp Met Val Gly Asp Ile Leu Ser His Pro Phe Asp Lys Asp Gly Lys
                245                 250                 255
Leu Ala Arg Asp Ile Asp Ser Ile Leu Val Ala Phe Pro Phe Ser Ala
                260                 265                 270
Leu Arg Lys Val Pro His Ser Val Gly Ile Ala Phe Gly Glu Glu Lys
            275                 280                 285
Val Asn Ala Ile Leu Ala Ala Leu Arg Gly Gly Leu Leu Asn Thr Leu
    290                 295                 300
Ile Thr Thr Glu Ala Thr Ala Lys Ala Ile Lys Glu Leu Ser
305                 310                 315

<210> SEQ ID NO 67
<211> LENGTH: 282
<212> TYPE: PRT
<213> ORGANISM: Lactobacillus rhamnosus

<400> SEQUENCE: 67

Met Pro Glu Leu Pro Glu Val Glu Thr Val Arg Arg Ser Leu Leu Pro
  1               5                  10                  15
Leu Val Lys Asn Lys Ile Thr Ala Ile Ser Thr Asn Trp Glu Lys
                 20                  25                  30
Ile Leu Ile Asn Gly Leu Ala Thr Phe Gln Lys Gln Val Val Gly Ala
             35                  40                  45
Ala Val Asn Thr Ile Asp Arg Arg Gly Lys Tyr Leu Leu Ile Arg Leu
 50                  55                  60
Asn Asn Gly Met Thr Ile Val Ser His Leu Arg Met Glu Gly Arg Tyr
 65                  70                  75                  80
Tyr Val Val Ser Asp Ala Lys Thr Pro Leu Asp Lys His Asp His Val
                 85                  90                  95
Thr Phe Thr Phe Gln Asp Gly Ser Gln Leu Arg Tyr Arg Asp Leu Arg
```

-continued

```
                100                 105                 110
Lys Phe Gly Arg Met Arg Leu Ile His Thr Gly Gln Glu Gln Leu Val
            115                 120                 125

Pro Ala Leu Ala Lys Leu Gly Pro Glu Pro Thr Ala Ala Thr Phe Ser
130                 135                 140

Glu Ser Asp Phe Ala Gln Lys Leu Lys Arg His His Lys Ala Ile Lys
145                 150                 155                 160

Ser Val Leu Leu Asp Gln Thr Val Val Ala Gly Ile Gly Asn Ile Tyr
                165                 170                 175

Ala Asp Glu Val Leu Trp Leu Ser Lys Leu Asn Pro Leu Gln Pro Ala
            180                 185                 190

Asn Thr Leu Thr Lys Ala Glu Val His Thr Leu His Asp Ala Ile Ile
                195                 200                 205

Lys Glu Leu Asp Asp Ala Ile Ala Ala Gly Gly Thr Ser Ala His Thr
            210                 215                 220

Tyr Val Asp Ala Lys Gly Asn Arg Gly Ser Phe Gln Asp Ala Leu His
225                 230                 235                 240

Val Tyr Asp Arg Glu Gly Thr Pro Cys Asp Arg Cys Gly Thr Thr Ile
                245                 250                 255

Val Lys Ile Lys Val Gly Gln Arg Gly Thr His Tyr Cys Pro His Cys
            260                 265                 270

Gln Pro Leu Arg Arg Arg Gly Gln Leu Ala
            275                 280
```

<210> SEQ ID NO 68
<211> LENGTH: 1741
<212> TYPE: PRT
<213> ORGANISM: Lactobacillus rhamnosus

<400> SEQUENCE: 68

```
Met Pro Ala Lys Thr Gln Gly Phe Asn Phe Asp Trp Ser Leu Lys Gly
1               5                   10                  15

Gln Asp Gly Val Thr Tyr Thr Gly His Tyr Ile Val His Leu Asp Asp
                20                  25                  30

Pro Val Ile Arg Ala His Asp Ile Ser Leu Phe Thr Gly Gln Val Trp
            35                  40                  45

Lys Pro Glu Leu Asn Phe Glu Asn Ala Ile Lys Ser Asp Gly Thr Glu
        50                  55                  60

Val Pro Leu Ser Glu Leu Thr Trp Ser Val Thr Asp Glu Lys Gly Asn
65                  70                  75                  80

Val Val Ala Ser Lys Asp Lys Asn Gly Val Val Thr Gly His Val Asp
                85                  90                  95

Asn Ser Gln Pro Thr Thr Tyr Val Val Thr Tyr Thr Tyr Gly Ala Glu
            100                 105                 110

Ser Gly Ser Ala Lys Ile Asn Tyr Lys Gln Arg Leu Ala Ala Ser Tyr
        115                 120                 125

Ala Leu Thr Gly Thr Gln Thr Val Thr Ala Thr Gly Ser Pro Ile Thr
130                 135                 140

Val Asp Val Ser Gln Phe Ala Leu Ser Leu Gly Asp Gly Phe Asp Ala
145                 150                 155                 160

Gly Lys Leu Glu Leu Ser Asp Leu Asn Phe Phe Asp Ala Asp Gly Lys
                165                 170                 175

Pro Val Ala Ala Asp Ala Leu Ile Lys Thr Gly Val Tyr Ser Val Glu
            180                 185                 190
```

-continued

```
Leu Ser Glu Ala Ala Trp Ala Arg Ile Ala Lys Leu Thr Asn Asp Glu
        195                 200                 205

Gly Gln Ser Ala Ala Gly Tyr Asp Phe Thr Gly Thr Ser Thr Ala Gln
    210                 215                 220

Leu Ile Ile Gly Leu Thr Ala Thr Gly His Leu Ser Asp Ser Gly Phe
225                 230                 235                 240

Val Tyr Asp Gly Lys Thr Thr Ala Ser Gln Ser Lys Asp Leu Ala Val
                245                 250                 255

Thr Val Thr Leu Ser Asp Gly Thr Gln Lys Glu Met Asn Leu Thr Ser
            260                 265                 270

Glu Asp Phe Ser Leu Val Glu Lys Asp Ser Ala Asn Val Gly Thr Tyr
        275                 280                 285

His Tyr Leu Leu Asn Ser Val Gly Phe Ala Arg Leu Gln Ala Leu Leu
    290                 295                 300

Gly Asp Thr Val Thr Ile Asp Gln Thr Ala Ile Asn Gln Asn Ser Gly
305                 310                 315                 320

Lys Ile Thr Ile Thr Pro Ala Pro Ala Thr Val Asn Ser Asn Ser Thr
                325                 330                 335

Asp Phe Glu Tyr Asp Gly Lys Thr Lys Ala Ser Glu Ala Lys Gly Ile
            340                 345                 350

Gln Ala Thr Val Lys Leu Gly Glu Thr Gly Lys Thr Ile Asp Leu Thr
        355                 360                 365

Ser Ala Asp Ile Val Val Glu Asn Asp Gly Val Asp Ala Gly Lys Tyr
    370                 375                 380

Ser Tyr Glu Leu Ser Asp Ala Gly Lys Ala Lys Leu Gln Ala Ala Thr
385                 390                 395                 400

Gly Asn Asn Tyr Gln Leu Thr Ala Asp Leu Ala Lys Val Thr Gly
                405                 410                 415

Ala Ile Thr Ile Thr Pro Ala Thr Thr Ser Val Asp Ser Asn Asp Val
            420                 425                 430

Ser Phe Glu Tyr Asp Gly Lys Thr Lys Ala Ser Glu Ala Ala Gly Ile
        435                 440                 445

Gln Ala Thr Ile Lys Leu Asp Thr Gly Lys Val Val Asp Leu Thr Ala
    450                 455                 460

Ala Asp Ile Ile Val Thr Asn Asp Asp Val Asn Ala Gly Gln Tyr Ser
465                 470                 475                 480

Tyr Gln Leu Ser Asp Ala Gly Lys Ala Lys Leu Gln Ala Ala Thr Gly
                485                 490                 495

Asn Asn Tyr Gln Leu Thr Ala Asp Asp Leu Ala Lys Val Ala Gly Thr
            500                 505                 510

Ile Thr Ile Thr Pro Ala Val Thr Thr Val Asp Ser Ser Asp Val Ser
        515                 520                 525

Phe Glu Tyr Asp Gly Lys Thr Lys Ala Ser Glu Ala Lys Gly Ile Gln
    530                 535                 540

Ala Thr Ile Lys Leu Asp Thr Gly Lys Val Val Asp Leu Thr Ala Ala
545                 550                 555                 560

Asp Ile Ile Val Thr Asn Asp Asp Val Asn Ala Gly Gln Tyr Ser Tyr
                565                 570                 575

Gln Leu Ser Asp Ala Gly Lys Ala Lys Leu Gln Ala Ala Thr Gly Asn
            580                 585                 590

Asn Tyr Gln Leu Thr Ala Asp Asp Leu Ala Lys Val Met Gly Thr Ile
        595                 600                 605

Thr Ile Thr Pro Ala Ala Val Thr Ala Asp Ser Asn Asp Leu Ser Phe
```

```
              610                 615                 620
Glu Tyr Asp Gly Lys Thr Lys Ala Ser Glu Ala Lys Gly Ile Gln Ala
625                 630                 635                 640

Met Val Lys Leu Gly Glu Thr Glu Lys Thr Val Asp Leu Thr Ser Ala
                645                 650                 655

Asp Ile Val Val Ala Asn Asp Val Asn Ala Gly Gln Tyr Ser Tyr
                660                 665                 670

Gln Leu Ser Asp Ala Gly Lys Ala Lys Leu Gln Ala Thr Gly Asn
        675                 680                 685

Asn Tyr Gln Leu Thr Ala Asp Gly Leu Ala Lys Val Ala Gly Thr Ile
690                 695                 700

Thr Ile Thr Pro Ala Thr Thr Ala Asp Ser Asn Asp Val Ser Phe
705                 710                 715                 720

Glu Tyr Asp Gly Lys Thr Lys Ala Ser Glu Ala Lys Gly Ile Gln Ala
                725                 730                 735

Thr Ile Lys Leu Gly Glu Ile Glu Lys Thr Val Asp Leu Ser Ser Ala
                740                 745                 750

Asp Ile Ile Val Ala Asn Asp Gly Val Ile Val Gly Lys Tyr Thr Tyr
            755                 760                 765

Ser Leu Ser Asp Ser Gly Lys Ser Lys Leu Gln Ala Ala Thr Gly Ser
770                 775                 780

Asn Tyr Gln Leu Thr Thr Glu Val Leu Asp Lys Val Ser Gly Ser Ile
785                 790                 795                 800

Thr Ile Thr Pro Ala Gly Ala Ile Ala Thr Gly Lys Asp Ala His Phe
                805                 810                 815

Glu Tyr Asp Gly Lys Thr Lys Ala Ser Glu Ala Lys Gly Ile Gln Ala
                820                 825                 830

Ile Leu Thr Ile Asp Gly Thr Glu Lys Thr Val Asp Leu Thr Ala Ala
            835                 840                 845

Asp Ile Val Val Ala Glu Asp Gly Val Asp Ala Gly Lys Tyr Ser Tyr
850                 855                 860

Arg Leu Ser Asp Ala Gly Lys Ser Lys Leu Gln Arg Glu Ala Gly Ser
865                 870                 875                 880

Asp His Gln Leu Thr Ala Asp Leu Ala Glu Val Thr Gly Thr Ile
        885                 890                 895

Thr Ile Thr Pro Ala Ile Ala Thr Ala Asp Ser Asn Asp Val Ser Phe
                900                 905                 910

Glu Tyr Asn Gly Lys Thr Lys Ala Ser Glu Ala Glu Gly Ile Gln Ala
        915                 920                 925

Thr Val Met Leu Gly Glu Ser Gly Gln Val Val Ala Leu Thr Ser Ala
        930                 935                 940

Asp Val Val Val Asn Asp Gly Val Asp Ala Gly Lys Tyr Ser Tyr
945                 950                 955                 960

Gln Leu Ser Asp Ala Gly Lys Ala Lys Leu Gln Ala Ala Thr Gly Asn
            965                 970                 975

Asn Tyr Gln Leu Thr Ala Asp Asp Leu Asp Lys Val Thr Gly Thr Ile
                980                 985                 990

Thr Ile Thr Pro Ala Thr Thr Val Asp Ser Asn Asp Val Ser Phe
                995                 1000                1005

Glu Tyr Asp Gly Lys Thr Lys Ala Gly Glu Ala Lys Gly Ile Gln Val
            1010                1015                1020

Thr Val Lys Leu Gly Glu Thr Glu Lys Thr Val Asp Leu Thr Ser Ala
1025                1030                1035                1040
```

```
Asp Ile Val Val Ala Asn Asp Val Asn Ala Gly Gln Tyr Ser Tyr
            1045                1050                1055

Gln Leu Ser Asp Ala Gly Lys Ala Lys Leu Gln Ala Ala Thr Gly Asn
        1060                1065                1070

Asn Tyr Gln Leu Thr Ala Asp Asp Leu Ala Lys Val Thr Gly Thr Ile
        1075                1080                1085

Thr Ile Thr Pro Ala Val Thr Thr Ala Asp Ser Asn Asp Val Ser Phe
        1090                1095                1100

Glu Tyr Asp Gly Lys Thr Lys Ala Ser Glu Ala Lys Gly Ile Gln Val
1105                1110                1115                1120

Ile Val Lys Leu Gly Glu Thr Glu Lys Thr Val Asp Leu Thr Ser Ala
            1125                1130                1135

Asp Ile Val Val Ala Asn Asp Val Asn Ala Gly His Tyr Ser Tyr
            1140                1145                1150

Gln Leu Ser Asp Ala Gly Lys Ala Lys Leu Gln Ala Ala Thr Gly Asn
        1155                1160                1165

Asn Tyr Gln Leu Thr Ala Asp Asp Leu Ala Lys Ile Thr Gly Thr Ile
        1170                1175                1180

Thr Ile Thr Pro Ala Val Ala Thr Ala Asp Ser Asn Asn Val Ser Phe
1185                1190                1195                1200

Glu Tyr Asn Gly Lys Thr Lys Ala Ser Glu Ala Arg Gly Ile Gln Ala
            1205                1210                1215

Thr Val Lys Leu Gly Glu Asn Gly Lys Thr Val Ala Leu Thr Ala Ala
            1220                1225                1230

Asp Ile Val Val Asn Asp Gly Val Asn Ala Gly Gln Tyr Asp Tyr
            1235                1240                1245

Lys Leu Ser Ala Ala Gly Met Thr Lys Leu Arg Gln Ala Thr Gly Thr
        1250                1255                1260

Asn Tyr Gln Phe Lys Lys Glu Asp Leu Thr Lys Leu Gly Gly Thr Val
1265                1270                1275                1280

Thr Ile Thr Pro Ala Thr Ala Leu Ala Asp Leu Asn Asp Val Ser Phe
            1285                1290                1295

Ser Tyr Asp Gly Gln Thr Lys Ala Ser Gln Ala His Asp Leu Thr Ala
        1300                1305                1310

Asn Ile Lys Leu Gly Thr Lys Val Val Ser Val His Leu Asn Ala Thr
        1315                1320                1325

Asp Ile Leu Val Thr Asp Asp Gly Val Gly Val Gly Gln Tyr Gln Tyr
        1330                1335                1340

Lys Leu Asp Ala Asn Gly Ile Ala Lys Leu Arg Gln Ala Ser Gly Asp
1345                1350                1355                1360

Asn Tyr Gln Phe Asp Ala Lys Val Leu Ala Gly Leu Thr Gly Thr Ile
            1365                1370                1375

Thr Ile Lys Pro Val Thr Gly Ala Val Thr Val Asn Asp Thr Ser Phe
        1380                1385                1390

Val Tyr Asp Gly His Thr Lys Ala Ser Ala Ala Ala Gly Leu Gln Ala
        1395                1400                1405

Ser Leu Tyr Leu Pro Gln Ala Glu Ala Lys Ala Thr Ile Gln Leu Thr
        1410                1415                1420

Arg Glu Asp Ile Leu Val Thr Asn Asp Gly Thr Ala Ala Gly Thr Tyr
1425                1430                1435                1440

Arg Tyr Arg Leu Ser Gln Thr Gly Ile Ala Lys Leu Gln Lys Ala Val
            1445                1450                1455
```

```
Gly Lys Asn Tyr Glu Leu Asp Gln Asp Glu Leu Ala Gly Leu Thr Gly
            1460                1465                1470

Thr Ile Thr Ile Thr Pro Leu Thr Val Asn Ala Thr Val Asn His Gly
        1475                1480                1485

Gln Phe Gln Tyr Asn Gly Val Thr Arg Ala Ser Gln Ala Gly Gly Leu
    1490                1495                1500

Ala Ile Thr Val Gln Leu Pro Glu Lys Ser Gln Lys Ile Ala Leu Thr
1505                1510                1515                1520

Asn Thr Asp Ile Ala Val Glu Asn Asp Ser Val Asn Val Gly Thr Tyr
            1525                1530                1535

Thr Tyr His Leu Thr Ala Ser Gly Leu Ala Lys Leu Ala Val Ala Ile
        1540                1545                1550

Gly Pro Asn Tyr Gln Val Thr Asp Gln Thr Phe Ser Gly Thr Ile Thr
    1555                1560                1565

Ile Thr Pro Ala Pro Ile Ser Ala Thr Leu Ser Gly Leu Gln Lys Lys
1570                1575                1580

Thr Tyr Asp Gly Gln Pro Gly Ala Leu Asn Asp Asp Tyr Tyr Arg Leu
1585                1590                1595                1600

Val Leu Gly Asp Gly Thr Glu Ile Gln Leu Gln Ala Gly Asp Leu Ile
            1605                1610                1615

Phe Val Asp Gly Gln Ala Pro Val Asn Pro Gly Ser Tyr Ala Val Ala
        1620                1625                1630

Leu Ser Thr Ser Gly Leu Gln Arg Ile Lys Ala Ser Leu Pro Asn Asn
    1635                1640                1645

Leu Leu Lys Asn Val Asn Thr Gln Gln Ala Ile Phe Glu Ile Val Ala
    1650                1655                1660

Leu Pro Ser Pro Asp Pro Gly Thr Gly Thr Thr Pro Asp Thr Pro Asp
1665                1670                1675                1680

His His Leu Pro Asn Thr Gly Thr Gly Thr Gln Gln Ser Glu Ile Ser
            1685                1690                1695

Thr His Asn Gly Thr Lys His Arg Leu Pro Gln Thr Gly Asp Thr Gln
        1700                1705                1710

Ser Gln Thr Leu Ser Leu Met Gly Leu Leu Ala Thr Met Ser Gly
    1715                1720                1725

Leu Phe Gly Leu Ala Gly Arg Lys Arg Lys Ala His Arg
    1730                1735                1740

<210> SEQ ID NO 69
<211> LENGTH: 1463
<212> TYPE: PRT
<213> ORGANISM: Lactobacillus rhamnosus

<400> SEQUENCE: 69

Val Arg Ala Met Val Lys Pro Lys Gln Ala Gly Ala Asn Val Ala Thr
1               5                   10                  15

Thr Thr Asn Ser Lys Ile Gly Gly Ser Gln Ser Ser Ala Lys Ala Ala
            20                  25                  30

Ser Ala Phe Lys Ser Ser Ala Ser Val Glu Ser Gly Gln Ile Lys
        35                  40                  45

Ser Thr Ser Leu Ala Ser Ala Gly Ser Asn Gly Glu Lys Ala Thr Ser
    50                  55                  60

Ala Leu Ser Ser Ala Val Asp Ala Ser Asp Gly Arg Ala Ser Gln
65                  70                  75                  80

Gly Val Gly Gly Thr Ser Ser Gly Ser Ser Asp Thr Ser Gln Ala
            85                  90                  95
```

-continued

```
Asn Glu Gly Asn Ser Ala Ala Ser Val Thr Ser Ala Ser Ala Asn Ser
            100                 105                 110
Ala Ser Ala Thr Asn Thr Ser Glu Gly Gln Thr Pro Val Asn Glu Ala
        115                 120                 125
Val Ser Asn Asp Ala Ser Ser Ala Asp Val Ser Thr Ala Ser Glu Phe
    130                 135                 140
Asp Ala Ala Met Ala Asp Ser Thr Val Ser Val Ile Asn Val Gln Ser
145                 150                 155                 160
Asp Phe Val Met Asp Val Ser Gly Asp Arg Gln Ser Tyr Ala Tyr Arg
                165                 170                 175
Pro Asn Leu Ile Ile Asn Gly Asn Asn His Thr Ile Asp Phe Gln Lys
            180                 185                 190
Lys Tyr Phe Glu Ala Asp Pro Thr Ser Ser Gln Asn Glu Ser Phe Thr
        195                 200                 205
Ile Asn Asp Leu Asn Met Tyr Gly Tyr Ser Trp Trp Gly Pro Val Thr
    210                 215                 220
Ile Lys Gly Ser Lys Pro Lys Asp Gly Ile Asp His Ser Val Val Phe
225                 230                 235                 240
Asn Asn Val Thr Tyr Thr Gly Ala Gln Leu Met Tyr Gly Ile Tyr Thr
                245                 250                 255
Lys Ala Phe Ile Lys Gly Asn Thr Lys Ile Gln Ser Val Gly Ser Tyr
            260                 265                 270
Val Ser Pro Leu Asp Gly Ser Thr Gln Thr Thr Gln Gly Leu Gly Asn
        275                 280                 285
Gln Gln Asn Phe Gln Ile Ser Tyr Leu Glu Val Leu Pro Gly Ala Thr
    290                 295                 300
Tyr Thr Gly Thr Thr Thr Gly Gly Thr Asn Val Glu Val Tyr Asp Gly
305                 310                 315                 320
Gly Ser Phe Ile Val Asp Lys Gly Ala Thr Val Asn Leu Gln Arg Thr
                325                 330                 335
Asp Ala Ser Lys Ser Asn Glu Arg Gly Thr Asn Ala Leu Ile Asp Thr
            340                 345                 350
Gln Gly Gly Asn Val Glu Phe Lys Asp Gly Ser Thr Val Ile Leu Asn
        355                 360                 365
Lys Asn Ala Leu Val Lys Asp Gly Phe Ala Pro Ile Tyr Ile Glu Asp
    370                 375                 380
Gly Gly Asn Leu Thr Val Asp Lys Asn Ala Thr Val Ser Ile Thr Gly
385                 390                 395                 400
Ala Thr Gly Asn Ile Pro Val Arg Ile Asp Gly Thr Gly Thr Val Asn
                405                 410                 415
Leu Asn Glu Gly Ser His Met Thr Ile Thr Gln Asn Gly Ala Pro Lys
            420                 425                 430
Leu Gly Tyr Gly Phe Ile Asn Ile Lys Gly Thr Gly Gly Phe Val
        435                 440                 445
Ala Ser Gly Ser Thr Leu Asp Leu Asn Val Thr Gly Thr Gly Thr Lys
    450                 455                 460
Ser Val Asn Ala Ile Asn Val Ala Asn Asp Gly Gln Leu Ser Phe Ala
465                 470                 475                 480
Gln Asp Ala Thr Ala Asn Leu Thr Ile Asp Gly Thr Gly Thr Gly Glu Ala
                485                 490                 495
His Leu Leu Lys Val Gly Asp Asp Ala Asn Ile Asn Ile Tyr Met Pro
            500                 505                 510
```

-continued

```
Lys Ser Val Leu Phe Lys Ile Thr Asp Asn Asp Asp Ala Asp Ser Ser
            515                 520                 525

Leu Phe Lys Val Ser Gly Thr Gly Thr Leu Thr Gly Gln Tyr Val Lys
        530                 535                 540

Ile Ile Pro Asp Asp Gly Asn Ala Tyr Gly Pro Tyr Lys Ser Ala Ile
545                 550                 555                 560

Tyr Thr Leu Lys Gly Asn Gly Ser Ser Asp Thr Ala Thr Val Glu
            565                 570                 575

Gly Glu Thr Ala Glu Asp Glu Gln Ser Gly Lys Ala Leu Ala Asp Thr
            580                 585                 590

Phe Ala Thr Asp Lys Ser Leu Glu Phe Val Ser Ala Ser Asp Asn Phe
            595                 600                 605

Ile Lys Val Asn Pro Val Thr Asp Glu Thr Thr Thr Leu Thr Gly Lys
            610                 615                 620

Thr Thr Ala Gly Ala Tyr Val Thr Ile Ser Gly Leu Lys Gly Ile Pro
625                 630                 635                 640

Glu Gly Ser Leu Thr Ala Asn Ser Tyr Asp Ser Thr Lys Tyr Leu Val
            645                 650                 655

Gln Ala Asp Lys Asp Gly Asn Trp Ser Tyr Glu Leu Pro Thr Gly Val
            660                 665                 670

Ser Leu Pro Ala Asn Ala Ser Phe Glu Val Ile Ser Ala Gly Phe
            675                 680                 685

Ile Val Lys Thr Ala Thr Val Val Ile Asn Asp Ala Glu Thr Pro Lys
            690                 695                 700

Gln Ala Ser Ser Ala Ala Gly Ser Leu Ile Asn Ala Asn Ser Ala Ala
705                 710                 715                 720

Asp Val Thr Ala Ser Gln Ala Lys Ala Thr Ser Ala Ala Ala Ser Asp
            725                 730                 735

Ala Ala Ser Tyr Ala Ser Glu Ala Gln Ser Ile Ala Gly Ser His Ala
            740                 745                 750

Asp Asn Met Glu Ile Lys Ser Leu Ala Ser Asp Ala Glu Lys Gln Ser
            755                 760                 765

Gln Ile Ala Leu Ala Ala Ser Lys Ser Ala Ala Ser Ser Ser Ala
            770                 775                 780

Ala Ala Ser Ala Ala Ile Val Ala Ser Ser Ala Ala Ser Glu Ala Ser
785                 790                 795                 800

Ser Ala Ala Ala Val Ser Asn Ala Asp Ala Ser Ala Asn Ser Ala
            805                 810                 815

Ala Ala Ala Tyr Asp Ser Tyr Ala Ser Glu Ala Ser Ala Ala Ser Ala
            820                 825                 830

Ala Asn Asp Ser Ser Gly Tyr Ala Thr Ala Ser Phe Ala Ala Ser Ser
            835                 840                 845

Ala Ala Ala Ala Met Ser Ala Ala Leu Ser Thr Ala Gln Val Ala Ala
            850                 855                 860

Lys Val Ala Val Ser Asp Ala Ala Ala Gly Ser Ala Ala Ala Val
865                 870                 875                 880

Ala Ser Ala Ala Gln Ser Asp Ser Lys Asn Lys Gln Ala Thr Ala Ala
            885                 890                 895

Thr Ala Arg Ser Gln Ala Leu Asp Asp Leu Asn Lys Ile Lys Ser Leu
            900                 905                 910

Thr Asp Tyr Ala Ser Gly Ala Ser Ser Ala Ser Glu Ala Gly Gln
            915                 920                 925

Ala Ser Thr Ala Thr Ser Ala Tyr Ala Ser Ala Ala Ser Ser Ser Ala
```

-continued

```
                930                 935                 940
Ser Glu Ala Gly Ser Tyr Ala His Gln Ala Gly Ser Ala Ser Asp
945                 950                 955                 960

Ala Val Gly Gln Ser Gly Ser Ala Ala Gln His Ala Ser Thr Ala Ala
                965                 970                 975

Ser Ala Ala Ser Ser Tyr Pro Lys Asp Ser Gly Ile Gln Ser Leu Ala
                980                 985                 990

Ser Gln Ala Ala Ser Glu Ala Ala Lys Ala Ser Ser Asn Ala Ser Ala
                995                 1000                1005

Ala Thr Ser Ala Ala Ala Val Gly Phe Ser Ala Ala Ser Asp Ala Ser
        1010                1015                1020

Glu Gln Ala Lys Thr Ala Ala Ser Ala Asp Val Val Ala Ser Ser Ala
1025                1030                1035                1040

Ala Ser Thr Ala Asn Ser Asn Ala Ser Ala Ala Ala Ser Ala Thr Lys
        1045                1050                1055

Ala Gly Asp Ser Lys Ala Ala Gly Phe Ser Ala Ala Ser Ala
        1060                1065                1070

Ala Ala Ser Ser Ala Lys Gly Ala Glu Ala Val Ala Ser Glu Ala Ala
        1075                1080                1085

Ser Ala Ala Ala Ser Asp Asp Ser Val Ala Ser Ala Ala Ser Ala
        1090                1095                1100

Ala Ala Gly Phe Asp Lys Ala Ala Ser Ala Ala Glu Gly Ala Ala Ser
1105                1110                1115                1120

Ser Ala Ala Ser Ala Ala Ala Ser Ala Ala Ala Gln Gly Thr Arg
        1125                1130                1135

Gly Gly Ala Ser Ser Ser Ala Ser Glu Ala Gly Gln Ala Ser Thr Ala
        1140                1145                1150

Thr Ser Val Tyr Ala Ser Ala Ser Ser Ala Ser Glu Ala Gly
        1155                1160                1165

Ser Tyr Ala His Gln Ala Gly Ser Ser Ala Glu Ala Thr Gly His
        1170                1175                1180

Ala Ser Ser Ala Thr Ser Gln Ala Ser Ala Ser Ser Ala Ala Ser
1185                1190                1195                1200

Arg Tyr Pro Ser Asp Ser Gly Ile Gln Ser Asp Val Ser Ile Ala Ser
        1205                1210                1215

Ser Ala Ala Ser Thr Ala Ser Ser Ala Ala Ser Ala Ala Gln Ser Glu
        1220                1225                1230

Ala Ser Thr Ala Ser Ser Ala Ala Ser His Ala Ser Glu Gln Ala Ser
        1235                1240                1245

Ile Ala Ser Ser Glu Asp Val Val Ser Ser Ala Ala Ser Val Ala
        1250                1255                1260

Ser Ser Ala Ala Ser Ala Ala Ser Ser Ala Ala Lys Ala Gly Asn Ser
1265                1270                1275                1280

Ser Ala Ala Gly Ile Tyr Ser His Ala Ala Ser Ala Ala Ala Ser Ser
        1285                1290                1295

Ala Lys Ser Ala Glu Ser Gln Ala Ser Ser Ala Ser Ala Ala Ala
        1300                1305                1310

Ser Asp Asp Ser Val Ala Ser Ser Ala Ala Ser Ala Ala Leu Ser Asp
        1315                1320                1325

Asp Ala Lys Ala Ser Ser Ala Ala Asp Val Ala Ser Ser Ala Thr Thr
        1330                1335                1340

Ala Ala Ile Ser Ser Ala Thr Ser Leu Ala Asp Gln Ser Ala Thr Gly
1345                1350                1355                1360
```

-continued

```
Ser Thr Ala Gly Ser His Ile Leu Pro Ser Thr Gly Glu Thr Thr
            1365                1370                1375

Gly Ser Ile Pro Ser Gly Gln Thr Pro Thr Gln Thr Lys Pro Thr Gln
        1380                1385                1390

Thr Lys Pro Thr Gln Thr Lys Pro Thr Gln Ala Gly Gln Thr Thr Gln
        1395                1400                1405

Thr Gly Ser Leu Pro Gln Thr Asp His Ala Gly Arg His Met Leu Pro
        1410                1415                1420

Gln Thr Gly Asp Asp Ala Glu Ser Gly Thr Ser Val Leu Gly Leu Leu
1425                1430                1435                1440

Ile Val Ser Leu Met Gly Leu Phe Gly Leu Ala Gly Thr Arg His Gln
            1445                1450                1455

Lys Asp Asn Lys Pro Ser Lys
            1460

<210> SEQ ID NO 70
<211> LENGTH: 1879
<212> TYPE: PRT
<213> ORGANISM: Lactobacillus rhamnosus

<400> SEQUENCE: 70

Met Gln Ala His Lys Ile Met Pro Glu Asp Trp Ile Ala Val Arg Met
1               5                   10                  15

Glu Thr Asn Arg Ile Glu Gly Lys His Pro Ile His Pro Ala Phe Arg
            20                  25                  30

Ser Thr Arg Ile Leu Glu Tyr Asn Asp Phe Gly Pro Ala Leu Asn Ala
        35                  40                  45

Lys Leu Leu Glu Ala Met Lys Lys Ala Ile Asp Asp Thr Ala Lys
    50                  55                  60

Asp Pro Lys Pro Val Gln Glu Val Lys Glu Lys Val Asp Pro Ile
65                  70                  75                  80

Thr Val Asp Glu Asp Phe Asp Lys Leu Ile Gln Glu Ile Val Leu Asn
            85                  90                  95

Ala His Lys Glu Gln Ala Lys Arg Asp Ile Asp Ala Glu Ala Ala Lys
            100                 105                 110

Val Ser Ala Glu Ile Glu Gln Asp Pro Thr Leu Thr Ala Thr Glu Lys
        115                 120                 125

Ala Lys Gln Lys Asp Gly Val Ala Ala Glu Ala Thr Lys Ala Lys Ala
130                 135                 140

Ala Ile Asp Gln Ala Gln Thr Glu Thr Gly Val Gln Gln Ala Arg Asp
145                 150                 155                 160

Ala Gly Ile Ala Ala Ile Asp Ala Gln His Gln Pro Gly Thr Gly Leu
            165                 170                 175

Asn Val Arg Arg Glu Glu Ala Lys Gln Ala Ile Asp Ala Glu Ala Ala
        180                 185                 190

Lys Val Thr Ala Glu Ile Glu Gln Asp Ser Thr Leu Ala Thr Ser Glu
        195                 200                 205

Lys Ala Ala Gln Lys Gln Gly Val Ala Asp Glu Ala Lys Ala Lys
    210                 215                 220

Thr Ala Ile Asp Gln Ala Gln Thr Ile Glu Ala Ile Asp Lys Ala Lys
225                 230                 235                 240

Asp Asp Gly Ile Lys Ala Ile Asp Ala Gln His Lys Gln Gly Ala Asp
            245                 250                 255

Phe Asp Thr Arg Lys Ala Gln Ala Lys Asp Ala Ile Asp Ala Glu Ala
```

-continued

```
                    260                 265                 270
Ala Lys Val Lys Asp Ala Ile Asp Gln Asp Pro Thr Leu Thr Ala Lys
            275                 280                 285
Asp Lys Thr Ala Gln Lys Gln Gly Val Gly Asp Glu Ala Thr Lys Ala
        290                 295                 300
Lys Thr Ala Ile Asp Gln Ala Lys Thr Ile Asp Gly Val Ile Gln Ala
305                 310                 315                 320
Lys Asp Asp Gly Ile Lys Ala Ile Asp Ala Gln His Gln Ala Gly Thr
                    325                 330                 335
Asp Leu Ala Thr Arg Lys Asp Ser Ala Lys Gln Ala Ile Asp Ala Glu
            340                 345                 350
Ala Ala Lys Ile Thr Asp Ala Ile Asn Gln Asp Asp Thr Leu Thr Ser
        355                 360                 365
Thr Glu Lys Asp Ala Gln Lys Gln Ala Val Ala Asp Glu Ala Ala Lys
    370                 375                 380
Ala Lys Ala Ala Ile Asp Gln Ala Gln Asn Ala Asp Ala Ile Leu Gln
385                 390                 395                 400
Ala Gln Ala Asp Gly Ile Lys Ala Ile Asp Ala Lys His Gln Ile Gly
                    405                 410                 415
Ala Asp Leu Asp Thr Gln Lys Thr Lys Ala Lys Gln Ala Ile Asp Lys
            420                 425                 430
Glu Ala Ala Lys Val Leu Thr Ala Ile Glu Gln Asp Pro Thr Leu Thr
        435                 440                 445
Ser Ala Glu Lys Lys Ala Gln Lys Gln Gly Val Ala Asp Glu Thr Ala
    450                 455                 460
Lys Ala Lys Thr Ala Ile Asp Ser Ala Arg Asn Ala Asp Glu Ile Ala
465                 470                 475                 480
Lys Ala Gln Ala Asp Gly Ile Lys Ala Ile Asp Ala Gln His Arg Leu
                    485                 490                 495
Gly Met Asp Leu Ala Lys Arg Lys Thr Asp Ala Gln Ala Ala Ile Asp
            500                 505                 510
Ala Glu Ala Ala Lys Val Gly Glu Ala Ile Asp Gln Asp Pro Thr Leu
        515                 520                 525
Thr Ser Gln Glu Lys Ala Ala Gln Lys Gln Thr Phe Ala Ala Glu Ala
    530                 535                 540
Thr Lys Ala Lys Asp Thr Ile Ala Lys Ala Gln Asp Ala Asp Gly Val
545                 550                 555                 560
Ile Gln Ala Glu Lys Ala Gly Ile Gln Ala Ile Asp Asp Gly His Gln
                    565                 570                 575
Ser Gly Ala Leu Leu Asp Thr Arg Lys Val Asp Ala Lys Lys Ala Ile
            580                 585                 590
Asp Ala Glu Ala Ala Lys Ile Asn Asp Ala Ile Asp Gln Asp Val Thr
        595                 600                 605
Leu Thr Ser Ala Glu Lys Ala Thr Gln Lys Gln Lys Val Thr Asp Glu
    610                 615                 620
Ala Val Lys Ala Lys Thr Ala Ile Asp Ala Lys Asn Ala Asp Thr
625                 630                 635                 640
Val Asp Gln Ala Lys Ala Ser Gly Ile Gln Ala Ile Asp Ala Val His
                    645                 650                 655
Gln Ser Gly Thr Leu Leu Asp Thr Arg Lys Gln Asp Ala Lys Lys Ala
            660                 665                 670
Ile Asp Ala Glu Ala Val Lys Val Ile Ala Ala Ile Gly Gln Asp Val
        675                 680                 685
```

-continued

```
Thr Leu Thr Gln Ala Glu Lys Leu Thr Gln Gln Ala Val Ala Asp
    690                 695                 700
Ala Ala Thr Gln Ala Lys Ala Ala Ile Asp Ala Ala Lys Asn Ala Asp
705                 710                 715                 720
Ala Val Asp Gln Ala Lys Ala Asp Gly Ile Lys Ala Ile Asp Ala Gln
                725                 730                 735
His Gln Ala Gly Leu Ala Leu Asn Glu Arg Lys Glu Ala Lys Lys
            740                 745                 750
Leu Ile Ala Glu Thr Ala Asp Lys Val Gln Ala Ile Gly Gln Asp
            755                 760                 765
Val Thr Leu Thr Ala Thr Gln Lys Ala Val Gln Arg Gln Ala Ile Thr
770                 775                 780
Val Glu Val Thr Lys Ala Asn Gln Ala Ile Asp Ala Ala Gly Asn Ala
785                 790                 795                 800
Asp Ala Val Asp Gln Ala Lys Asn Ala Gly Val Lys Ala Ile Tyr Asp
                805                 810                 815
Gln His Gln Ser Gly Gln Ala Leu Ala Asp Arg Lys Arg Asp Ala Lys
            820                 825                 830
Gln Ala Ile Asp Ala Glu Ala Ala Lys Glu Thr Ala Ala Ile Asp Gln
            835                 840                 845
Asp Ala Thr Leu Thr Ala Asn Glu Lys Ala Ser Gln Lys Gln Ala Val
            850                 855                 860
Ala Asp Glu Ala Thr Lys Ala Lys Glu Ala Ile Asp Ala Ala Lys Gln
865                 870                 875                 880
Ala Asp Ala Val Asp Gln Ala Lys Asn Asp Gly Ile Arg Ala Ile Asp
                885                 890                 895
Ala Gln His His Ala Gly Gln Ala Val Ala Asp Arg Lys Ala Ala Ala
            900                 905                 910
Lys Gln Ala Ile Asp Ala Glu Ala Ala Lys Val Thr Gly Asn Ile Asp
            915                 920                 925
Gln Asp Glu Thr Leu Thr Ala Thr Glu Lys Ala Ala Gln Lys Gln Ala
            930                 935                 940
Val Ala Thr Glu Ala Asp Asn Ala Lys Gln Ala Ile Asp Lys Gly Gln
945                 950                 955                 960
Asn Ala Asp Ala Val Asp Lys Ala Lys Thr Gly Gly Ile Lys Ala Ile
                965                 970                 975
Asp Ala Gln His Gln Ser Gly Gln Ala Ile Lys Ala Arg Gln Asn Asp
            980                 985                 990
Ala Lys Gln Ala Ile Asp Ala Glu Ala Ala Lys Val Thr Lys Ala Ile
            995                 1000                1005
Asp Gln Asp Pro Thr Leu Thr Ala Ala Glu Lys Lys Ala Gln Lys Gln
            1010                1015                1020
Ala Val Thr Asp Ala Glu Thr Lys Ala Lys Ala Ala Ile Asp Ala Thr
1025                1030                1035                1040
Leu Val Ala Asp Ala Ile Asp Gln Ala Leu Ala Asp Gly Ile Lys Thr
                1045                1050                1055
Ile Asp Ala Gln Tyr Gln Thr Gly Ile Ala Leu Asp Lys Gln Lys Ala
            1060                1065                1070
Ala Ala Lys Gln Thr Ile Asp Ala Glu Ala Ala Lys Val Ser Glu Ala
            1075                1080                1085
Ile Asp Gln Asp Val Thr Leu Thr Ala Asp Gln Lys Ala Thr Gln Lys
            1090                1095                1100
```

-continued

```
Gln Ala Val Ala Asp Glu Ala Thr Lys Ala Lys Ala Ala Ile Asp Gln
1105                1110                1115                1120

Ala Ser Asp Ala Asp Ala Val Ile Gln Ala Thr Ile Asp Gly Ile Glu
            1125                1130                1135

Ala Ile Asp Ala Gln His Gln Ser Ala Thr Ala Leu Asp Lys Gln Lys
        1140                1145                1150

Gln Gln Ala Lys Gln Ala Ile Asp Ala Glu Ala Ala Lys Val Ser Lys
    1155                1160                1165

Ala Ile Asp Gln Asp Val Thr Leu Thr Ala Thr Gln Lys Ala Asp Gln
1170                1175                1180

Lys Gln Ala Val Ile Ala Glu Ala Asp Lys Ala Lys Lys Leu Ile Asp
1185                1190                1195                1200

Ala Ala Gly Asn Ala Asp Gly Ile Lys Gln Ala Glu Ser Asp Gly Ile
            1205                1210                1215

Lys Ala Ile Asp Ala Gln His Gln Ser Ser Gln Ala Leu Ala Asp Arg
        1220                1225                1230

Lys Arg Asp Ala Lys Thr Ala Ile Asp Ala Glu Ala Ala Lys Glu Thr
    1235                1240                1245

Ala Ala Ile Asp His Asp Ala Thr Leu Thr Ala Asn Glu Lys Ala Ser
1250                1255                1260

Gln Lys Gln Ala Val Thr Asp Glu Ala Thr Lys Ala Lys Lys Ala Ile
1265                1270                1275                1280

Asp Ala Ala Lys Gln Ala Asp Ala Val Asp Gln Ala Lys Thr Asp Gly
            1285                1290                1295

Ile Lys Ala Ile Asp Ala Gln His His Ser Gly Gln Ala Leu Asp Asp
        1300                1305                1310

Arg Lys Ala Asp Ala Lys Gln Val Ile Asp Ala Glu Ala Ala Lys Val
    1315                1320                1325

Thr Ala Ala Ile Asp Gln Asp Asn Thr Leu Thr Lys Ala Gln Lys Ala
1330                1335                1340

Ala Gln Lys Gln Gly Val Ala Thr Glu Ala Asp Lys Ala Lys Gln Ala
1345                1350                1355                1360

Ile Asp Ala Ala Gly Asp Ala Asp Ala Val Asp Gln Ala Lys Thr Ala
            1365                1370                1375

Gly Ile Gln Ala Ile Asp Ala Gln His Lys Ala Gly Lys Thr Ile Asp
        1380                1385                1390

Ser Arg His Asp Asp Ala Lys Gln Ala Ile Asp Glu Glu Ala Ala Lys
    1395                1400                1405

Val Ile Lys Ala Ile Asp Gln Asp Pro Thr Leu Thr Ala Ala Gln Lys
1410                1415                1420

Glu Ala Gln Lys Gln Ala Val Ala Thr Glu Ala Asp Lys Ala Lys Lys
1425                1430                1435                1440

Ala Ile Asp Ala Ala Gly Asp Ala Asp Ala Val Asp Gln Ala Lys Thr
            1445                1450                1455

Ala Gly Ile Lys Ala Ile Asp Glu Gln His Lys Ser Gly Gln Thr Val
        1460                1465                1470

Asp Ala Arg Lys Glu Asp Ala Lys Lys Ala Ile Asp Ala Glu Ala Gly
    1475                1480                1485

Lys Val Thr Asp Ala Ile Asp His Asp Ala Thr Leu Thr Ala Ala Gln
1490                1495                1500

Lys Glu Ala Gln Lys Gln Ala Val Ala Asp Glu Ala Asp Lys Ala Lys
1505                1510                1515                1520

Lys Ala Ile Asp Ala Ala Gly Asn Ala Asp Ala Ile Asp Gln Ala Lys
```

```
                        1525                1530                1535

Ser Ala Gly Ile Lys Ala Ile Asp Glu Gln His Lys Ser Gly Gln Ser
                    1540                1545                1550

Ile Asp Thr Arg Lys Asp Asp Ala Lys Lys Ala Ile Asp Gly Glu Val
                1555                1560                1565

Ala Lys Ile Thr Asp Ala Ile Asp His Asp Pro Thr Leu Thr Asp Ala
            1570                1575                1580

Glu Lys Ala Thr Gln Lys Gln Ala Val Ile Ala Glu Ala Asp Lys Ala
1585                1590                1595                1600

Lys Lys Ala Ile Asp Ala Ala Gly Asp Ala Asp Ala Val Asp Gln Ala
                1605                1610                1615

Gln Lys Ala Gly Ile Lys Ala Ile Asp Gln Gln His Lys Ser Gly Gln
            1620                1625                1630

Ala Leu Ala Ile Arg Lys Asp Ala Ala Lys Lys Ala Ile Asp Glu Glu
        1635                1640                1645

Ala Ala Lys Val Ser Glu Ala Ile Asp His Asp Val Thr Leu Thr Asp
    1650                1655                1660

Ser Glu Lys Gly Thr Gln Lys Gln Ala Val Ala Asp Glu Ala Lys Lys
1665                1670                1675                1680

Ala Lys Gln Ala Ile Asp Thr Ala Asp Asn Ala Asp Gly Val Asp Gln
                1685                1690                1695

Ala Val Thr Lys Gly Ile Gln Ile Ile Asp Ala Gln His Gln Ser Gly
            1700                1705                1710

Gln Ala Leu Thr Asp Arg Lys Ala Ala Lys Lys Ala Ile Asp Ala
        1715                1720                1725

Glu Ala Ala Lys Val Gly Gln Ala Ile Glu Gln Asp Pro Thr Leu Thr
    1730                1735                1740

Ala Thr Glu Lys Lys Arg Gln Lys Gln Ala Val Ala Asp Glu Ala Thr
1745                1750                1755                1760

Lys Ala Lys Ala Ala Ile Asp Thr Ala Ala Asn Ala Ser Ala Val Asp
                1765                1770                1775

Gln Ala Lys Asn Ala Gly Ile Lys Ala Ile Asp Ala Gln His Val Ser
            1780                1785                1790

Gly Lys Ala Phe Asp Leu Ser Lys Asp Glu Ala Lys Lys Ala Ile Asp
        1795                1800                1805

Ala Glu Ala Thr Lys Val Gln Gly Glu Ile Asp Gln Asp Pro Thr Leu
    1810                1815                1820

Thr Ala Thr Ala Lys Lys Gln Gln Lys Glu Ala Val Pro Thr Glu Ala
1825                1830                1835                1840

Gly Lys Ala Lys Gln Ala Phe Asp Gln Ala Lys Asn Ile Glu Glu Val
                1845                1850                1855

Arg Pro Pro Lys Thr Lys Ala Ser Lys Arg Leu Met Arg Asn Ile Ser
            1860                1865                1870

Gln Asp Lys Gln Leu His Thr
        1875

<210> SEQ ID NO 71
<211> LENGTH: 293
<212> TYPE: PRT
<213> ORGANISM: Lactobacillus rhamnosus

<400> SEQUENCE: 71

Met Pro Leu Val Asn Ala Ala Glu Leu Val Lys Ala Ala His Lys Gly
1               5                   10                  15
```

```
His Tyr Cys Ile Gly Ala Phe Asn Thr Asn Asn Leu Glu Trp Thr Arg
            20                  25                  30

Ala Ile Leu Ala Gly Ala Gln Glu Leu Asn Val Pro Val Ile Ile Gln
        35                  40                  45

Thr Ser Met Gly Ala Ala Lys Tyr Met Gly Gly Tyr Glu Phe Cys Gln
    50                  55                  60

Thr Met Ile Glu Ala Ala Val Lys Ala Met Asp Ile Thr Val Pro Val
65                  70                  75                  80

Val Ile His Leu Asp His Gly Asn Tyr Glu Ala Lys Glu Ala Ile
                85                  90                  95

Ala Ala Gly Tyr Asn Ser Val Met Phe Asp Gly His Asp Leu Asp Phe
            100                 105                 110

Glu Asp Asn Leu Glu Lys Thr Lys Glu Ile Val Lys Leu Ala His Ala
            115                 120                 125

Lys Gly Ile Ser Val Glu Ala Glu Val Gly Ser Ile Gly Gly Glu Glu
    130                 135                 140

Asp Gly Val Val Gly Glu Gly Glu Leu Ala Asp Val Glu Glu Ala Lys
145                 150                 155                 160

Thr Leu Ala Ala Thr Gly Ile Asp Phe Leu Ala Gly Ile Gly Asn
                165                 170                 175

Ile His Gly Gln Tyr Pro Asp Asn Trp Lys Gly Leu His Phe Asp Arg
            180                 185                 190

Leu Gln Glu Leu Asn Asp Ala Val Lys Met Pro Leu Val Leu His Gly
            195                 200                 205

Gly Ser Gly Ile Pro Gln Glu Gln Val Gln Lys Ala Ile Thr Met Gly
    210                 215                 220

Ile Ser Lys Leu Asn Ile Asn Thr Glu Cys Gln Leu Ala Phe Ala Lys
225                 230                 235                 240

Ala Thr Arg Glu Tyr Ile Glu Ala Gly Lys Asp Gln Gly Lys Gly
            245                 250                 255

Phe Asp Pro Arg Lys Met Leu Lys Pro Gly Thr Asp Ala Ile Thr Asp
            260                 265                 270

Thr Phe Lys Glu Ile Thr Gly Trp Ile Gly Asn Lys Pro Val Lys Met
        275                 280                 285

Val Pro Glu Ala Leu
        290

<210> SEQ ID NO 72
<211> LENGTH: 174
<212> TYPE: PRT
<213> ORGANISM: Lactobacillus rhamnosus

<400> SEQUENCE: 72

Met Ser Lys Val Ile Gly Ile Asp Leu Gly Thr Thr Asn Ser Ala Val
1               5                   10                  15

Ala Val Leu Glu Gly Asn Gln Pro Lys Ile Ile Thr Asn Pro Glu Gly
            20                  25                  30

Asn Arg Thr Thr Pro Ser Val Val Ala Phe Lys Asp Gly Glu Ile Gln
        35                  40                  45

Val Gly Glu Val Ala Lys Arg Gln Ala Ile Thr Asn Pro Asp Thr Ile
    50                  55                  60

Val Ser Ile Lys Arg His Met Gly Glu Ala Asn Tyr Lys Val Lys Val
65                  70                  75                  80

Gly Asp Lys Glu Tyr Thr Pro Gln Glu Ile Ser Ala Met Ile Leu Gln
            85                  90                  95
```

```
Tyr Ile Lys Lys Phe Ser Glu Asp Tyr Leu Gly Glu Pro Val Lys Asp
            100                 105                 110

Ala Val Ile Thr Val Pro Val Tyr Phe Asn Asp Ser Glu Arg Gln Ala
            115                 120                 125

Asn Lys Asp Ala Gly Lys Ile Ala Gly Leu Asn Val Gln Arg Ile Ile
            130                 135                 140

Asn Glu Pro Thr Ala Ser Ala Leu Ala Tyr Gly Leu Asp Lys Gly Asp
145                 150                 155                 160

Lys Glu Lys Arg Phe Gly Leu Arg Leu Cys Arg Arg His Ile
                165                 170
```

<210> SEQ ID NO 73
<211> LENGTH: 282
<212> TYPE: PRT
<213> ORGANISM: Lactobacillus rhamnosus

<400> SEQUENCE: 73

```
Gln Val Ile Ala Asp Gly Val Val Thr Lys Tyr Thr Pro Ala Asn Ala
1               5                   10                  15

Met Ile Val Ala Thr His Arg His Thr Ala Lys Gln Leu Leu Ala Ala
            20                  25                  30

Ala Gly Ile Pro Val Ala Arg Gly Ala Lys Phe Thr Lys Trp Pro Asp
            35                  40                  45

Ala Lys Ala Ala Phe Glu His Ser Phe Ala His Lys Ser Ile Val Val
            50                  55                  60

Lys Pro Glu Ala Arg Ser Gln Gly Lys Ala Val Glu Gln Phe Ser Ile
65                  70                  75                  80

Pro Pro Thr Glu Lys Gln Phe Asp Arg Ala Phe His Glu Ala Asn Arg
                85                  90                  95

His His Gly Val Leu Ile Glu Met Met Ala Arg Gly Thr Thr Tyr His
            100                 105                 110

Phe Thr Ile Ile Gly Gln Gln Val Leu Ser Val Leu Glu Thr Ala Ala
            115                 120                 125

Ala Asn Val Val Gly Asp Gly Arg Lys Ala Ile Lys Glu Leu Ile Ala
            130                 135                 140

Leu Lys Asn Gly His Arg Ala Thr Ser Arg Gln Leu Gln Leu Asp Ala
145                 150                 155                 160

Ser Ala Arg Arg Gln Leu Lys Ala Gln Ala Leu Thr Pro Glu Thr Val
                165                 170                 175

Leu Gln Arg Gly Gln Gln Val Phe Leu Thr Thr Ala Ala His Pro Gln
            180                 185                 190

Thr Gly Gly Asp Leu Tyr Asp Val Thr Asp Glu Ile Asp Asp Ser Tyr
            195                 200                 205

Lys Gln Leu Ala Leu Lys Ala Ala Thr Leu Asp Leu Pro Val Ala
            210                 215                 220

Ala Val Asp Ile Val Ile Asp Asn Leu Tyr Ala Pro Tyr Asp Pro Glu
225                 230                 235                 240

Ala Asp Gly Gln Ala Ile Val Ile Ser Leu Asn Pro Val Pro Asp Leu
                245                 250                 255

Ala Val Pro Leu His Pro Asp Met Gly Glu Ser Arg Ala Leu Ala Pro
            260                 265                 270

Ala Leu Leu Asn Trp Leu Phe Ala Val Arg
            275                 280
```

<210> SEQ ID NO 74
<211> LENGTH: 261
<212> TYPE: PRT
<213> ORGANISM: Lactobacillus rhamnosus

<400> SEQUENCE: 74

Met Tyr Arg Asp Leu Asn Gly Lys Val Ala Val Thr Gly Gly Ser
1               5                   10                  15

Lys Gly Ile Gly Ala Gly Ile Ala Glu Arg Phe Gly Gln Glu His Met
            20                  25                  30

Ala Val Val Ile Asn Tyr Leu Gly Asp His Glu Gly Ala Arg Lys Thr
        35                  40                  45

Ala Asp Thr Val Ile Lys Asn Gly Gly Gln Ala Val Ser Ile His Ala
50                  55                  60

Asp Val Ser Thr Glu Ala Gly Ile Ala Ser Leu Val Lys Thr Ala Glu
65                  70                  75                  80

Ser Glu Phe Gly Arg Leu Asp Val Trp Val Asn Asn Ala Gly Met Glu
                85                  90                  95

Ile Lys Ala Pro Thr His Glu Val Ser Leu Asp Asp Trp Asn Lys Val
            100                 105                 110

Ile Ala Ile Asn Gln Thr Gly Val Phe Leu Gly Ala Arg Ala Ala Leu
        115                 120                 125

Asn Tyr Phe Leu Asp His His Gln Pro Gly Asn Ile Ile Asn Ile Ser
130                 135                 140

Ser Val His Glu Gln Ile Pro Trp Pro Thr Phe Ala Ser Tyr Ala Ala
145                 150                 155                 160

Ala Lys Gly Ser Val Lys Leu Phe Thr Glu Thr Ile Ala Met Glu Tyr
                165                 170                 175

Ala Asn Arg Gly Ile Arg Val Asn Ala Ile Gly Pro Gly Ala Ile Glu
            180                 185                 190

Thr Pro Ile Asn Ala Glu Lys Phe Ala Asp Lys Ala Gln Tyr Asp Gln
        195                 200                 205

Thr Val Ala Met Ile Pro Gln Gly Arg Leu Gly Lys Pro Glu Asp Val
    210                 215                 220

Ala Ala Gly Ala Ala Trp Leu Ala Ser Thr Glu Ser Ser Tyr Val Thr
225                 230                 235                 240

Gly Thr Thr Leu Phe Ile Asp Gly Gly Met Thr Leu Tyr Pro Ala Phe
                245                 250                 255

Lys Asp Gly Gln Gly
            260

<210> SEQ ID NO 75
<211> LENGTH: 396
<212> TYPE: PRT
<213> ORGANISM: Lactobacillus rhamnosus

<400> SEQUENCE: 75

Met Ala Lys Ile Leu Ala Val Asn Ala Gly Ser Ser Thr Leu Lys Trp
1               5                   10                  15

Lys Leu Phe Asp Met Pro Ala Glu Val Gln Leu Ala Glu Gly Leu Val
            20                  25                  30

Asp Arg Leu Gly Gln Pro Gln Ser Lys Val Lys Ile Lys Tyr Gly Asp
        35                  40                  45

Gly Gln Lys Tyr Glu Ser Asp Thr Pro Ile Ala Asn Tyr Gln Glu Ala
    50                  55                  60

Val Ala Ser Leu Met Gly Asn Ile Lys Ala Leu Gly Leu Val Glu His

-continued

```
            65                  70                  75                  80
        Leu His Glu Ile Ile Gly Val Gly His Arg Val Ala Gly Gly Glu
                            85                  90                  95
        Ile Phe Ala Glu Ser Val Val Asp Asp Glu Thr Leu Leu Gln Ile
                        100                 105                 110
        Gln Asn Leu Arg Asp Tyr Ala Pro Leu His Asn Pro Val Glu Ala Asp
                    115                 120                 125
        Tyr Ile Ser Val Phe Arg Lys Met Met Pro Trp Ala Asn Glu Val Ala
                130                 135                 140
        Val Phe Asp Thr Ala Phe His Gln Thr Met Gln Pro Glu Asn Phe Leu
        145                 150                 155                 160
        Tyr Ser Ile Pro Tyr Glu Tyr Tyr Gln Tyr Gly Ala Arg Lys Tyr
                            165                 170                 175
        Gly Ala His Gly Thr Ser Val Arg Tyr Val Ser Ala Arg Ala Ala Glu
                        180                 185                 190
        Met Leu Gly Lys Pro Leu Glu Asp Leu Arg Met Ile Val Met His Leu
                    195                 200                 205
        Gly Ser Gly Ser Ser Ile Thr Ala Val Gln Gly Gln Ser Ile Asp
                210                 215                 220
        Thr Ser Met Gly Phe Thr Pro Leu Ala Gly Val Thr Met Gly Thr Arg
        225                 230                 235                 240
        Ser Gly Asp Ile Asp Pro Ser Leu Val Gly Tyr Leu Met Lys Lys Leu
                            245                 250                 255
        Ala Ile Pro Asp Val Gly Gln Met Ile His Ile Leu Asn Asn Asp Ser
                        260                 265                 270
        Gly Leu Leu Gly Ile Ser Gly Leu Ser Asn Asp Met Arg Asp Leu Glu
                    275                 280                 285
        Ala Ala Glu Asp Thr Asn Thr Arg Ala Lys Leu Ala Leu Asp Ile Phe
                290                 295                 300
        Val Asn Arg Val Val Lys Tyr Val Gly Ser Tyr Val Ala Leu Met Asp
        305                 310                 315                 320
        Gly Val Asp Val Leu Val Phe Thr Ala Gly Ile Gly Glu Asn Gly Asp
                            325                 330                 335
        Glu Ile Arg Asp Lys Ile Met Arg Ser Leu Asp Tyr Leu Gly Ala Lys
                        340                 345                 350
        Ile Asp Asn Asp Leu Asn Tyr Lys Ser His Gly Val Glu Ala Asp Leu
                    355                 360                 365
        Ser Thr Ala Asp Ser Thr Val Lys Thr Leu Leu Val Pro Thr Asn Glu
                370                 375                 380
        Glu Leu Met Ile Val Arg Asp Val Met Ala Leu Ser
        385                 390                 395
```

<210> SEQ ID NO 76
<211> LENGTH: 11
<212> TYPE: PRT
<213> ORGANISM: Lactobacillus rhamnosus
<220> FEATURE:
<221> NAME/KEY: PEPTIDE
<222> LOCATION: (0)...(0)

<400> SEQUENCE: 76

```
Met Arg Thr Pro Phe Ile Ala Gly Asn Leu Lys
 1               5                  10
```

<210> SEQ ID NO 77
<211> LENGTH: 10

```
<212> TYPE: PRT
<213> ORGANISM: Lactobacillus rhamnosus
<220> FEATURE:
<221> NAME/KEY: PEPTIDE
<222> LOCATION: (0)...(0)

<400> SEQUENCE: 77

Pro Leu Val Asn Ala Ala Glu Leu Val Lys
 1               5                  10

<210> SEQ ID NO 78
<211> LENGTH: 11
<212> TYPE: PRT
<213> ORGANISM: Lactobacillus rhamnosus
<220> FEATURE:
<221> NAME/KEY: PEPTIDE
<222> LOCATION: (0)...(0)

<400> SEQUENCE: 78

Met Glu Lys Arg Glu Phe Asn Ile Ala Ala Glu
 1               5                  10

<210> SEQ ID NO 79
<211> LENGTH: 12
<212> TYPE: PRT
<213> ORGANISM: Lactobacillus rhamnosus
<220> FEATURE:
<221> NAME/KEY: PEPTIDE
<222> LOCATION: (0)...(0)

<400> SEQUENCE: 79

Ser Lys Val Ile Gly Ile Asp Pro Gly Thr Gly Asn
 1               5                  10

<210> SEQ ID NO 80
<211> LENGTH: 12
<212> TYPE: PRT
<213> ORGANISM: Lactobacillus rhamnosus
<220> FEATURE:
<221> NAME/KEY: PEPTIDE
<222> LOCATION: (0)...(0)

<400> SEQUENCE: 80

Thr Val Lys Ile Gly Ile Asn Gly Phe Gly Arg Ile
 1               5                  10

<210> SEQ ID NO 81
<211> LENGTH: 13
<212> TYPE: PRT
<213> ORGANISM: Lactobacillus rhamnosus
<220> FEATURE:
<221> NAME/KEY: PEPTIDE
<222> LOCATION: (0)...(0)

<400> SEQUENCE: 81

Ser Val Lys Ile Thr Ala Gly Gln Leu Glu His Leu Lys
 1               5                  10

<210> SEQ ID NO 82
<211> LENGTH: 12
<212> TYPE: PRT
<213> ORGANISM: Lactobacillus rhamnosus
<220> FEATURE:
<221> NAME/KEY: PEPTIDE
<222> LOCATION: (0)...(0)

<400> SEQUENCE: 82

Ala Lys Leu Ile Val Ser Asp Leu Asp Val Lys Asp
```

```
                         -continued
1               5              10

<210> SEQ ID NO 83
<211> LENGTH: 12
<212> TYPE: PRT
<213> ORGANISM: Lactobacillus rhamnosus
<220> FEATURE:
<221> NAME/KEY: PEPTIDE
<222> LOCATION: (0)...(0)

<400> SEQUENCE: 83

Ser Ile Ile Thr Asp Val Leu Ala Arg Glu Val Leu
1               5                  10
```